(12) United States Patent
Termin et al.

(10) Patent No.: US 7,569,604 B2
(45) Date of Patent: Aug. 4, 2009

(54) HETEROCYCLIC DERIVATIVES FOR MODULATION OF CALCIUM CHANNELS

(75) Inventors: Andreas Termin, Encinitas, CA (US); Esther Martinborough, San Diego, CA (US); Nicole Zimmerman, San Diego, CA (US); Charles Cohen, Poway, CA (US); Corey Gutierrez, Cardiff-by-the-Sea, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/165,254

(22) Filed: Jun. 22, 2005

(65) Prior Publication Data

US 2006/0074076 A1   Apr. 6, 2006

Related U.S. Application Data

(60) Provisional application No. 60/582,013, filed on Jun. 22, 2004.

(51) Int. Cl.
*A61K 31/343* (2006.01)
*A61K 31/443* (2006.01)
*A61K 31/4525* (2006.01)
*A61K 31/4545* (2006.01)
*A61K 31/495* (2006.01)
*A61K 31/5377* (2006.01)
*C07D 405/12* (2006.01)
*C07D 405/14* (2006.01)
*C07D 407/14* (2006.01)

(52) U.S. Cl. ............ 514/469; 514/217.03; 514/233.05; 514/254.11; 514/256; 514/278; 514/314; 514/316; 514/320; 544/297; 544/153; 544/141; 544/364; 546/16; 546/187; 546/193; 546/196; 540/596; 549/414; 549/467

(58) Field of Classification Search ............ 514/217.03, 514/233.5, 254.11, 256, 278, 314, 316, 320, 514/469; 544/297, 153, 141, 364; 549/414, 549/467; 546/16, 187, 193, 196; 540/596
See application file for complete search history.

(56) References Cited

U.S. PATENT DOCUMENTS 7,265,152 B2 *   9/2007   Saha et al. .................. 514/469

FOREIGN PATENT DOCUMENTS

| WO | WO 02/098852 | 12/2002 |
| WO | WO 00/30683 | 10/2003 |
| WO | WO 2004041202 A2 * | 5/2004 |

OTHER PUBLICATIONS

Database WPI Section ch, Week 200039 Derwent Publications Ltd., London, GB; AN 2000-451668, XP002350808 & WO 00/30683 A1 (Shionogi & CO LTD) Jun. 2, 2000 abstract pp. 51, 52; compounds I-24, I-32, I-33, I-62.

* cited by examiner

*Primary Examiner*—Rebecca L Anderson
*Assistant Examiner*—Jason Nolan
(74) *Attorney, Agent, or Firm*—Wei-Chuan Chen

(57) ABSTRACT

Heterocyclic derivatives act as Ca channel antagonists. The compositions are useful for treating or relieving Ca channel mediated conditions.

31 Claims, No Drawings

HETEROCYCLIC DERIVATIVES FOR MODULATION OF CALCIUM CHANNELS

CROSS-REFERENCES TO RELATED APPLICATIONS

The present application claims priority under 35 U.S.C. § 119 to U.S. Provisional Application No. 60/582,013, filed Jun. 22, 2004, the entire contents thereof being incorporated herein by reference.

FIELD OF THE INVENTION

This invention relates to heterocyclic derivatives that can act as Ca channel antagonists. The preferred embodiments are useful for treating or relieving Ca channel mediated conditions.

BACKGROUND OF THE INVENTION

Voltage-gated calcium channels are membrane-spanning, multi-subunit proteins that open in response to membrane depolarization, allowing Ca entry from the extracellular milieu. Calcium channels were initially classified based on the time and voltage-dependence of channel opening and on the sensitivity to pharmacological block. The categories were low-voltage activated (primarily T-type) and high-voltage activated (L, N, P, Q or R-type). This classification scheme was replaced by a nomenclature based upon the molecular subunit composition, as summarized in Table I (Hockerman G H, Peterson B Z, Johnson B D, Catterall W A. 1997. *Annu Rev Pharmacol Toxicol* 37: 361-96.)

There are four primary subunit types that make up calcium channels—$\alpha_1$, $\alpha_2\delta$, $\beta$ and $\gamma$ (See, e.g., De Waard et al. Structural and functional diversity of voltage-activated calcium channels. In Ion Channels, (ed. T. Narahashi) 41-87, (Plenum Press, New York, 1996)). The $\alpha_1$ subunit is the primary determinant of the pharmacological properties and contains the channel pore and voltage sensor (Hockennan G H, Peterson B Z, Johnson B D, Catterall W A. 1997. *Annu Rev Pharmacol Toxicol* 37: 361-96; Striessnig J. 1999. *Cell Physiol Biochem* 9: 242-69). Ten isoforms of the $\alpha_1$ subunit are known, as indicated in Table I. The $\alpha_2\delta$ subunit consists of two disulfide linked subunits, $\alpha_2$, which is primarily extracellular and a transmembrane $\delta$ subunit. Four isoforms of $\alpha_2\delta$ are known, $\alpha_2\delta$-1, $\alpha_2\delta$-2, $\alpha_2\delta$-3 and $\delta_2\delta$-4. The $\beta$ subunit is a non-glycosylated cytoplasmic protein that binds to the $\alpha_1$ subunit. Four isoforms are known, termed $\beta_1$ to $\beta_4$. The $\gamma$ subunit is a transmembrane protein that has been biochemically isolated as a component of $Ca_v1$ and $Ca_v2$ channels. At least 8 isoforms are known ($\gamma_1$ to $\gamma_8$) [Kang M G, Campbell K P. 2003. *J Biol Chem* 278: 21315-8]. The nomenclature for voltage-gated calcium channels is based upon the content of the $\alpha_1$ subunit, as indicated in Table I. Each type of $\alpha_1$ subunit can associate with a variety of $\beta$, $\alpha_2\delta$ or $\gamma$ subunits, so that each $Ca_v$ type corresponds to many different combinations of subunits.

| Cav Nomenclature | $\alpha_1$ subunit | Pharmacological name |
| --- | --- | --- |
| $Ca_v1.1$ | $\alpha_{1S}$ | L-type |
| $Ca_v1.2$ | $\alpha_{1C}$ | L-type |
| $Ca_v1.3$ | $\alpha_{1D}$ | L-type |
| $Ca_v1.4$ | $\alpha_{1F}$ | |
| $Ca_v2.1$ | $\alpha_{1A}$ | P- or Q-type |
| $Ca_v2.2$ | $\alpha_{1B}$ | N-type |
| $Ca_v2.3$ | $\alpha_{1E}$ | R-type |
| $Ca_v3.1$ | $\alpha_{1G}$ | T-type |
| $Ca_v3.2$ | $\alpha_{1H}$ | T-type |
| $Ca_v3.3$ | $\alpha_{1I}$ | T-type |

$Ca_v2$ currents are found almost exclusively in the central and peripheral nervous system and in neuroendocrine cells and constitute the predominant forms of presynaptic voltage-gated calcium current. Presynaptic action potentials cause channel opening and neurotransmitter release is steeply dependent upon the subsequent calcium entry. Thus, $Ca_v2$ channels play a central role in mediating neurotransmitter release.

$Ca_v2.1$ and $Ca_v2.2$ contain high affinity binding sites for the peptide toxins $\omega$-conotoxin-MVIIC and $\omega$-conotoxin-GVIA, respectively, and these peptides have been used to determine the distribution and function of each channel type. $Ca_v2.2$ is highly expressed at the presynaptic nerve terminals of neurons from the dorsal root ganglion and neurons of lamina I and II of the dorsal horn (Westenbroek R E, Hoskins L, Catterall W A. 1998. *J Neurosci* 18: 6319-30; Cizkova D, Marsala J, Lukacova N, Marsala M, Jergova S, et al. 2002. *Exp Brain Res* 147: 456-63) $Ca_v2.2$ channels are also found in presynaptic terminals between second and third order interneurons in the spinal cord. Both sites of neurotransmission are very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain, on the other hand, may last for much longer periods of time and its intensity is more graded. Inflammation may occur for many reasons including tissue damage, autoimmune response, and pathogen invasion. Inflammatory pain is mediated by a variety of agents that are released during inflammation, including substance P, histamines, acid, prostaglandin, bradykinin, CGRP, cytokines, ATP, and other agents (Julius D, Basbaum A I. 2001. *NATURE* 413 (6852): 203-10). The third class of pain is neuropathic and involves nerve damage arising from nerve injury or viral infection and results in reorganization of neuronal proteins and circuits yielding a pathologic "sensitized" state that can produce chronic pain lasting for years. This type of pain provides little or no adaptive benefit and is particularly difficult to treat with existing therapies (Bridges D, Thompson S W N, Rice A S C (2001) Mechanisms of neuropathic pain. Br J Anaesth 87:12-26).

Pain, particularly neuropathic and intractable pain is a large unmet medical need. Millions of individuals suffer from severe pain that is not well controlled by current therapeutics. The current drugs used to treat pain include non-steroidal anti-inflammatory drugs (NSAIDs), cyclo-oxygenase 2 (COX-2) inhibitors, opioids, tricyclic antidepressants, and anticonvulsants. Neuropathic pain has been particularly difficult to treat as it does not respond well to opioids until high doses are reached. Gabapentin is currently the most widely used therapeutic for the treatment of neuropathic pain, although it works in only 60% of patients and has modest efficacy. The drug is generally safe, although sedation is an issue at higher doses.

Validation of $Ca_v2.2$ as a target for the treatment of neuropathic pain is provided by studies with ziconotide (also known as ω-conotoxin-MVIIA), a selective peptide blocker of this channel (Bowersox S S, Gadbois T, Singh T, Pettus M, Wang Y X, Luther R R. 1996. *J Pharmacol Exp Ther* 279: 1243-9; Jain K K. 2000. *Exp. Opin. Invest. Drugs* 9: 2403-10; Vanegas H, Schaible H. 2000. *Pain* 85: 9-18). In man, intrathecal infusion of Ziconotide is effective for the treatment of intractable pain, cancer pain, opioid resistant pain, and neuropathic pain. The toxin has an 85% success rate for the treatment of pain in humans with a greater potency than morphine. An orally available antagonist of $Ca_v2.2$ should have similar efficacy without the need for intrathecal infusion. $Ca_v2.1$ and $Ca_v2.3$ are also in neurons of nociceptive pathways and antagonists of these channels could be used to treat pain.

Antagonists of $Ca_v2.1$, $Ca_v2.2$ or $Ca_v2.3$ should also be useful for treating other pathologies of the central nervous system that apparently involve excessive calcium entry. Cerebral ischaemia and stroke are associated with excessive calcium entry due to depolarization of neurons. The $Ca_v2.2$ antagonist ziconotide is effective in reducing infarct size in a focal ischemia model using laboratory animals, suggesting that $Ca_v2.2$ antagonists could be used for the treatment of stroke. Likewise, reducing excessive calcium influx into neurons may be useful for the treatment of epilepsy, traumatic brain injury, Alzheimer's disease, multi-infarct dementia and other classes of dementia, amyotrophic lateral sclerosis, amnesia, or neuronal damage caused by poison or other toxic substances. The distribution of $Ca_v2$ channels in the central nervous system also suggests that antagonists are likely to provide efficacy against a number of psychiatric disorders, such as anxiety and depression and will also ameliorate insomnia.

$Ca_v2.2$ also mediates release of neurotransmitters from neurons of the sympathetic nervous system and antagonists could be used to treat cardiovascular diseases such as hypertension, cardiac arrhythmias, angina pectoris, myocardial infarction, and congestive heart failure. Inhibition of neurotransmission in the gut can be useful for treating irritable bowel disease and other gastrointestinal disorders.

Block of $Ca_v3$ channels can also result in therapeutically useful effects. Low-voltage activated calcium currents associated with these channels were first described in dorsal root ganglia neurons and suppression of $Ca_v3.2$ with antisense provides efficacy in the chronic constriction model for neuropathic pain (Bourinet E, Alloui A, Monteil A, re C B, Couette B, Poirot O, Pages A, McRory J, Snutch T P, Eschalier A, Nargeot J I (2005) Silencing of the $Ca_v3.2$ T-type calcium channel gene in sensory neurons demonstrates its major role in nociception. EMBO Journal 24:315-324). Block of $Ca_v3$ channels is also likely to result in efficacy against inflammatory pain and acute pain. Current through these channels supports pacemaker electrical activity in the central nervous system, and antagonists are likey to have activity as anti-convulsant agents. Unlike $Ca_v2$ channels, $Ca_v3$ channels are widely distributed in vascular smooth muscle and myocardial cells. $Ca_v3$ antagonists may thus have utility against hypertension, angina and arrhythmias.

$Ca_v2$ and $Ca_v3$ channels are also found in a variety of endocrine cells and antagonists may be useful for the treatment of endocrine disorders such as diabetes.

SUMMARY OF THE INVENTION

The present invention discloses Ca channel antagonists of formula I-A, formula I-B, or formula I-C:

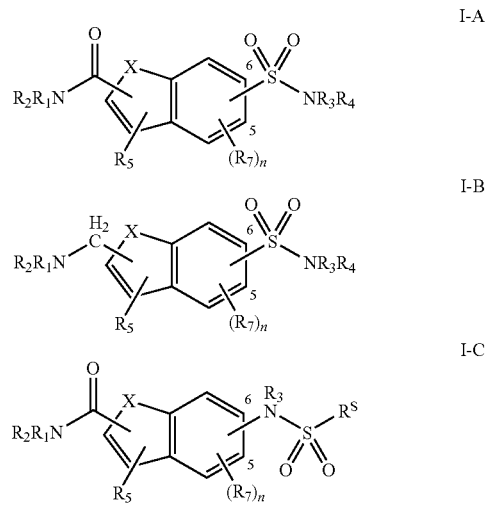

wherein $R_1$, $R_2$, $R_3$, $R_4$, $R_5$, $R_7$, X, and n are as defined below.

DETAILED DESCRIPTION OF THE INVENTION

The term "alkyl" used herein refers to a monovalent straight or branched chain radical from one to ten carbon atoms, including, but not limited to, methyl, ethyl, n-propyl, isopropyl, n-butyl, isobutyl, tert-butyl, n-hexyl, and the like.

The term "halo" used herein refers to fluoro, chloro, bromo, or iodo.

The term "alkoxy" used herein refers to straight or branched chain alkyl radical covalently bonded to the parent molecule through an —O— linkage. Examples of alkoxy groups include, but not limited to, methoxy, ethoxy, propoxy, isopropoxy, n-butoxy, sec-butoxy, t-butoxy and the like.

The term "alkenyl" used herein refers to a monovalent straight or branched chain radical from two to six carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical from two to six carbon atoms containing a carbon triple bond including, but not limited to, 1-propynyl, 1-butynyl, 2-butynyl, and the like.

The term "aryl" used herein refers to homocyclic aromatic radical whether fused or not fused. Examples of aryl groups include, but are not limited to, phenyl, naphthyl, biphenyl, phenanthrenyl, naphthacenyl, and the like.

The term "cycloalkyl" used herein refers to saturated aliphatic ring system radical having 3 to 10 carbon atoms including, but not limited to, cyclopropyl, cyclopentyl, cyclohexyl, cycloheptyl, and the like.

The term "cycloalkenyl" used herein refers to aliphatic ring system radical having 3 to 10 carbon atoms having at least one carbon-carbon double bond in the ring. Examples of cycloalkenyl groups include, but are not limited to, cyclopropenyl, cyclopentenyl, cyclohexenyl, cycloheptenyl, and the like.

The term "polycycloalkyl" used herein refers to saturated aliphatic ring system radical having at least two rings that are fused with or without bridgehead carbons. Examples of polycycloalkyl groups include, but are not limited to, bicyclo [4.4.0]decanyl, bicyclo[2.2.1]heptanyl, adamantyl, norbornyl, and the like.

The term "polycycloalkenyl" used herein refers to aliphatic ring system radical having at least two rings that are fused with or without bridgehead carbons in which at least one of the rings has a carbon-carbon double bond. Examples of polycycloalkenyl groups include, but are not limited to, norbornylenyl, 1,1'-bicyclopentenyl, and the like.

The term "polycyclic hydrocarbon" used herein refers to a ring system radical in which all of the ring members are carbon atoms. Polycyclic hydrocarbons can be aromatic or can contain less than the maximum number of non-cumulative double bonds. Examples of polycyclic hydrocarbon include, but are not limited to, naphthyl, dihydronaphthyl, indenyl, fluorenyl, and the like.

The term "heterocyclic" or "heterocyclyl" used herein refers to cyclic ring system radical having at least one ring system in which one or more ring atoms are not carbon, namely heteroatom. Heterocycles can be nonaromatic or aromatic. Examples of heterocyclic groups include, but are not limited to, morpholinyl, tetrahydrofuranyl, dioxolanyl, pyrolidinyl, oxazolyl, pyranyl, pyridyl, pyrimidinyl, pyrrolyl, and the like.

The term "heteroaryl" used herein refers to heterocyclic group formally derived from an arene by replacement of one or more methine and/or vinylene groups by trivalent or divalent heteroatoms, respectively, in such a way as to maintain the aromatic system. Examples of heteroaryl groups include, but are not limited to, pyridyl, pyrrolyl, oxazolyl, indolyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "cycloalkylalkyl" used herein refers to one or more cycloalkyl groups appended to an alkyl radical. Examples of cycloalkylalkyl include, but are not limited to, cyclohexylmethyl, cyclohexylethyl, cyclopentylmethyl, cyclopentylethyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiophenylethyl, and the like.

The term "heterocyclylalkyl" used herein refers to one or more heterocyclyl groups appended to an alkyl radical. Examples of heterocyclylalkyl include, but are not limited to, morpholinylmethyl, morpholinylethyl, morpholinylpropyl, tetrahydro furanylmethyl, pyrrolidinylpropyl, and the like.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group. When substituted, the substituent group(s) is (are) one or more group(s) individually and independently selected from alkyl, alkenyl, alkynyl, cycloalkyl, aryl, fused aryl, heterocyclyl, heteroaryl, hydroxy, alkoxy, aryloxy, arylalkyl, mercapto, alkylthio, arylthio, cyano, halo, carbonyl, thiocarbonyl, alkoxycarbonyl, nitro, silyl, trihalomethanesulfonyl, and amino, including mono- and di-substituted amino groups, and the protected derivatives thereof. The protecting groups that can form the protective derivatives of the above substituents are known to those of skill in the art and can be found in references such as Greene and Wuts *Protective Groups in Organic Synthesis*; John Wiley and Sons: New York, 1999. Wherever a substituent is described as "optionally substituted" that substituent can be substituted with the above substituents.

Asymmetric carbon atoms can be present. All such isomers, including diastereomers and enantiomers, as well as the mixtures thereof are intended to be included in the scope. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated.

One family of compounds is defined by compounds of formula I-A, formula I-B, or formula I-C:

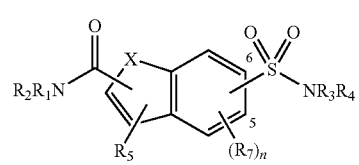

I-A

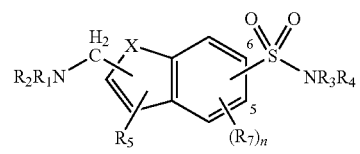

I-B

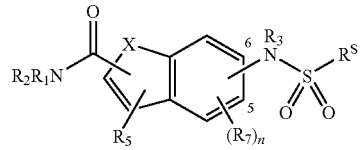

I-C wherein $R_5$ and $R_7$ are independently defined by $-ZR_6$, wherein Z is a bond or is an optionally substituted $C_1$-$C_6$ alkyl, alkenyl, or alkynyl, chain wherein up to two carbon units of Z are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, —NR'SO$_2$—, or —NR'SO$_2$NR'—; and $R_6$ is defined below;

wherein $R_1$, $R_2$, $R_3$, $R_4$ are independently selected from the group consisting of hydrogen, alkyl, substituted alkyl, cycloalkyl, substituted cycloalkyl, heterocyclylalkyl, substituted heterocyclylalkyl, arylalkyl, substituted arylalkyl, heteroarylalkyl, substituted heteroarylalkyl, cycloalkylalkyl, substituted cycloalkylalkyl, polycyclic hydrocarbon, substituted polycyclic hydrocarbon, or $R_1$ and $R_2$ together form an unsubstituted or substituted 3 to 7-membered ring, wherein the members of the ring contain 0-4 heteroatoms selected from nitrogen, oxygen, and sulfur; or $R_3$ and $R_4$ together form a ring wherein together form an unsubstituted or substituted 3 to 7-membered ring, wherein the members of the ring are selected from the group consisting of carbon, nitrogen, oxygen, and sulfur; and the group $SO_2NR_3R_4$ is linked to the phenyl ring either at position 5 or 6;

X is O, S, or N-Z—$R_6$;

n is 0-3;

$R_6$ is independently R', halogen, $NO_2$, CN, $CF_3$, or $OCF_3$;

$R^S$ is an optionally substituted 5-7 membered, saturated, unsaturated, or aromatic ring having 0-3 heteroatoms selected from N, O, or S;

R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, the following compounds are excluded from compounds of formula IA:

a. When $R_3$ and $R_4$, together with the intervening nitrogen atom, form a piperidyl ring, X is S, then $R_5$ is not $NH_2$;
b. When $R_3$ and $R_4$, together with the intervening nitrogen atom, form a 4-benzyl-piperidin-1-yl ring, $R_5$ is hydrogen, X is NH, then $R_1$ and $R_2$ are not simultaneously hydrogen; and
c. When X is O, then $R_5$ is not methyl.

In one embodiment, $R_1$ and $R_2$, are independently selected from the group consisting of hydrogen, alkyl, substituted alkyl, cycloalkyl, substituted cycloalkyl, heterocyclylalkyl, substituted heterocyclylalkyl, arylalkyl, substituted arylalkyl, heteroarylalkyl, substituted heteroarylalkyl, cycloalkylalkyl, substituted cycloalkylalkyl, polycyclic hydrocarbon, substituted polycyclic hydrocarbon.

In another embodiment, $R_1$ and $R_2$ together form an unsubstituted or substituted 3 to 7-membered ring, wherein the members of the ring contain 0-4 heteroatoms selected from nitrogen, oxygen, and sulfur.

In one embodiment, $R_3$ and $R_4$ are independently selected from the group consisting of hydrogen, alkyl, substituted alkyl, cycloalkyl, substituted cycloalkyl, heterocyclylalkyl, substituted heterocyclylalkyl, arylalkyl, substituted arylalkyl, heteroarylalkyl, substituted heteroarylalkyl, cycloalkylalkyl, substituted cycloalkylalkyl, polycyclic hydrocarbon, substituted polycyclic hydrocarbon.

In another embodiment, $R_3$ and $R_4$ together form a ring wherein together form an unsubstituted or substituted 3 to 7-membered ring, wherein the members of the ring are selected from the group consisting of carbon, nitrogen, oxygen, and sulfur.

In one embodiment, X is O, Or, X is S.

In another embodiment, X is N-Z—$R_6$. In one embodiment, Z—$R_6$ together is hydrogen. In another embodiment, Z is a bond. Or, C1-C6 alkylene, wherein up to two carbon units are replaced independently by $SO_2$, C(O), or C(O)O. In one embodiment, Z is $SO_2$.

In one embodiment, R' has 0-3 substituents selected from halo, CN, $CF_3$, $NO_2$, $CF_3$, $OCF_3$, or C1-C6 alkyl, wherein up to two carbon units are optionally and independently replaced by —CO—, —CS—, —COCO—, —CONR"—, —CONR"NR"—, —$CO_2$—, —OCO—, —NR"$CO_2$—, —O—, —NR"CONR"—, —OCONR"—, —NR"NR", —NR"NR"CO—, —NR"CO—, —S—, —SO, —$SO_2$—, —NR"—, —$SO_2$NR"—, NR"$SO_2$—, or —NR"$SO_2$NR"—, wherein R" is hydrogen, C1-C6 alkyl, aryl, arylalkyl, cycloalkylalkyl, heterocyclylalkyl, or heteroarylalkyl.

In one embodiment, R' is hydrogen. Or, R' is an optionally substituted group $C_1$-$C_8$ aliphatic group. Or, R' is an optionally substituted 3-8-membered saturated, partially unsaturated, or fully unsaturated monocyclic ring having 0-3 heteroatoms independently selected from nitrogen, oxygen, or sulfur.

In another embodiment, R' is an 8-12 membered saturated, partially unsaturated, or fully unsaturated bicyclic ring system having 0-5 heteroatoms independently selected from nitrogen, oxygen, or sulfur.

Another family of compounds is defined by the following formula IIA or formula IIB:

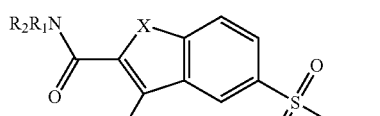

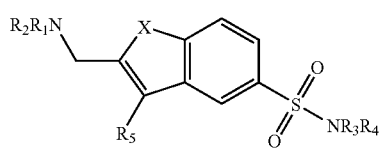

wherein $R_5$ is selected from the group consisting of hydrogen, $C_1$-$C_5$ alkyl, halo, hydroxyl, $C_1$-$C_5$ alkoxy, $C_1$-$C_5$ mercapto, cyano, nitro, and amino;

wherein $R_1$ and $R_2$ are independently selected from the group consisting of hydrogen, alkyl, substituted alkyl, cycloalkyl, substituted cycloalkyl, heterocyclylalkyl, substituted heterocyclylalkyl, arylalkyl, substituted arylalkyl, heteroarylalkyl, substituted heteroarylalkyl, cycloalkylalkyl, substituted cycloalkylalkyl, polycyclic hydrocarbon, substituted polycyclic hydrocarbon, or $R_1$ and $R_2$ together form an unsubstituted or substituted 3 to 7-membered ring, wherein the members of the ring are selected from the group consisting of carbon, nitrogen, oxygen, and sulfur; and wherein $R_3$ and $R_4$ are independently selected from the group consisting of hydrogen, alkyl, cycloalkyl; or $R_3$ and $R_4$ together form an unsubstituted or substituted 3 to 7-membered ring, wherein the members of the ring are selected from the group consisting of carbon, nitrogen, oxygen, and sulfur; and X is O, S, or N-Z—$R_6$.

In one embodiment, $R_1$ and $R_2$ are selected from hydrogen, alkyl, cycloalkyl, heterocyclylalkyl, arylalkyl, or heteroarylalkyl; $R_1$ and $R_2$ form an unsubstituted or substituted six-membered ring, wherein the members of the ring are selected from carbon or nitrogen. In another embodiment, substituents on the substituted ring include alkyl, alkoxycarbonyl, and fused aryl.

In another embodiment, $R_1$ and $R_2$ are selected from hydrogen, alkyl, cycloalkyl, or heterocyclylalkyl; or such that $R_1$ and $R_2$ form an unsubstituted or substituted six-membered ring, wherein the members of the ring are selected from carbon or nitrogen. Preferred substituents on the substituted ring include alkyl, alkoxycarbonyl, and fused aryl.

In another embodiment, $R_3$ and $R_4$ are alkyl; or $R_3$ and $R_4$ form an unsubstituted or substituted 6 to 7-membered ring, wherein the members of the ring are selected from carbon or nitrogen. A preferred substituent on these substituted rings include alkyl group.

In another embodiment, $R_3$ and $R_4$ form an unsubstituted or substituted 6 to 7-membered ring, wherein the members of the ring are selected from carbon or nitrogen. A preferred substituent on these substituted rings include alkyl group.

Preferred compounds of Genus I comprise $R_5$ is alkyl. More preferred compounds of Genus I comprise $R_5$ is methyl.

In one embodiment, X is O. Or, X is S.

In another embodiment, X is N-Z—$R_6$. In one embodiment, Z—$R_6$ together is hydrogen; i.e., X is NH. In another embodiment, Z is a bond. Or, C1-C6 alkylene, wherein up to two carbon units are replaced independently by $SO_2$, C(O), or C(O)O. In one embodiment, Z is $SO_2$.

In one embodiment, $R_6$ is alkyl, cycloalkyl, cycloalkylalkyl, heterocyclyl, heterocyclylalkyl, aryl, arylalkyl, aryl, arylalkyl, heteroaryl, heteroarylalkyl, wherein $R_6$ is substituted with up to three substituents selected from halo, OH, $NO_2$, CN, $CF_3$, $OCF_3$, C1-C6 alkyl, wherein up to two carbon units are independently and optionally replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, or —NR'$SO_2$NR'—

In one embodiment, $R_3$ and $R_4$ taken together form a 5-7 membered saturated ring, having 0-2 additional heteroatoms selected from nitrogen, oxygen, or sulfur. In another embodiment, $R_3$ and $R_4$ taken together form a 5-7 membered saturated ring having no additional heteroatoms. Exemplary such rings include pyrrolidinyl, piperidinyl, or azepanyl. Or, $R_3$ and $R_4$ taken together form a 5-7 membered saturated ring having one additional heteroatom. Exemplary such rings include piperazinyl, morpholinyl, or thiomorpholinyl.

In another embodiment, $R_5$ is hydrogen or C1-C6 alkyl. Or, $R_5$ is hydrogen. Or, $R_5$ is C1-C6 alkyl.

In one embodiment, $R_1$ is hydrogen. In another embodiment, $R_1$ is C1-C4 alkyl.

In one embodiment, $R_2$ is alkyl, arylalkyl, cycloalkyl, cycloalkenyl, cycloalkyl-alkyl, cycloalkenyl-alkyl, heterocyclyl, heterocyclyl-alkyl, heteroaryl, or heteroarylalkyl, wherein $R_2$ has 0-4 substituents selected from Z—$R_6$.

In one embodiment, $R_2$ is an optionally substituted arylalkyl group. Exemplary $R_2$ groups include benzyl, 2-methoxybenzyl, 4-methoxybenzyl, 4-halobenzyl, 1-phenyl-1-methyl-methyl, phenylethyl, phenylpropyl, etc.

In another embodiment, $R_2$ is a cycloalkyl or cycloalkyl-alkyl group wherein $R_2$ has 0-4 substituents selected from Z—$R_6$. Exemplary $R_2$ include cyclopropyl, cyclopentyl, cyclohexyl, methylcyclohexyl, azepanyl, cyclopropyl-C1-C4 alkyl, cyclopentyl-C1-C4 alkyl, cyclohexyl-C1-C4 alkyl, methylcyclohexyl-C1-C4 alkyl, azepanyl-C1-C4 alkyl, etc.

In another embodiment, $R_2$ is a cycloalkenyl or cycloalkenyl-alkyl group wherein $R_2$ has 0-4 substituents selected from Z—$R_6$. Exemplary $R_2$ include cyclohexenyl, tetralin-4-yl, cyclohexenyl-C1-C4 alkyl, etc.

In another embodiment, $R_2$ is a heterocyclyl, or heterocyclyl-alkyl group wherein $R_2$ has 0-4 substituents selected from Z—$R_6$. Exemplary $R_2$ include pyrrolidinyl, pyrrolidin-2-one-1-yl, piperidinyl, piperazinyl, morpholinyl, tetrahydrofuranyl, tetrahydropyranyl, pyrrolidinyl-C1-C4 alkyl, piperidinyl-C1-C4 alkyl, piperazinyl-C1-C4 alkyl, morpholinyl-C1-C4 alkyl, tetrahydrofuranyl-C1-C4 alkyl, tetrahydropyranyl-C1-C4 alkyl, tetrahydroisoquinolin-2-yl, etc.

In another embodiment, $R_2$ is heteroaryl or heteroarylalkyl group, wherein $R_2$ has 0-4 substituents selected from Z—$R_6$. Exemplary $R_2$ include pyridinyl, pyridinyl-C1-C4 alkyl, etc.

In one embodiment, $R_1$ is C1-C4 alkyl, and $R_2$ is an optionally substituted arylalkyl group. Exemplary $R_2$ groups include benzyl, 2-methoxybenzyl, 4-methoxybenzyl, 4-halobenzyl, 1-phenyl-1-methyl-methyl, etc.

In another embodiment, $R_1$ and $R_2$ taken together form a 5-7 membered heterocyclic ring containing up to two additional heteroatoms selected from oxygen, nitrogen, or sulfur, wherein said ring has 0-4 substituents selected from Z—$R_6$. Exemplary such rings include optionally substituted tetrahydrofuranyl, pyrrolidinyl, piperidinyl, piperazinyl, morpholinyl, or thiomorpholinyl. Exemplary substituents on such rings includes halo, C1-C6 alkyl, OC1-C6 alkyl, C(O)C1-C6 alkyl, C(O)OC1-C6 alkyl, C(O)NH(C1-C4 alkyl), and ethylenedioxy.

In another embodiment, $R^S$ is a phenyl ring having 0-4 substituents selected from Z—$R_6$. Or, $R^S$ is a cycloalkyl ring having 0-4 substituents selected from Z—$R_6$. Exemplary such rings include cyclopropyl, cyclopentyl, or cyclohexyl.

Another family of compounds is defined by the following subgenus (Subgenus III):

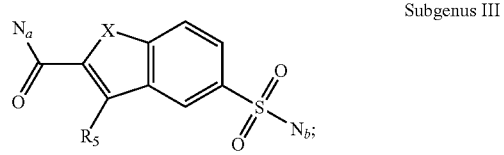

Subgenus III wherein:

X is O or N-Z—$R_6$;

$R_5$ is selected from the group consisting of hydrogen, $C_1$-$C_5$ alkyl, halo, hydroxyl, $C_1$-$C_5$ alkoxy, $C_1$-$C_5$ mercapto, cyano, nitro, and amino;

$N_a$ is selected from the group consisting of

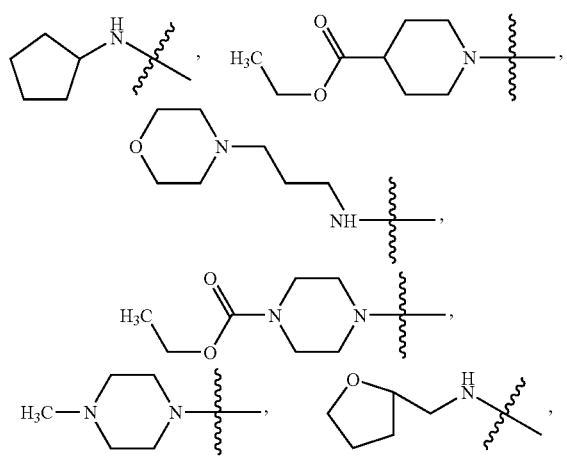

-continued
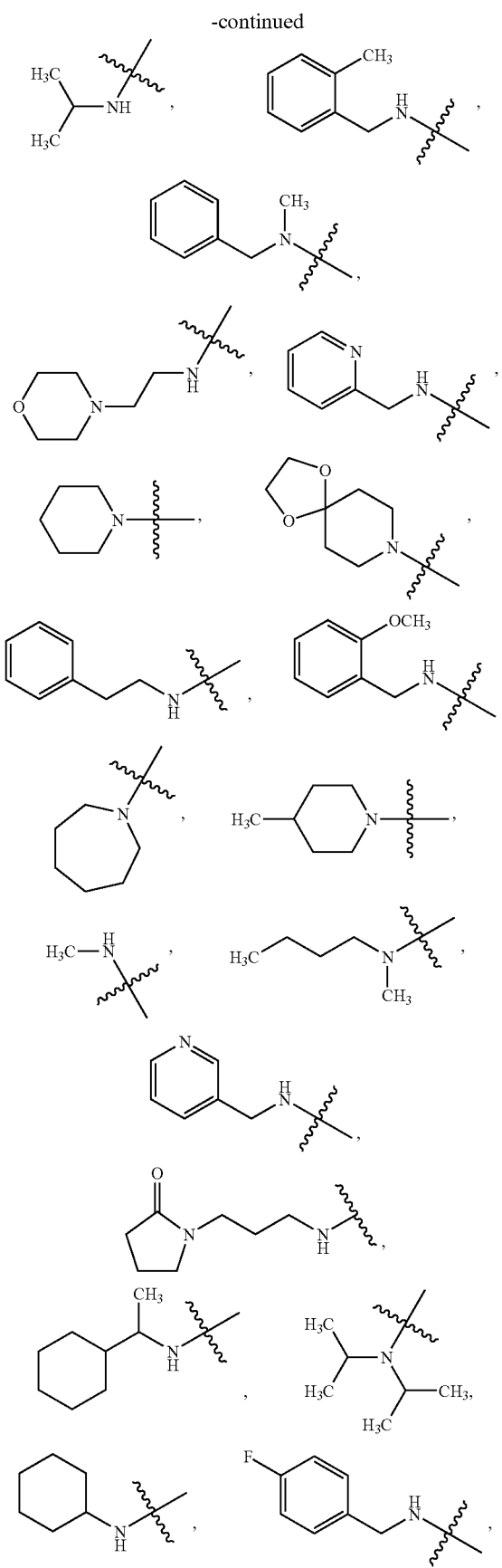
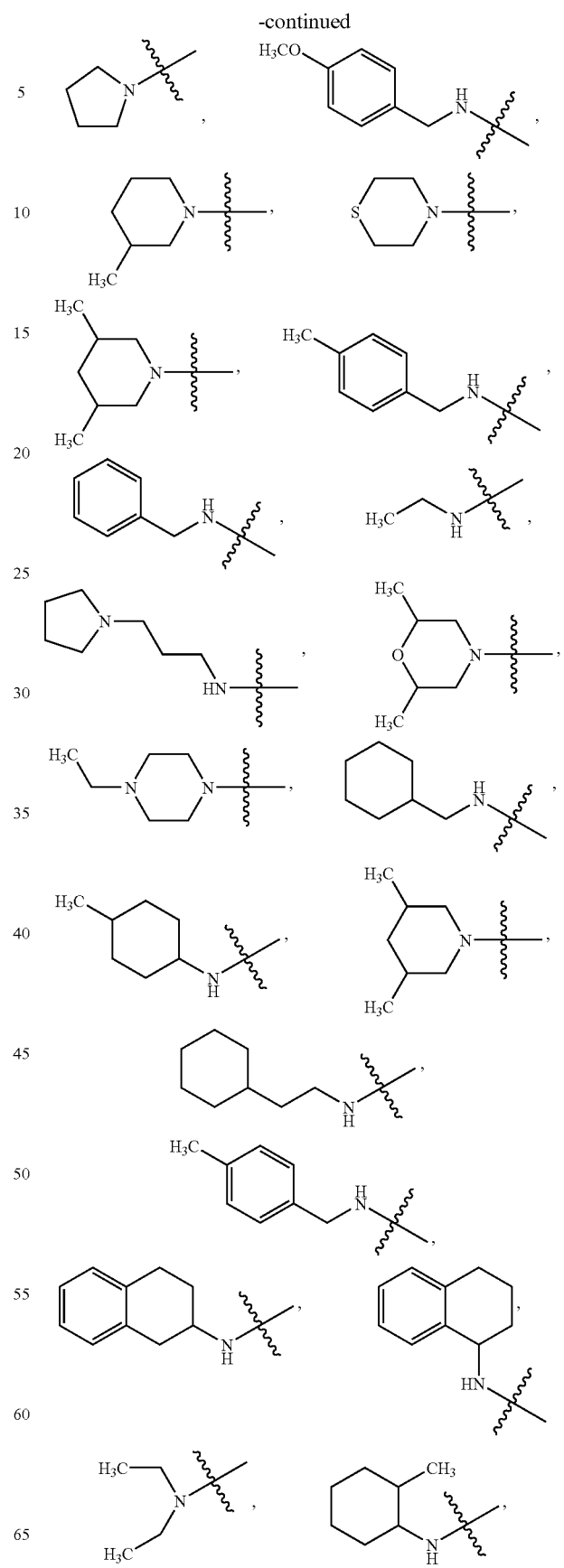

-continued

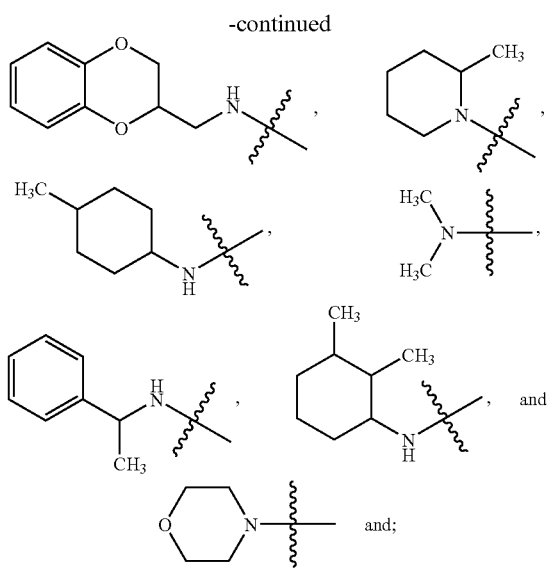

$N_b$ is selected from the group consisting of

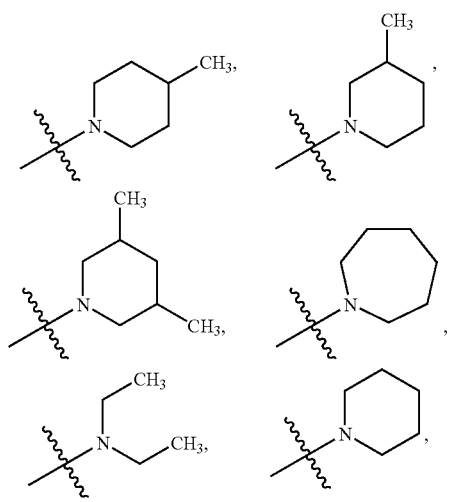

-continued

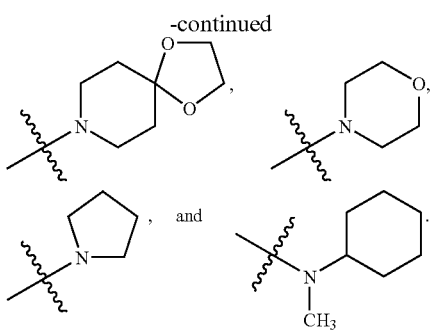

In one embodiment, $N_a$ in compounds of the present invention is selected from any of the embodiments as shown in Table 1 below.

In another embodiment, $N_b$ in compounds of the present invention is selected from any of the embodiments as shown in Table 1 below.

In another embodiment, the present invention provides compounds of formula IV:

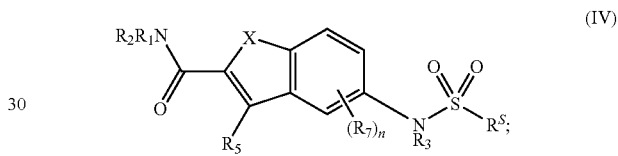

(IV)

wherein:

$R^3$ is C1-C6 aliphatic, C5-C10 cycloaliphatic, or aralkyl, wherein $R^3$ has 0-4 substituents selected from Z—$R_6$; and $R^S$ is phenyl optionally substituted with 0-4 substituents selected from Z—$R^6$;

wherein $R^1$, $R^2$, $R^5$, $R^7$, n, Z and R6 are as defined above.

In one embodiment, $R^3$ is C1-C6 alkyl, e.g., cyclopropyl or cyclohexyl. Or, $R^3$ is C3-C6 cycloalkyl-alkyl, e.g., cyclopropylmethyl. Or, $R^3$ is arylalkyl, e.g., benzyl or phenylethyl.

Exemplary compounds of the present invention are recited below in Table 1.

TABLE 1

| Cmpd No. | Structure |
| --- | --- |
| 1 | 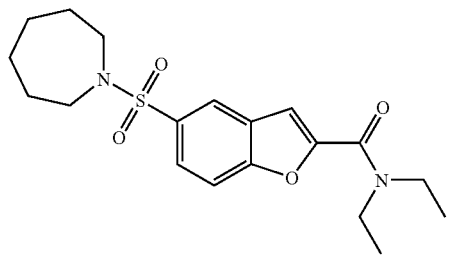 |

-continued
2 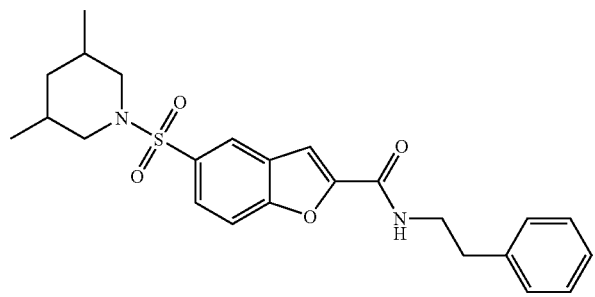
3 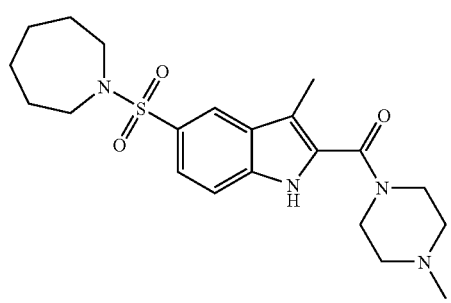
4 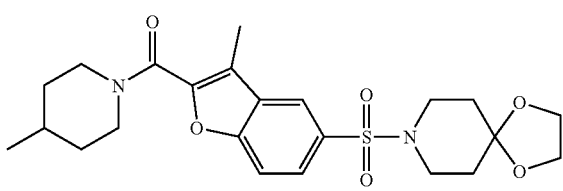
5 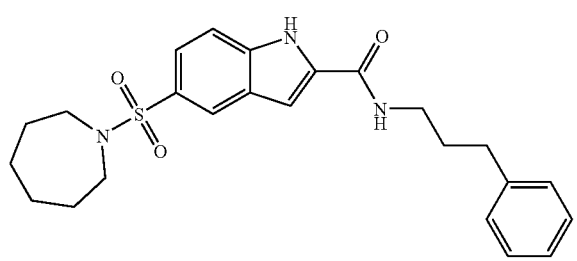
6 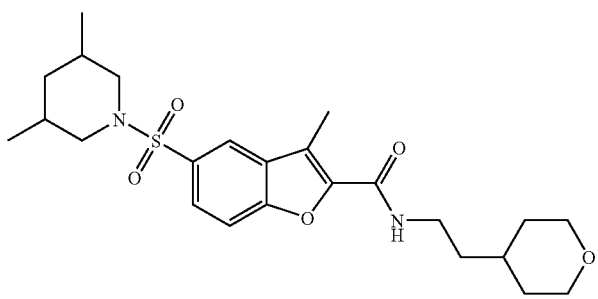

-continued
7
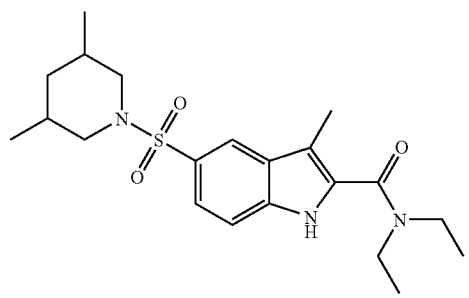
8
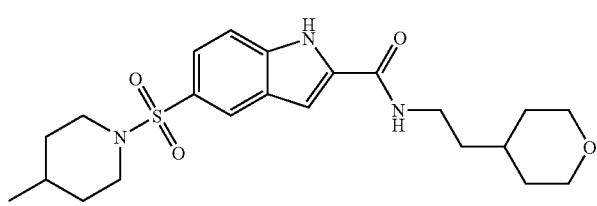
9
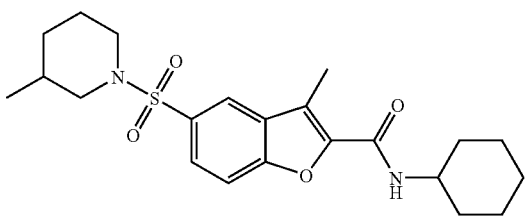
10
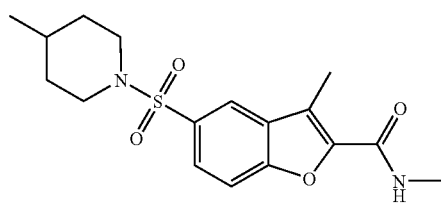
11
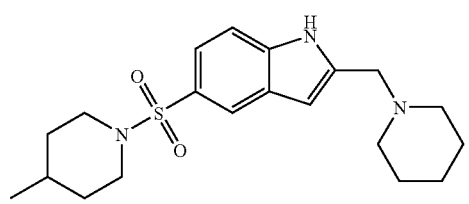
12
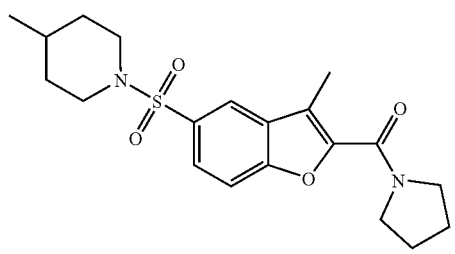

-continued
13
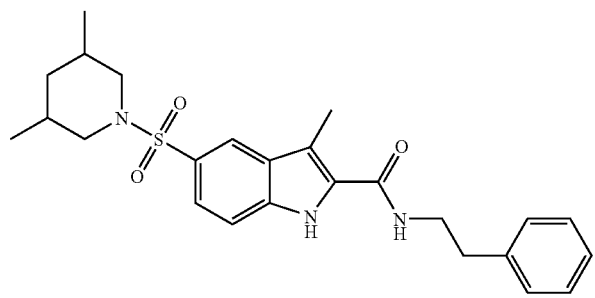
14
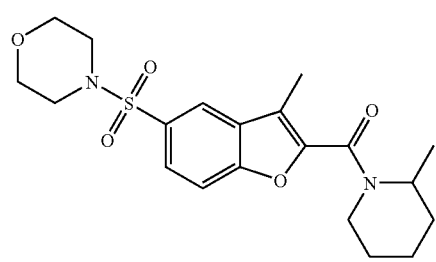
15
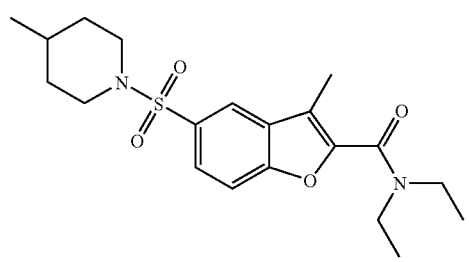
16
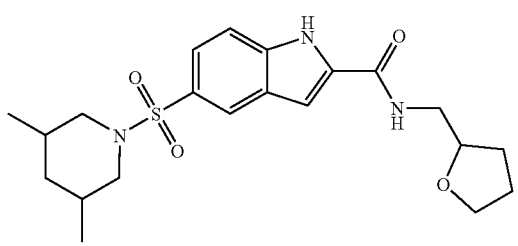
17
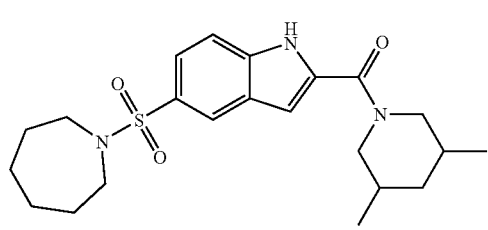
18
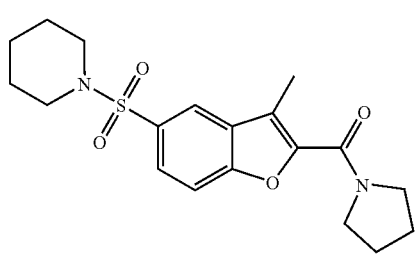

-continued
19
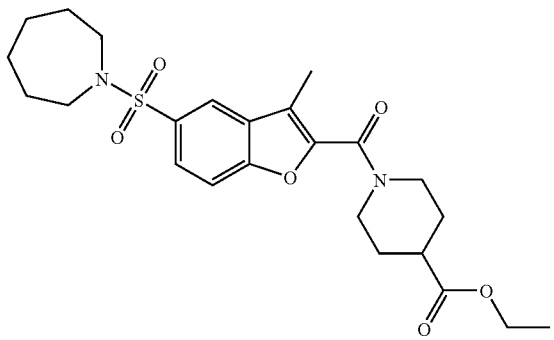
20
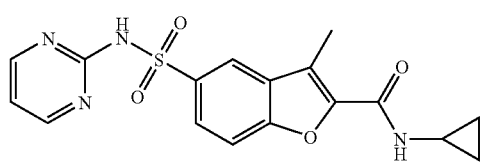
21
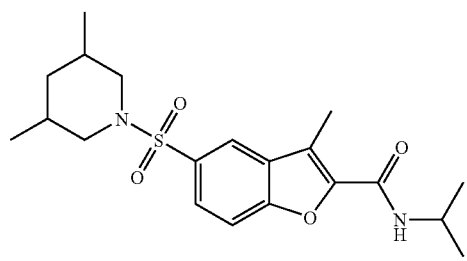
22
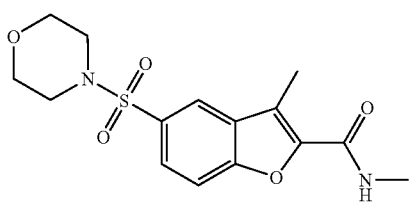
23
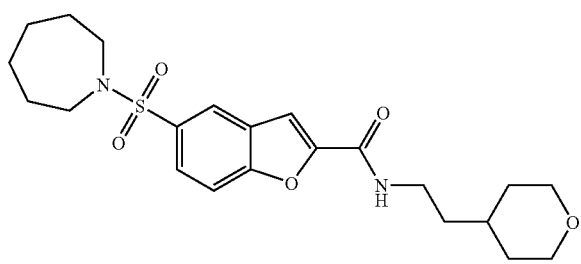
24
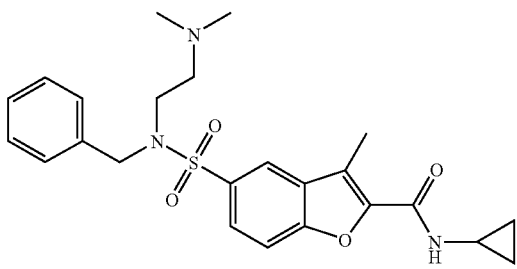

-continued
25 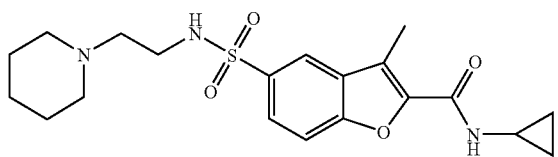
26 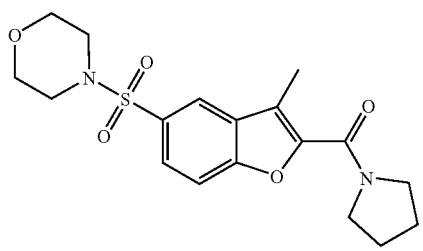
27 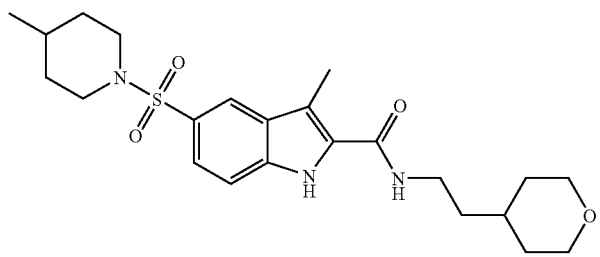
28 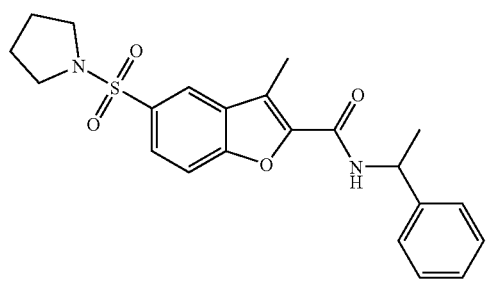
29 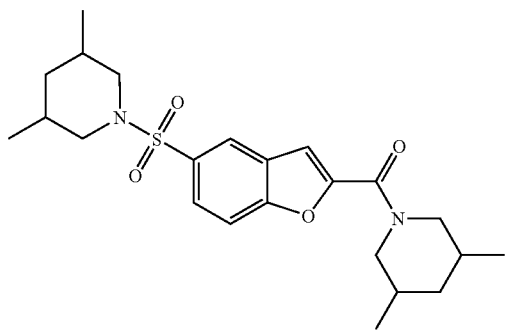
30 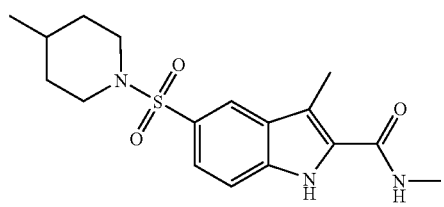

-continued
31 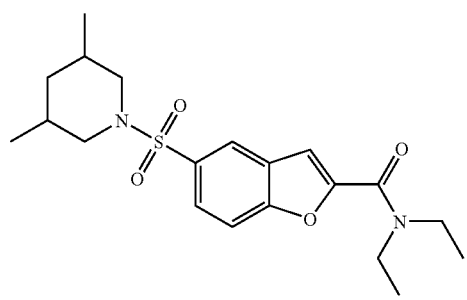
32 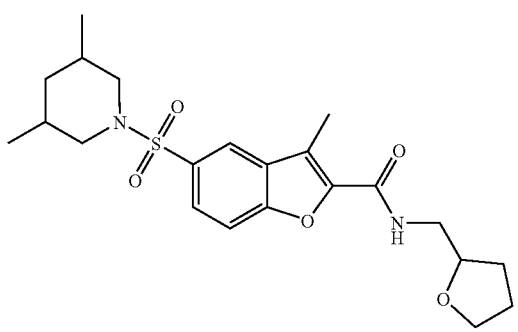
33 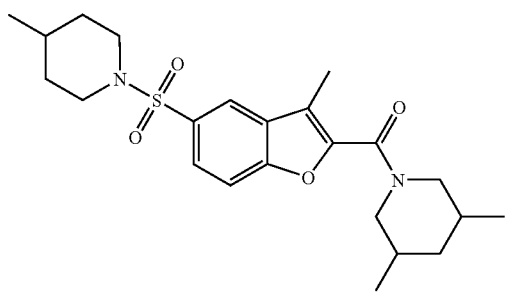
34 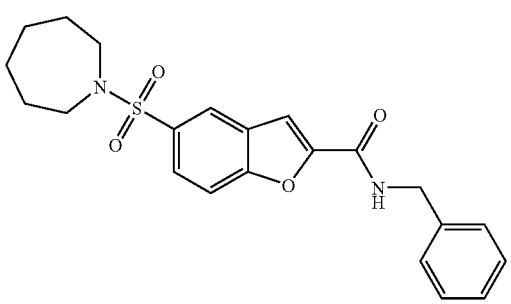
35 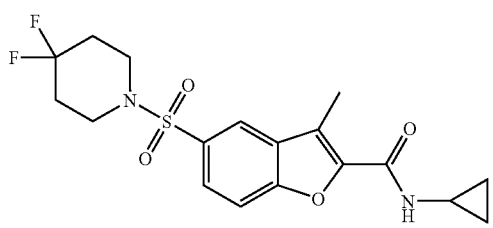

-continued
36
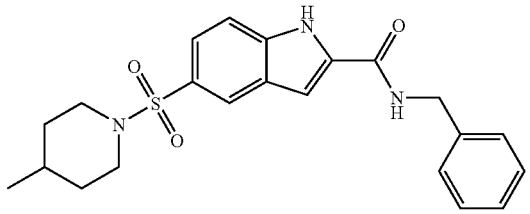
37
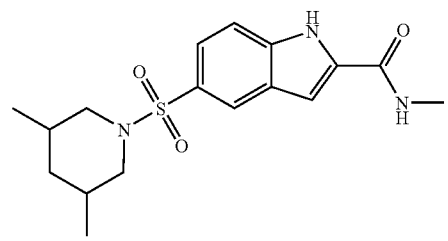
38
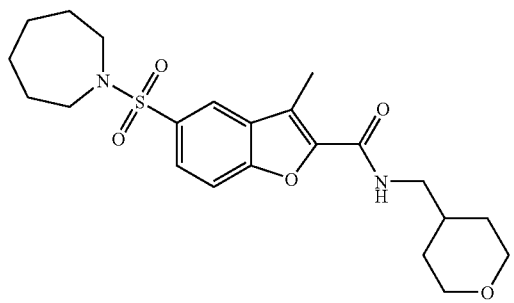
39
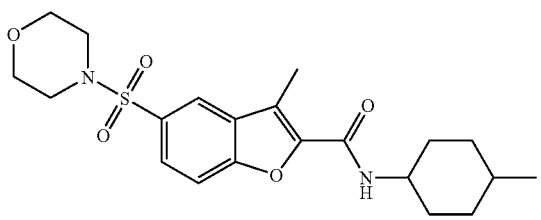
40
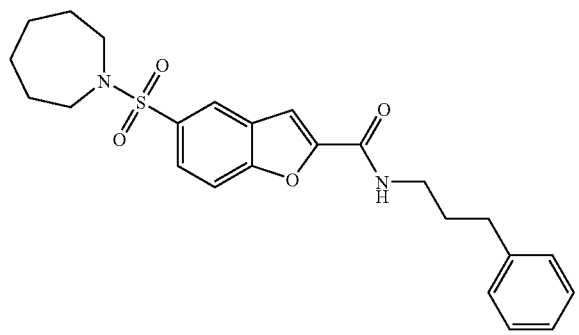
41
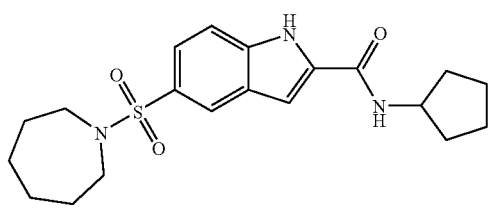

-continued
| | |
|---|---|
| 42 | 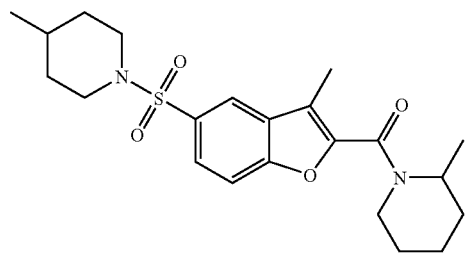 |
| 43 | 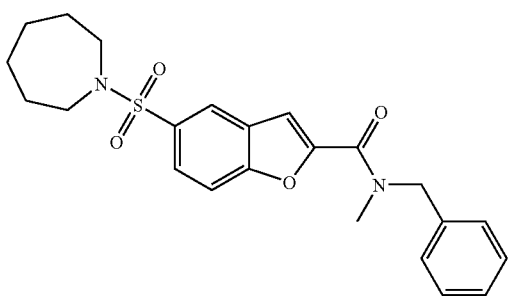 |
| 44 | 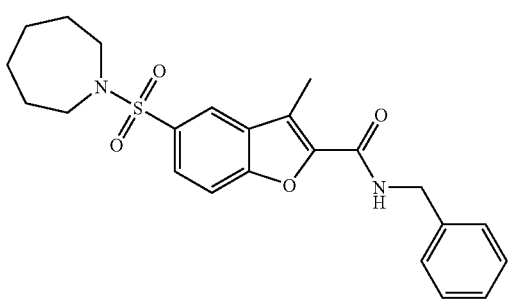 |
| 45 | 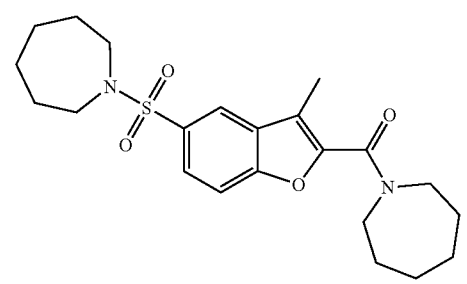 |
| 46 | 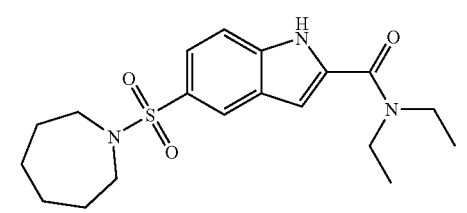 |
| 47 | 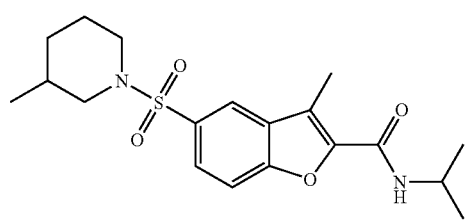 |

-continued
| | |
|---|---|
| 48 | 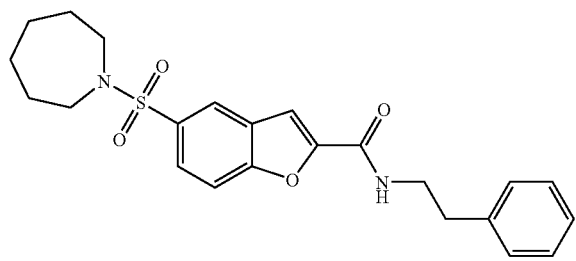 |
| 49 | 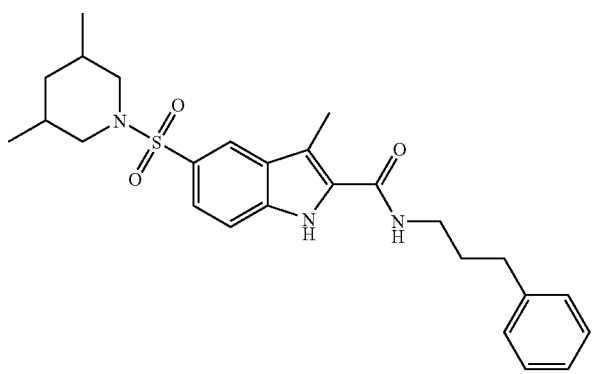 |
| 50 | 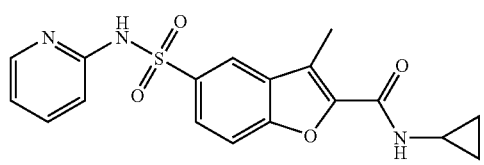 |
| 51 | 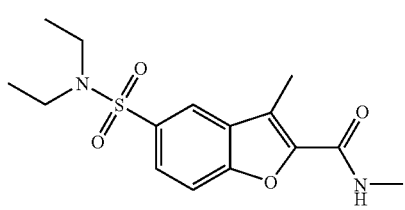 |
| 52 | 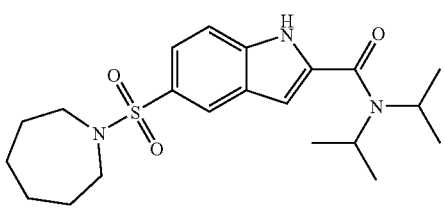 |
| 53 | 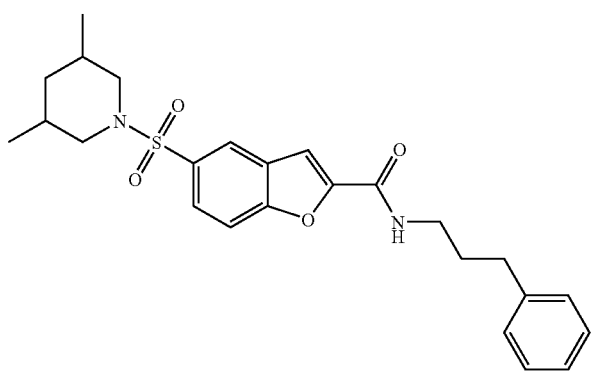 |

-continued
54
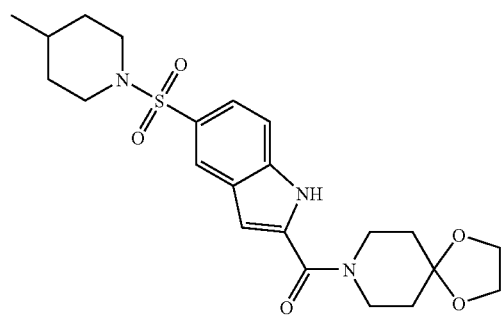
55
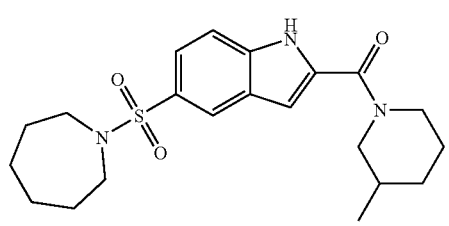
56
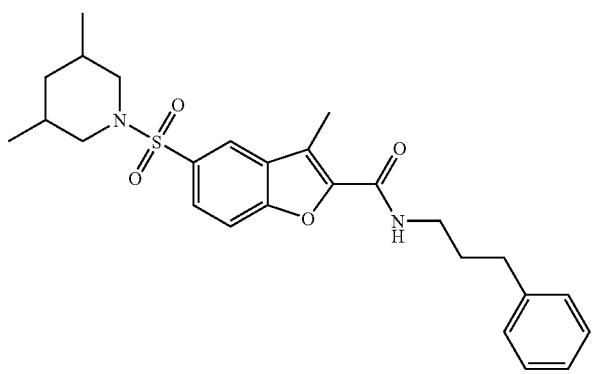
57
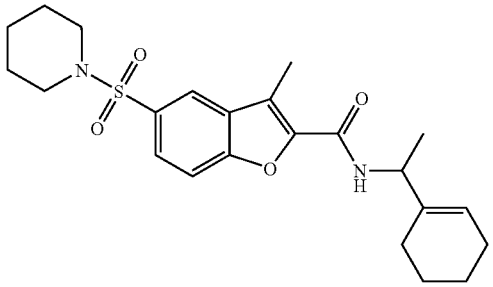
58
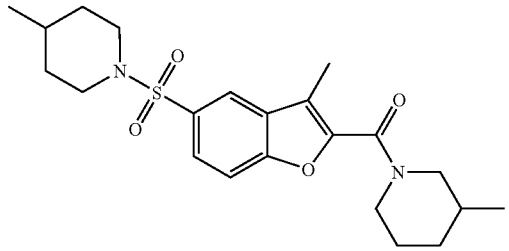

-continued
| | |
|---|---|
| 59 | 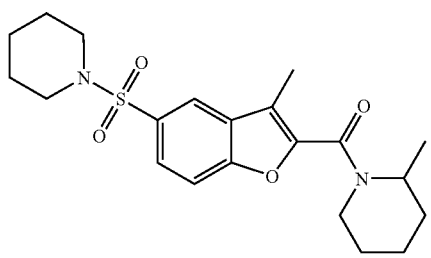 |
| 60 | 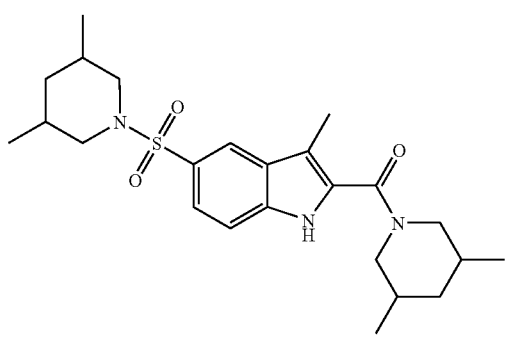 |
| 61 | 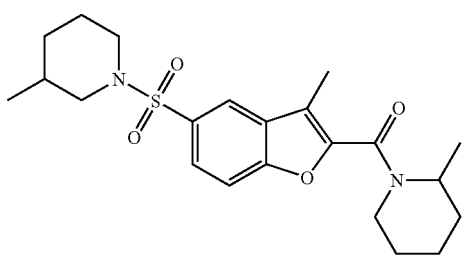 |
| 62 | 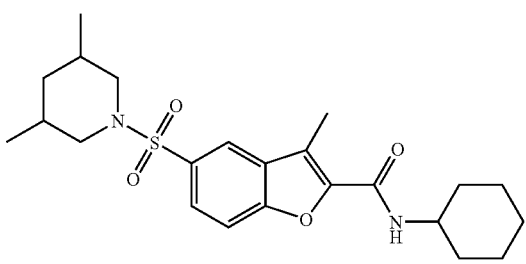 |
| 63 | 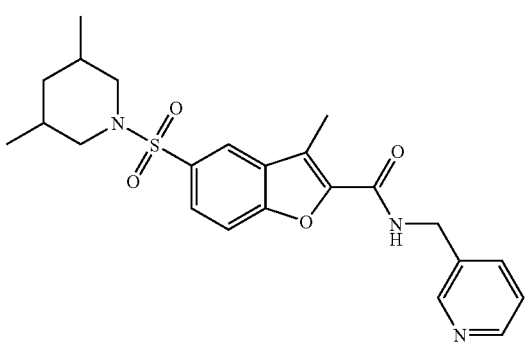 |

-continued
64 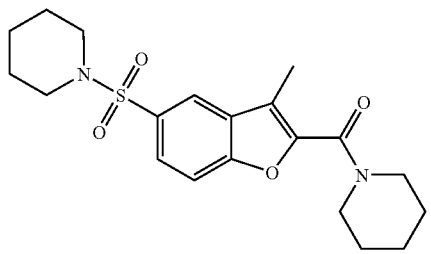
65 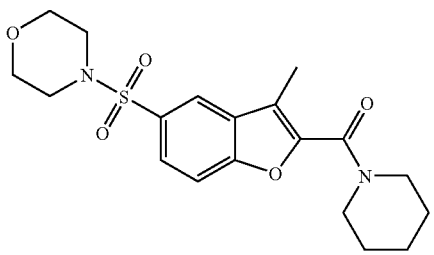
66 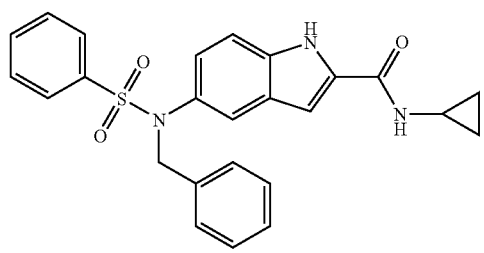
67 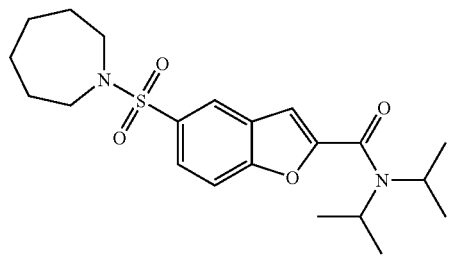
68 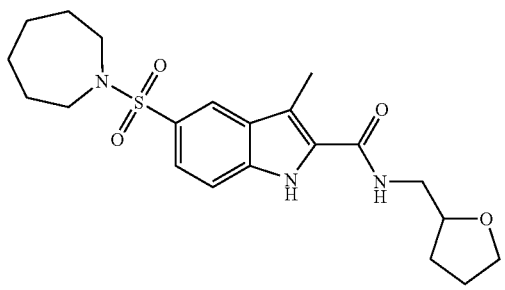
69 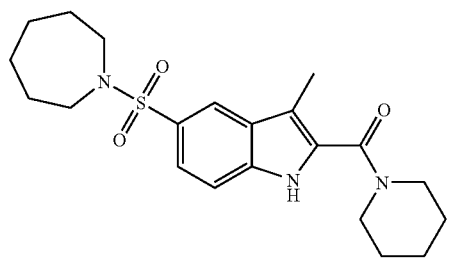

-continued
| | |
|---|---|
| 70 | 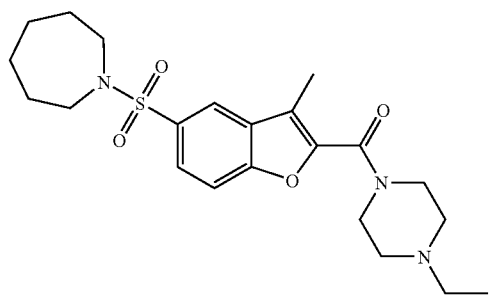 |
| 71 | 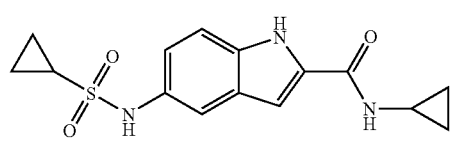 |
| 72 | 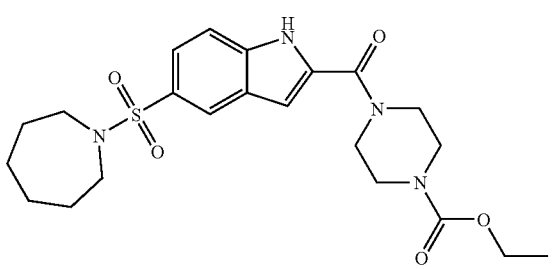 |
| 73 | 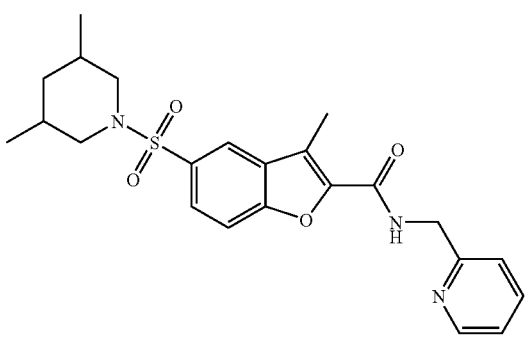 |
| 74 | 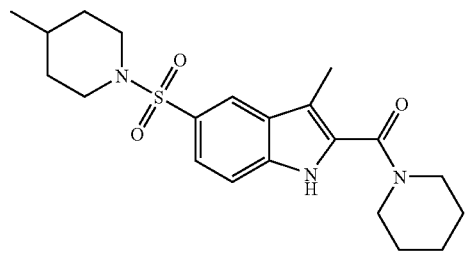 |
| 75 | 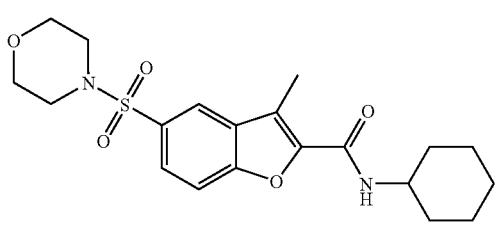 |

-continued
| | |
|---|---|
| 76 | 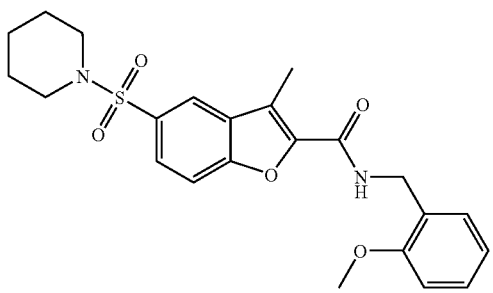 |
| 77 | 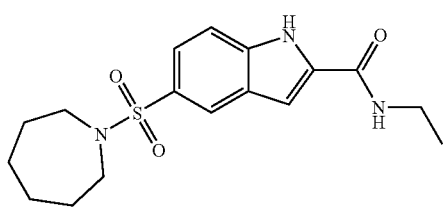 |
| 78 | 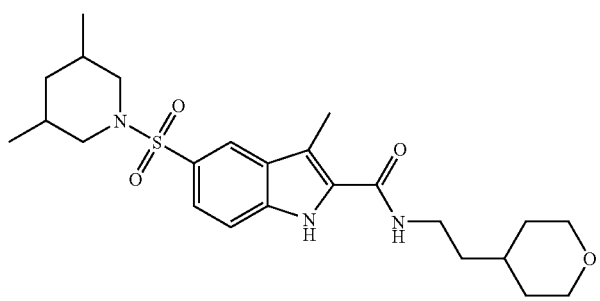 |
| 79 | 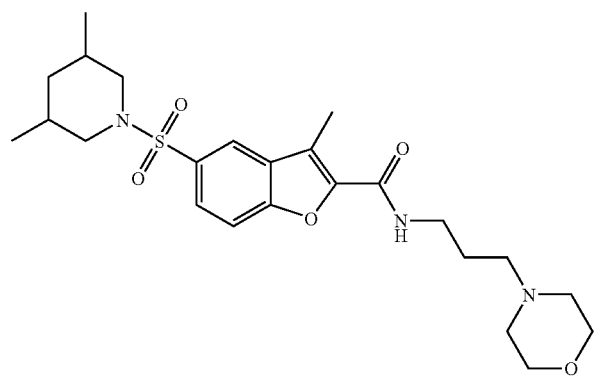 |
| 80 | 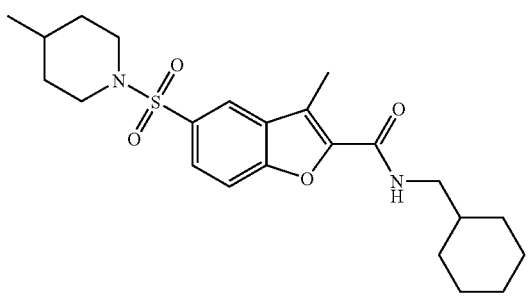 |

-continued
81 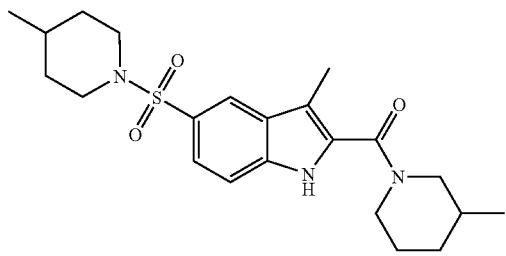
82 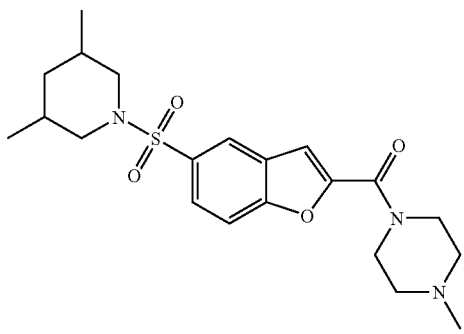
83 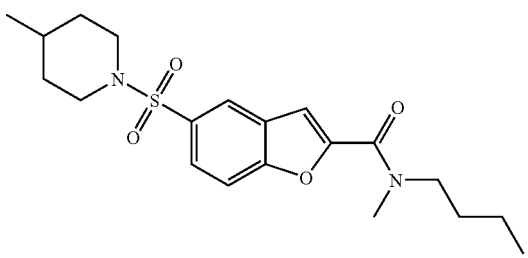
84 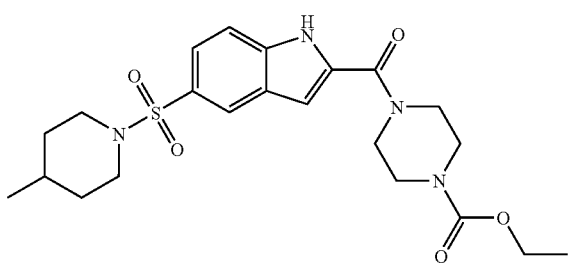
85 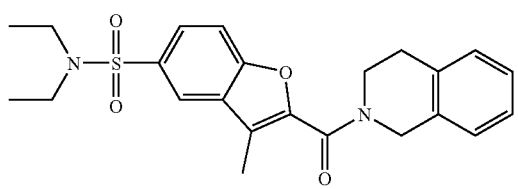
86 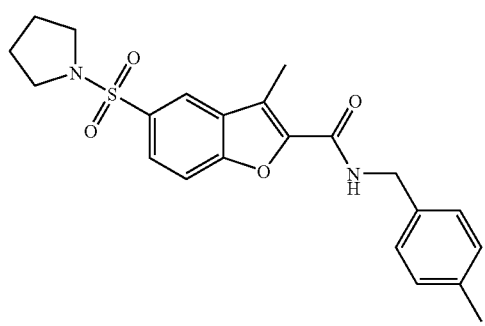

-continued
87 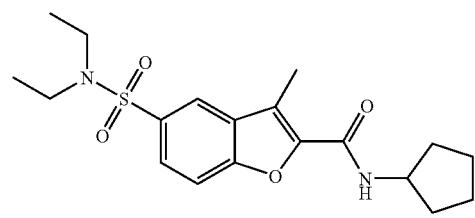
88 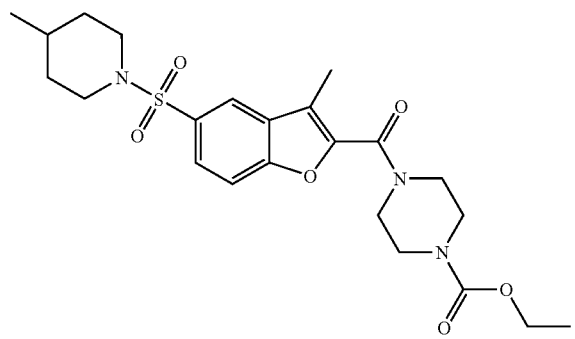
89 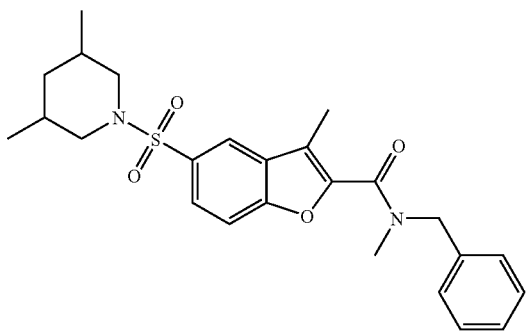
90 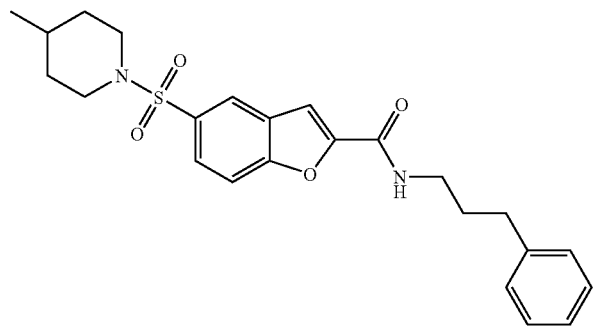
91 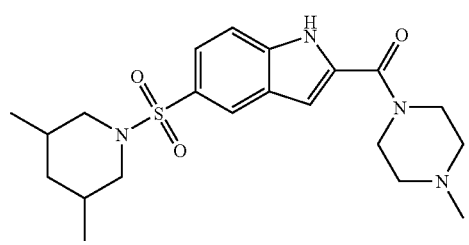

-continued
92 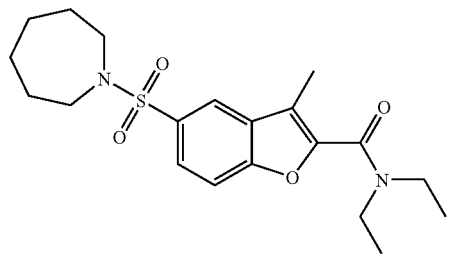
93 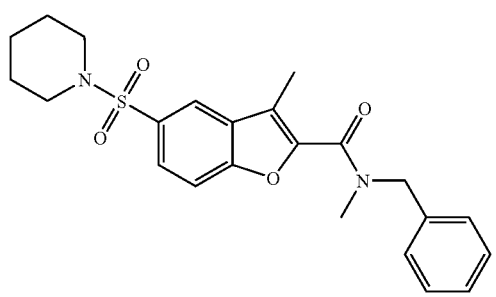
94 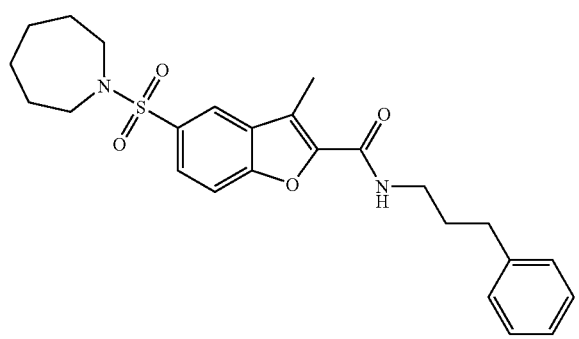
95 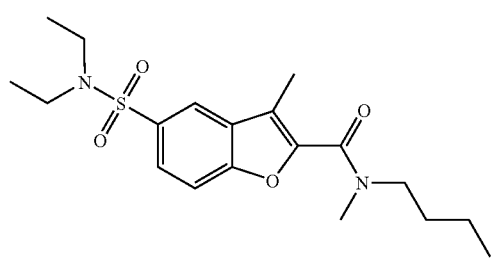
96 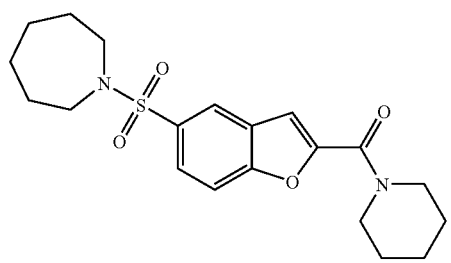

-continued
| | |
|---|---|
| 97 | 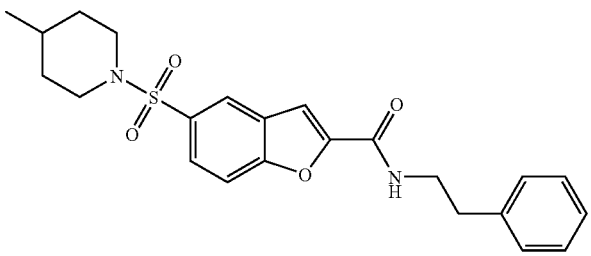 |
| 98 | 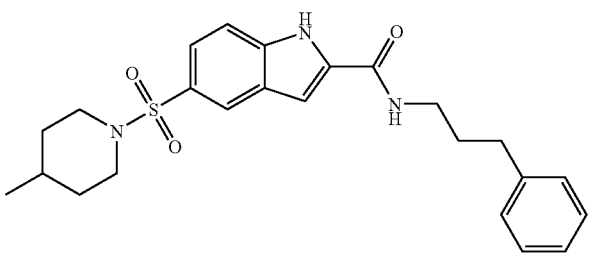 |
| 99 |  |
| 100 | 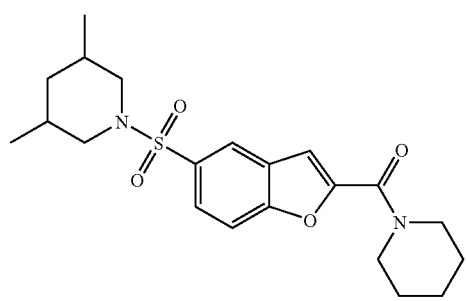 |
| 101 | 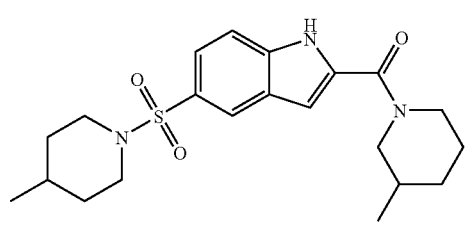 |
| 102 | 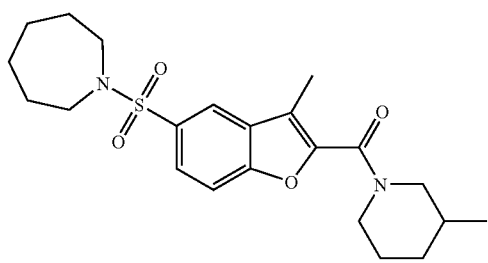 |

-continued
103
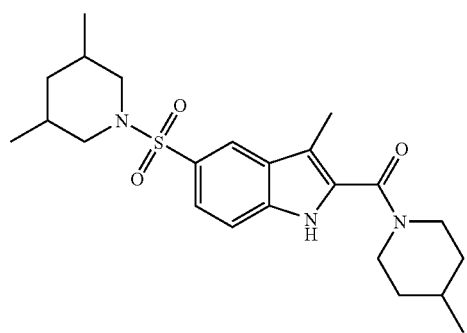
104
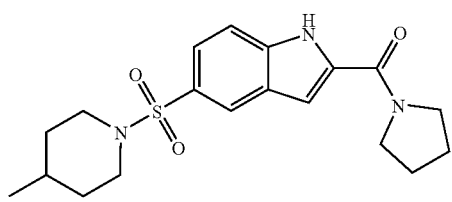
105
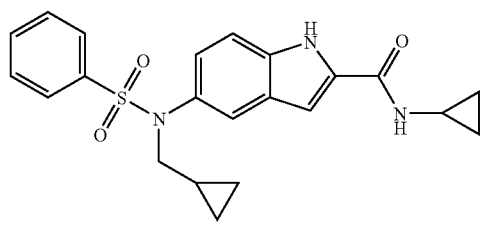
106
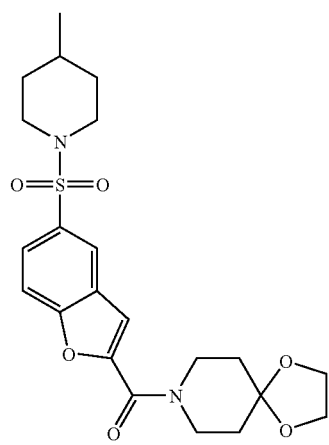

107 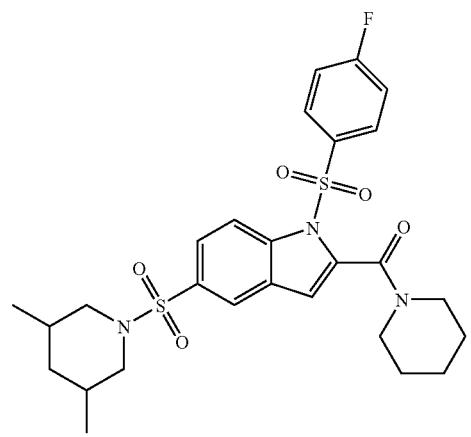
108 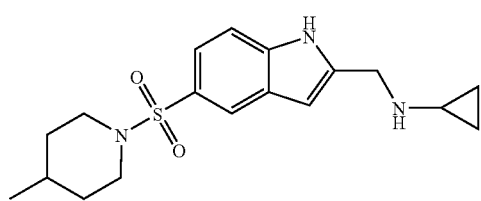
109 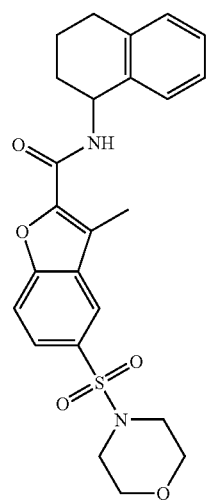
110 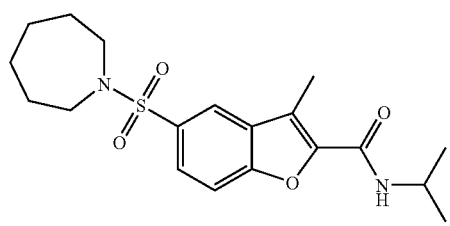

-continued
111
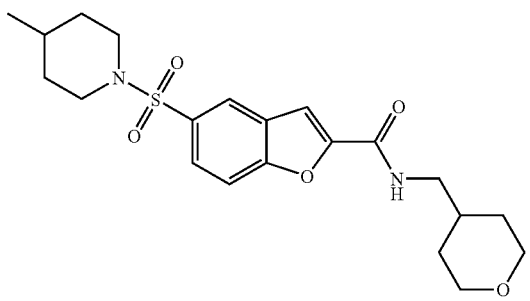
112
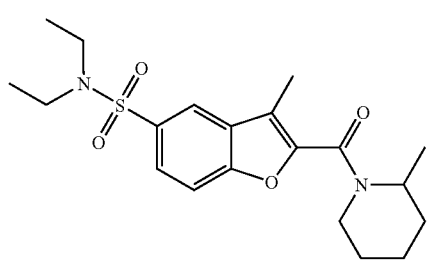
113
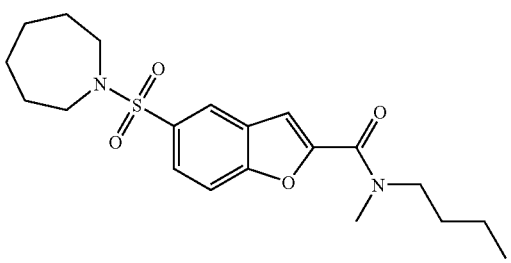
114
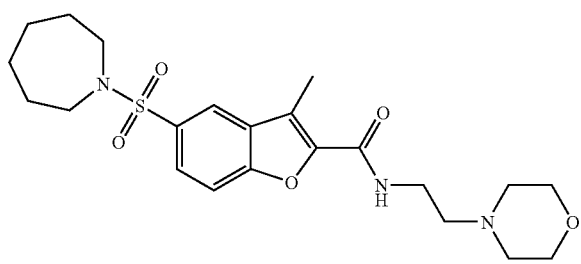
115
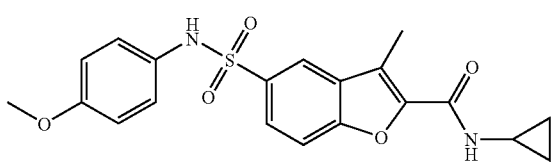
116
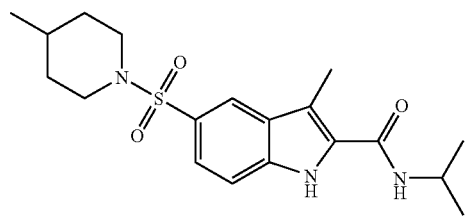

-continued
| 117 | 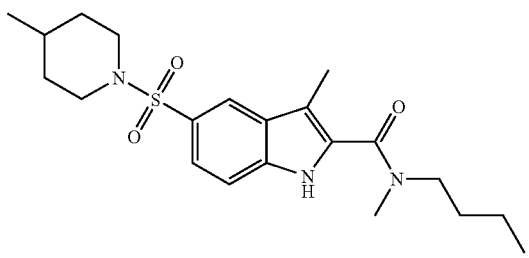 |
| 118 | 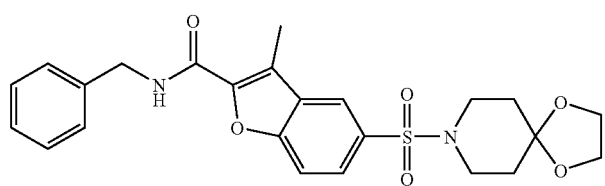 |
| 119 | 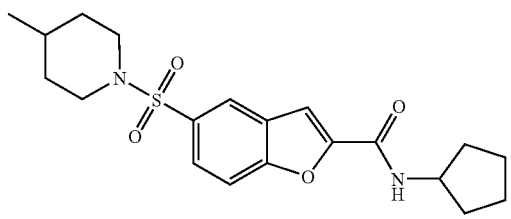 |
| 120 | 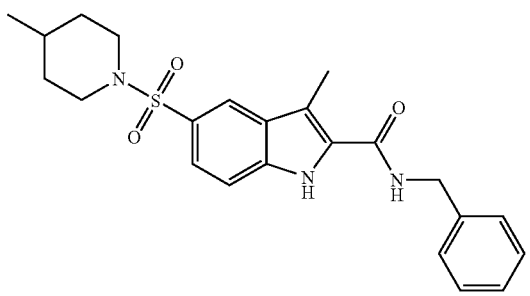 |
| 121 | 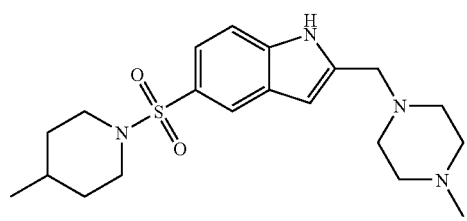 |
| 122 | 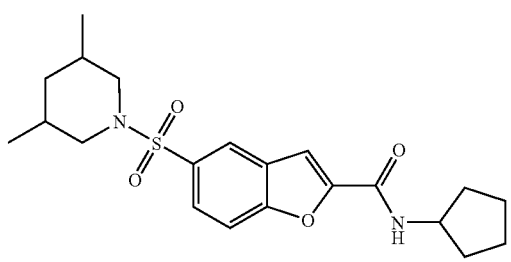 |

-continued
123
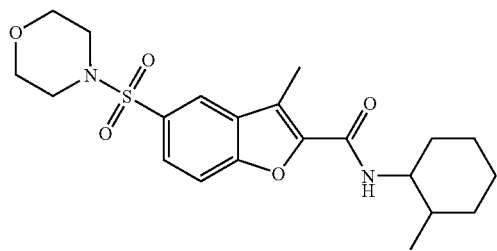
124
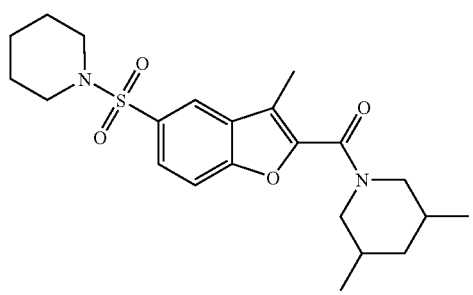
125
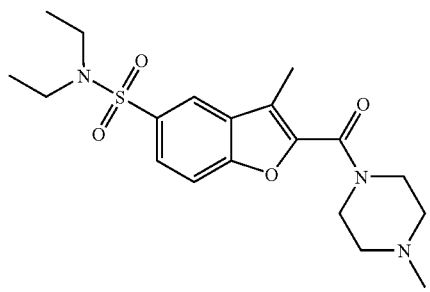
126
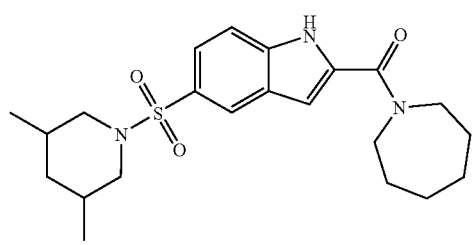
127
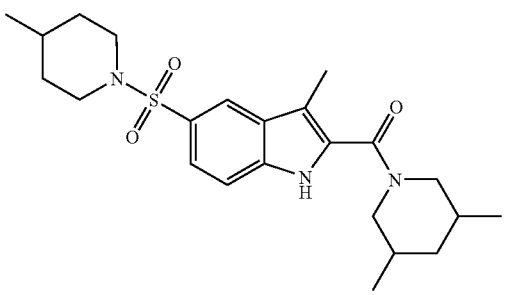

-continued
128
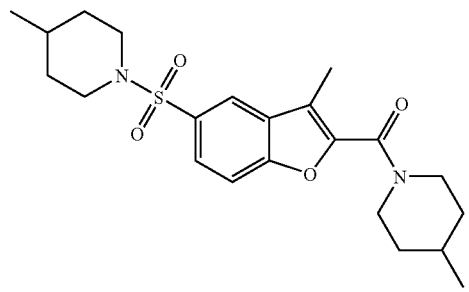
129
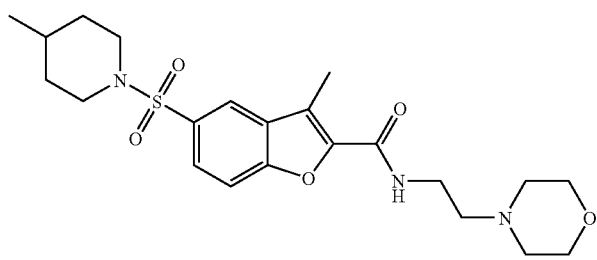
130
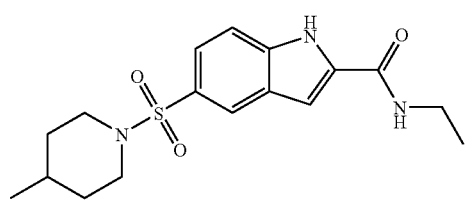
131
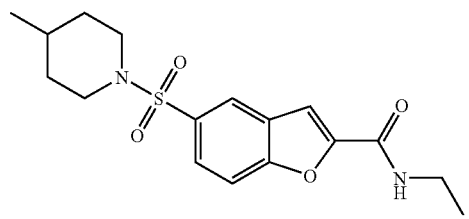
132
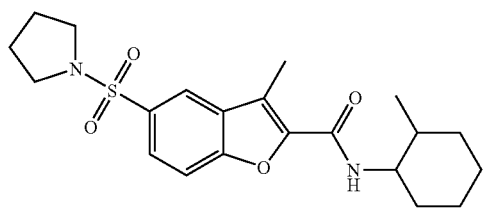
133
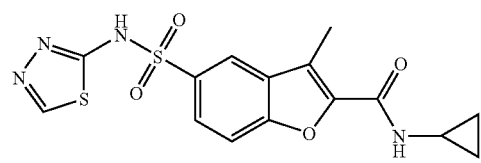

-continued
| | |
|---|---|
| 134 | 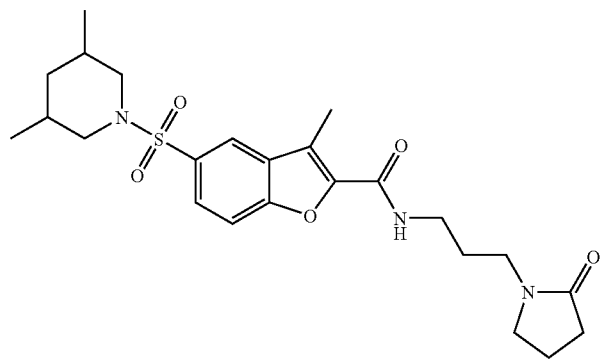 |
| 135 | 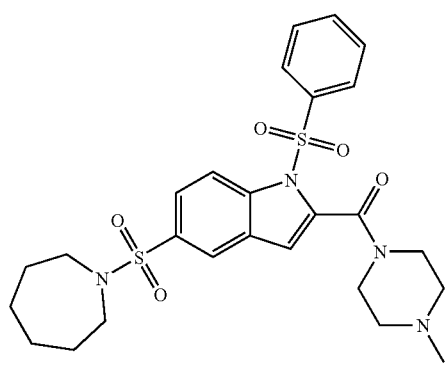 |
| 136 | 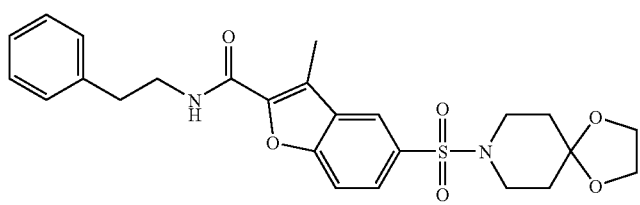 |
| 137 | 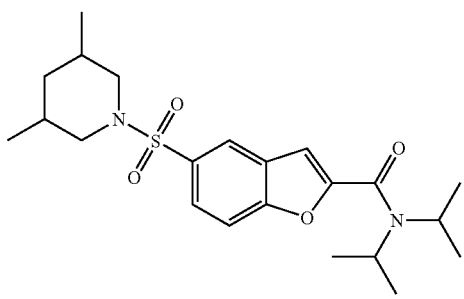 |
| 138 | 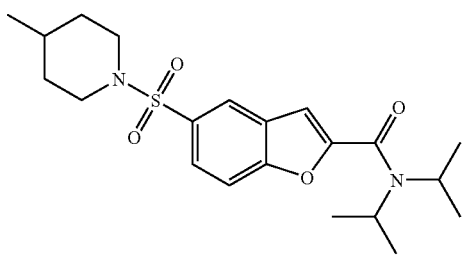 |

-continued
| | |
|---|---|
| 139 | 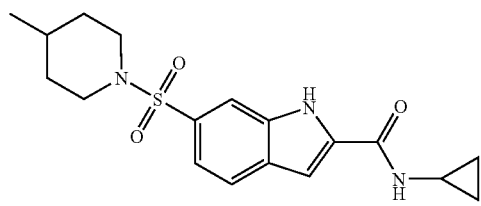 |
| 140 | 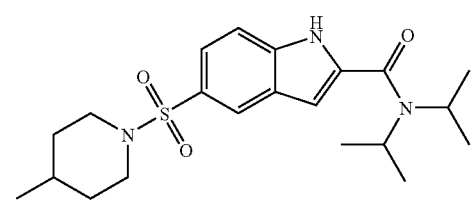 |
| 141 | 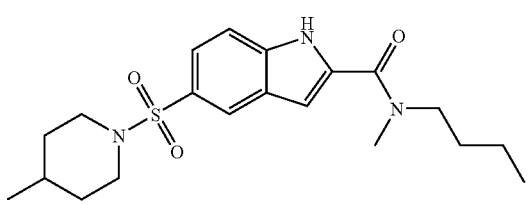 |
| 142 | 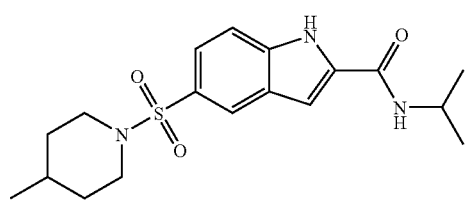 |
| 143 | 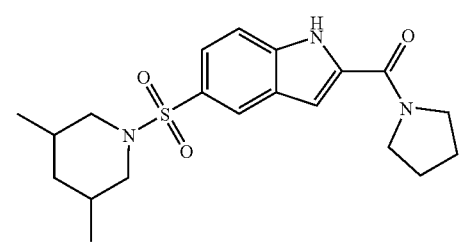 |
| 144 | 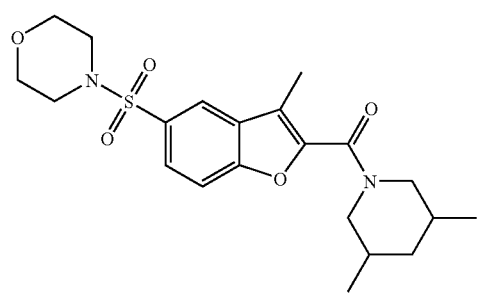 |
| 145 | 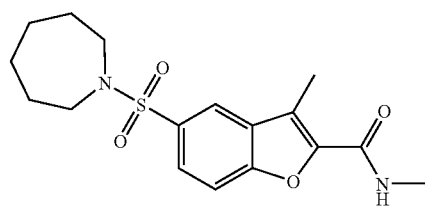 |

-continued
146 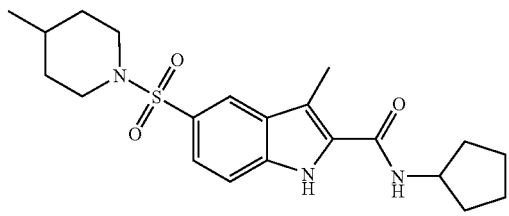
147 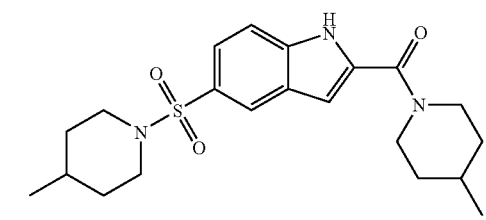
148 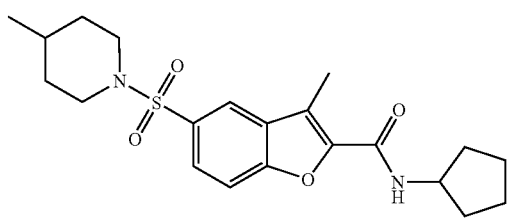
149 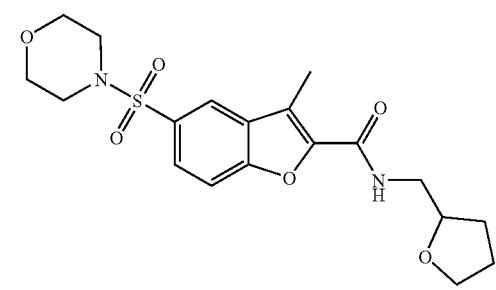
150 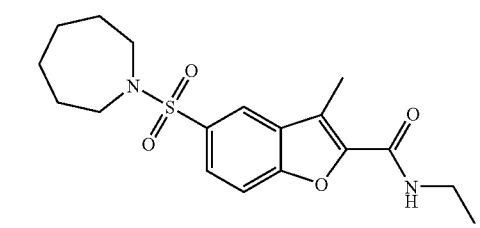
151 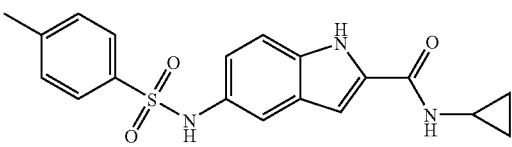
152 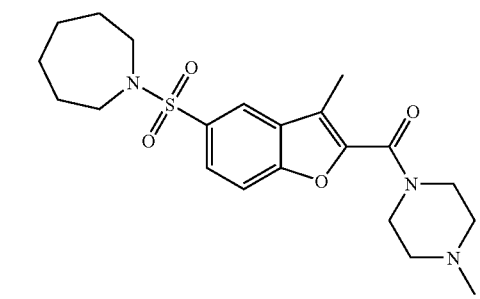

-continued
153 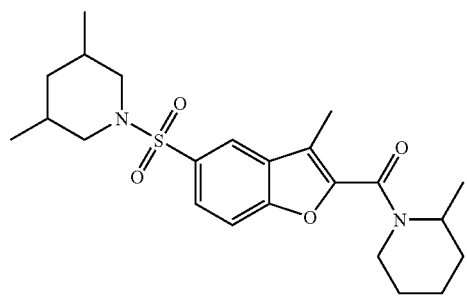
154 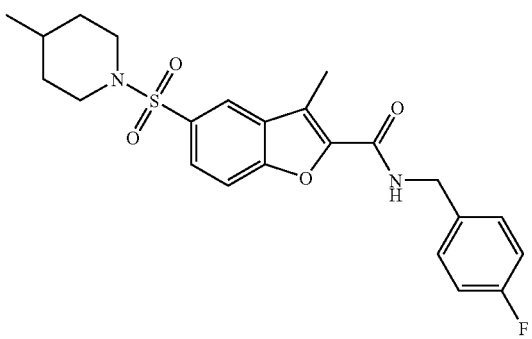
155 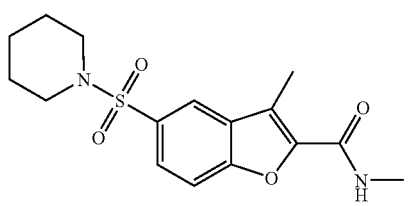
156 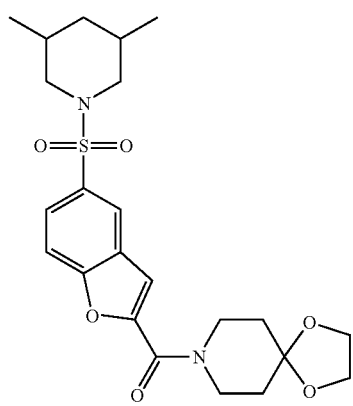
157 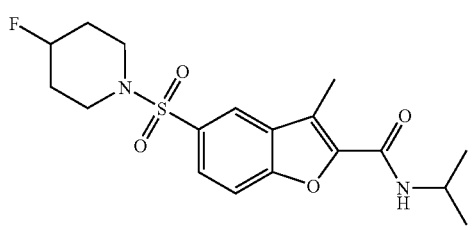

-continued
158 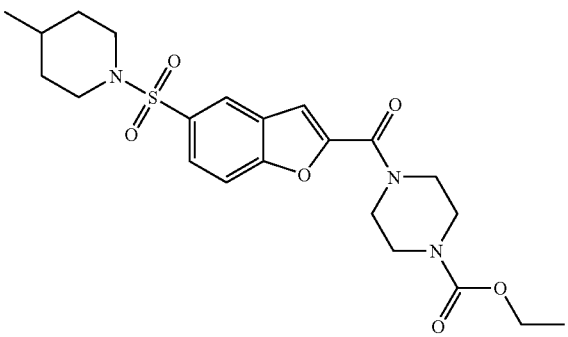
159 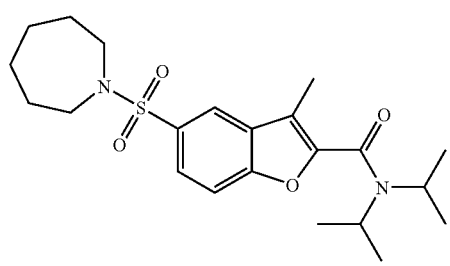
160 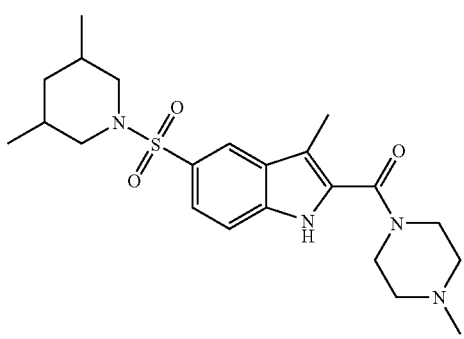
161 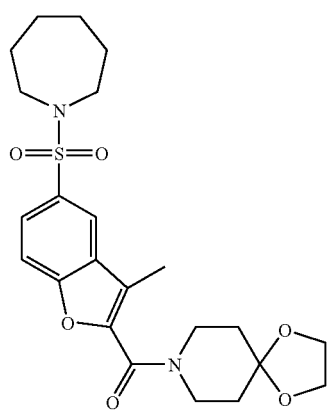
162 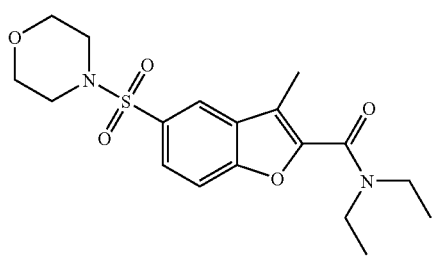

-continued
163 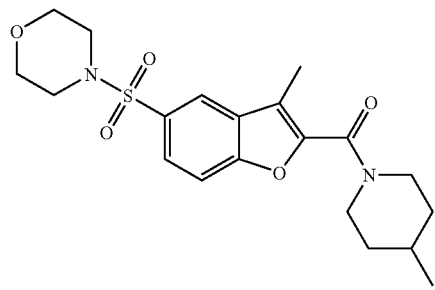
164 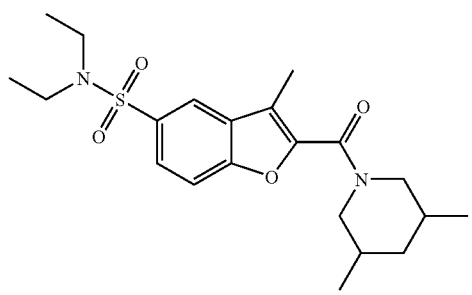
165 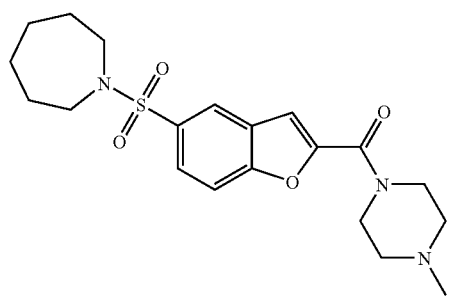
166 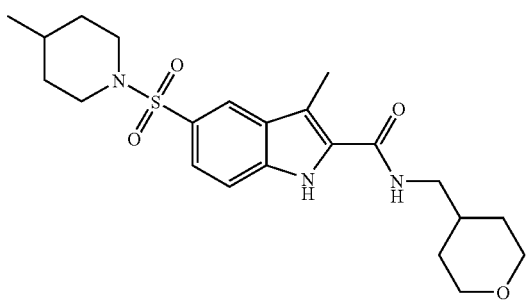
167 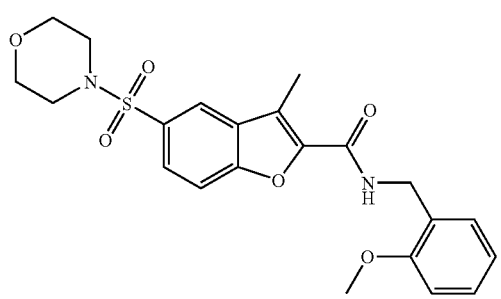

-continued
168 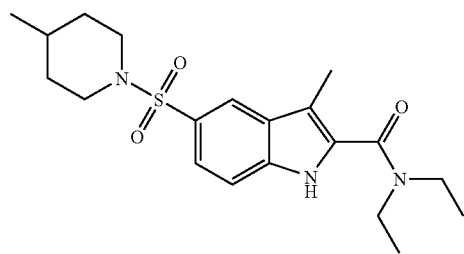
169 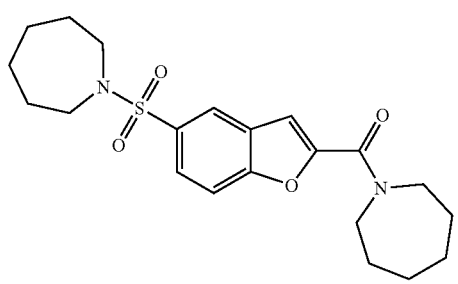
170 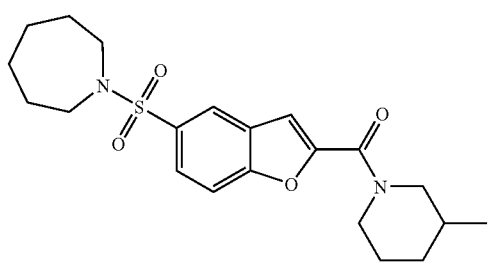
171 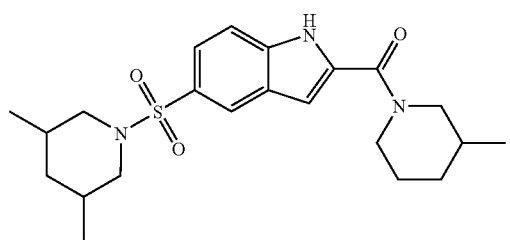
172 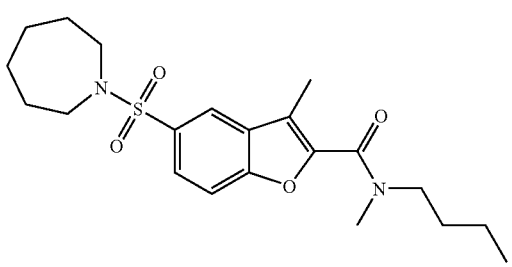

-continued
| | |
|---|---|
| 173 | 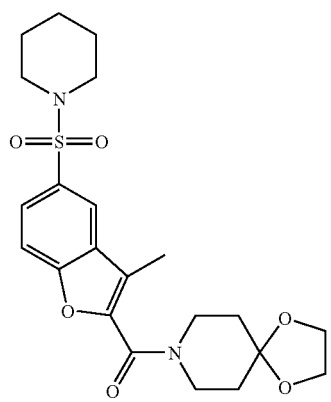 |
| 174 | 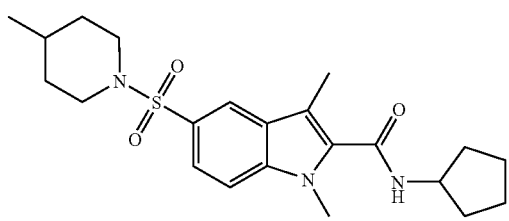 |
| 175 | 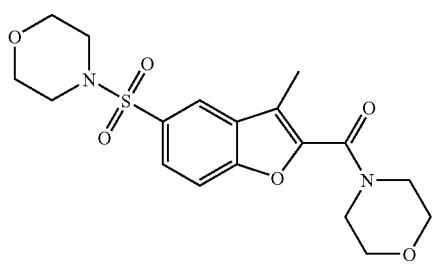 |
| 176 | 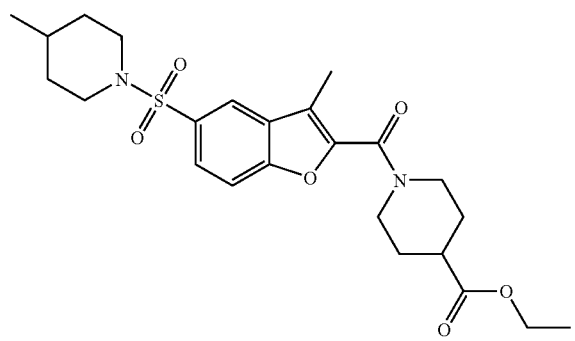 |
| 177 | 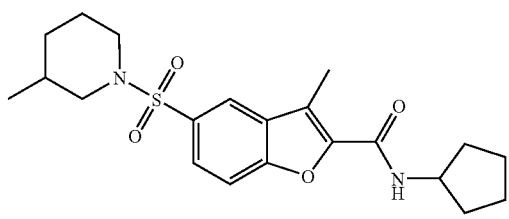 |

-continued
178 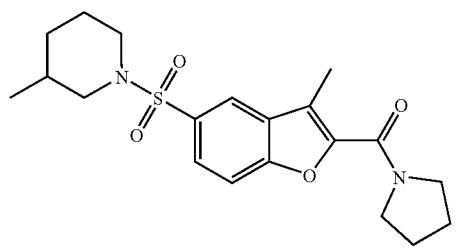
179 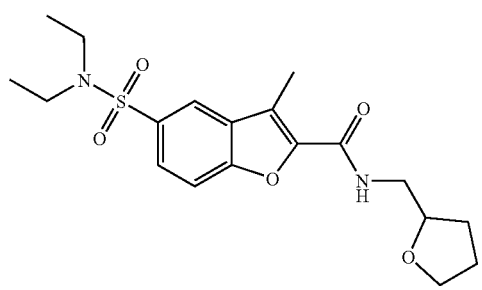
180 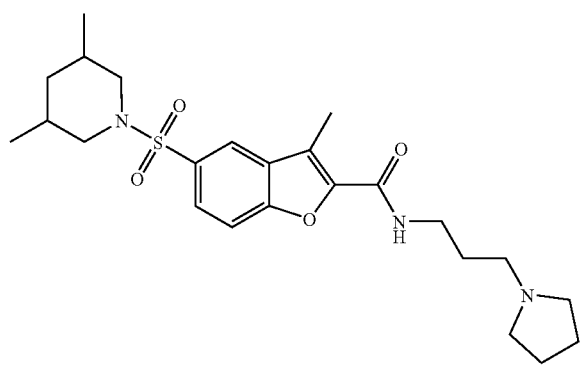
181 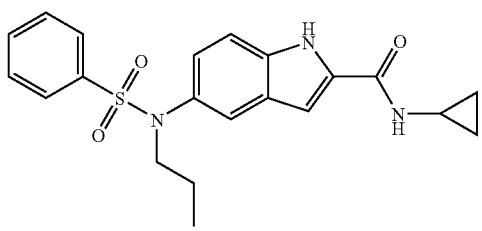
182 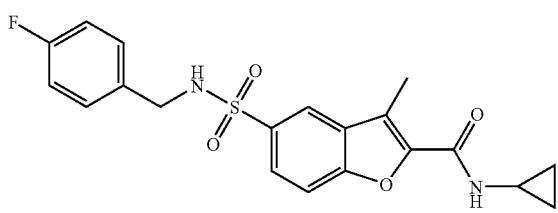

183 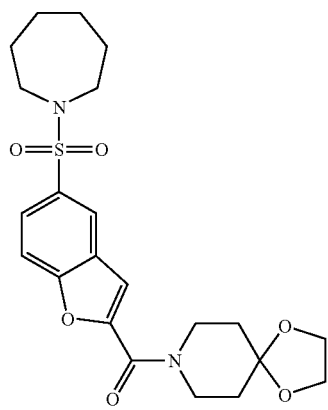
184 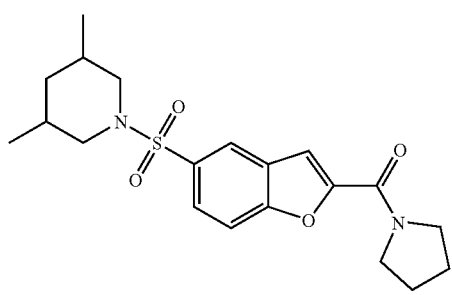
185 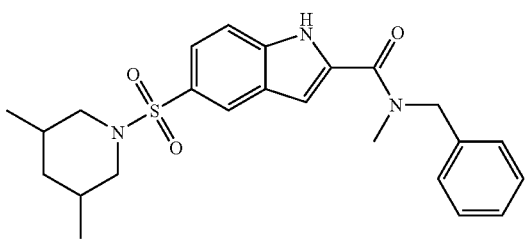
186 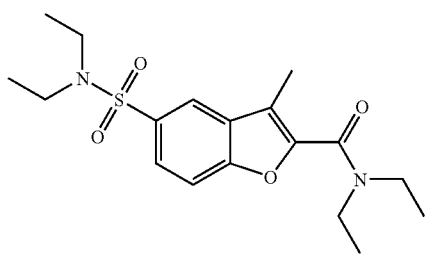
187 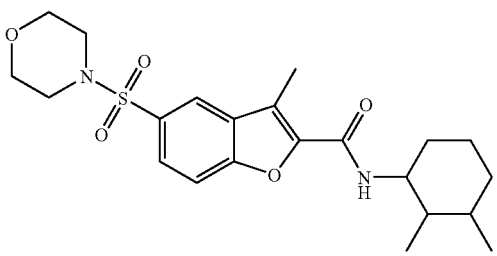

-continued
| | |
|---|---|
| 188 | 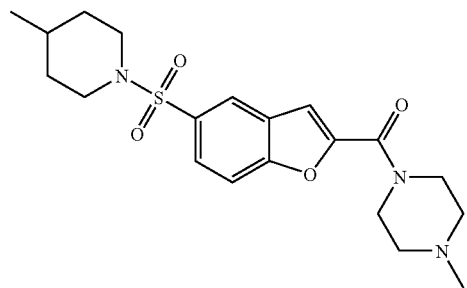 |
| 189 | 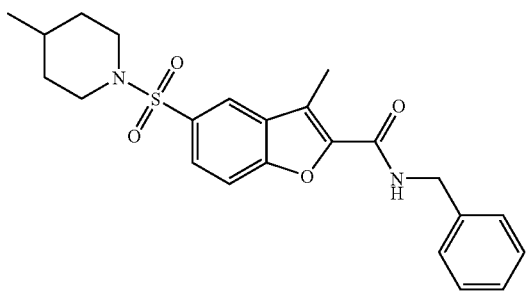 |
| 190 | 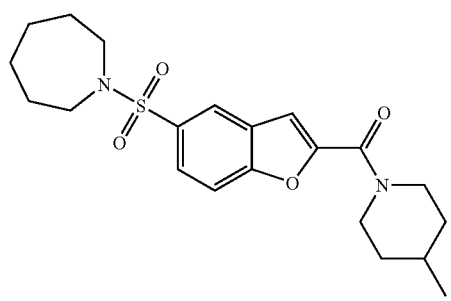 |
| 191 | 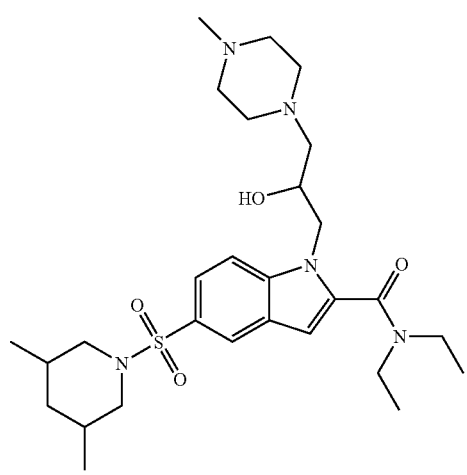 |
| 192 | 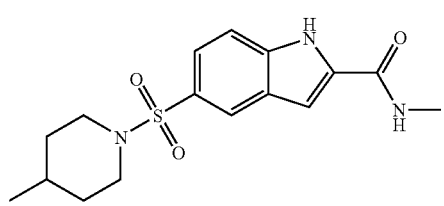 |

-continued
193 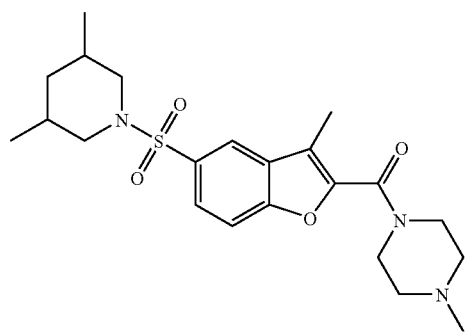
194 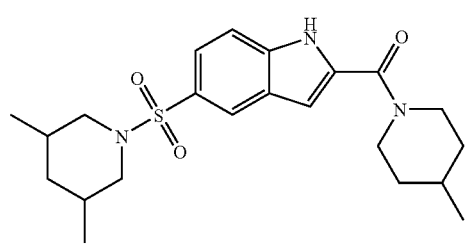
195 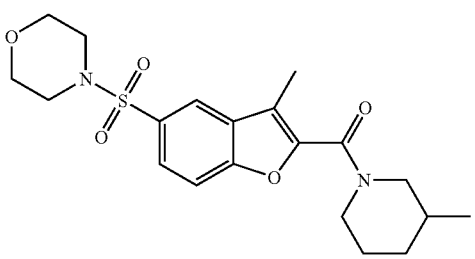
196 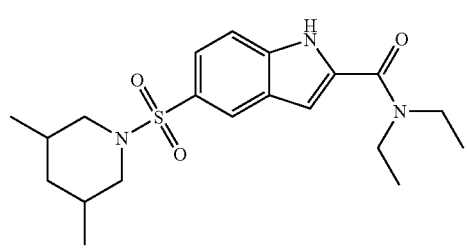
197 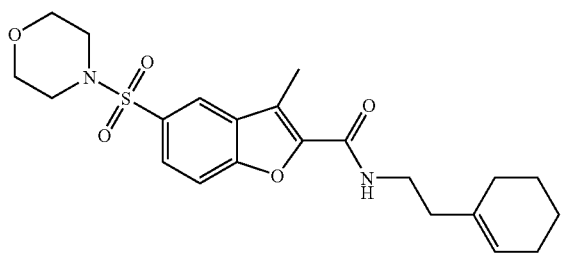

-continued
198
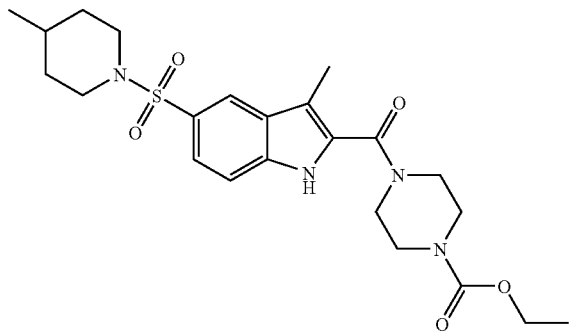
199
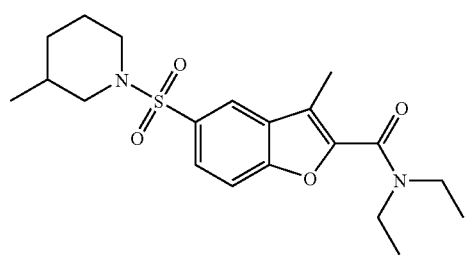
200
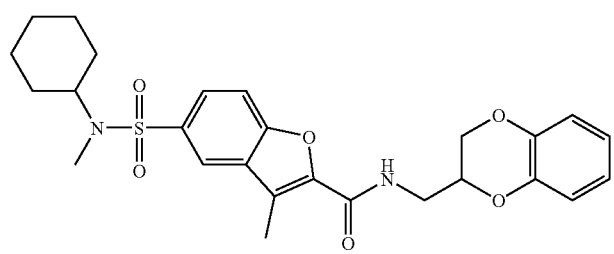
201
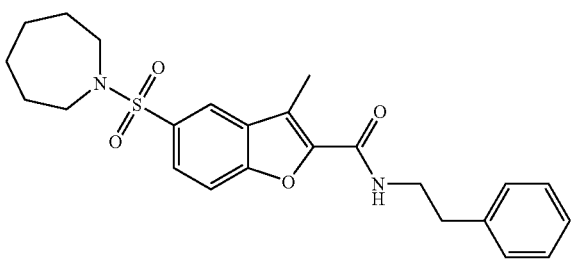
202
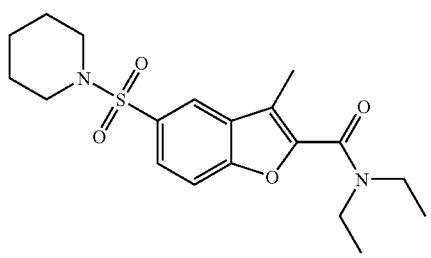

-continued
| | |
|---|---|
| 203 | 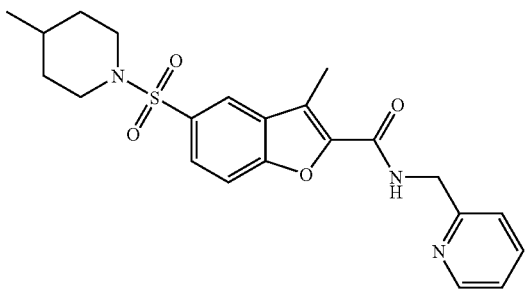 |
| 204 | 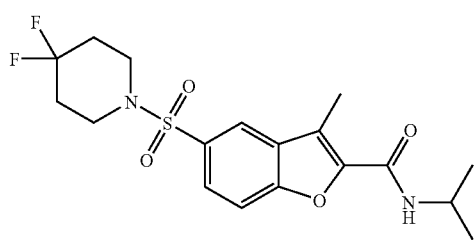 |
| 205 | 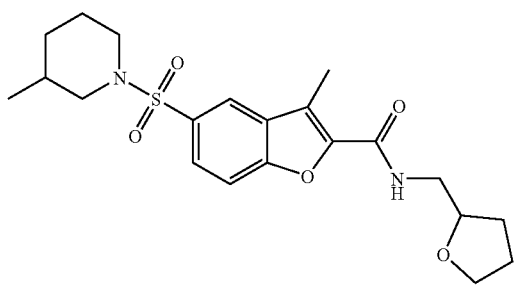 |
| 206 | 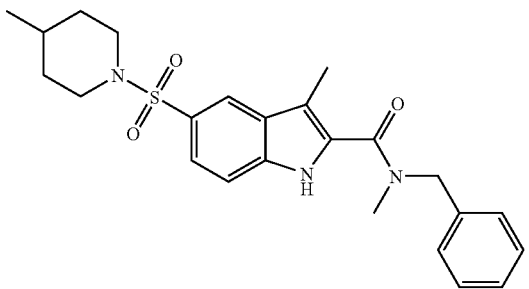 |
| 207 | 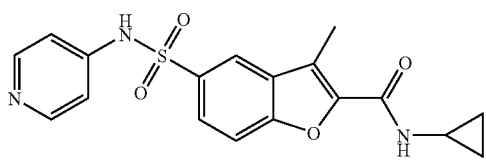 |
| 208 | 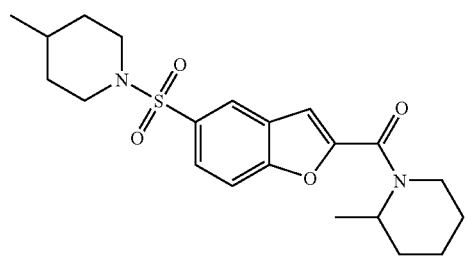 |

| | |
|---|---|
| 209 | 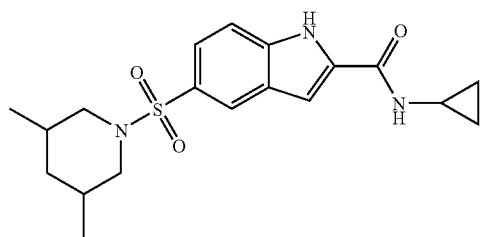 |
| 210 | 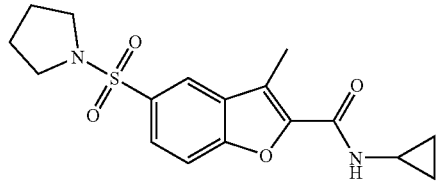 |
| 211 | 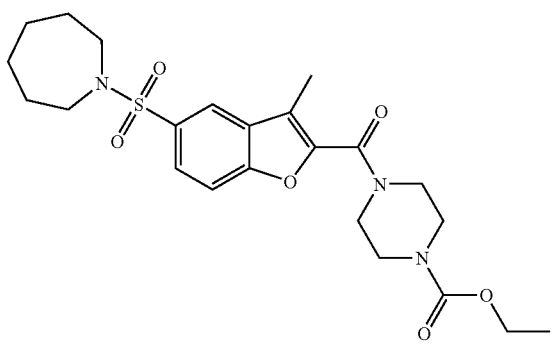 |
| 212 | 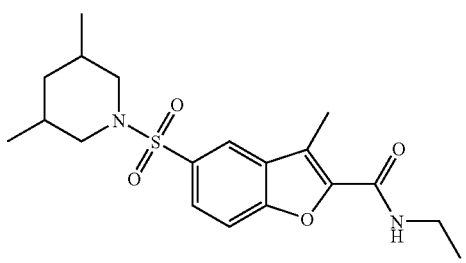 |
| 213 | 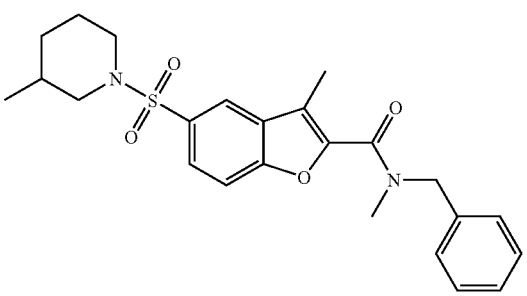 |
| 214 | 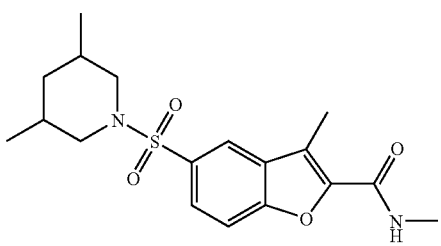 |

-continued
215 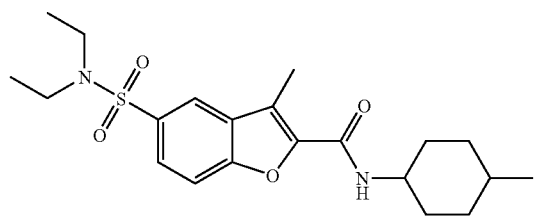
216 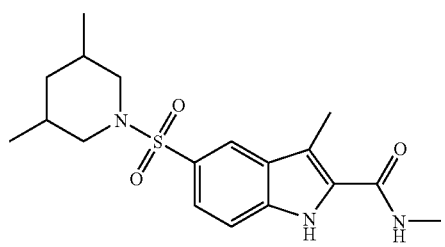
217 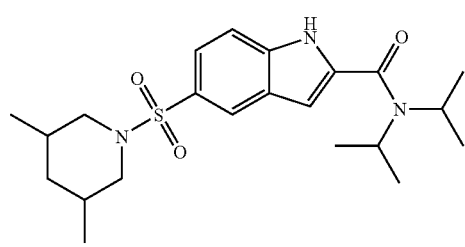
218 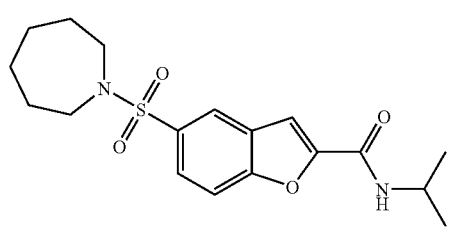
219 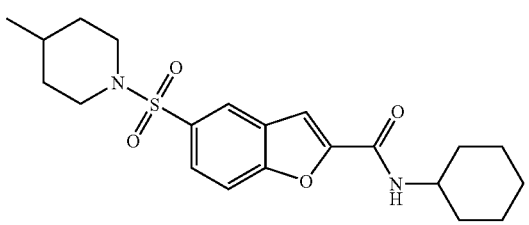
220 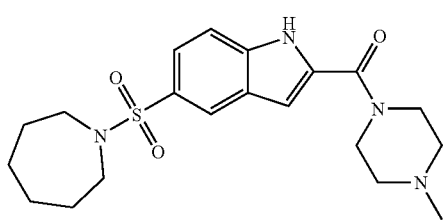

-continued
221 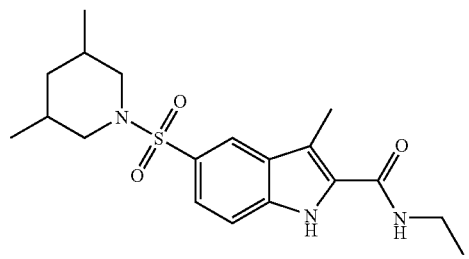
222 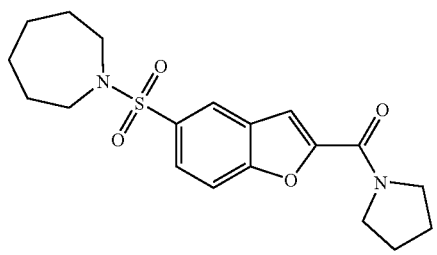
223 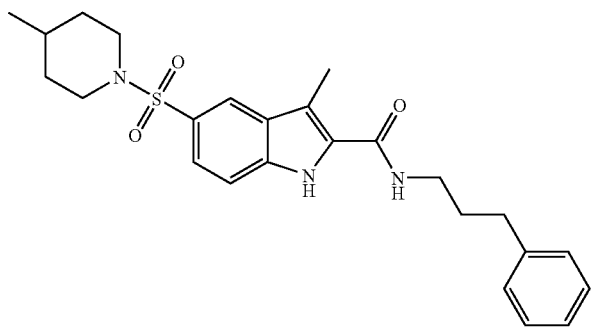
224 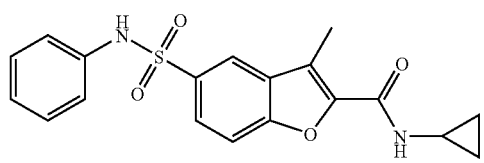
225 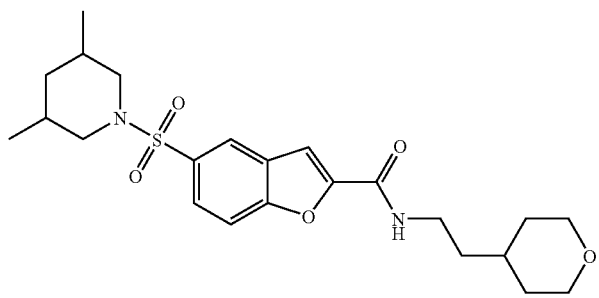
226 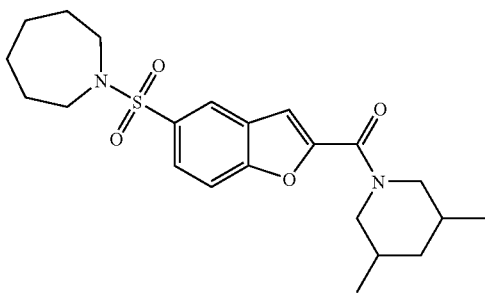

| | |
|---|---|
| 227 | 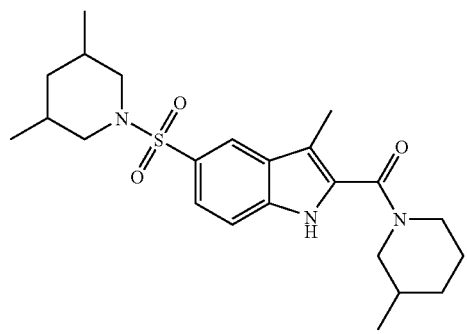 |
| 228 | 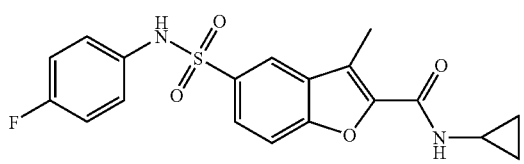 |
| 229 | 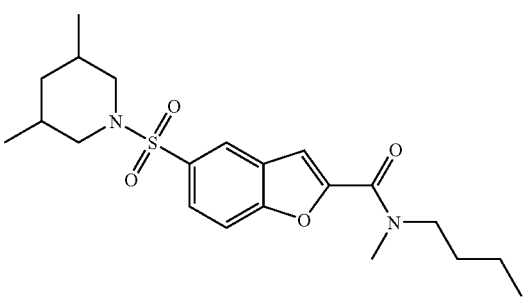 |
| 230 | 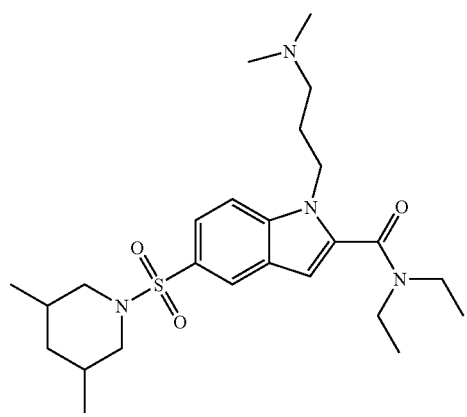 |
| 231 | 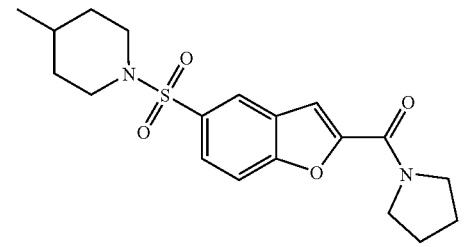 |

-continued
232 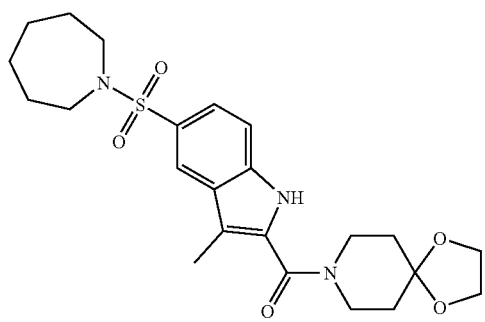
233 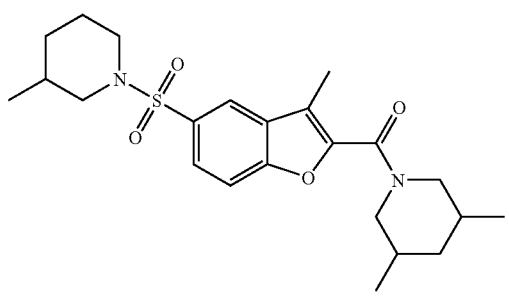
234 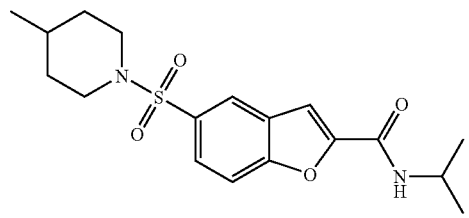
235 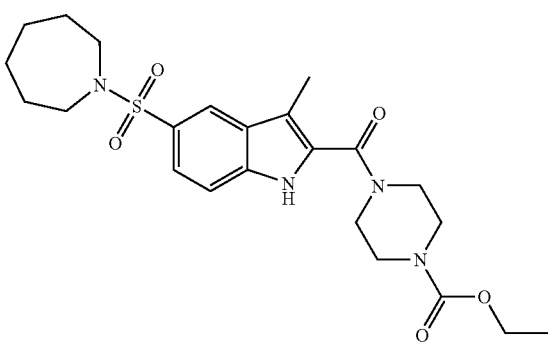
236 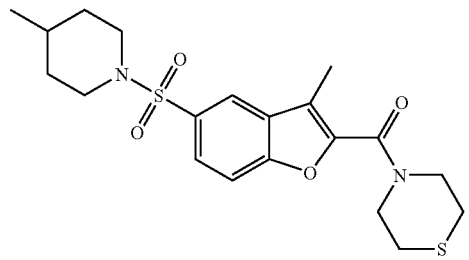

-continued
237
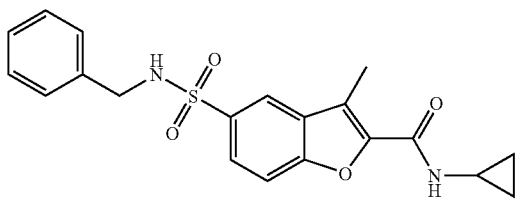
238
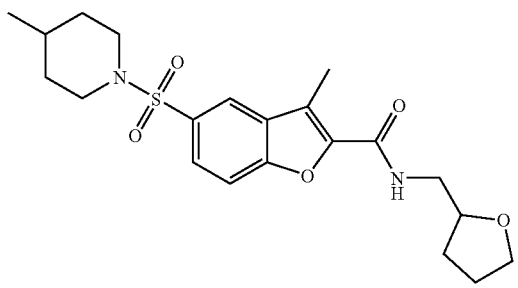
239
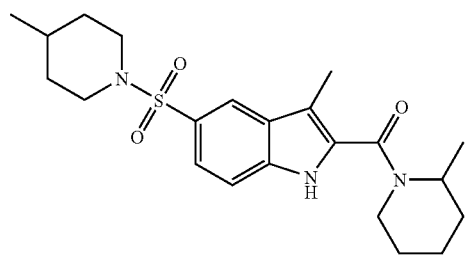
240
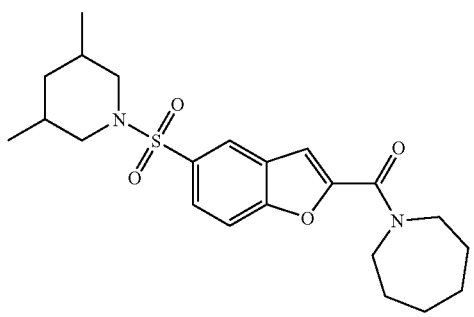
241
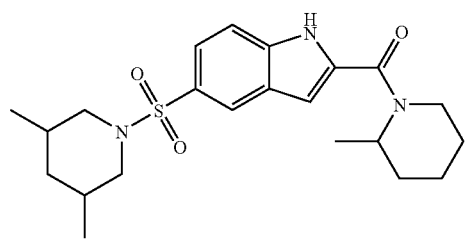

-continued
242
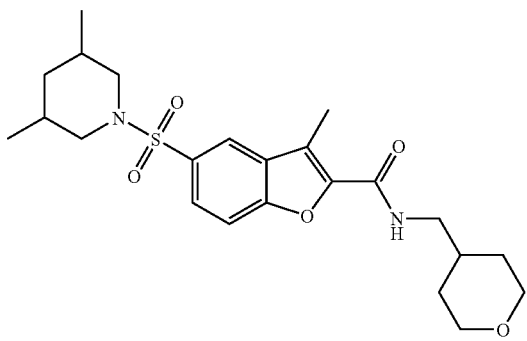
243
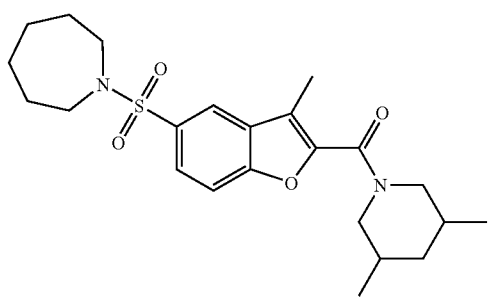
244
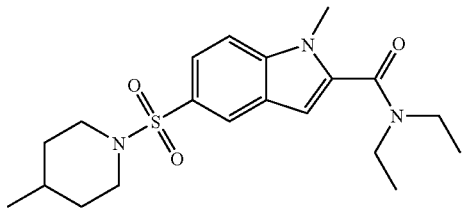
245
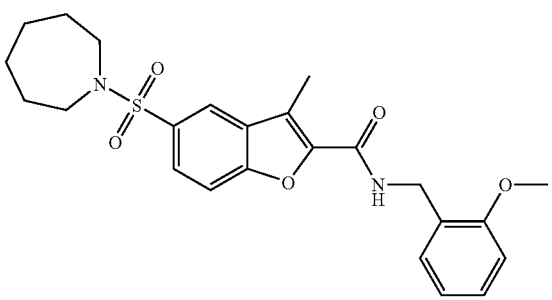
246
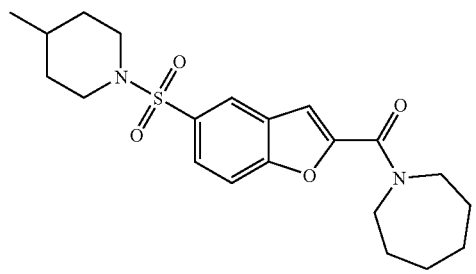

-continued
247 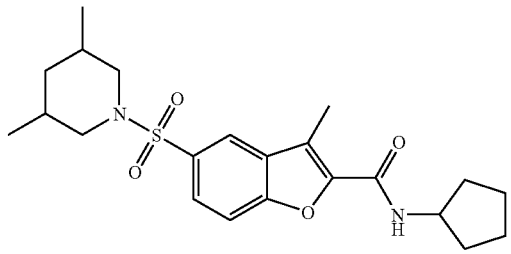
248 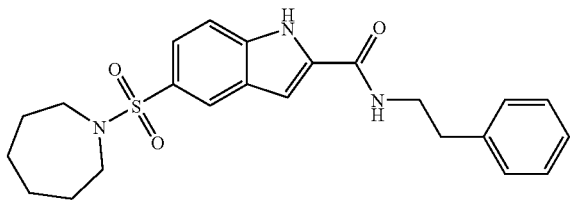
249 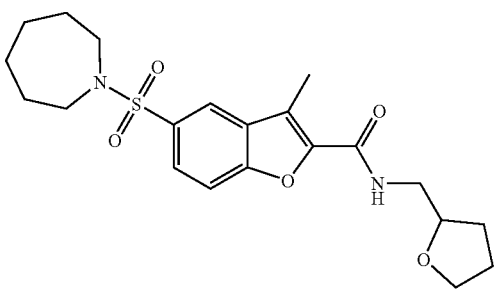
250 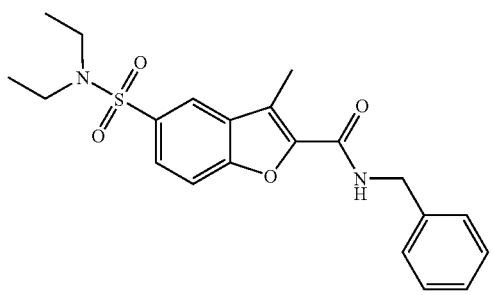
251 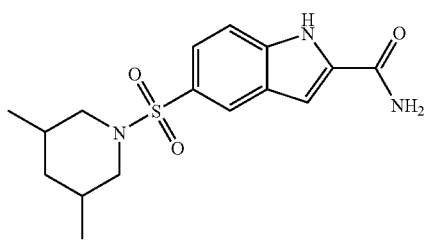
252 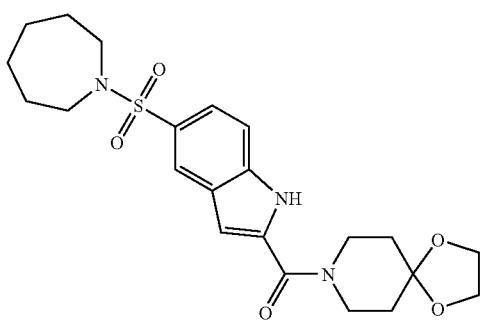

-continued
253 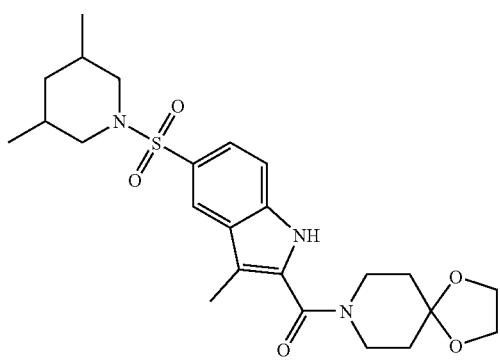
254 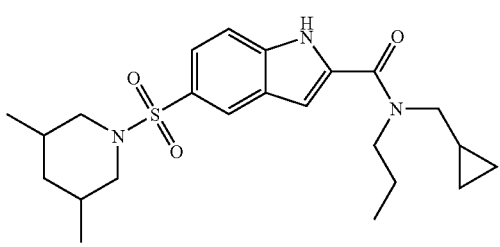
255 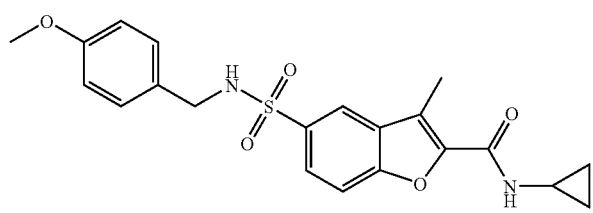
256 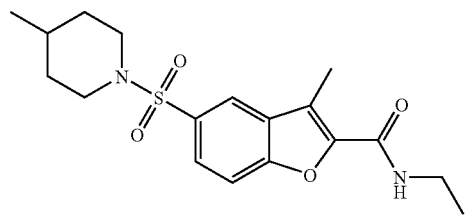
257 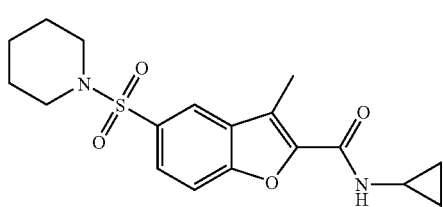
258 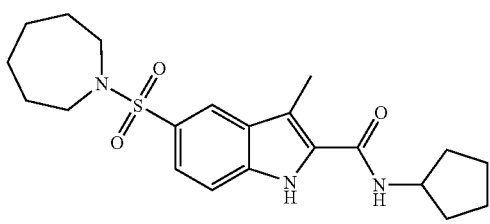

-continued
| | |
|---|---|
| 259 | 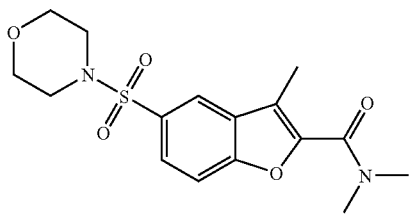 |
| 260 | 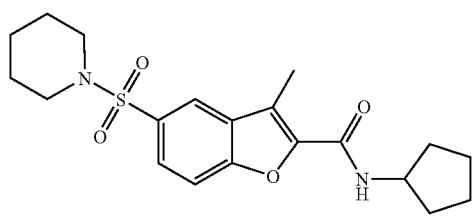 |
| 261 | 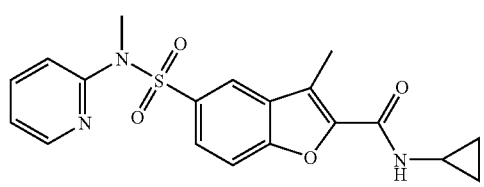 |
| 262 | 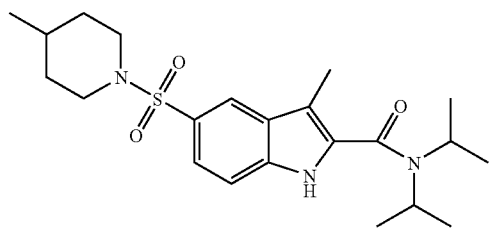 |
| 263 | 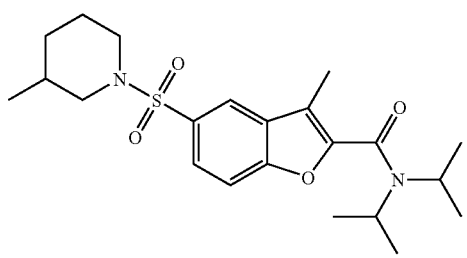 |
| 264 | 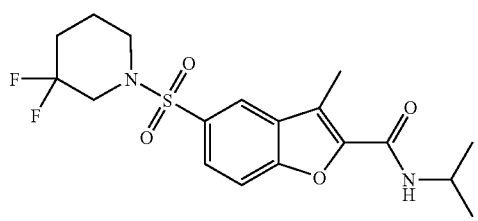 |
| 265 | 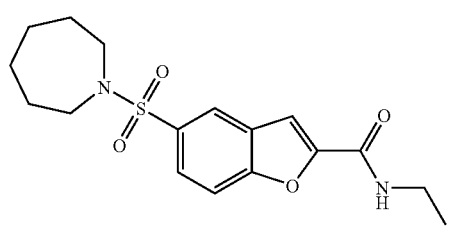 |

-continued
| 266 | 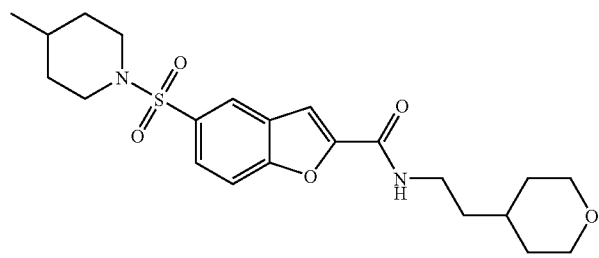 |
| 267 | 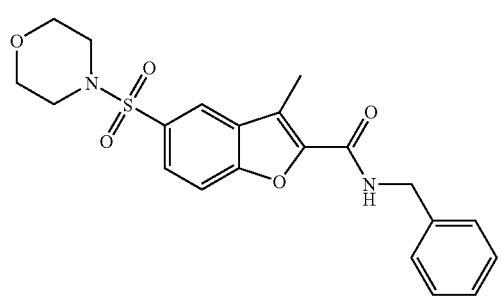 |
| 268 | 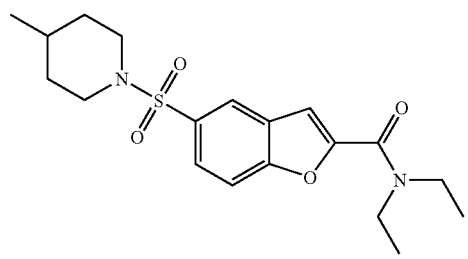 |
| 269 | 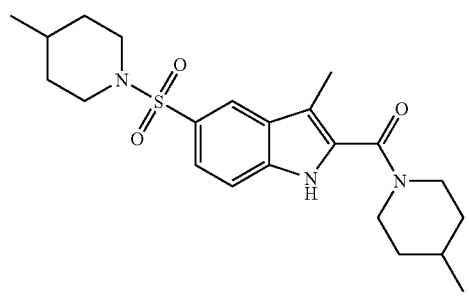 |
| 270 | 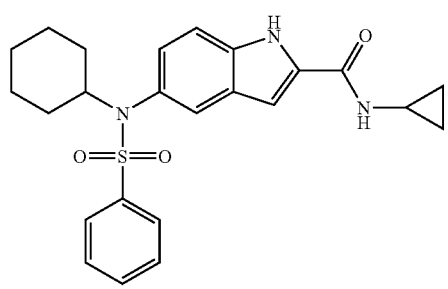 |

-continued
271 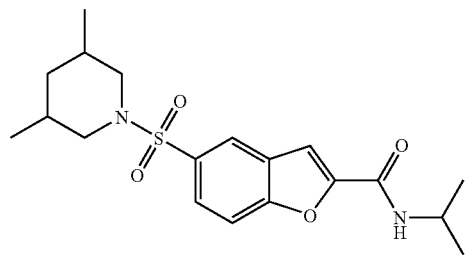
272 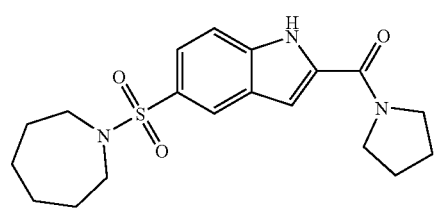
273 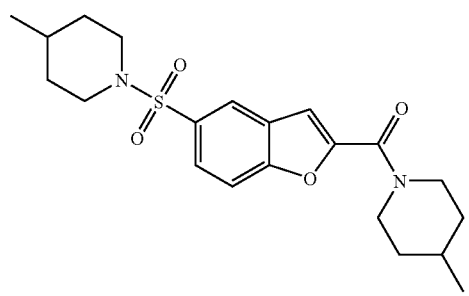
274 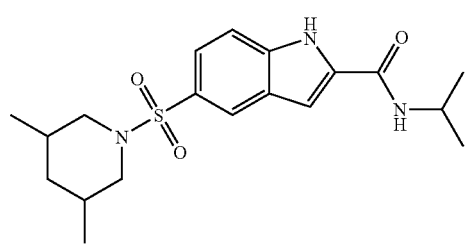
275 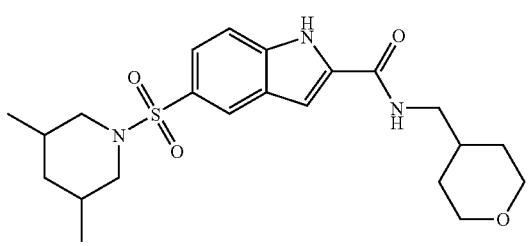
276 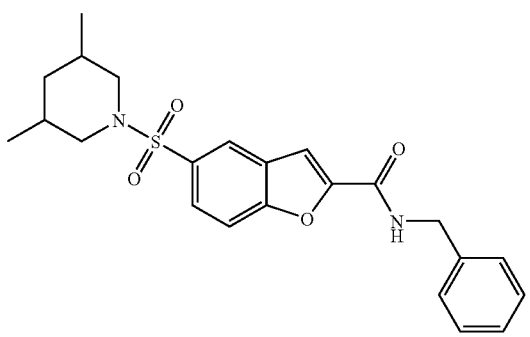

-continued
277 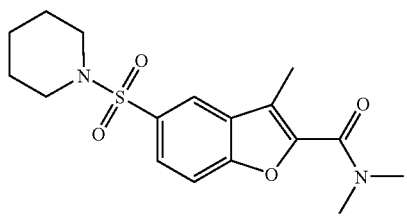
278 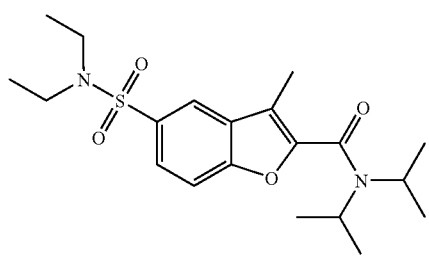
279 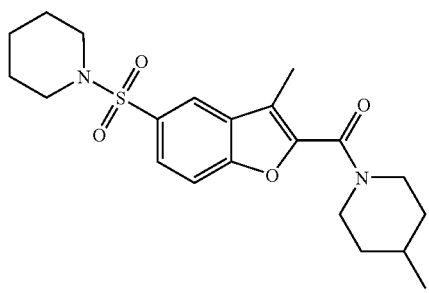
280 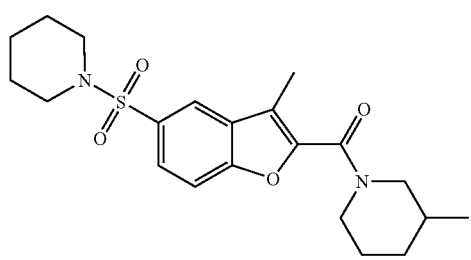
281 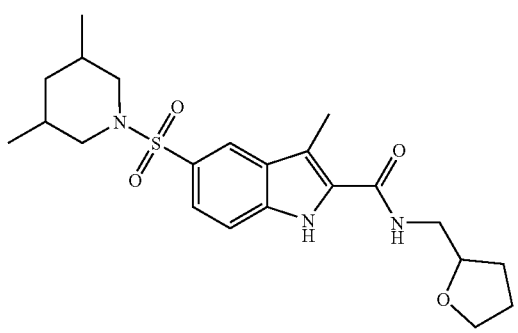

-continued
282 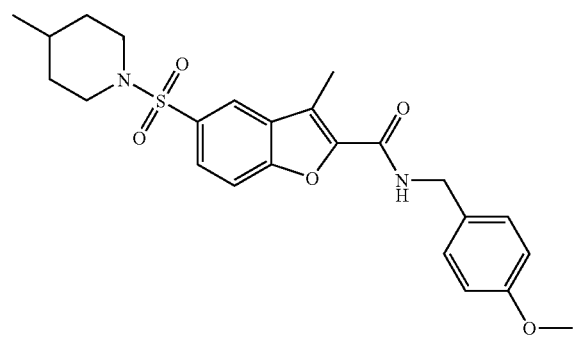
283 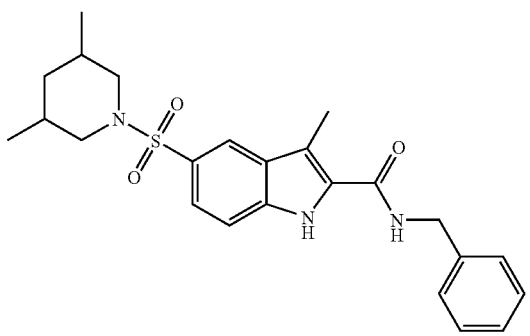
284 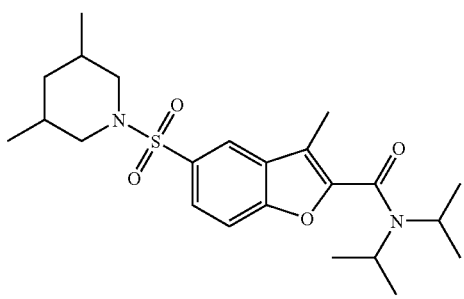
285 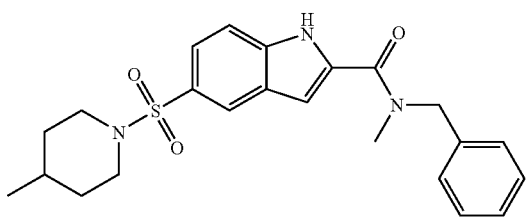
286 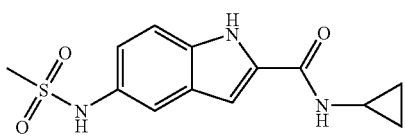

-continued
287 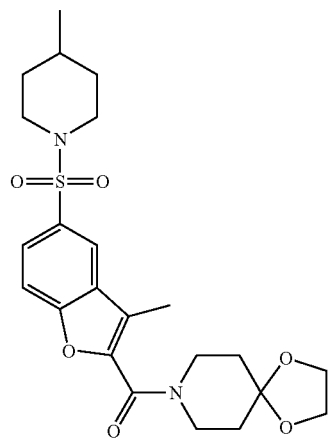
288 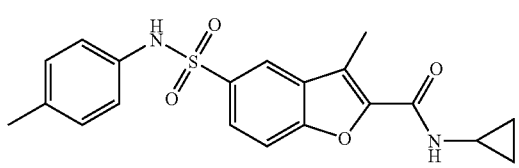
289 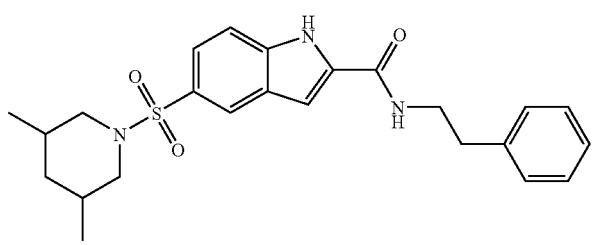
290 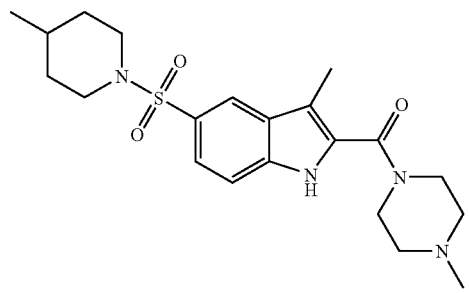
291 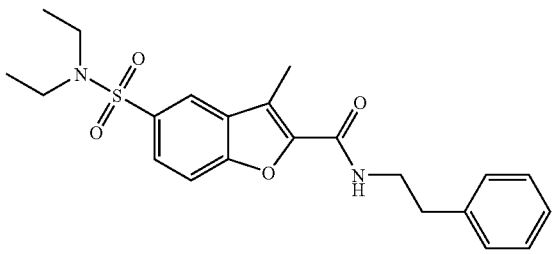

-continued
292
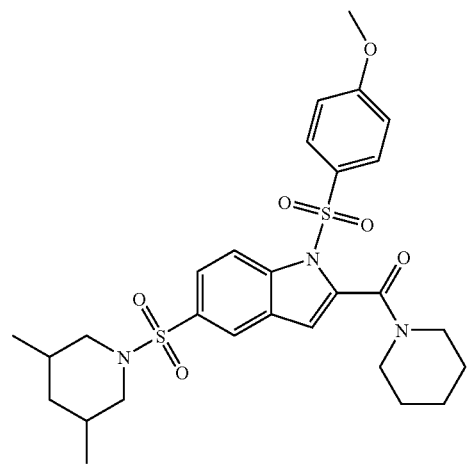
293
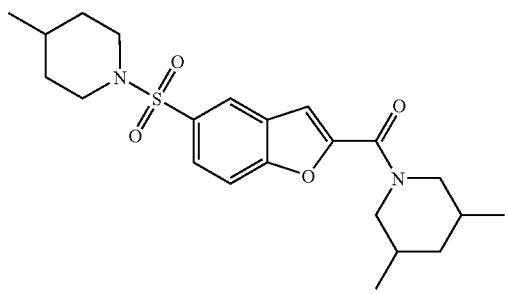
294
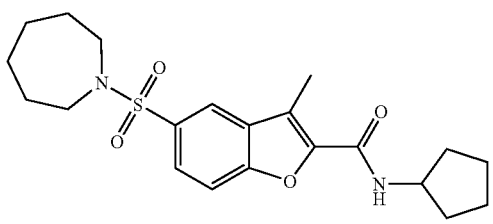
295
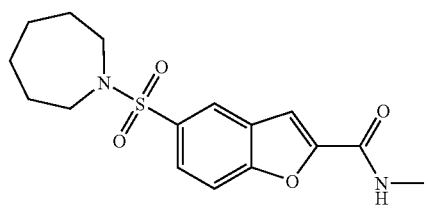
296
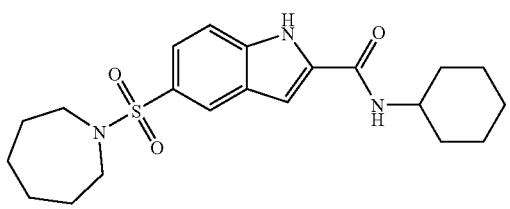

-continued
297 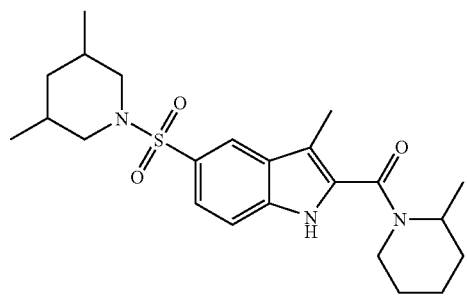
298 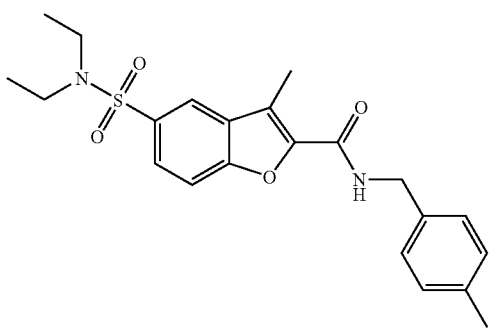
299 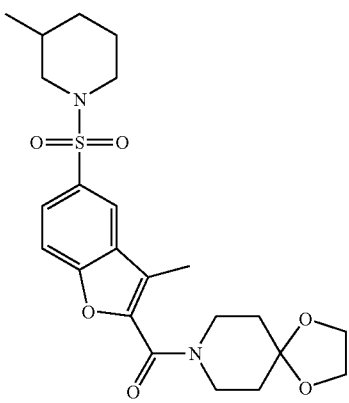
300 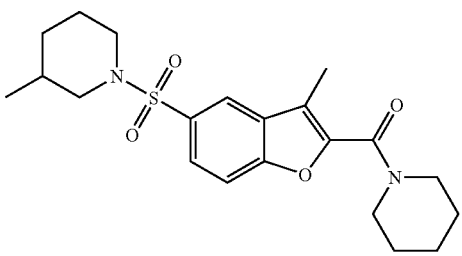
301 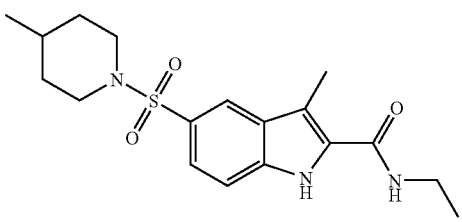

-continued
302 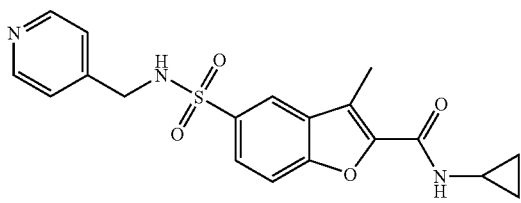
303 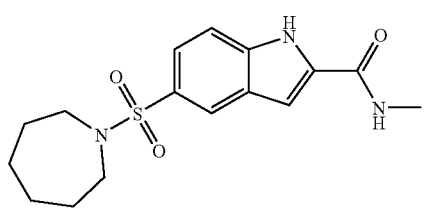
304 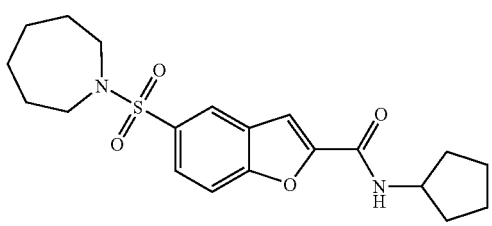
305 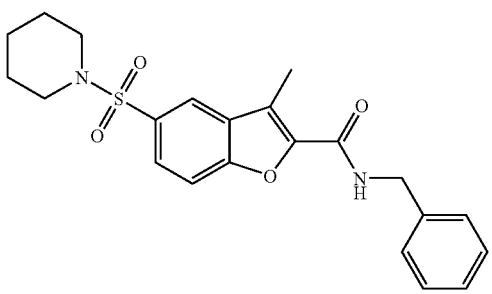
306 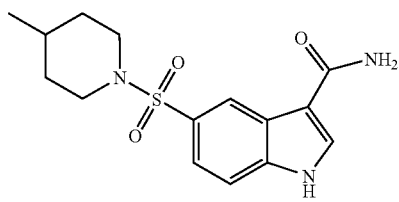
307 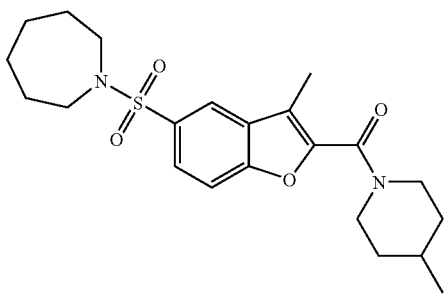

-continued
308 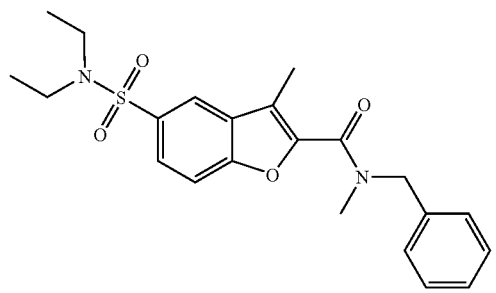
309 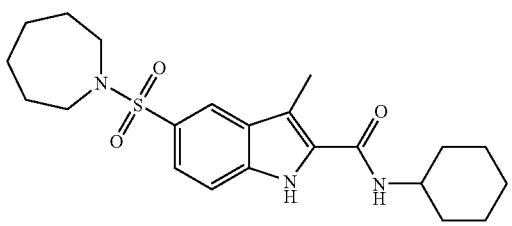
310 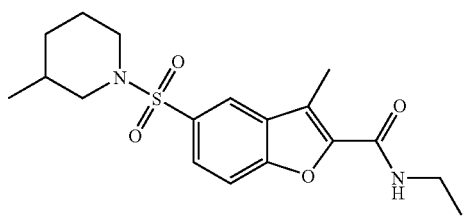
311 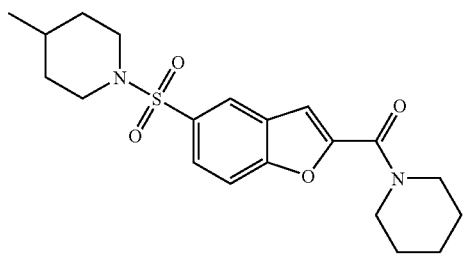
312 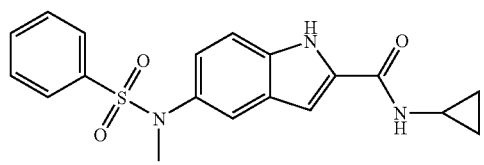
313 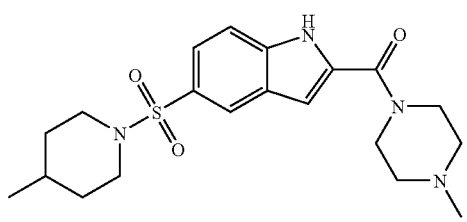

-continued
314
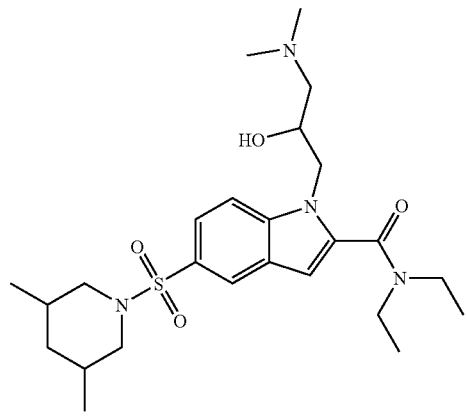
315
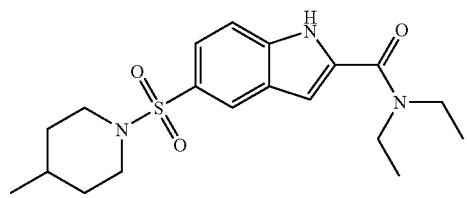
316
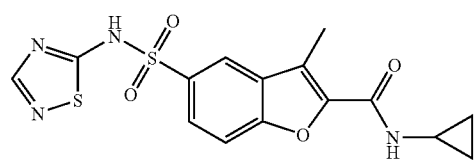
317
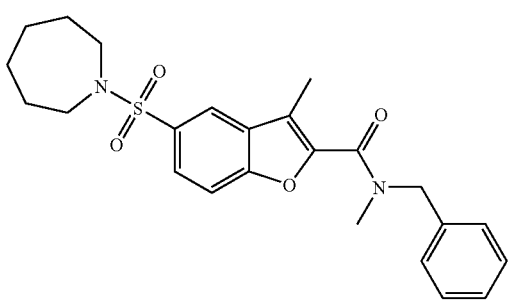
318
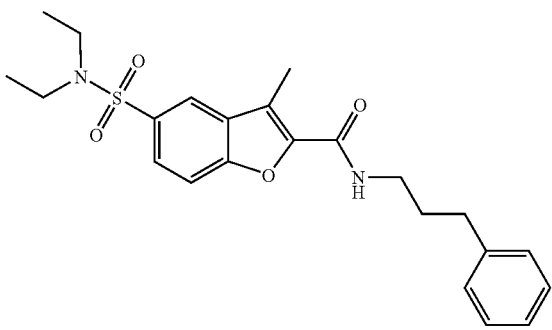

-continued
| | |
|---|---|
| 319 | 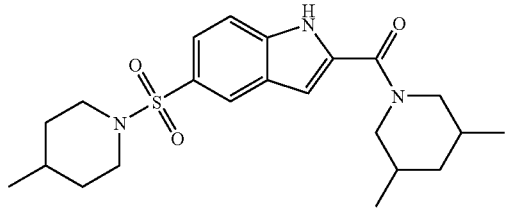 |
| 320 | 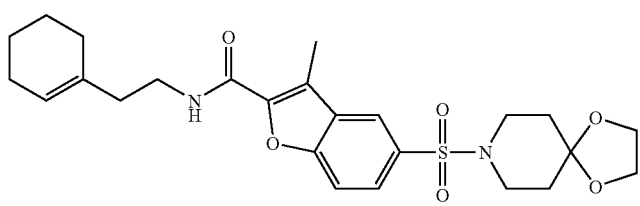 |
| 321 | 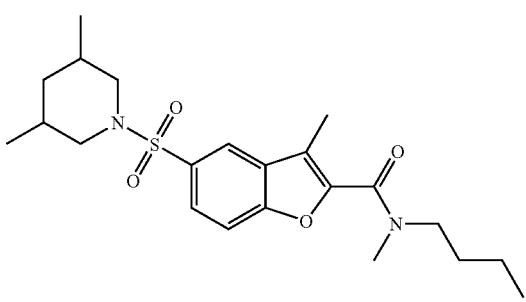 |
| 322 | 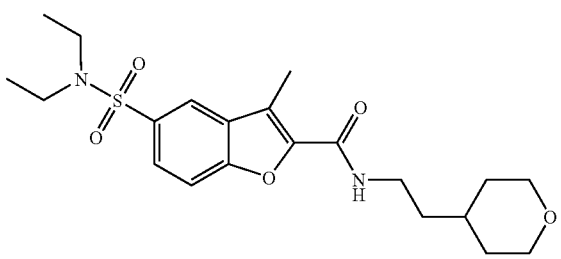 |
| 323 | 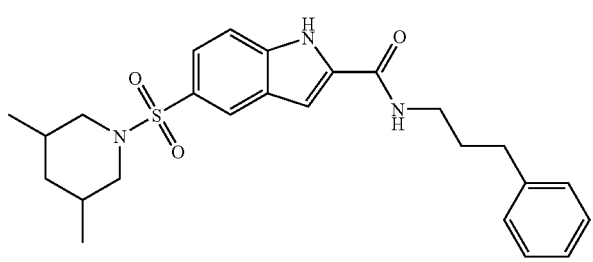 |
| 324 | 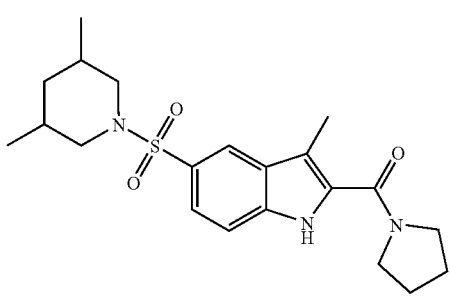 |

-continued
| 325 | 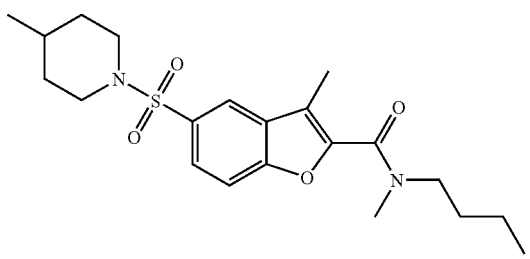 |
| 326 | 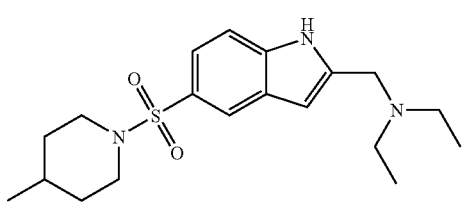 |
| 327 | 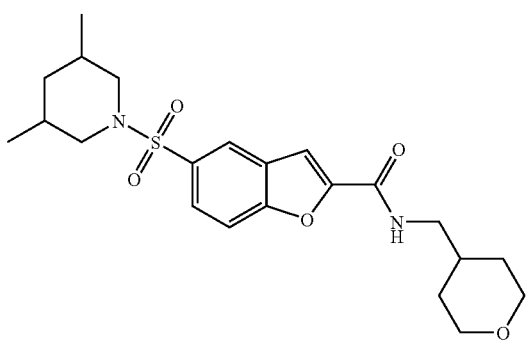 |
| 328 | 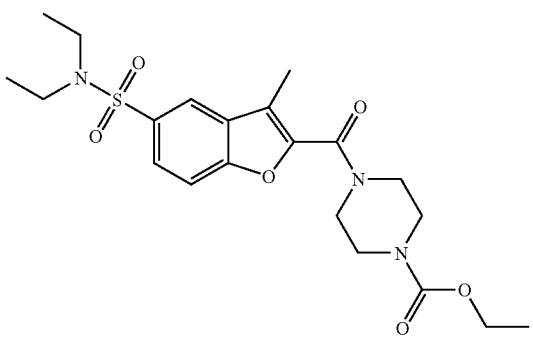 |
| 329 | 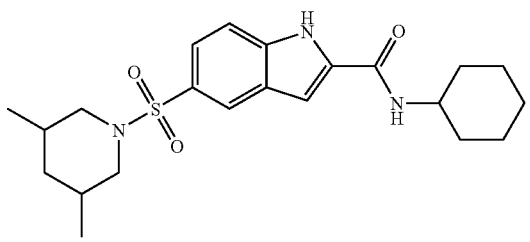 |

-continued
| | |
|---|---|
| 330 | 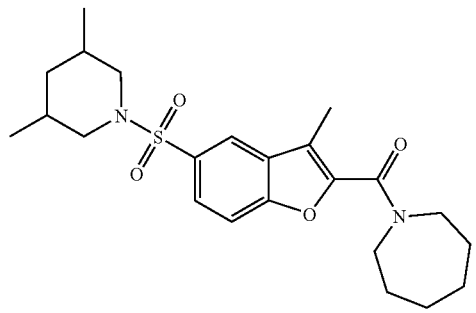 |
| 331 | 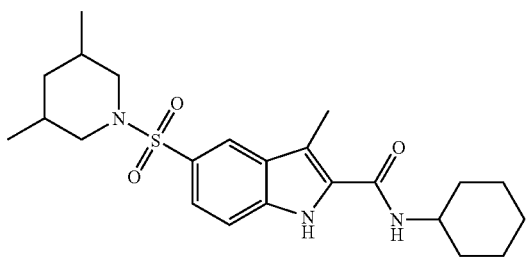 |
| 332 | 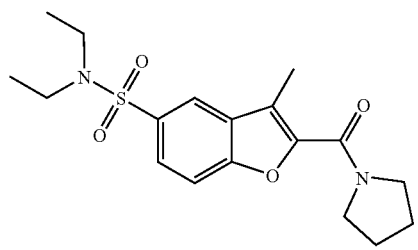 |
| 333 | 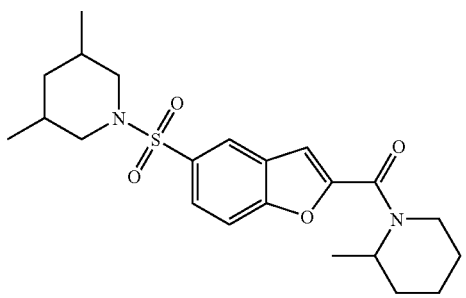 |
| 334 | 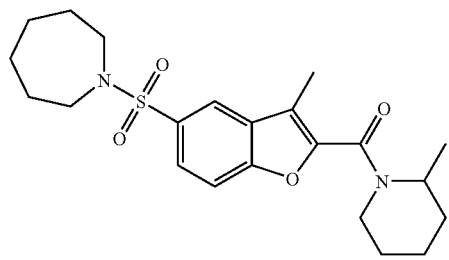 |
| 335 | 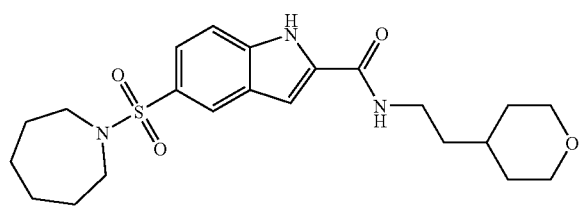 |

-continued
336 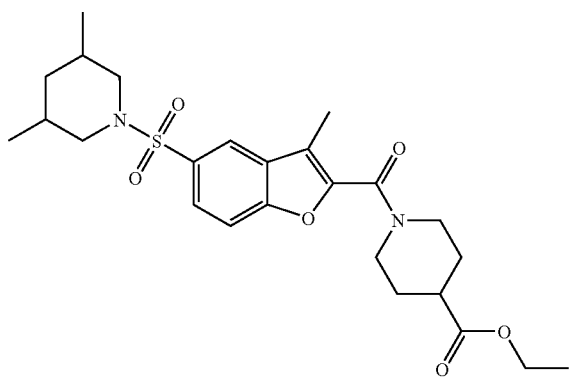
337 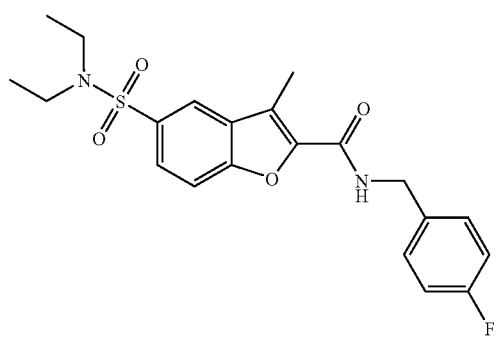
338 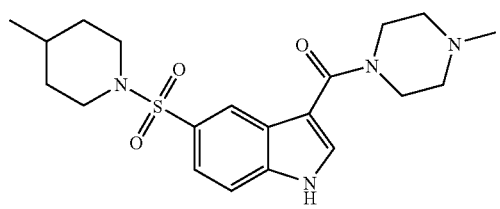
339 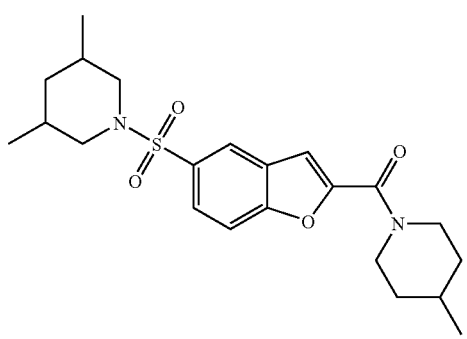
340 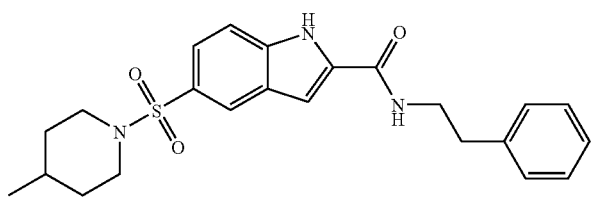

-continued
341 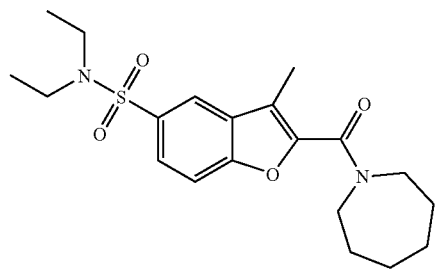
342 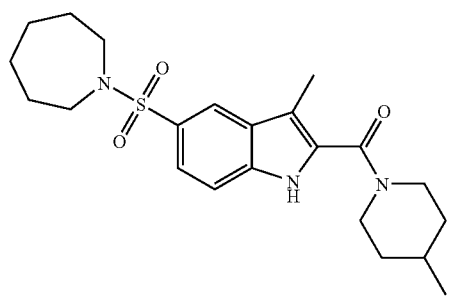
343 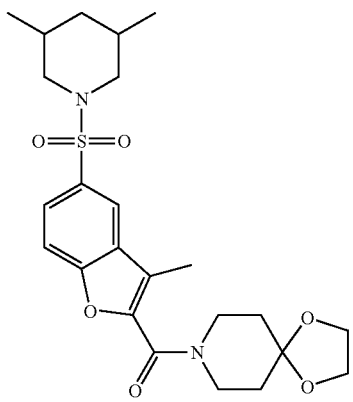
344 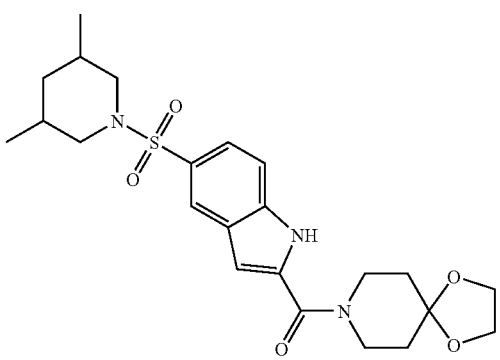
345 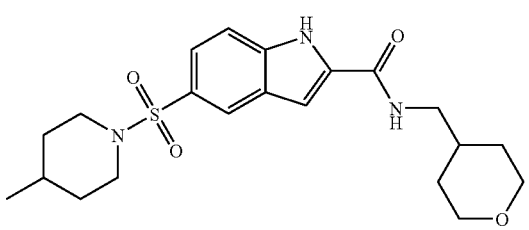

-continued
346
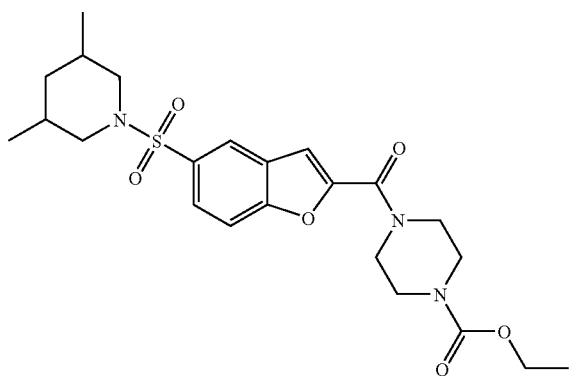
347
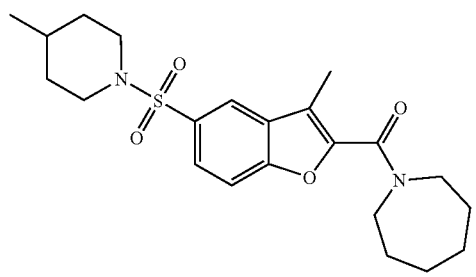
348
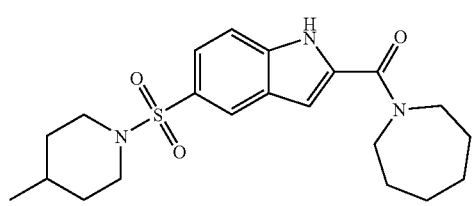
349
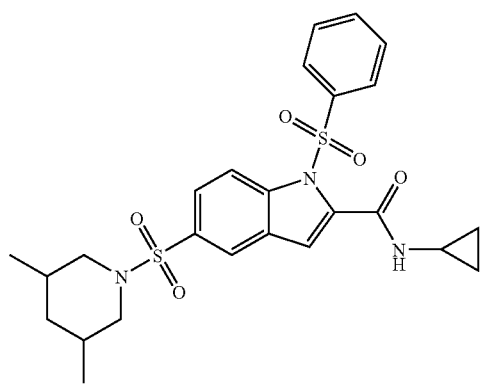

350 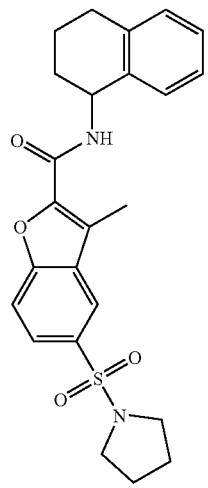
351 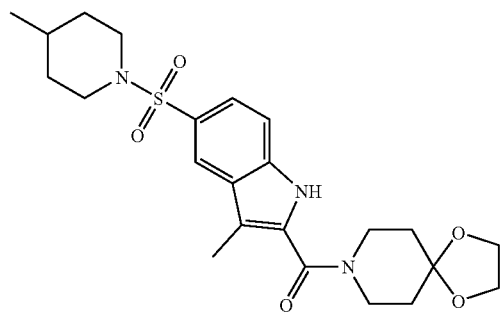
352 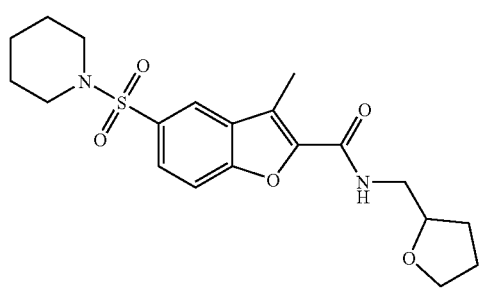
353 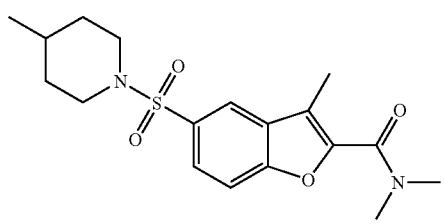
354 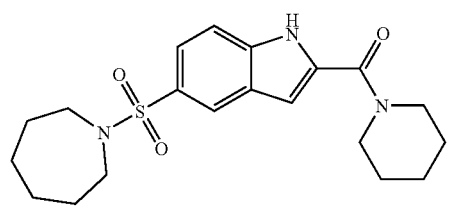

-continued
355 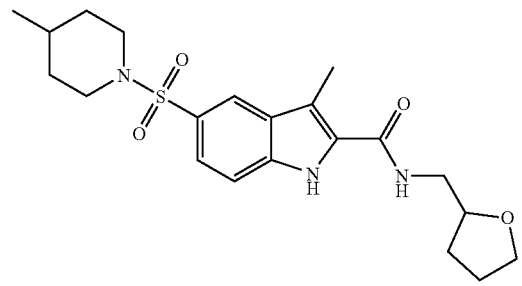
356 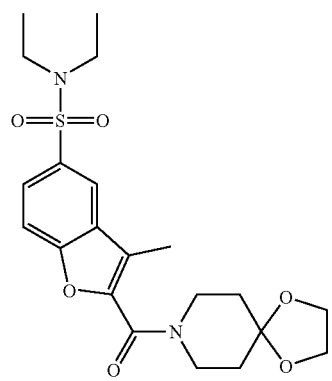
357 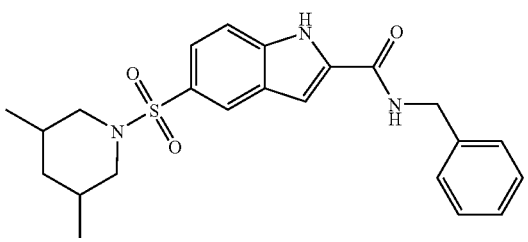
358 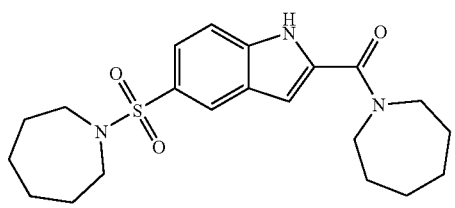
359 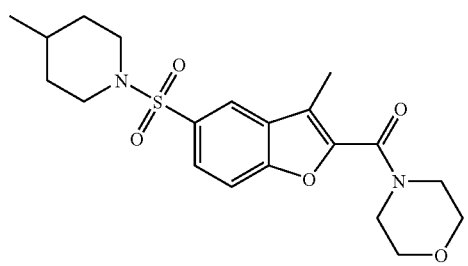

-continued
360 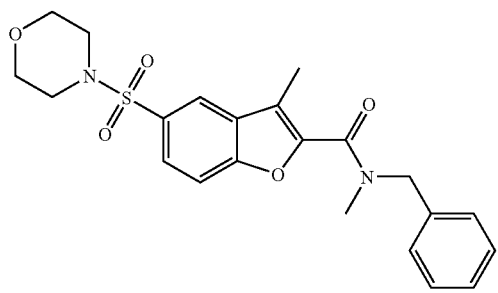
361 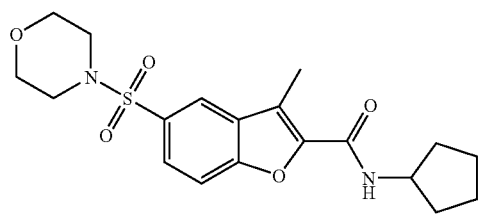
362 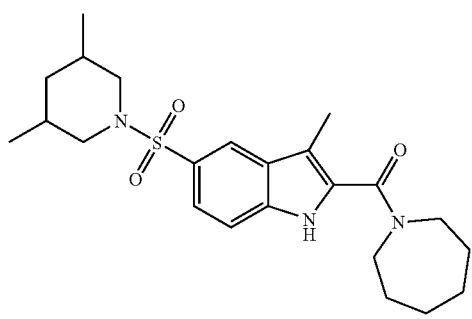
363 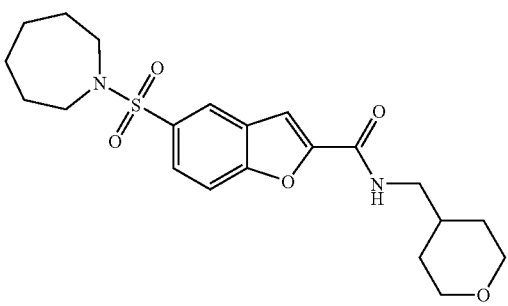
364 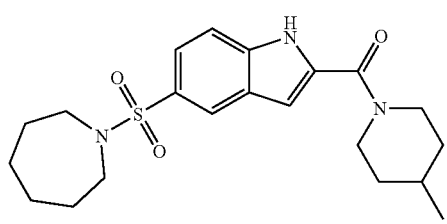
365 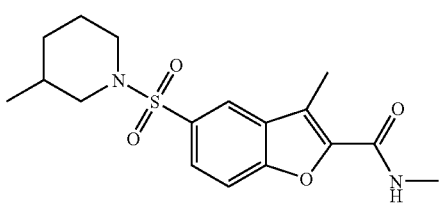

-continued
366
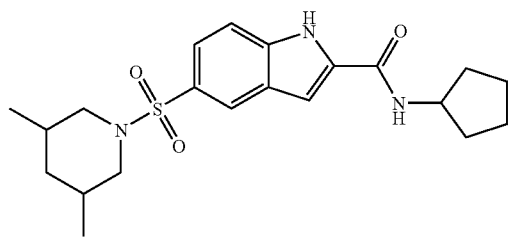
367
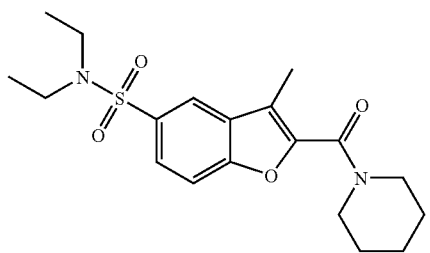
368
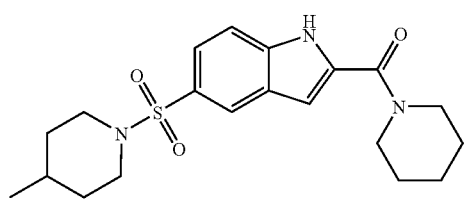
369
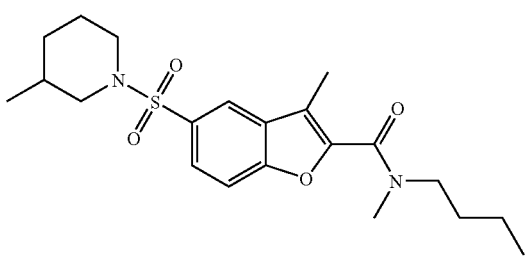
370
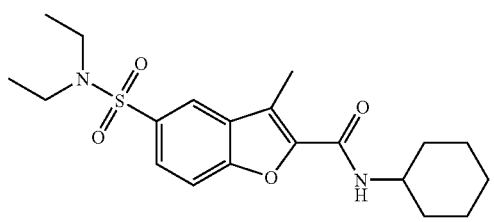
371
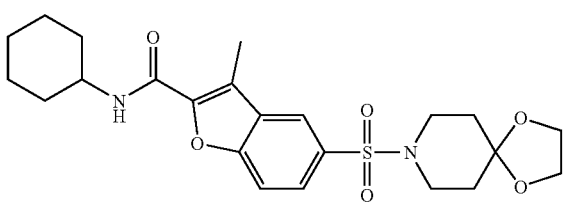

-continued
| | |
|---|---|
| 372 | 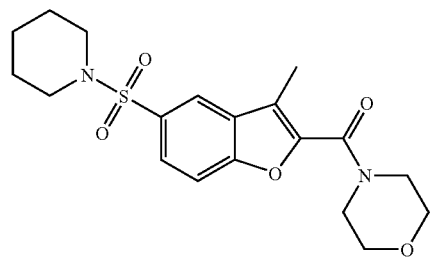 |
| 373 | 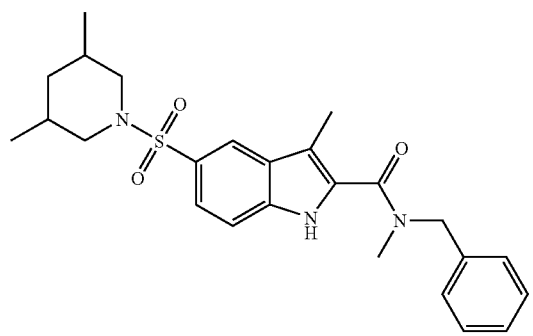 |
| 374 | 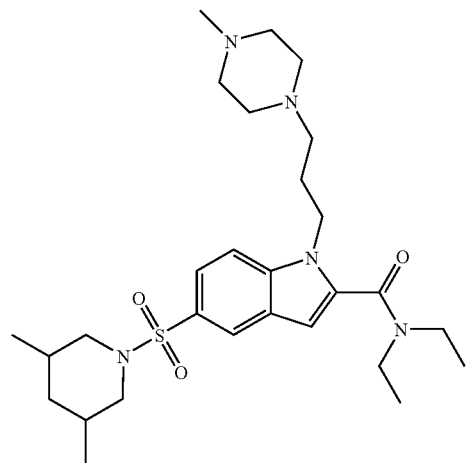 |
| 375 | 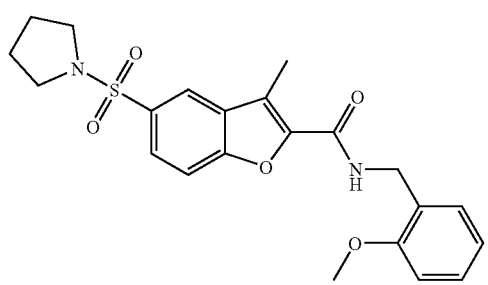 |

-continued
| | |
|---|---|
| 376 | 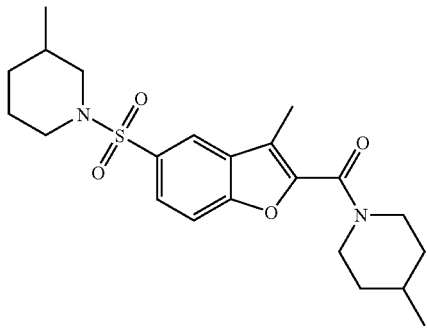 |
| 377 | 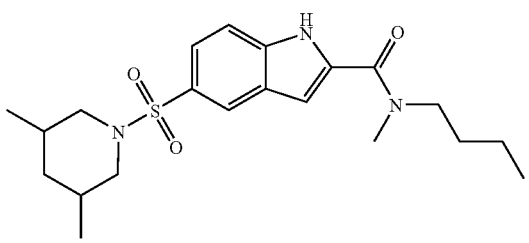 |
| 378 | 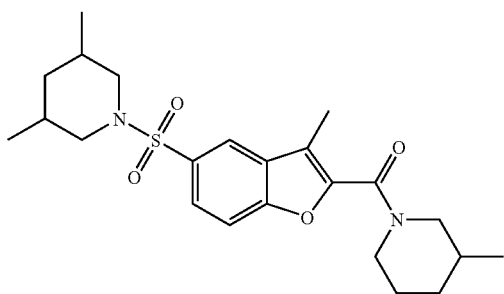 |
| 379 | 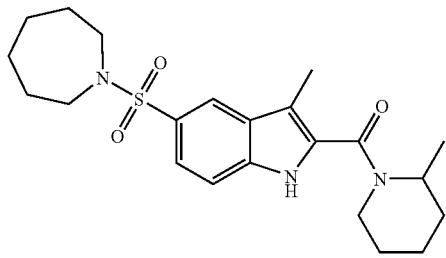 |
| 380 | 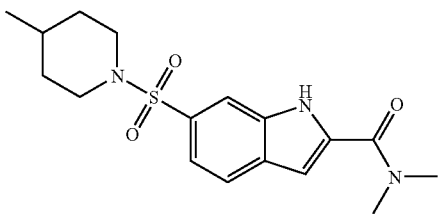 |
| 381 | 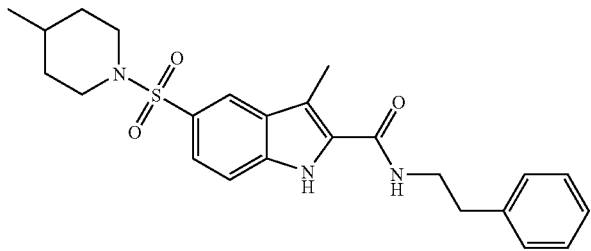 |

-continued
| | |
|---|---|
| 382 | 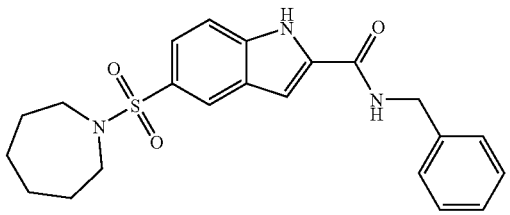 |
| 383 | 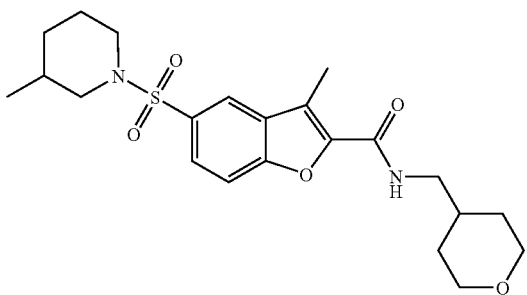 |
| 384 | 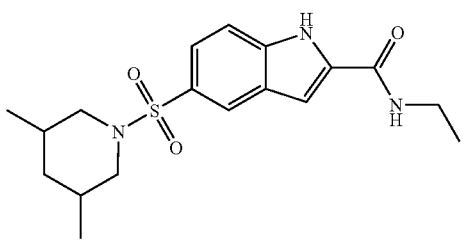 |
| 385 | 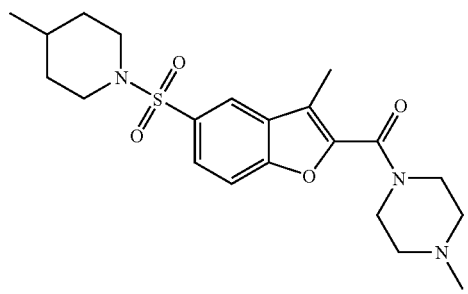 |
| 386 | 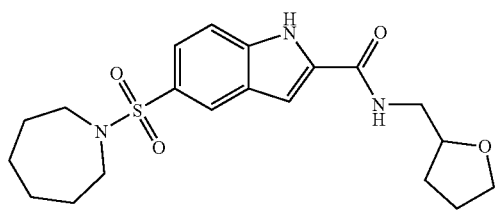 |

-continued
387
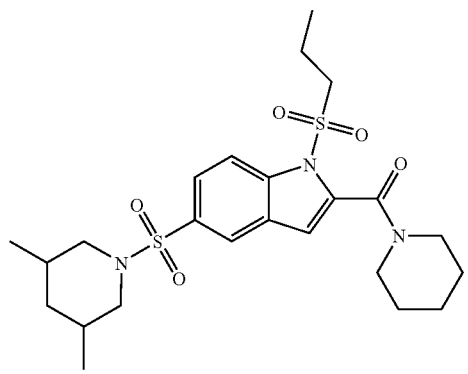
388
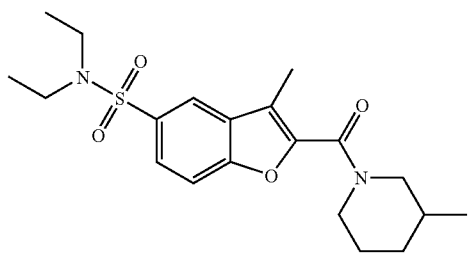
389
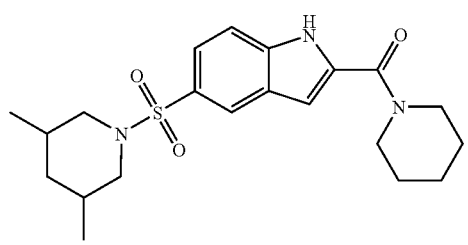
390
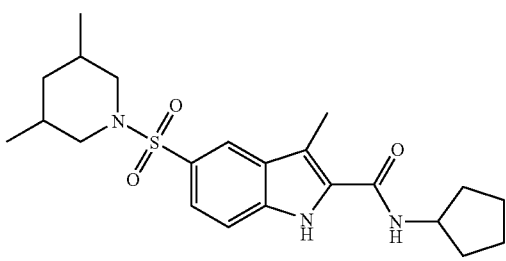
391
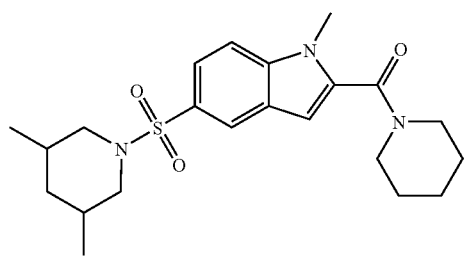

-continued
392
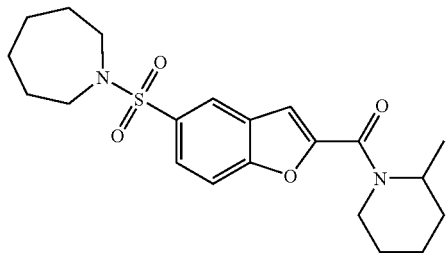
393
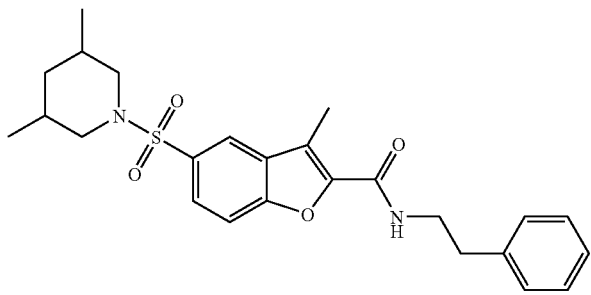
394
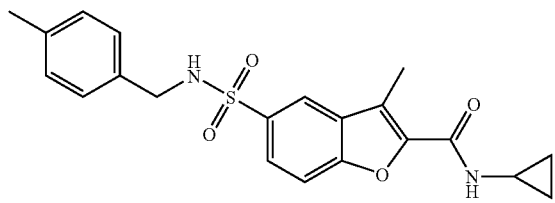
395
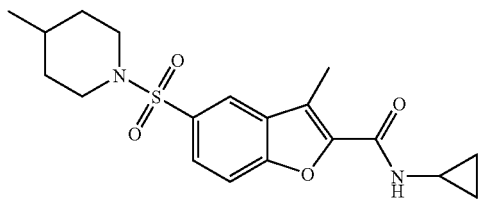
396
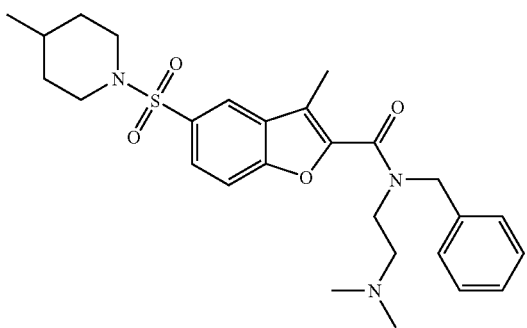
397
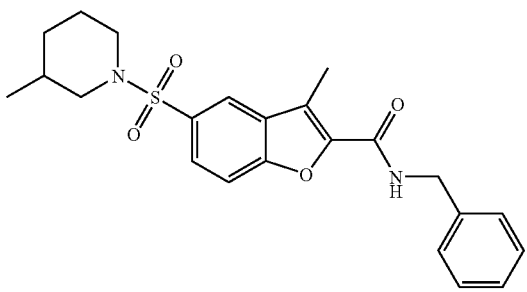

-continued
| | |
|---|---|
| 398 | 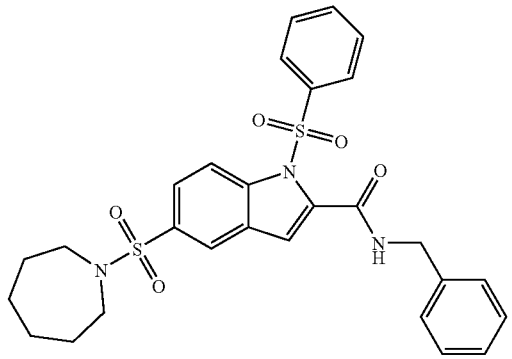 |
| 399 | 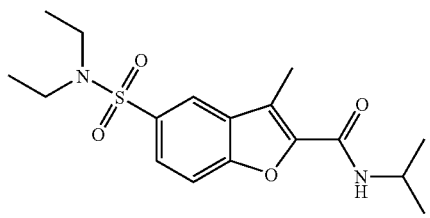 |
| 400 | 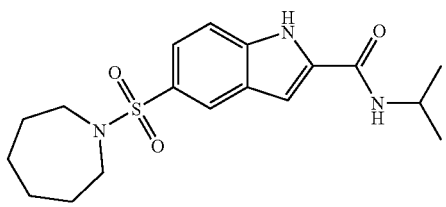 |
| 401 | 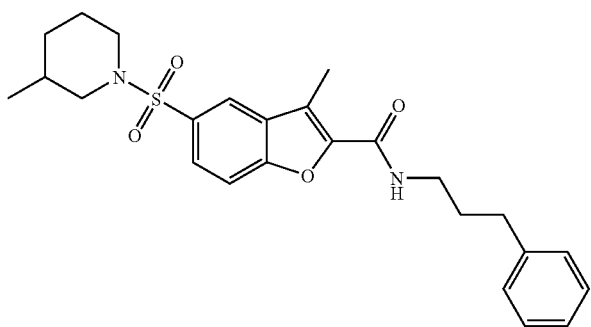 |
| 402 | 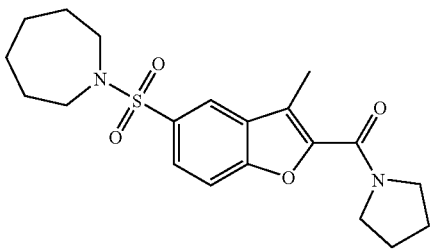 |

-continued
403
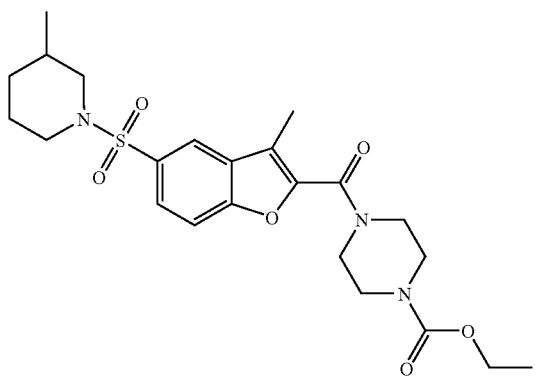
404
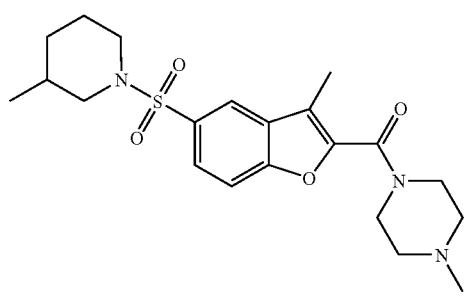
405
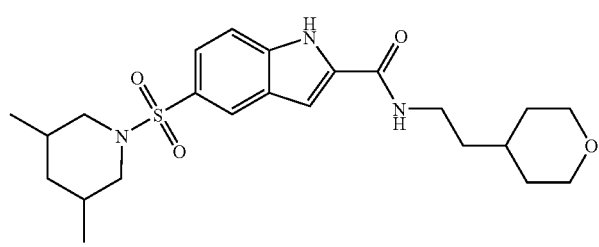
406
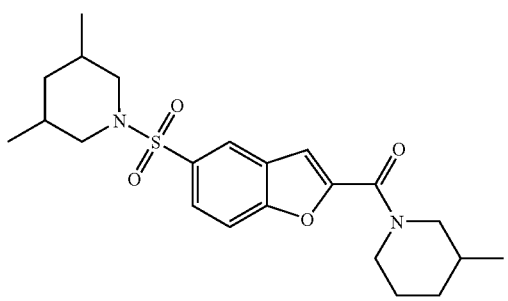
407
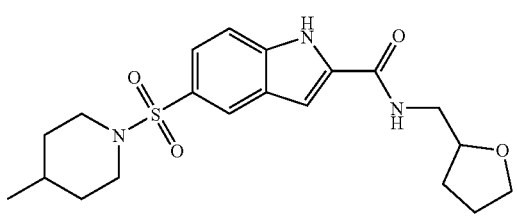

-continued
408 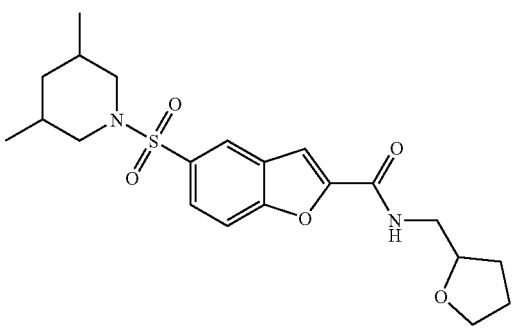
409 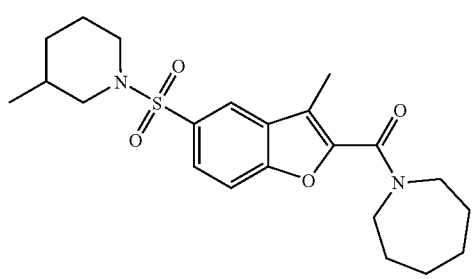
410 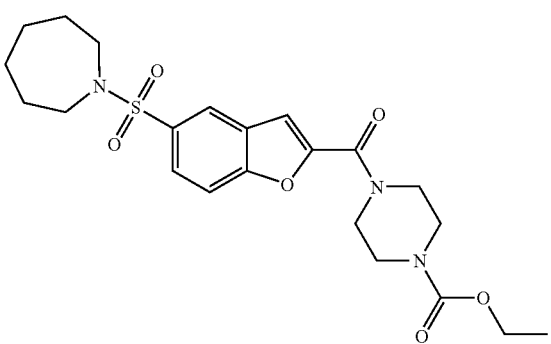
411 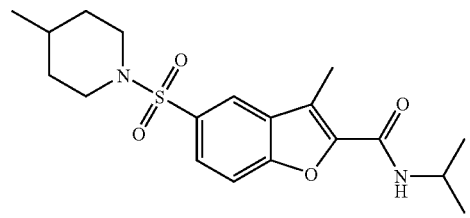
412 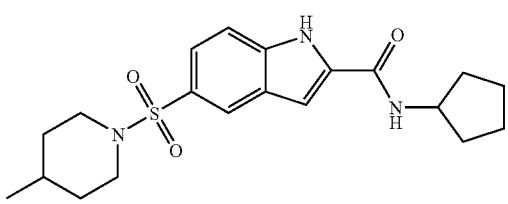

-continued
| | |
|---|---|
| 413 | 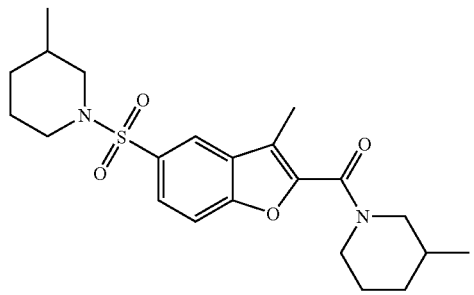 |
| 414 | 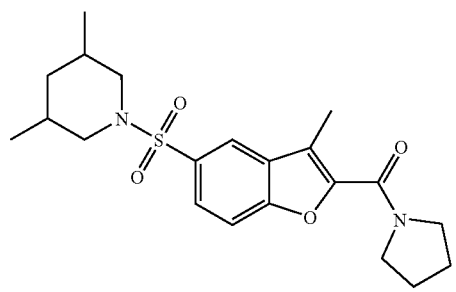 |
| 415 | 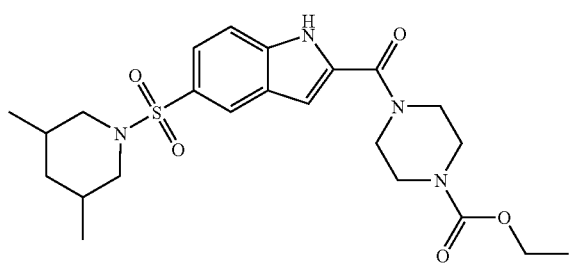 |
| 416 | 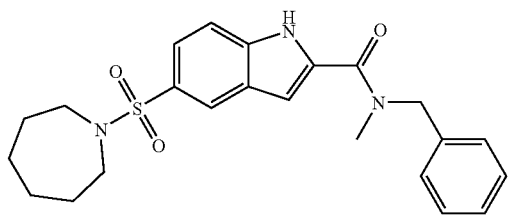 |
| 417 | 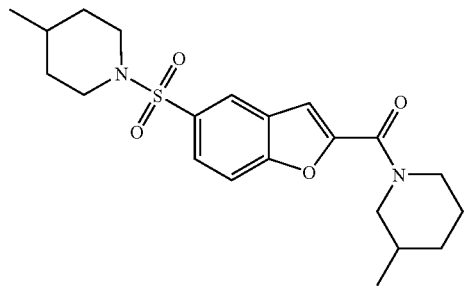 |
| 418 | 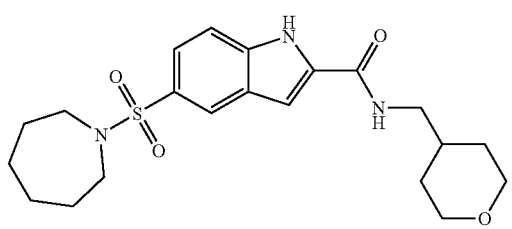 |

-continued
419 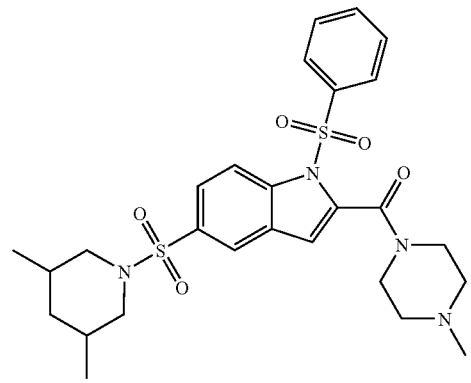
420 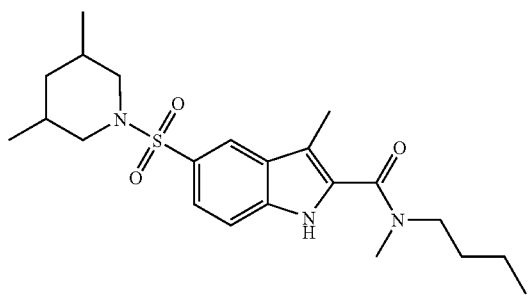
421 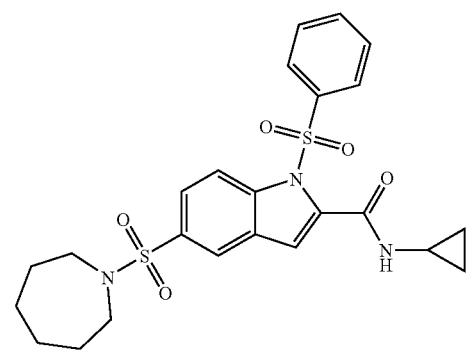
422 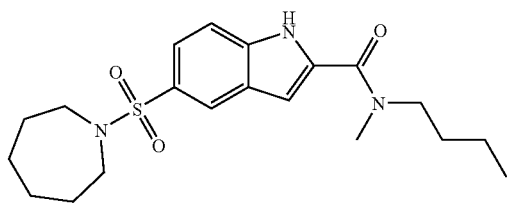
423 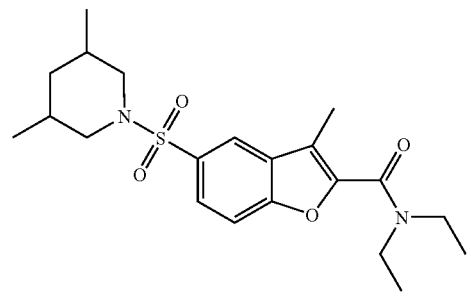

-continued
424 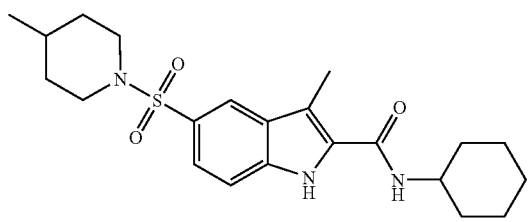
425 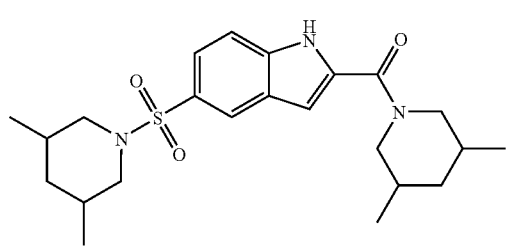
426 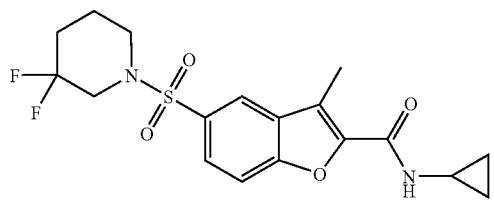
427 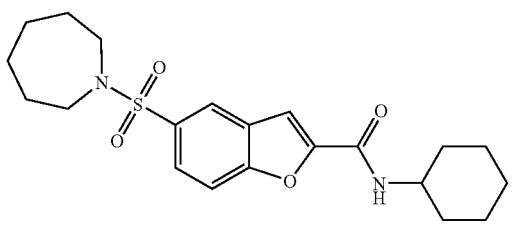
428 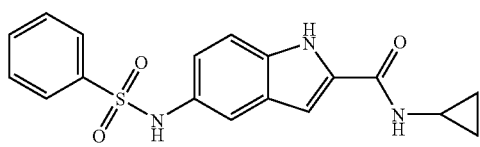
429 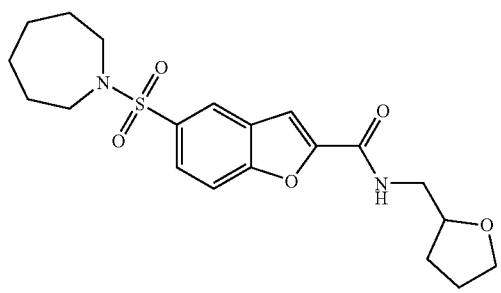

-continued
430 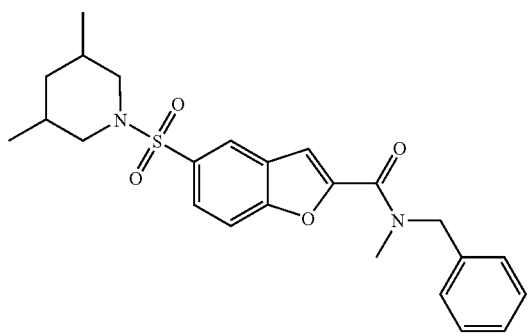
431 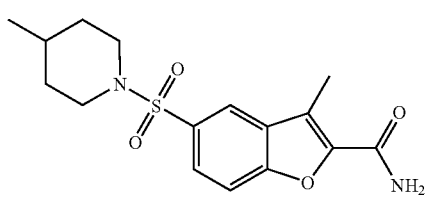
432 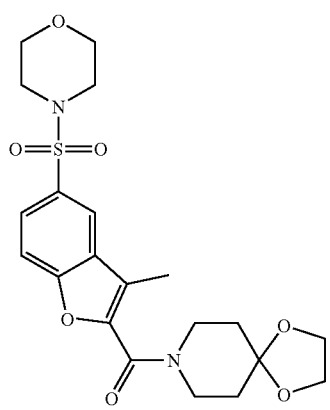
433 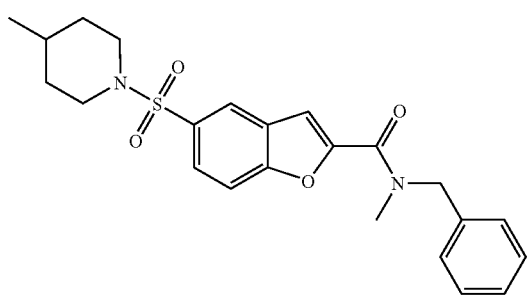
434 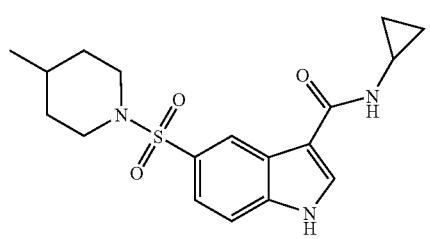

-continued
| | |
|---|---|
| 435 | 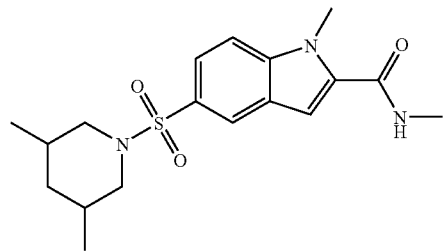 |
| 436 | 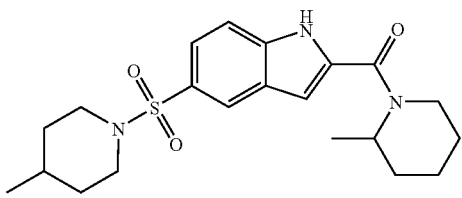 |
| 437 | 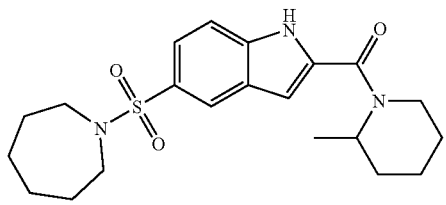 |
| 438 | 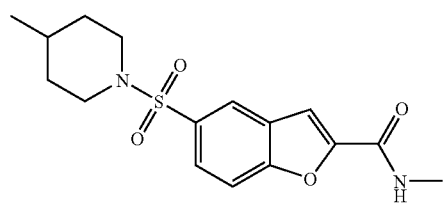 |
| 439 | 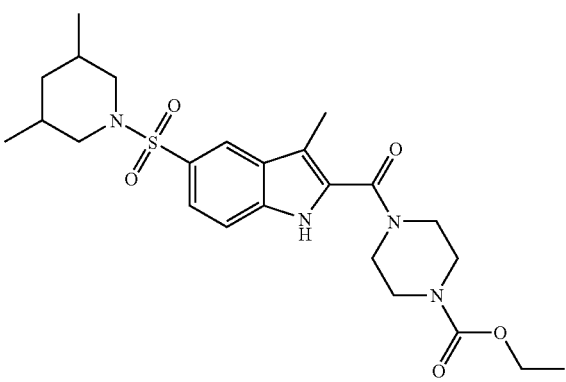 |
| 440 | 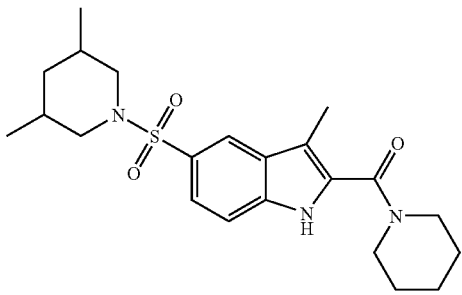 |

-continued
441
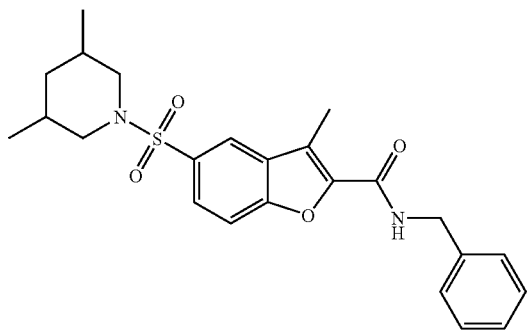
442
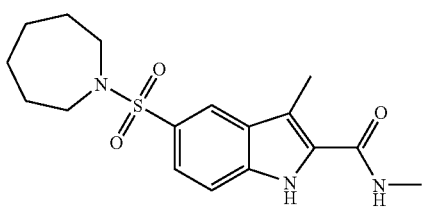
443
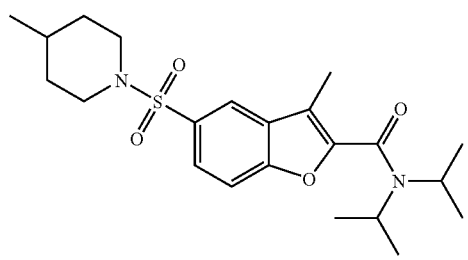
444
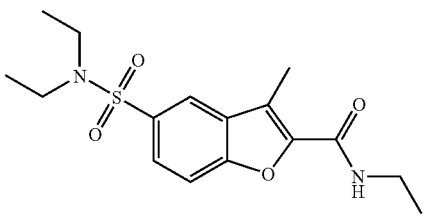
445
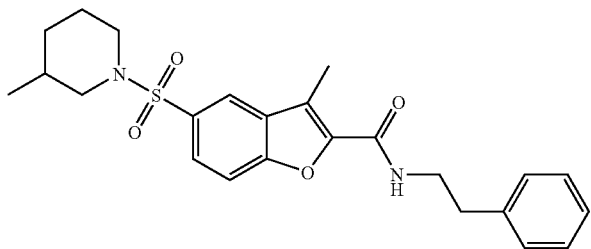
446
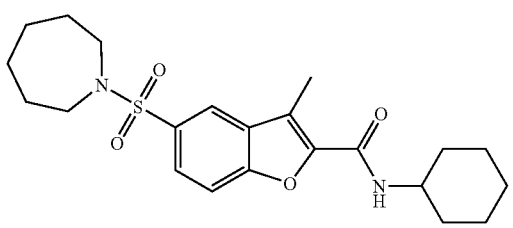

-continued
| | |
|---|---|
| 447 | 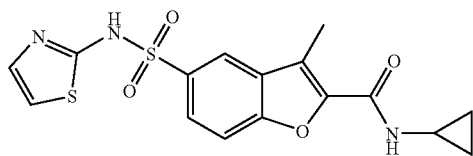 |
| 448 | 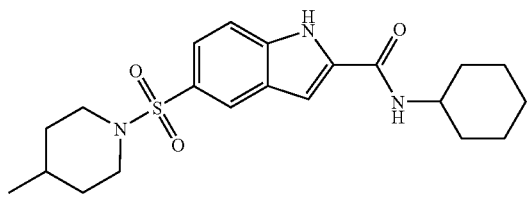 |
| 449 | 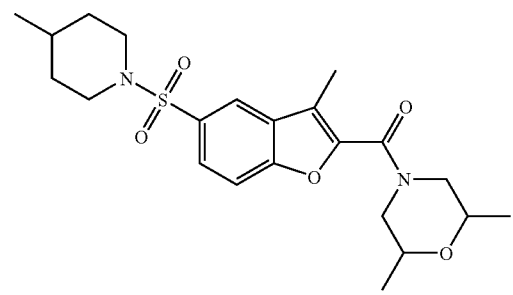 |
| 450 | 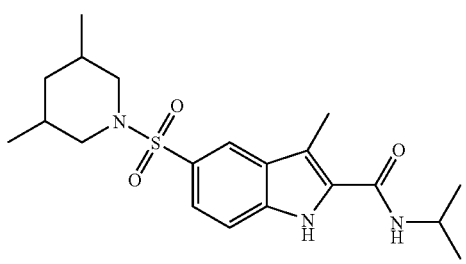 |
| 451 | 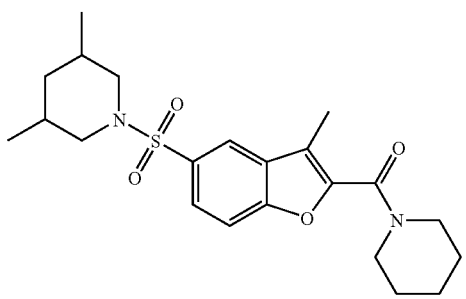 |
| 452 | 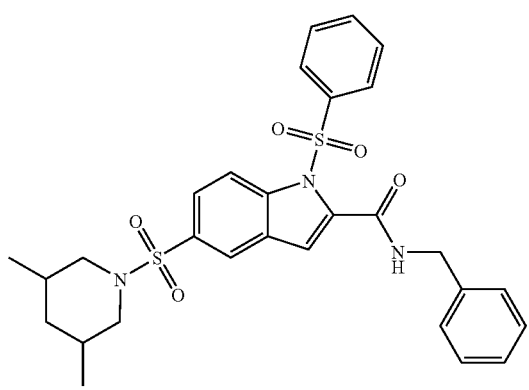 |

-continued
| | |
|---|---|
| 453 | 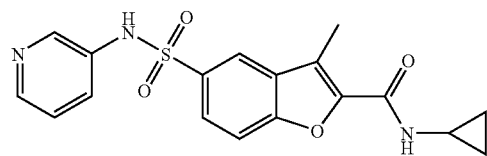 |
| 454 | 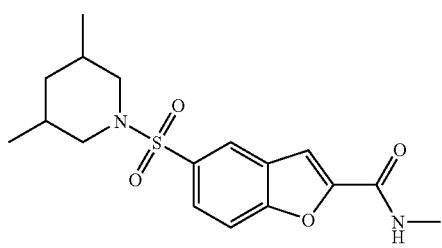 |
| 455 | 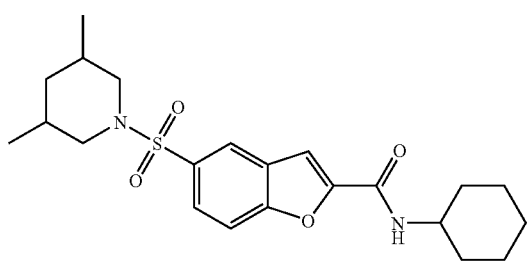 |
| 456 | 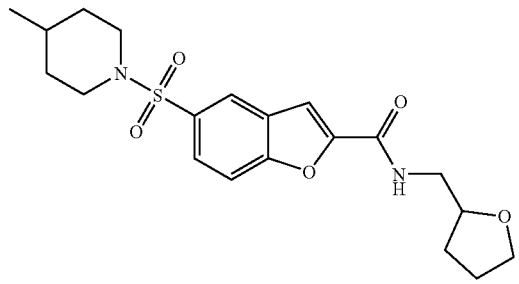 |
| 457 | 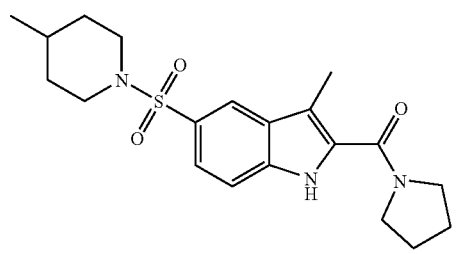 |
| 458 | 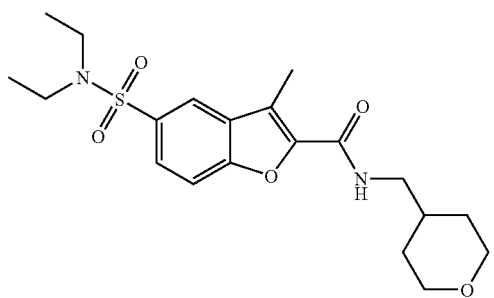 |

-continued
459 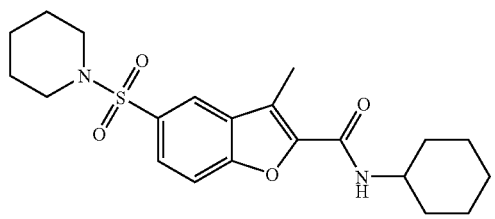
460 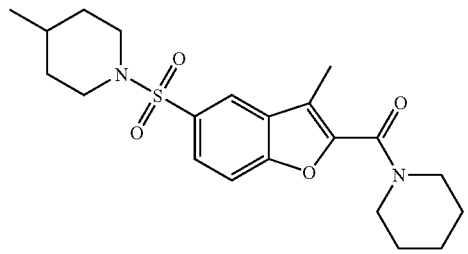
461 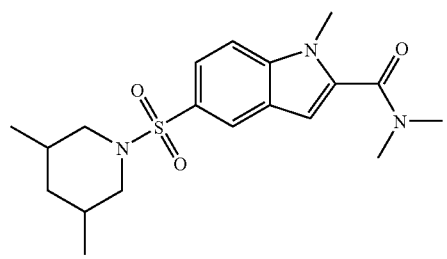
462 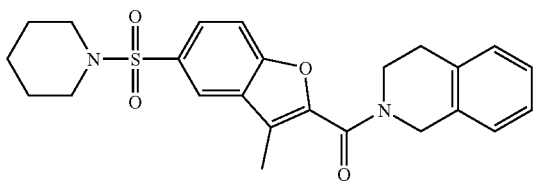
463 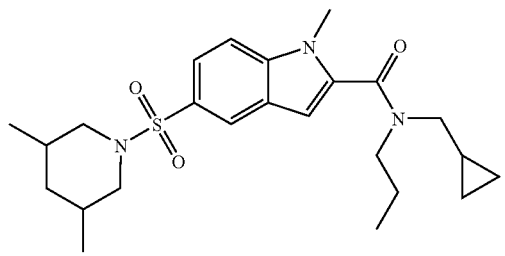
464 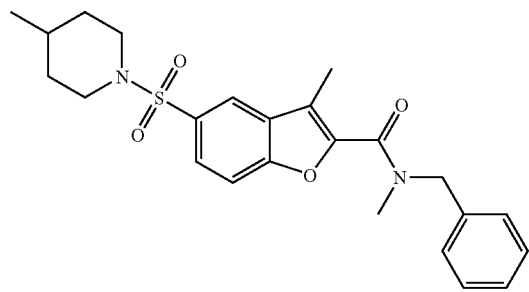

-continued
465
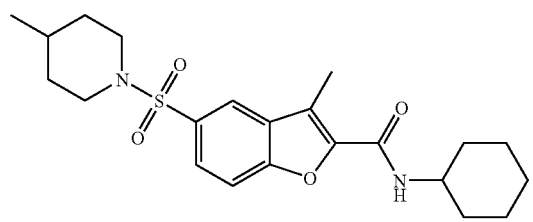
466
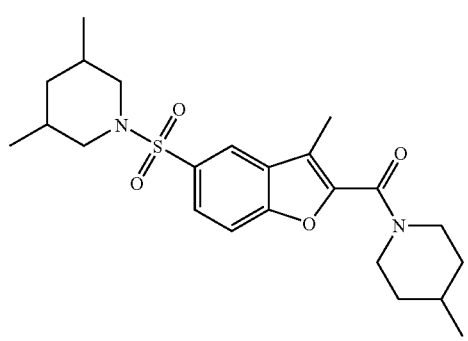
467
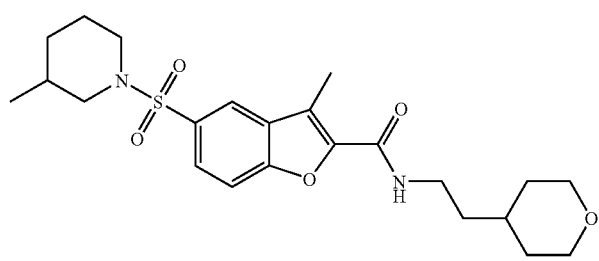
468
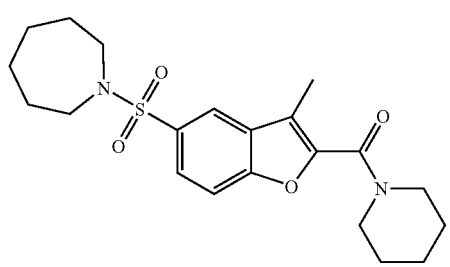
469
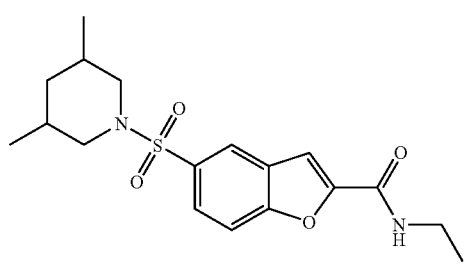

470
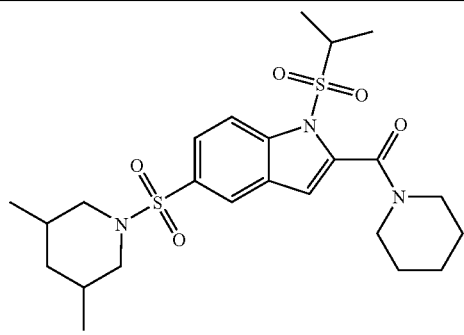
Synthetic Methods
The compounds of the present invention may be readily prepared by methods known in the art. Exemplary synthetic methods to prepare the compounds of the present invention are illustrated below.
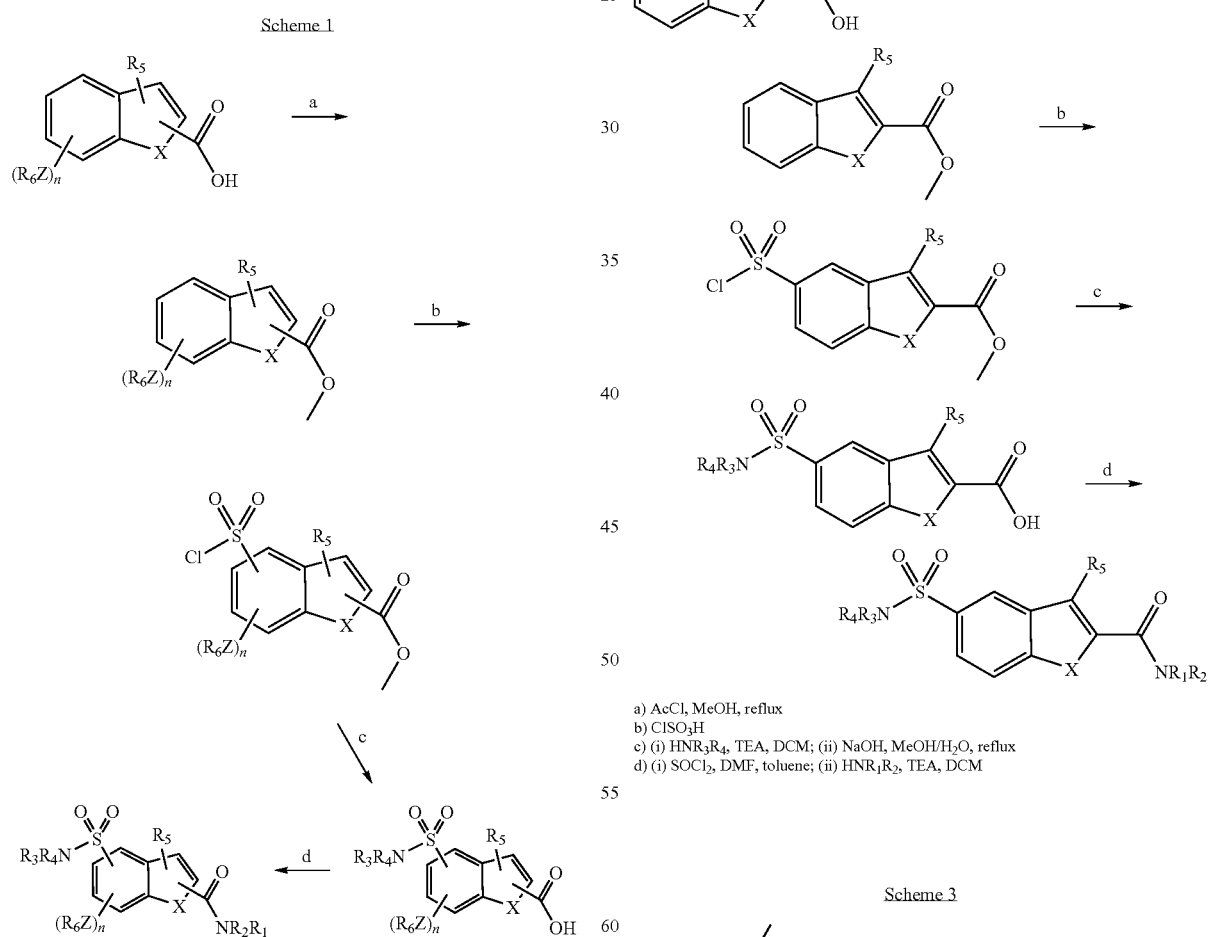
a) AcCl, MeOH, reflux
b) ClSO₃H
c) (i) HNR₃R₄, TEA, DCM; (ii) NaOH, MeOH/H₂O, reflux
d) (i) SOCl₂, DMF, toluene; (ii) HNR₁R₂, TEA, DCM
Scheme 3
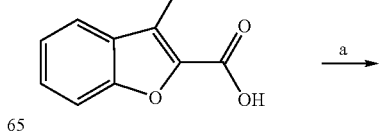

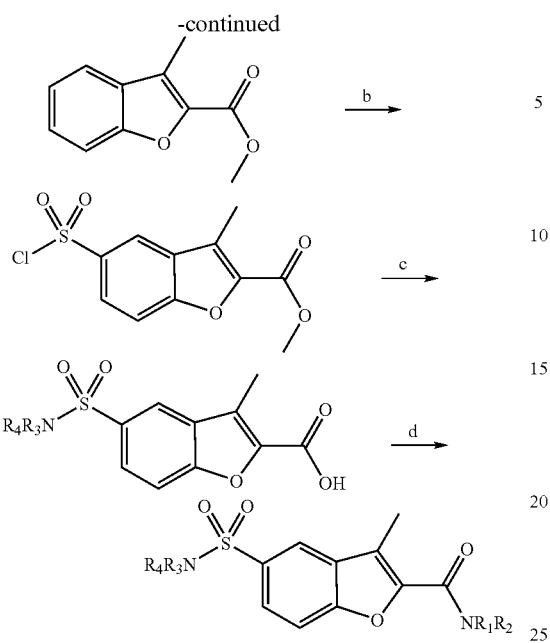
a) AcCl, MeOH, reflux
b) ClSO₃H
c) (i) HNR₃R₄, TEA, DCM; (ii) NaOH, MeOH/H₂O, reflux
d) (i) SOCl₂, DMF, toluene; (ii) HNR₁R₂, TEA, DCM
Scheme 4: Benzofuran Sulfonamide Variations
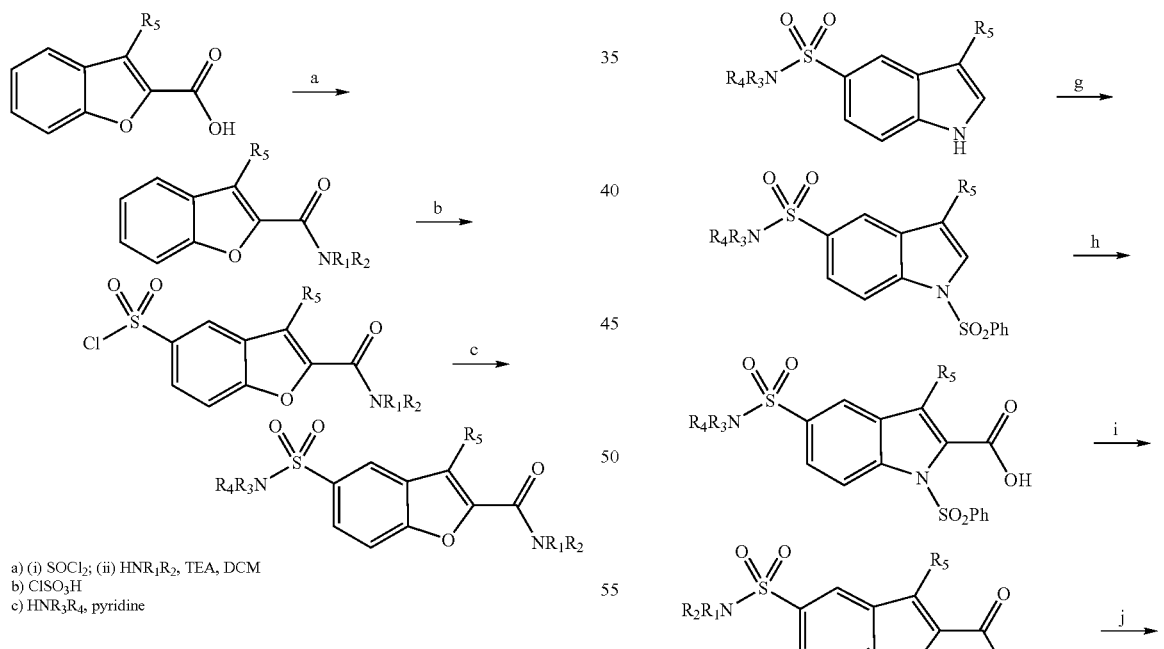
a) (i) SOCl₂; (ii) HNR₁R₂, TEA, DCM
b) ClSO₃H
c) HNR₃R₄, pyridine
Scheme 5: General Synthetic Scheme
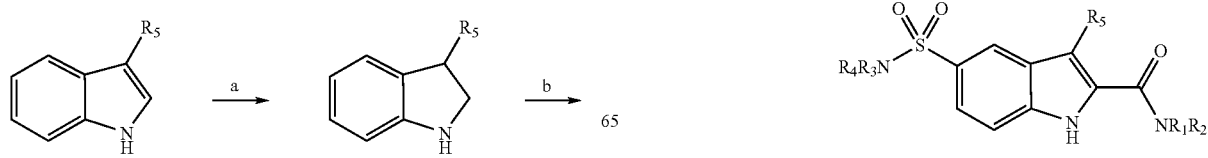
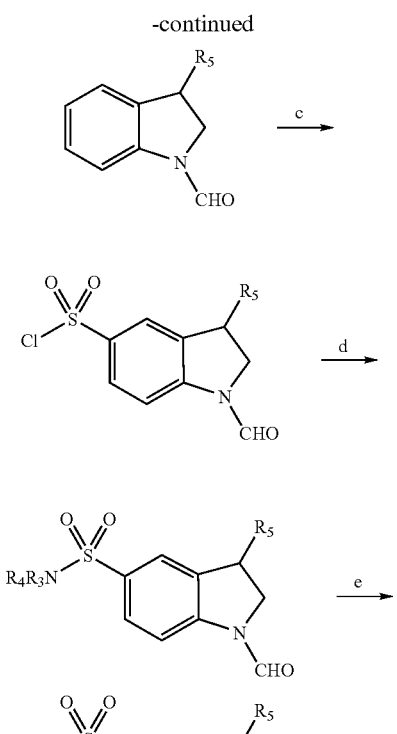

191

-continued a) NaCNBH$_3$, AcOH
b) HCO$_2$H, toluene, Dean-Stark
c) ClSO$_3$H
d) HNR$_1$R$_2$, TEA, DCM
e) 30% HCl, MeOH, reflux
f) MnO$_2$, DCM
g) PhSO$_2$Cl, NaH, DMF
h) LDA, CO$_2$, THF
i) (i) SOCl$_2$; (ii) HNR$_3$R$_4$, TEA, DCM
j) 2M NaOH, MeOH Scheme 6: General Synthetic Scheme

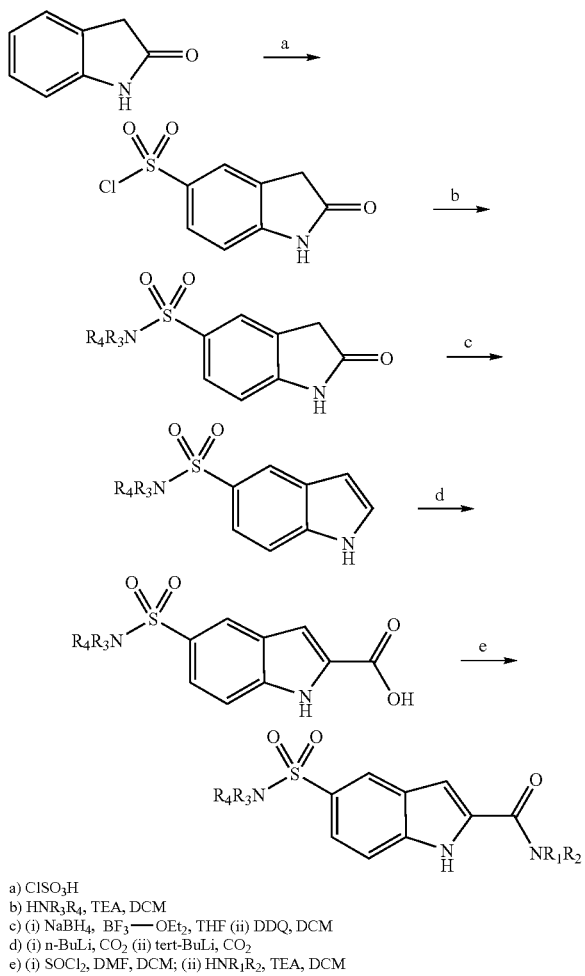

a) ClSO$_3$H
b) HNR$_3$R$_4$, TEA, DCM
c) (i) NaBH$_4$, BF$_3$—OEt$_2$, THF (ii) DDQ, DCM
d) (i) n-BuLi, CO$_2$ (ii) tert-BuLi, CO$_2$
e) (i) SOCl$_2$, DMF, DCM; (ii) HNR$_1$R$_2$, TEA, DCM General Synthetic Scheme

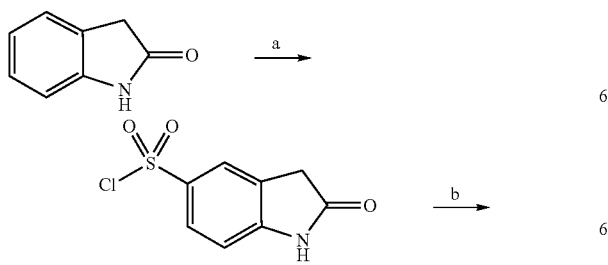

192

-continued

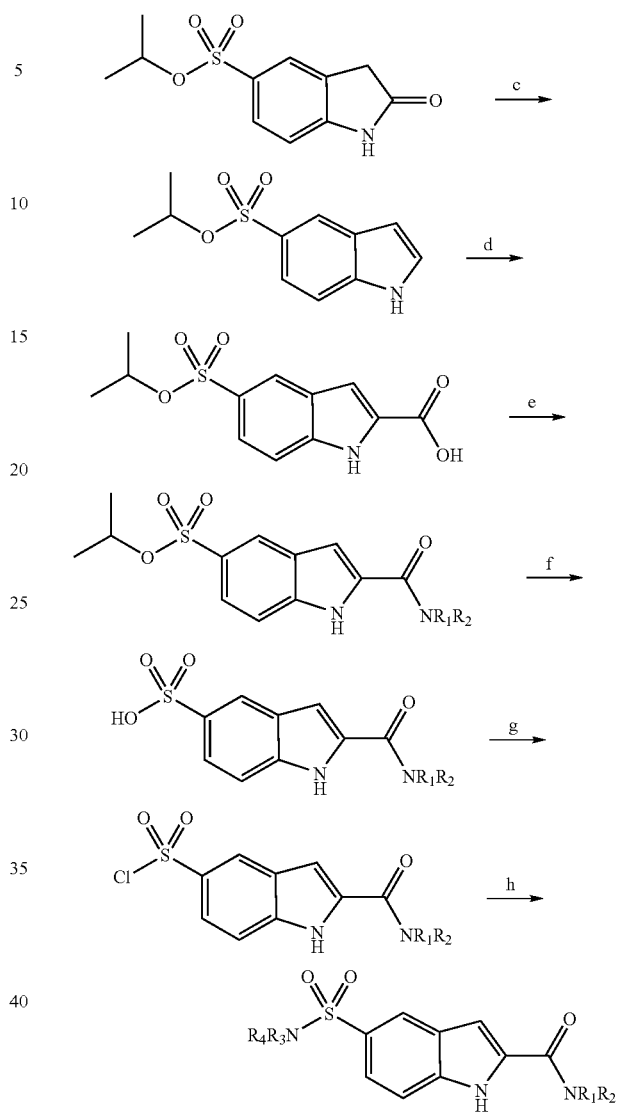

a) ClSO$_3$H
b) i-PrOH, pyridine
c) (i) NaBH$_4$, BF$_3$—OEt$_2$, THF (ii) DDQ, DCM
d) (i) n-BuLi, CO$_2$ (ii) tert-BuLi, CO$_2$
e) (i) SOCl$_2$, DMF, DCM; (ii) HNR$_1$R$_2$, TEA, DCM
f) 1M NaOH, MeOH
g) cyanuric chloride, TEA, acetone, MW: 120° C./600 s
h) HNR$_3$R$_4$, pyridine C-3 Amides

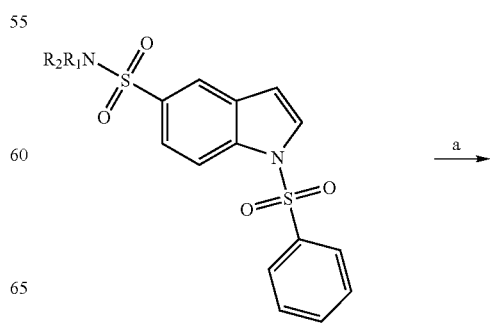

193
-continued
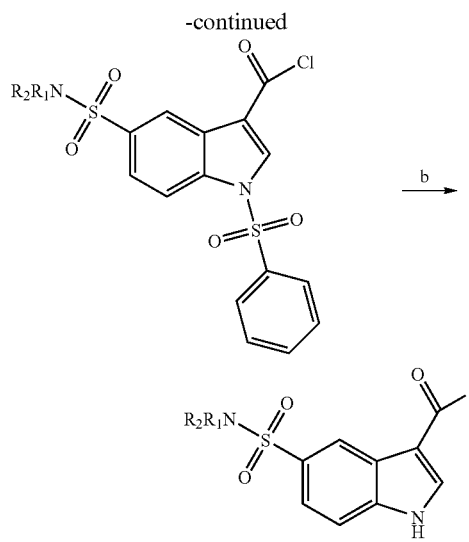
a) AlCl₃, oxalyl chloride, DCM
b) (i) HNR₁R₂, TEA, DCM; (ii) NaOH, MeOH
Reduced Amides
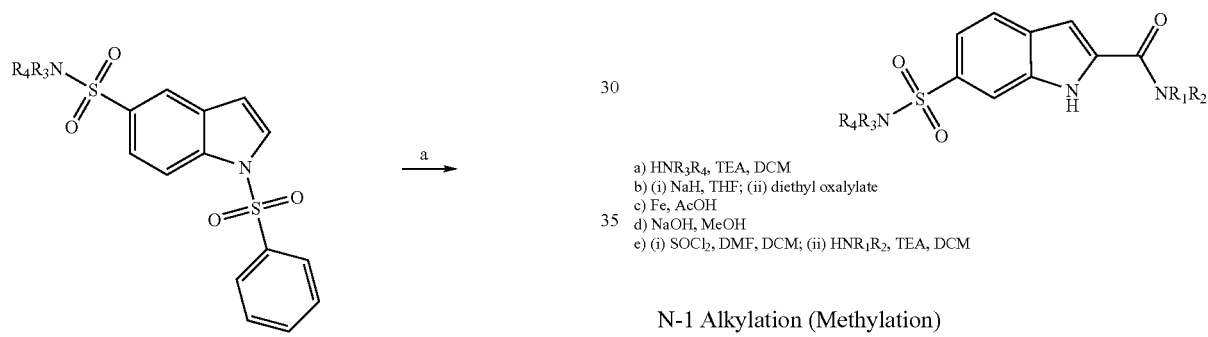
a) (i) LDA, THF; (ii) DMF
b) HNR₁R₂, NaBH₃CN, AcOH, DCE; (ii) NaOH, MeOH
6-Sulfonamides
194
-continued
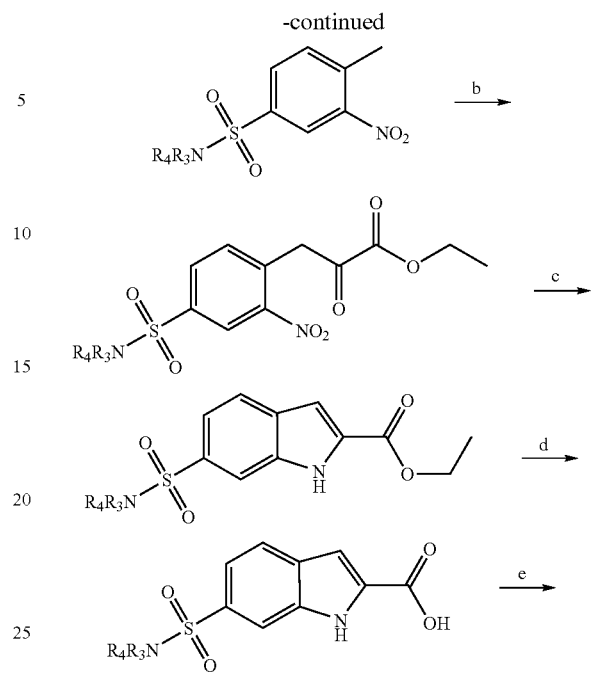
a) HNR₃R₄, TEA, DCM
b) (i) NaH, THF; (ii) diethyl oxalylate
c) Fe, AcOH
d) NaOH, MeOH
e) (i) SOCl₂, DMF, DCM; (ii) HNR₁R₂, TEA, DCM
N-1 Alkylation (Methylation)
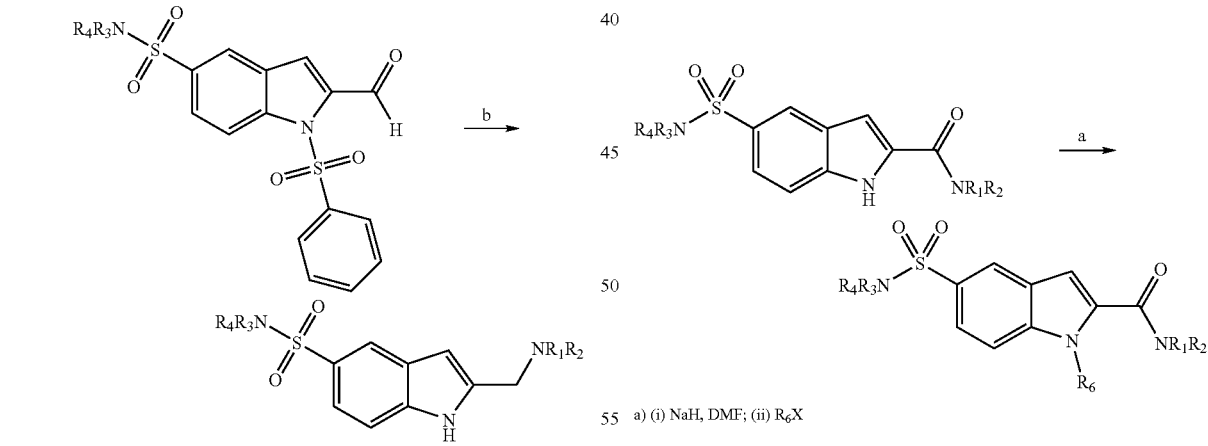
a) (i) NaH, DMF; (ii) R₆X
N-1 Sulfonamides

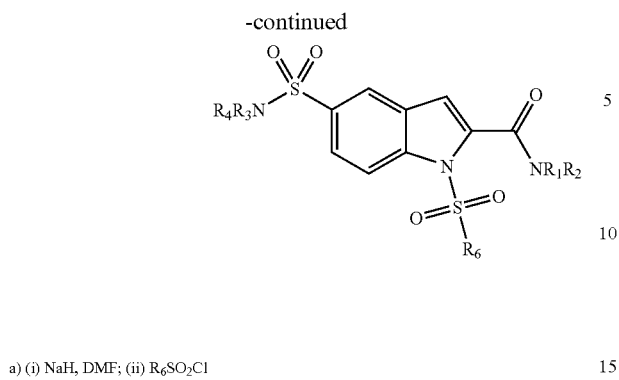

a) (i) NaH, DMF; (ii) R₆SO₂Cl

N-1 Alkylations and Further Amine Formation

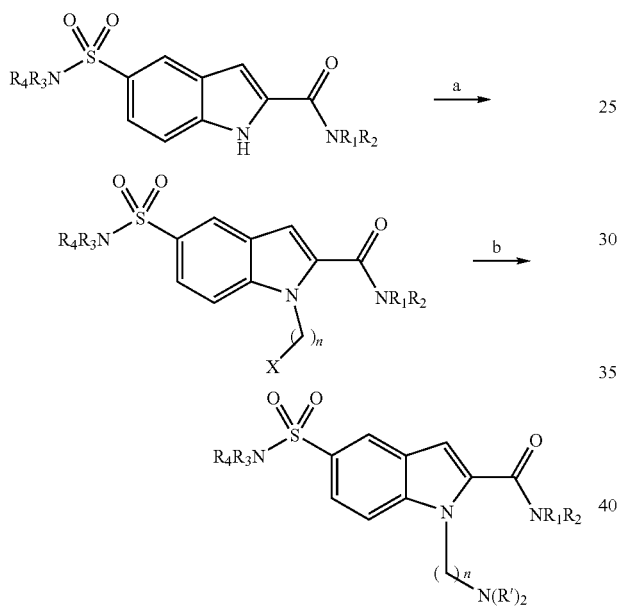

a) (i) NaH, DMF; (ii) X(CH₂)ₙX
b) HNR'R', (n-Bu)₄NI (cat.)

N-1 Alkylations with Epichlorohydrin

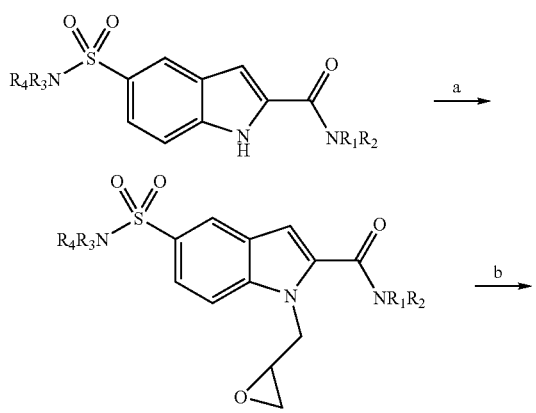

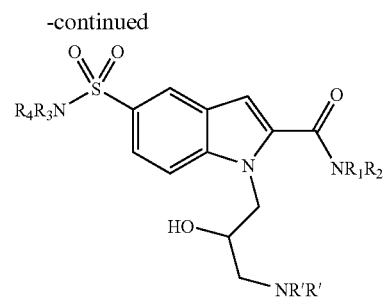

a) (i) NaH, DMF; (ii) epichlorohydrin
b) HNR'R'

Reversed Indole Sulfonamides (Compounds of Formula I-C)

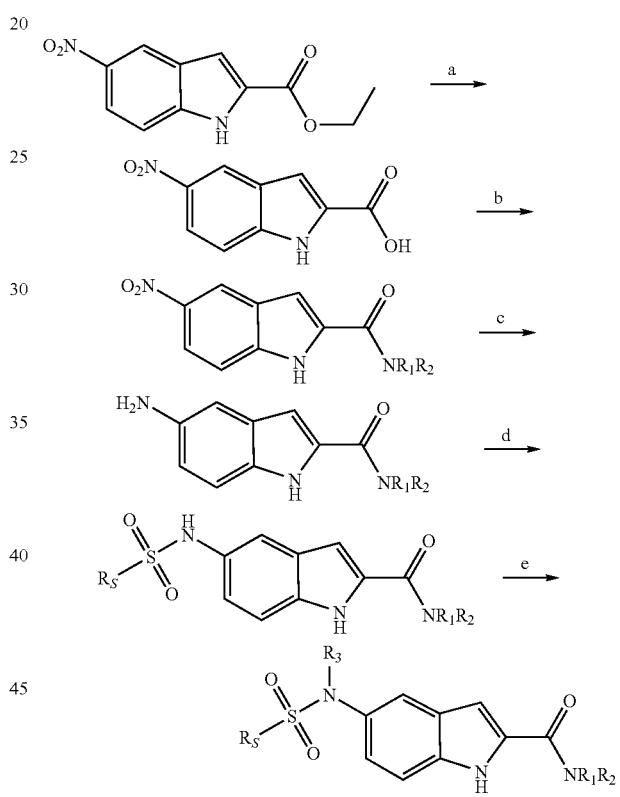

a) NaOH, MeOH
b) (i) SOCl₂, DMF, DCM; (ii) HNR₁R₂, TEA, DCM;
c) Fe,AcOH or Pd/C, H₂;
d) R₅SO₂Cl, Py
e) R₃OH, DEAD, P(Ph)₃, THF

Synthesis of Sulfones and Sulfoxides

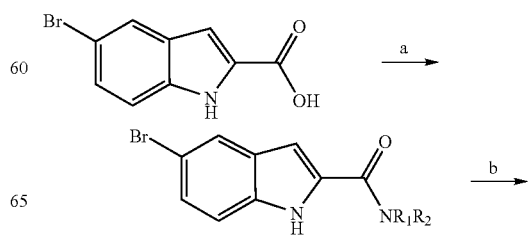

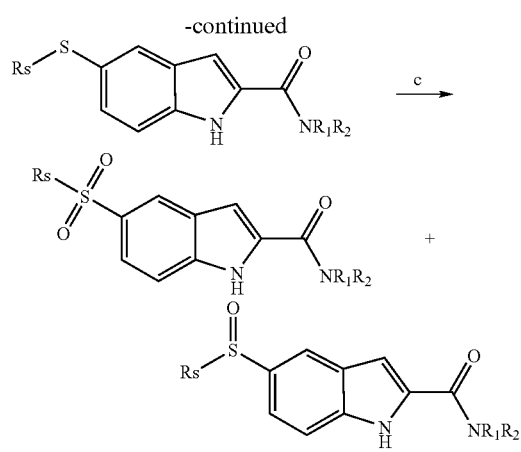

a) (i) SOCl$_2$, DMF, DCM; (ii) HNR$_1$R$_2$, TEA, DCM
b) R$_S$—SH, Xantphos, Pd$_2$dba$_3$, d$^i$PEA, dioxane
c) m-CPBA, DCM Pharmaceutically Acceptable Compositions As discussed above, the embodiments provide compounds that are inhibitors of voltage-gated calcium channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another embodiment, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of the embodiments can exist in free form for treatment, or where appropriate, as a pharmaceutically acceptable derivative thereof. According to the embodiments, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of the embodiments that, upon administration to a recipient, is capable of providing, either directly or indirectly, a compound of the embodiments or an inhibitory active metabolite or residue thereof. As used herein, the term "inhibitory active metabolite or residue thereof" means that a metabolite or residue thereof is also an inhibitor of a voltage-gated calcium channel.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of the embodiments include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. The embodiments also envision the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the embodiments additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the embodiments, such as by producing any undesirable biological effect or otherwise interacting in a deleterious manner with any other component(s) of the pharmaceutically acceptable composition, its use is contemplated to be within the scope of the embodiments. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, or cancer pain is provided comprising administering an effective amount of a compound or a pharmaceutically acceptable composition to a subject in need thereof.

In certain embodiments, an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

The compounds and compositions, according to the method of the embodiments, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain. The exact amount required will vary from subject to subject, depending on the species, age, and general condition of the subject, the severity of the infection, the particular agent, its mode of administration, and the like. The compounds of the embodiments are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the embodiments will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of the embodiments can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the embodiments may be administered orally or parenterally at dosage levels of about 0.01 mg/kg to about 50 mg/kg, and in some embodiments, from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the embodiments, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of the embodiments with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the embodiments include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of the embodiments. Additionally, the embodiments contemplate the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the embodiments are useful as inhibitors of voltage-gated calcium channels, preferably N-type calcium channels. In one embodiment, the compounds and compositions of the embodiments are inhibitors of $Ca_v2.2$, and thus, without wishing to be bound by any particular theory, the compounds and compositions are particularly useful for treating or lessening the severity of a disease, condition, or disorder where activation or hyperactivity of $Ca_v2.2$ is implicated in the disease, condition, or disorder ("$Ca_v2.2$-mediated condition or disorder"). Accordingly, in another aspect, the embodiments provide a method for treating or lessening the severity of a disease, condition, or disorder where activation or hyperactivity of $Ca_v2.2$ is implicated in the disease state.

It will also be appreciated that the compounds and pharmaceutically acceptable compositions of the embodiments can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the embodiments. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of the embodiments will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of the embodiments or pharmaceutically acceptable compositions thereof may also be incorporated into compositions for coating an implantable medical device, such as prostheses, artificial valves, vascular grafts, stents and catheters. Accordingly, the embodiments, in another aspect, include a composition for coating an implantable device comprising a compound of the embodiments as described generally above, and in classes and subclasses herein, and a carrier suitable for coating said implantable device. In still another aspect, the embodiments include an implantable device coated with a composition comprising a compound of the embodiments as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the embodiments relates to inhibiting CaV2.2 activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of CaV2.2 activity in a biological sample is useful for a variety of purposes that are known to one of skill in the art. Examples of such purposes include, but are not limited to, the study of calcium ion channels in biological and pathological phenomena; and the comparative evaluation of new calcium ion channel inhibitors.

Assays for Detecting and Measuring CaV Inhibition Properties of Compounds

A) Optical Methods for Assaying CaV Inhibition Properties of Compounds:

Compounds of the embodiments are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® Optical Membrane Potential Assay Method with Electrical Stimulation

The following is an example of how CaV2.2 inhibition activity is measured using the optical membrane potential method. Other subtypes are performed in an analogous mode in a cell line expressing the CaV of interest.

HEK293 cells stably expressing CaV2.2 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM DiSBAC$_6$(3) (Aurora #00-100-010) in dry DMSO 10 mM CC2-DMPE (Aurora #00-100-008) in dry DMSO 200 mM Acid Yellow 17 (Aurora #VABSC) in H$_2$O 370 mM Barium Chloride (Sigma Cat# B6394) in H$_2$O Bath X 160 mM NaCl (Sigma Cat# S-9888)

4.5 mM KCl (Sigma Cat# P-5405)

1 mM MgCl2 (Fluka Cat# 63064)

10 mM HEPES (Sigma Cat# H-4034)

pH 7.4 using NaOH

Loading Protocol:

2×CC2-DMPE=20 μM CC2-DMPE: 10 mM CC2-DMPE is vortexed with an equivalent volume of 10% Pluronic, followed by vortexing in required amount of HBSS containing 10 mM HEPES. Each cell plate will require 5 mL of 2×CC2-DMPE. 50 μL of 2×CC2-DMPE is added to wells containing washed cells, resulting in a 10 μM final staining concentration. The cells are stained for 30 minutes in the dark at RT.

2×CC2DMPE & DISBAC$_6$(3)=8 μM CC2DMPE & 2.5 μM DISBAC$_6$(3): Vortex together both dyes with an equivalent volume of 10% Pluronic (in DMSO). Vortex in required amount of Bath X with beta-cyclodextrin. Each 96 well cell plate will require 5 ml of 2×CC2DMPE. Wash plate with ELx405 with Bath X, leaving a residual volume of 50 μL/well. Add 50 μL of 2×CC2DMPE & DISBAC$_6$(3) to each well. Stain for 30 minutes in the dark at RT.

5×AY17=750 μM AY17 with 15 mM BaCl$_2$: Add Acid Yellow 17 to vessel containing Bath X. Mix well. Allow solution to sit for 10 minutes. Slowly mix in 370 mM BaCl$_2$. This solution can be used to solvate compound plates. Note that compound plates are made at 1.5× drug concentration and not the usual 2×. Wash CC2 stained plate, again, leaving residual volume of 50 μL. Add 100 uL/well of the AY17 solution. Stain for 15 minutes in the dark at RT. Run plate on the optical reader.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Assay Protocol

Insert or use electrodes into each well to be assayed.

Use the current-controlled amplifier to deliver stimulation wave pulses for 3-5 s. Two seconds of pre-stimulus recording are performed to obtain the un-stimulated intensities. Five seconds of post-stimulation recording are performed to examine the relaxation to the resting state.

Alternative Assay Method

Block of Ca$_v$2 channels was evaluated using cell lines with the target channel expressed in HEK-293 cells. Block was quantified using conventional patch voltage clamp techniques and/or E-VIPR (Electric Field Stimulation and Voltage Ion Probe Reader) assays. The opening of calcium permeable channels can be monitored with a fluorescent dye that reports changes in cell calcium. Typically the dyes used are fluo-3 with or without fura-red. Channel opening can also be monitored with FRET dyes that monitor changes in membrane potential produced by calcium influx.

Cells are cultured on 96-well or 384-well plates (Costar tissue culture treated flat bottom plates, Corning), pre-coated with 0.5% Growth Factor Reduced matrigel matrix in DMEM. The cell seeding density for 96-well plates is in the range of 30,000-60,000 cells/well. Cells are assayed after 18-36 hrs in culture at 37° C.

For assays measuring changes in cell calcium, cells are washed, loaded with 4 μM each of the calcium indicator dyes fluo-3/AM and fura-red/AM (60-90 minutes at room temperature) and maintained in 1 mM probenacid to inhibit loss of dye after cleavage of the acetylmethoxy derivatives. The washing and external bath solution used in the assays is: 160 mM NaCl, 4.5 mM KCl, 1 mM MgCl$_2$, 2 mM CaCl$_2$, 10 mM glucose, 10 mM HEPES-NaOH, pH 7.4 with NaOH.

After dye loading, cells are washed and maintained in external saline modified to contain 10-12 mM CaCl$_2$ and 0.5 mM Probenecid. Test compounds are prepared from DMSO stock solutions. The compounds are added to a multi-well plate at 2× the desired concentration in external saline with 10 mM CaCl$_2$. The solution with test compound is transferred to the cell plate and thereby diluted 2-fold. After 30 min incubation with test compounds, fluorescence responses of target cells are measured in the E-VIPR system. The stimulation protocols, including waveform, timing, frequency, and repetition of stimulations, are defined via a graphical user interface of a custom program. A custom-designed amplifier is used to generate the final voltage pulses. These voltage pulses are delivered with 8 pairs of electrodes to simultaneously create electrical field in a column of 8 wells of a 96-well plate.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as mibefradil, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for CaV Activity and Inhibition of Test Compounds

Patch clamp electrophysiology was used to assess the efficacy of calcium channel blockers expressed in HEK293 cells. HEK293 cells expressing CaV2.2 have been visually identified and probed with fine tip glass electrodes connected to an amplifier (Axon Instruments). The "voltage clamp" mode has been used to assess the compound's IC50 holding the cells at −100 mV. The results of these experiments have contributed to the definition of the efficacy profile of the compounds.

Voltage-Clamp Assay in HEK293 Cells Expressing CaV2.2

CaV2.2 calcium currents were recorded from HEK293 cells using the whole-cell variation of the patch clamp technique. Recordings were made at room temperature (~22° C.) with thick walled borosilicate glass electrodes (WPI; resistance 3-4 MΩ using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +20 mV for 50 ms at frequencies of 0.1, 1, 5, 10, 15, and 20 Hz. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $BaCl_2$ (10), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10).

(A) Following these procedures, representative compounds of the embodiments were found to possess desired N-type calcium channel modulation activity and selectivity.

The disclosure below is of specific examples setting forth preferred methods for making preferred compounds. These examples are not intended to limit the scope, but rather to exemplify preferred embodiments.

EXAMPLES

General Scheme

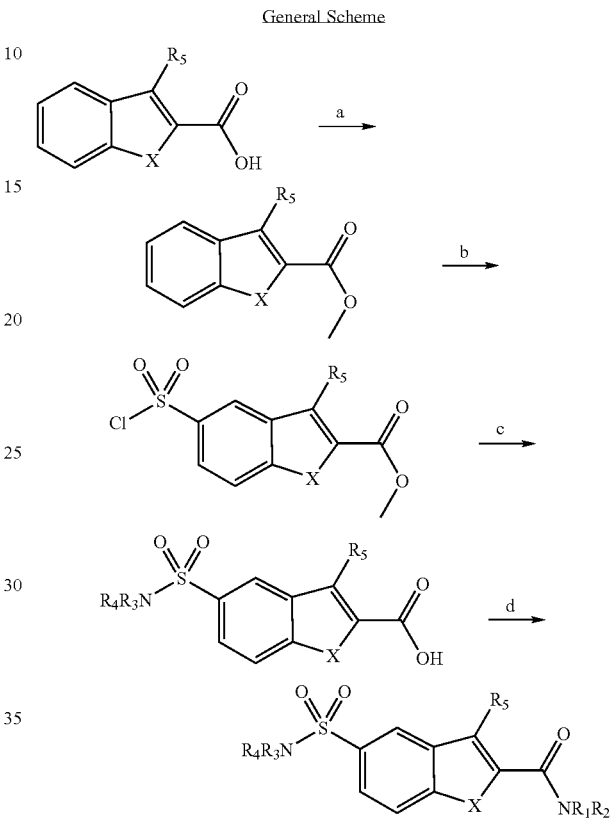

a) AcCl, MeOH, reflux
b) ClSO$_3$H
c) (i) HNR$_3$R$_4$, TEA, DCM; (ii) NaOH, MeOH/H$_2$O, reflux
d) (i) SOCl$_2$, DMF, toluene; (ii) HNR$_1$R$_2$, TEA, DCM 3-Methyl-benzofuran-2-carboxylic acid methyl ester

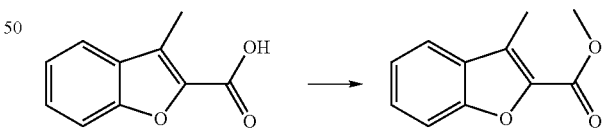

Acetylchloride (6.7 mL, 91 mmol) was added dropwise to 750 mL dry methanol cooled on an ice-bath under $N_2$ atmosphere. After completion of the addition, the solution was stirred at RT for 30 min. Subsequently, 16.0 g (90 mmol) 3-methyl benzo[b]furan-2-carboxylic acid was added and the solution was refluxed for 17 h under $N_2$ atmosphere. The solution was cooled on an ice-bath to 0° C. and 500 mL ice-cold water was added. The resulting white precipitate was collected by filtration and washed with cold methanol. Yield: 16.1 g (94%) of a white solid. $^1$H-NMR (200 MHz, CDCl$_3$):

δ 7.72 (d, J=8 Hz, 1H), 7.60 (t, J=8 Hz, 1H), 7.53 (t, J=8 Hz, 1H), 7.41 (d, J=8 Hz, 1H), 4.08 (s, 3H), 2.73 (s, 3H) ppm.

5-Chlorosulfonyl-3-methyl-benzofuran-2-carboxylic acid methyl ester

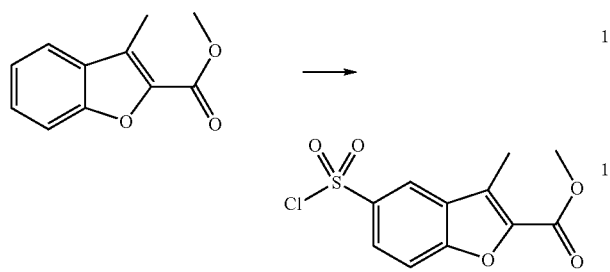

Benzofuran (15.0 g, 79 mmol) was slowly added to 26 ml (400 mmol) chlorosulfonic acid, cooled to 0-5° C. on an ice-bath under $N_2$. After completion of the addition, the solution was left stirring at RT for 1 hr. The suspension turned to a clear brown solution with evolution of gas (HCl). After 1 hr at r.t. the solution was heated to 50° C. for 5 min to drive the reaction to completion (HCl evolution ceased upon heating). The mixture was slowly poured on ice and a white precipitate formed. The suspension was extracted with DCM. The organic phase was washed with water, brine, dried over $Na_2SO_4$, filtered, and evaporated to dryness under reduced pressure. Yield: 7.8 g (34%). $^1$H-NMR (200 MHz, CDCl$_3$): δ 8.48 (d, J=2 Hz, 1H), 8.21 (dd, J=7, 2 Hz, 1H), 7.82 (d, J=7 Hz, 1H), 4.12 (s, 3H), 2.77 (s, 3H) ppm.

General Procedure for the Preparation of Sulfonamides

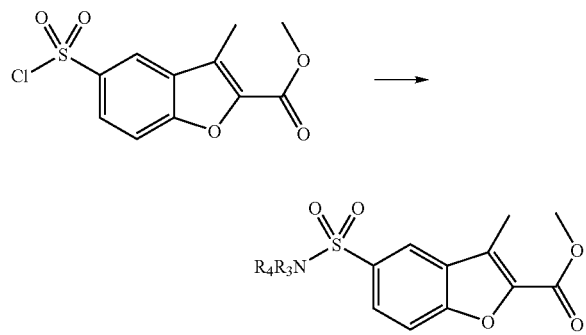

To a solution the amine (HNR$_3$R$_4$) in DCM at about 0.1 M was added 1 equivalent TEA and subsequently about 0.9 equivalents of the sulfonyl chloride. The resulting solution was left stirring overnight under nitrogen atmosphere at RT. The solution was washed twice with 1 M aq. HCl and with brine. After drying over $Na_2SO_4$ and filtration, the solution was concentrated to dryness under vacuum. The crude material was purified by column chromatography over silica gel.

3-Methyl-5-(4-methyl-piperidine-1-sulfonyl)-benzofuran-2-carboxylic acid methyl ester

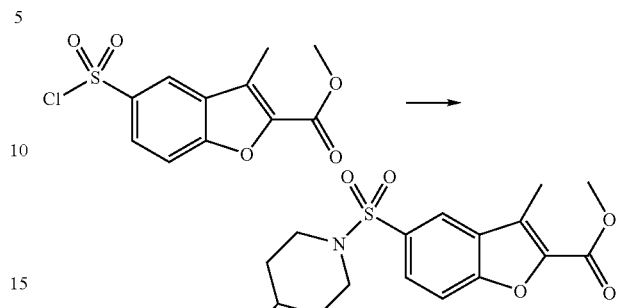

The general procedure was followed with 1.3 ml (11.4 mmol) 4-methyl-piperidine, 1.6 ml (11.5 mmol) TEA, and 3.0 g (10.4 mmol). Purification by column chromatography with EtOAc/heptanes (1:2 V/V) as the eluent. Yield: 3.3 g (90%) of a white solid. $^1$H-NMR (200 MHz, CDCl$_3$): δ 8.19 (d, J=2 Hz, 1H), 7.92 (dd, J=8, 2 Hz, 1H), 7.72 (d, J=8 Hz, 1H), 4.09 (s, 3H), 3.92-3.82 (m, 2H), 2.70 (s, 3H), 2.41-2.25 (m, 2H), 1.83-1.72 (m, 2H), 1.50-1.32 (m, 3H), 1.00 (d, J=5 Hz, 3H) ppm.

General Procedure for the Preparation of Acid Chlorides

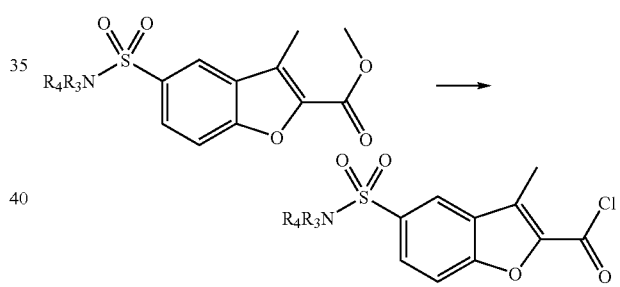

A solution of the methyl ester was refluxed in a mixture of methanol and aqueous 1N NaOH for 1 hr. After cooling to RT, the resulting suspension was acidified with aqueous 1 M HCl and the precipitate was collected by filtration and washed twice with water. The acid was dried under air at 40° C. A mixture of the acid in 50 mL DCM with 5 equivalents thionyl chloride and 0.5 ml N,N-dimethylformamide (DMF) was refluxed until a clear solution was formed (1-2 h). After cooling to RT, the mixture was evaporated to dryness and subsequently co-evaporated three times with toluene in order to remove residual thionyl chloride and DMF.

3-Methyl-5-(4-methyl-piperidine-1-sulfonyl)-benzofuran-2-carbonyl chloride

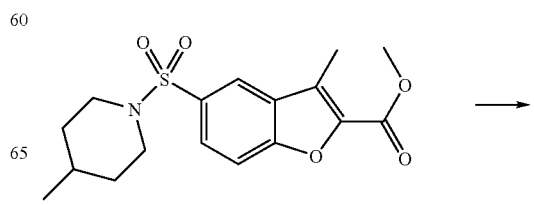

-continued

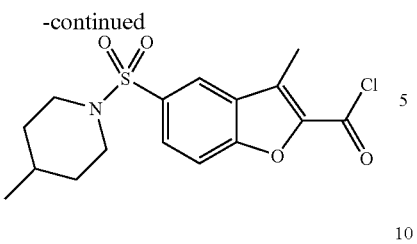

According to the general procedure with 3.3 g ester, 60 ml methanol, and 30 mL 1M NaOH for the hydrolysis and and 3.0 ml SOCl$_2$ for the chlorination. Yield: 3.45 g. $^1$H-NMR (200 MHz, CDCl$_3$): δ 8.22 (d, J=2 Hz, 1H), 8.02 (dd, J=2, 8 Hz, 1H), 7.81 (d, J=8 Hz, 1H), 3.92-3.81 (m, 0.2H), 2.79 (s, 3H), 2.45-2.28 (m, 2H), 1.82-1.73 (m, 2H), 1.50-1.29 (m, 3H), 1.00 (d, J=6 Hz, 3H) ppm.

General Procedure for the Preparation of Amides

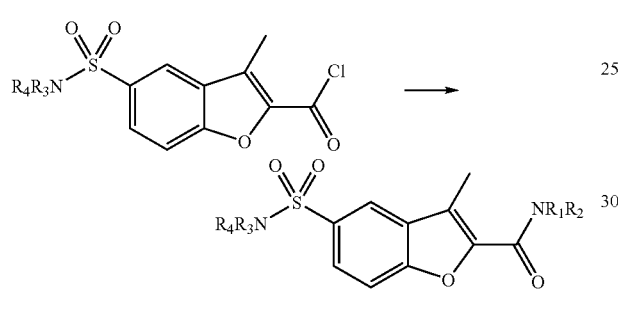

Parallel library generation was performed using 10 mL borosilicate glass reaction vessels in a 24 position Mettler-Toledo MiniblockXT™. The vessels were loaded with the individual amines HNR$_1$R$_2$ (0.3 mmol) to which dry CH$_2$Cl$_2$ (0.5 mL) was added. Subsequently, a solution of the acid chloride in dry CH$_2$Cl$_2$ (0.1 M, 1 mL, 0.1 mmol) was added to the vessels. The reactions were stirred for 16 h, after which they were quenched by the addition of a saturated aqueous NaHCO$_3$ solution (2 mL). For the work-up, the reactions blocks were then transferred to a Mettler-Toledo ALLEXis automated liquid-liquid extraction robot. The work-up comprised separation of the layers and washing of the organic phase with aqueous hydrochloric acid (0.5 M, 2 mL). Finally, removal of the CH$_2$Cl$_2$ under reduced pressure using a Genevac EZ2+ centrifugal parallel evaporation unit, afforded the final products in good purity as shown by HPLC analysis. For dibasic amines, the acidic wash was replaced with an additional bicarbonate wash.

3-Methyl-5-(4-methyl-piperidine-1-sulfonyl)-benzo-furan-2-carboxylic acid cyclo-hexylmethyl-amide

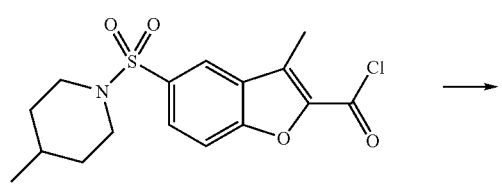

-continued

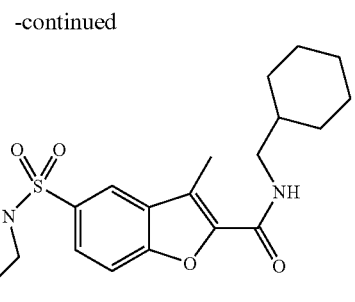

$^1$H-NMR (300 MHz, CDCl$_3$): δ 8.02 (d, J=2 Hz, 1H), 7.77 (dd, J=2, 9 Hz, 1H), 7.55 (d, J=9 Hz, 1H+), 6.76-6.68 (m, 1H), 3.76 (d, J=11 Hz, 2H), 3.29 (t, J=7 Hz, 2H), 3.10 (d, J=7 Hz, 1H), 2.63 (s, 3H), 2.28-2.18 (m, 2H), 1.75-1.55 (m, 6H), 1.40 (s, 3H), 1.30-1.10 (m, 4H), 1.05-0.90 (m, 2H), 0.88 (d, J=5 Hz, 3H) ppm.

(2,6-Dimethyl-morpholin-4-yl)-[3-methyl-5-(4-methyl-piperidine-1-sulfonyl)-benzo-furan-2-yl]-methanone

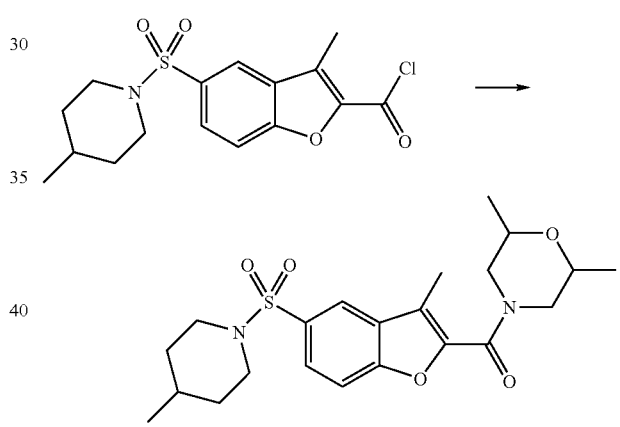

$^1$H-NMR (300 MHz, CDCl$_3$): δ 8.01 (d, J=2 Hz, 1H), 7.76 (dd, J=2, 9 Hz, 1H), 7.56 (d, J=9 Hz, 1H), 4.58-4.42 (m, 1H), 3.96-3.81 (m, 1H), 3.76 (d, J=11 Hz, 2H), 3.72-3.56 (m, 3H), 3.03-2.85 (m, 1H), 2.67-2.50 (m, 1H), 2.44 (s, 3H), 2.26-2.18 (m, 2H), 1.68-1.63 (m, 2H), 1.32-1.15 (m, 8H), 0.88 (d, 6 Hz, 3H) ppm.

Benzofuran Sulfonamide Derivatives

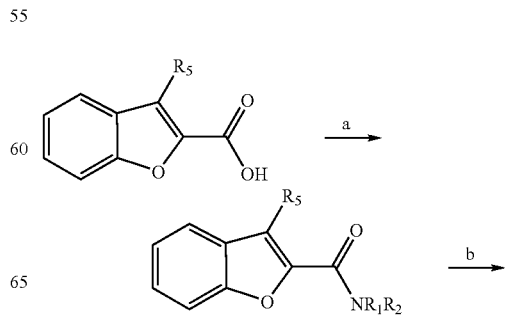

213

-continued

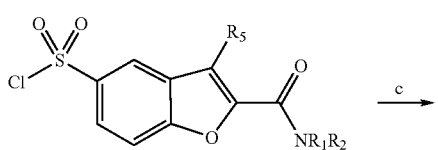

a) (i) SOCl$_2$; (ii) HNR$_1$R$_2$, TEA, DCM
b) ClSO$_3$H
c) HNR$_3$R$_4$, pyridine

General Procedure for the Preparation of 3-Methyl-benzofuran-2-carboxylic Acid Amides

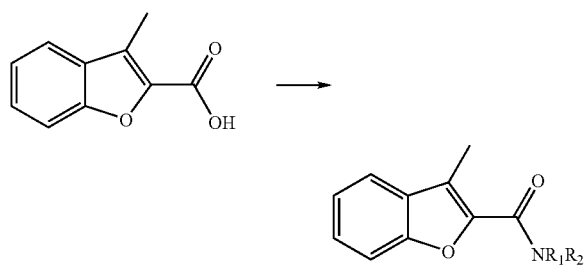

A suspension of the acid (11.4 mmol), thionyl chloride (28.9 mmol) and cat. DMF (1.8 mL) in DCM (100 mL) was heated to reflux for 4 h. The reaction solution was concentrated, coevaporated with toluene (2×20 mL), dried under HV and redissolved in DCM (50 mL). This solution was added to a solution of the amine (34.2 mmol) and TEA (3.2 mL, 22.8 mmol) in DCM (100 mL) at 0° C. After stirring for 16 h at RT, the reaction mixture was washed with 1M HCl (3×50 mL), brine (100 mL), dried over MgSO$_4$ and concentrated.

3-Methyl-benzofuran-2-carboxylic acid cyclopropylamide

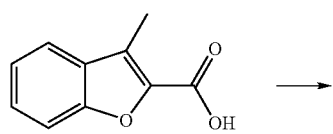

Yield: 2.37 g (97%). $^1$H-NMR (400 MHz, DMSO-d6): δ 8.58 (d, J=4.3 Hz, 1H), 7.74-7.72 (m, 1H), 7.56 (d, J=8.3 Hz, 1H), 7.48-7.44 (m, 1H), 7.35-7.32 (m, 1H), 2.90-2.83 (m, 1H), 2.53 (s, 3H), 0.72-0.62 (m, 4H). LC/MS (10-99%): M/Z: M$^+$ (obs)=216; t$_R$=2.61 min.

General Procedure for the Preparation of 2-carbamoyl-3-methyl-benzofuran-5-sulfonyl Chlorides

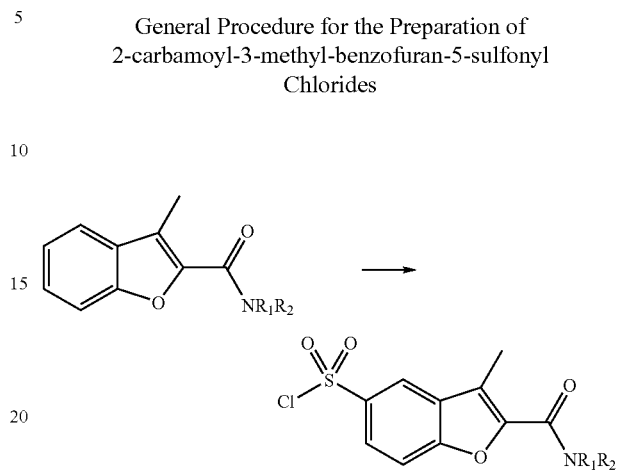

To a solution of chlorosulfonic acid (0.78 mL, 11.7 mmol) at 0° C. was slowly added the amine. The resulting solution was stirred at RT for 2 h and then heated to 50° C. for 15 min until gas evolution ceased. After cooling to RT, the reaction mixture was carefully poured onto ice. A white precipitate formed which was filterred off, washed with ice-water and dried under HV.

2-Cyclopropylcarbamoyl-3-methyl-benzofuran-5-sulfonyl chloride

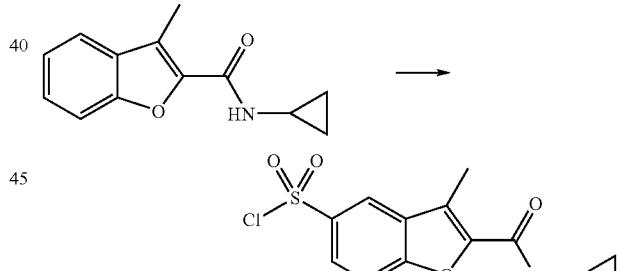

Yield: 553 mg (76%). LC/MS (10-99%): M/Z: M$^+$(obs) =314; t$_R$=3.65 min.

General Procedure for the Formation of 2-cyclopropylcarbamoyl-3-methyl-benzofuran-5-sulfonamides

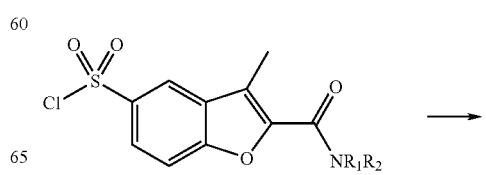

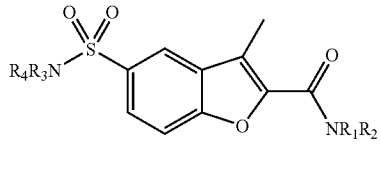

A solution of the sulfonyl chloride (47 mg, 0.15 mmol) and amine (0.15 mmol) in pyridine (0.5 mL) was stirred at RT for 24-48 h. The reaction mixture was diluted with MeOH: DMSO (1:1, 0.5 mL), and purification by HPLC afforded the desired products.

3-Methyl-5-phenylsulfamoyl-benzofuran-2-carboxylic acid cyclopropyl amide

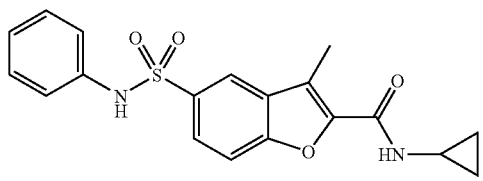

LC/MS (10-99%): M/Z: M+(obs) 371; $t_R$=2.90 min.

3-Methyl-5-(pyridin-4-ylsulfamoyl)-benzofuran-2-carboxylic acid cyclopropylamide

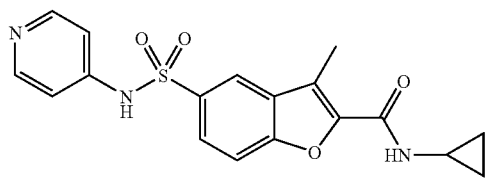

LC/MS (10-99%): M/Z: M+(obs)=372; $t_R$=2.01 min.

5-Dipropylsulfamoyl-3-methyl-benzofuran-2-carboxylic acid cyclopropylamide

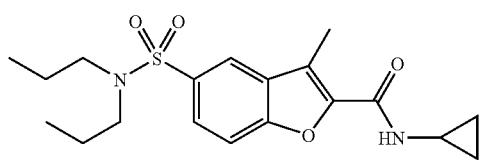

LC/MS (10-99%): M/Z: M+(obs)=379; $t_R$=1.88 min.

General Scheme

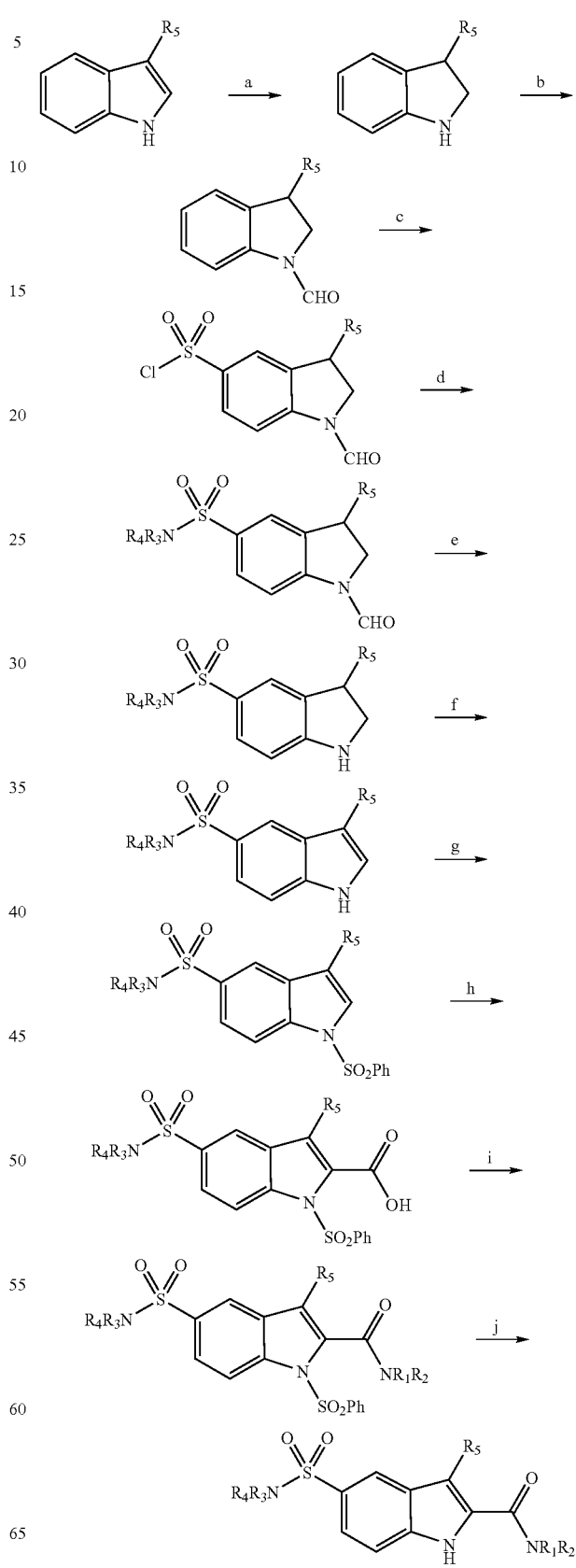

-continued a) NaCNBH₃, AcOH
b) HCO₂H, toluene, Dean-Stark
c) ClSO₃H
d) HNR₃R₄, TEA, DCM
e) 30% HCl, MeOH, reflux
f) MnO₂, DCM
g) PhSO₂Cl, NaH, DMF
h) LDA, CO₂, THF
i) (i) SOCl₂; (ii) HNR₁R₂, TEA, DCM
j) 2M NaOH, MeOH 3-Methyl-2,3-dihydro-1H-indole

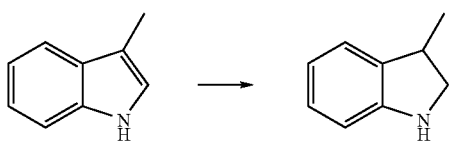

Skatole (26.5 g, 202 mmol) was dissolved in acetic acid (500 mL) and cooled to 15° C. Sodium cyanoborohydride (40 g, 637 mmol) was added in portions to this cooled solution. After the addition was complete, stirring was continued for 1 h at RT. Subsequently, water (100 mL) was added and after 15 min at RT, the mixture was evaporated under reduced pressure at 60° C. To the residue was added 0.5 L 5% aq. NaHCO₃ and 0.5 L TBME and the organic layer was washed with 5% aq. NaHCO₃ (2×250 mL), water (0.5 L), 1M aq. NaOH (100 mL), 5% aq. NaHCO₃ (250 mL), and brine (250 mL). After drying over Na₂SO₄ and filtration, the solvent was removed by evaporation under reduced pressure. Yield: 23.3 g (87%).

2,3-Dihydro-indole-1-carbaldehyde

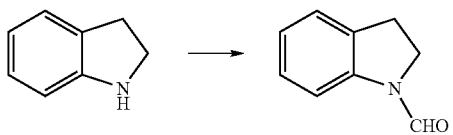

A solution of indoline (47.4 g, 398 mmol) and formic acid (30 g, 652 mmol, 1.64 eq.) in toluene (175 mL) was heated at reflux with azeotropic removal of water. After 3 h, the reaction mixture was cooled to RT. The solution was washed with water and brine, dried over Na₂SO₄ and concentrated. The residue was triturated with TBME and heptanes. The precipitate was filtered off, washed with heptanes and pentane and dried in vacuo at 45° C. for 4 h. Yield: 50.46 g, (86%).

3-Methyl-2,3-dihydro-indole-1-carbaldehyde

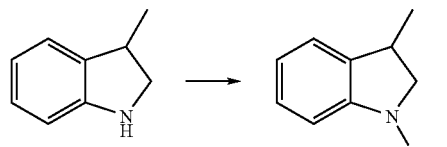

Indoline (23.3 g, 175 mmol) with formic acid (11.5 ml, 305 mmol) was refluxed in toluene (250 mL) with a Dean-Stark trap to collect the formed water. After 1 h of reflux, 6 mL of water was tapped off and the reaction mixture was cooled to RT, some greenish solid was formed in the mixture. Water (250 mL) was added and the organic layer was washed with another portion of water (250 mL) and with brine (250 mL), dried over Na₂SO₄, filtered and evaporated to dryness. Yield: 22.5 g (80% of a yellow oil, identified as 3 by $^1$H-NMR. This crude material was crystallized from 2-propanol, the formed crystals were collected by filtration and washed with 2-propanol. Yield: 3.0 g (11%). The mother liquor was evaporated to dryness and the residue was purified by column chromatography (Silica, EtOAc: heptanes=1:3→1:1). Yield: 15.5 g (55%) of a yellowish oil that crystallized upon standing. The two portions were combined and used as such in the next step.

General Procedure for the Preparation of 1-Formyl-3-R⁵-2,3-dihydro-1H-indole-5-sulfonyl chlorides

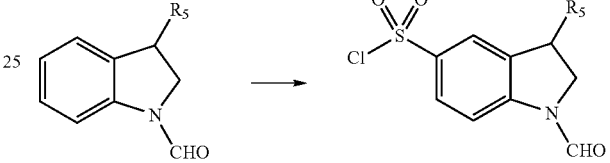

Chlorosulfonic acid (115 mL, 1.7 mol) was cooled to 0-5° C. and the indoline (116 mmol) was slowly added at that temperature. After completion of the addition, stirring was continued for 1 h at 0-5° C. and then the mixture was heated to 100° C. for 15 min. After cooling to 0-5° C., the mixture was carefully added dropwise to 1.5 L ice water with vigorous stirring, the temperature was kept below 5° C. by the addition of more crushed ice during the addition. The formed solid was collected by filtration and was washed with 50 mL water portions until the filtrate was pH neutral (5 washings were needed). The pinkish-colored solid was air-dried at 45° C. for three days. Yield: 85%.

General Procedure for the Preparation of 1-Formyl-3-R⁵-2,3-dihydro-1H-indole-5-sulfonic Acid Amides

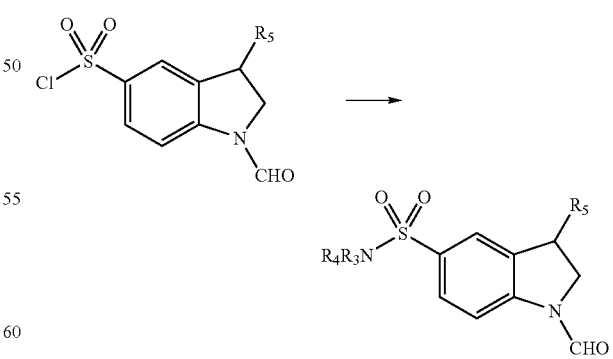

To an ice-cooled solution of the N-formyl indoline (40.7 mmol) and Et₃N (6.5 mL, 4.72 g, 46.6 mmol) in CH₂Cl₂ (100 mL) was added secondary amine (40.7 mmol). The reaction mixture was stirred at RT for 1 h, washed with 1M aq. HCl, sat. aq. NaHCO₃, and brine, dried over Na₂SO₄, and concentrated. The resulting solid was recrystallized from ethanol, filtered off and air-dried at 45° C. overnight. Yields: 68-74%.

General Procedure for the Preparation of 3-R$^5$-2,3-dihydro-1H-indole-5-sulfonic Acid Amides

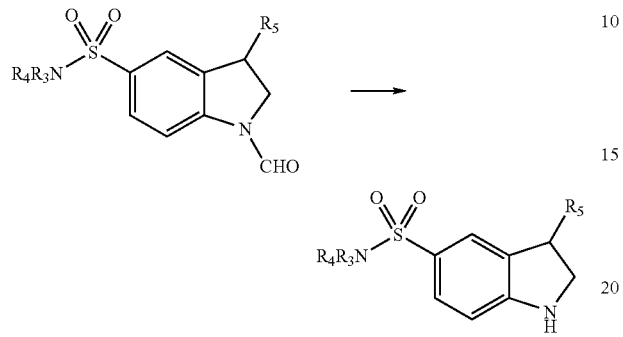

To a solution of the sulfonamide (16 mmol) in MeOH (80 mL) was added 30% aq. HCl (7 mL). The mixture was heated at reflux for 90 min and concentrated. The residue was suspended in water and cooled in ice. The suspension was neutralized by addition of 30% aq. NaOH. The white suspension was filtered off, washed with water and air-dried at 45° C. overnight to give the product as a white solid. Yields: 78-99%.

5-(4-Methyl-piperidine-1-sulfonyl)-2,3-dihydro-1H-indole

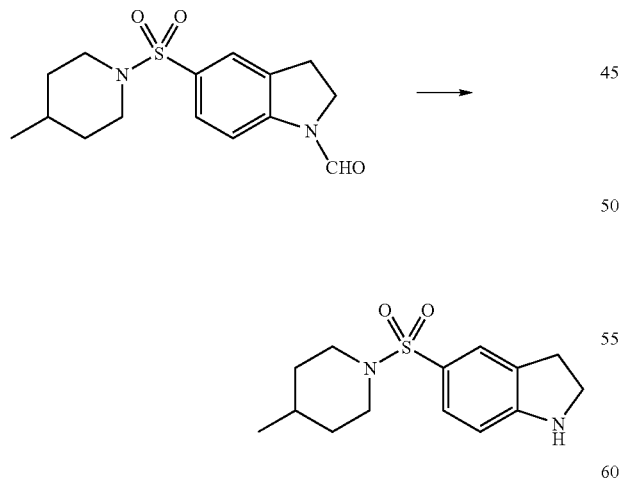

$^1$H-NMR (400 MHz, CDCl$_3$) δ 7.12 (s, 1H), 7.08 (d, J=8.2 Hz, 1H), 6.68 (d, J=8.2 Hz, 1H), 3.87 (s br, 4H), 3.59 (d, J=11.0 Hz, 2H), 2.18-2.11 (m, 2H), 1.57 (d, J=9.4 Hz, 2H), 1.20-1.18 (m, 3H), 0.83 (d, J=5.3 Hz, 3H); LC/MS (10-99%): M/Z: M$^+$(obs)=280; t$_R$=2.85 min. LC/MS (10-99%): M/Z: M$^+$(obs)=281; t$_R$=4.02 min.

5-(3,5-Dimethyl-piperidine-1-sulfonyl)-2,3-dihydro-1H-indole

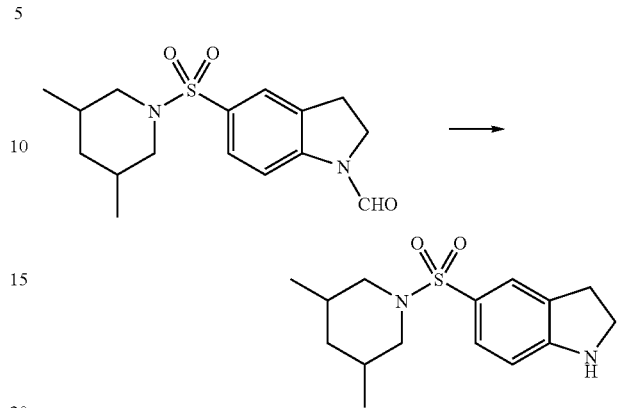

LC/MS (10-99%): M/Z: M$^+$(obs)=295; t$_R$=4.88 min.

5-(Azepane-1-sulfonyl)-2,3-dihydro-1H-indole

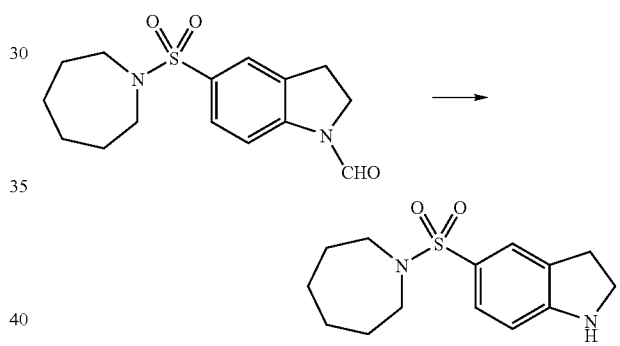

LC/MS (10-99%): M/Z: M$^+$(obs)=281; t$_R$=3.94 min.

General Procedure for the Preparation of 3-R$^5$-1H-indole-5-sulfonic Acid Amides

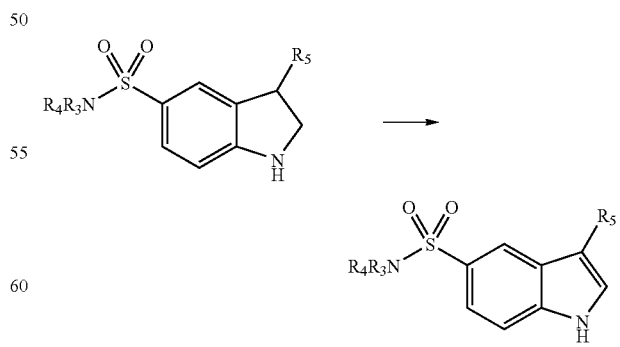

MnO$_2$ (5.58 g, 64.2 mmol) was added to a solution of the indoline (16.0 mmol) in CH$_2$Cl$_2$ (200 mL). The mixture was heated at reflux for 24 h. The solids were filtered off over 5-(4-Methyl-piperidine-1-sulfonyl)-1H-indole

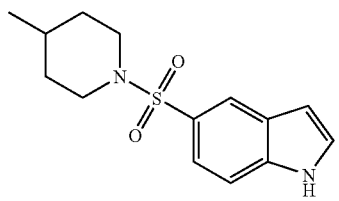

¹H-NMR (400 MHz, CDCl₃) δ 8.83 (s, 1H, NH), 8.13 (s, 1H), 7.60-7.51 (m, 2H), 7.37 (dd, J=2.8, 2.8 Hz, 1H), 6.69 (dd, J=2.2, 2.2 Hz, 1H), 3.80 (d, J=11.8 Hz, 2H), 2.28-2.22 (m, 2H), 1.66 (d, J=10.2 Hz, 2H), 1.37-1.19 (m, 3H), 0.90 (d, J=5.9 Hz, 3H); LC/MS (10-99%): M/Z: M⁺(obs)=279; $t_R$=3.34 min.

General Procedure for the Preparation of 1-Benzene-sulfonyl-3-R⁵-1H-indole-5-sulfonic Acid Amides

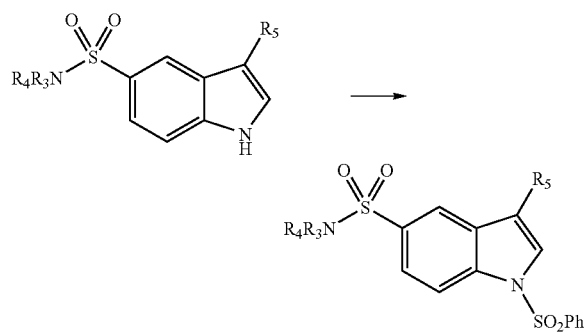

To a suspension of pentane-washed NaH (0.53 g, ca. 60% dispersion in oil, 13.3 mmol) in DMF (20 mL) was added the indole (13.2 mmol). The mixture was stirred at RT for 2 h. PhSO₂Cl (1.73 mL, 2.39 g, 13.5 mmol) was added dropwise. The resulting suspension was stirred at RT overnight. The mixture was poured into sat. aq. NaHCO₃ (150 mL) and extracted with TBME (3×75 mL). The combined organic layers were washed with water and brine, dried over Na₂SO₄, and concentrated. The crude product was purified by column chromatography (silica, EtOAc/heptanes 1:3) or crystallized from ethanol. Yields 83-87%.

1-Benzenesulfonyl-5-(4-methyl-piperidine-1-sulfo-nyl)-1H-indole

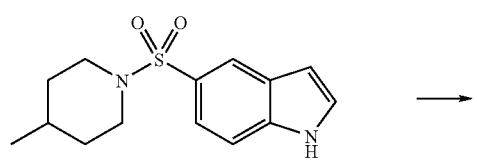

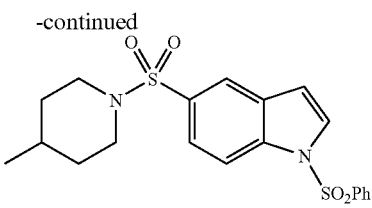

¹H-NMR (400 MHz, CDCl₃) δ 8.13 (d, J=8.8 Hz, 1H), 8.01 (d, J=1.5 Hz, 1H), 7.94 (m, 1H), 7.92 (dd, J=1.6, 1.6 Hz, 1H), 7.73 (d, J=3.8 Hz, 1H), 7.70 (d, J=1.8 Hz, 1H), 7.64-7.60 (m, 1H), 7.52 (d, J=8.3 Hz, 1H), 7.50 (d, J=1.6 Hz, 1H), 6.80-6.79 (m, 1H), 3.78 (d, J=11.7 Hz, 2H), 2.25 (t, J=11.2 Hz, 2H), 1.72-1.66 (m, 2H), 1.36-1.28 (m, 3H), 0.91 (d, J=5.6 Hz, 3H); LC/MS (10-99%): M/Z: M⁺(obs)=419; $t_R$=3.71 min.

1-Benzenesulfonyl-5-(3,5-dimethyl-piperidine-1-sulfonyl)-1H-indole

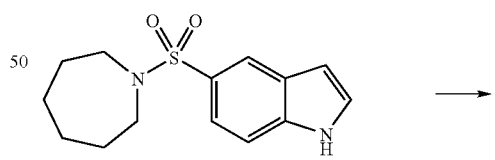

LC/MS (10-99%): M/Z: M⁺(obs)=433; $t_R$=6.53 min.

5-(Azepane-1-sulfonyl)-1-benzenesulfonyl-1H-indole

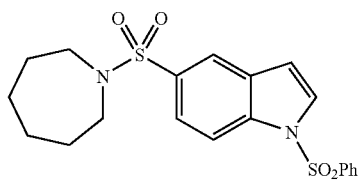

LC/MS (10-99%): M/Z: M⁺(obs)=419; $t_R$=6.13 min.

223

1-Benzenesulfonyl-3-methyl-5-(4-methyl-piperidine-1-sulfonyl)-1H-indole

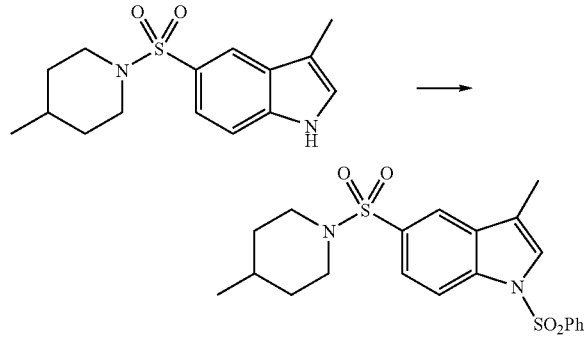

LC/MS (10-99%): M/Z: M$^+$(obs)=433; $t_R$=6.58 min.

1-Benzenesulfonyl-5-(3,5-dimethyl-piperidine-1-sulfonyl)-3-methyl-1H-indole

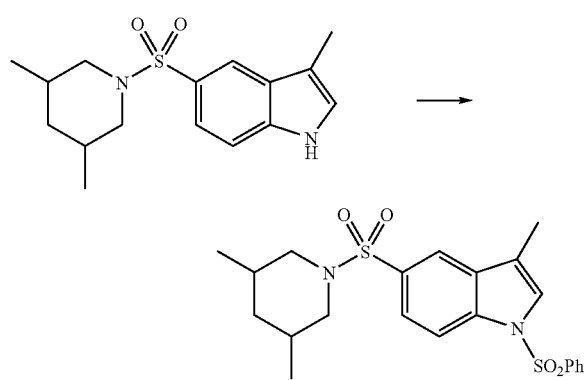

LC/MS (10-99%): M/Z: M$^+$(obs)=447; $t_R$=6.80 min.

5-(Azepane-1-sulfonyl)-1-benzenesulfonyl-3-methyl-1H-indole

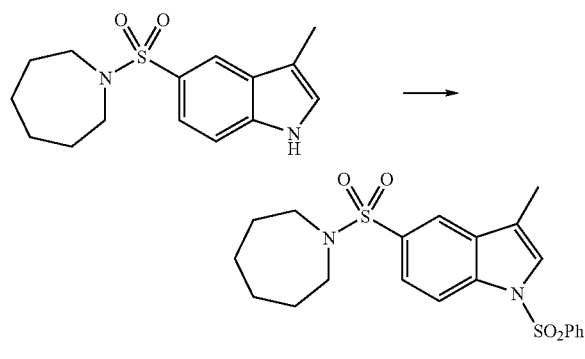

LC/MS (10-99%): M/Z: M$^+$(obs) 433; $t_R$=6.42 min.

224

General Procedure for the Preparation of 1-Benzenesulfonyl-5-sufamoyl-3-R$^5$-1H-indole-2-carboxylic Acids

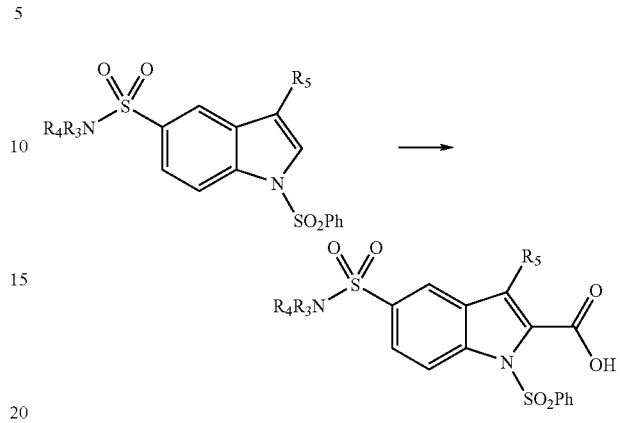

To a solution of LDA (prepared from (i-Pr)$_2$NH (1.2 mL) and n-BuLi (3.4 mL, 2.5 M)) in THF (10 mL) was added the indole (7.65 mmol) at 0° C. The reaction mixture was stirred at 0° C. for 30 min. After cooling the solution to −80° C., excess dry ice was added. The reaction mixture was allowed to warm to RT overnight. Acetic acid (0.5 mL) was added to quench the reaction. The mixture was diluted with CH$_2$Cl$_2$, washed with 1M aq. HCl, water (2×) and half-saturated brine. The organic layers were dried over Na$_2$SO$_4$, and concentrated. Diisopropylamine was added to a solution of the resulting foam in a small volume of ethanol. The precipitate that formed was filtered off, washed twice with ethanol and air-dried (3.4 grams). Of this salt 1.60 g was suspended in CH$_2$Cl$_2$, washed with 0.1M aq. HCl (2×20 mL), water (2×20 mL) and half-saturated brine. The organic layer was dried over Na$_2$SO$_4$, and concentrated to give the product as a yellow foam. Yields: 10-75%.

1-Benzenesulfonyl-5-(4-methyl-piperidine-1-sulfonyl)-1H-indole-2-carboxylic acid

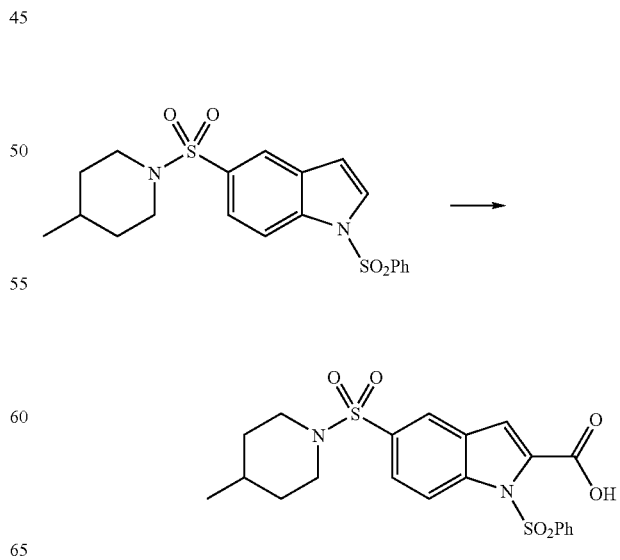

LC/MS (10-99%): M/Z: M$^+$(obs)=463; $t_R$=2.91 min.

225
1-Benzenesulfonyl-5-(3,5-dimethyl-piperidine-1-sulfonyl)-1H-indole-2-carboxylic acid

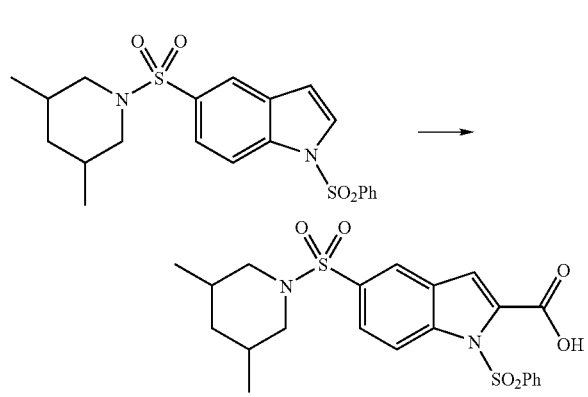

LC/MS (10-99%): M/Z: M$^+$(obs)=477; $t_R$=4.13 min.

5-(Azepane-1-sulfonyl)-1-benzenesulfonyl-1H-indole-2-carboxylic acid

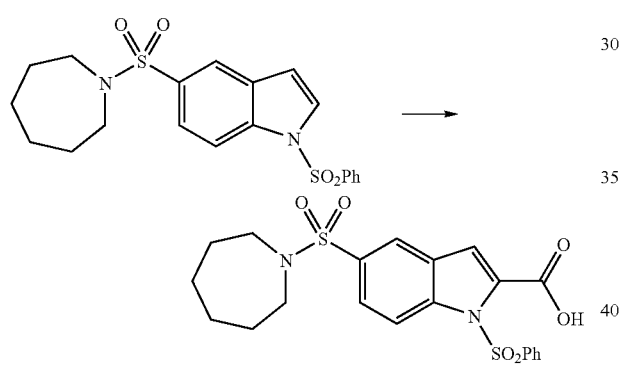

LC/MS (10-99%): M/Z: M$^+$(obs)=463; $t_R$=2.45 min.

1-Benzenesulfonyl-3-methyl-5-(4-methyl-piperidine-1-sulfonyl)-1H-indole-2-carboxylic acid

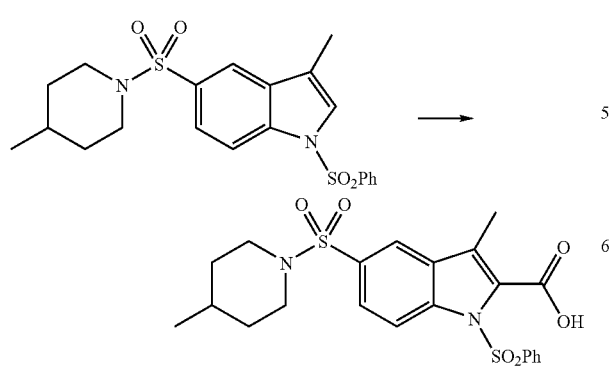

LC/MS (10-99%): M/Z: M$^+$(obs)=477; $t_R$=3.06 min.

226
1-Benzenesulfonyl-5-(3,5-dimethyl-piperidine-1-sulfonyl)-3-methyl-1H-indole-2-carboxylic acid

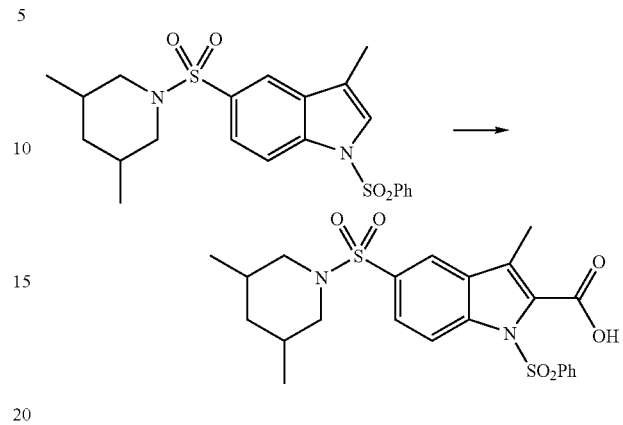

LC/MS (10-99%): M/Z: M$^+$(obs)=491; $t_R$=4.16 min.

5-(Azepane-1-sulfonyl)-1-benzenesulfonyl-3-methyl-1H-indole-2-carboxylic acid

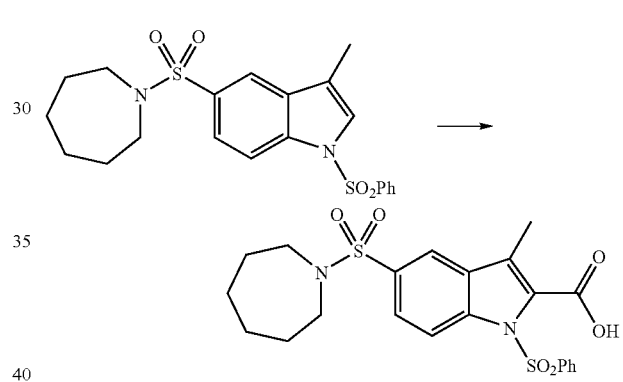

LC/MS (10-99%): M/Z: M$^+$(obs)=477; $t_R$=2.47 min.

General Procedure for the Preparation of 1-Benzenesulfonyl-5-sulfamoyl-3-R$^5$-1H-indole-2-carboxamides

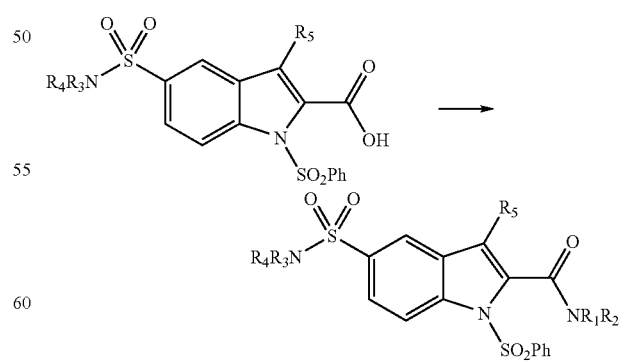

A solution of the acid (3.31 mmol) in SOCl$_2$ was heated at reflux for 1 h. Excess SOCl$_2$ was removed in vacuo. The resulting foam was dried at 0.01 mm Hg for several h to give the acid chloride in quantitative yield.

Parallel library generation was performed using 10 mL borosilicate glass reaction vessels in a 24 position Mettler-Toledo MiniblockXT™. The vessels were loaded with the individual amines (0.3 mmol) to which dry CH$_2$Cl$_2$ (0.5 mL) was added. Subsequently, a solution of the acid chloride scaffold in dry CH$_2$Cl$_2$ (0.1 M, 1 mL, 3 equiv) was added to the vessels. The reactions were stirred for 16 h, after which they were quenched by the addition of a saturated aqueous NaHCO$_3$ solution (2 mL). For the work-up, the reactions blocks were then transferred to a Mettler-Toledo ALLEXis automated liquid-liquid extraction robot. The work-up consisted of separation of the layers and washing of the organic phase with aqueous hydrochloric acid (0.5 M, 2 mL). Finally, removal of the CH$_2$Cl$_2$ under reduced pressure using a Genevac EZ2+ centrifugal parallel evaporation unit, afforded the coupled products. These were used without further purification in the next reaction step.

[1-Benzenesulfonyl-5-(3,5-dimethyl-piperidine-1-su/fonyl)-1H-indol-2-yl]-piperidin-1-yl-methanone

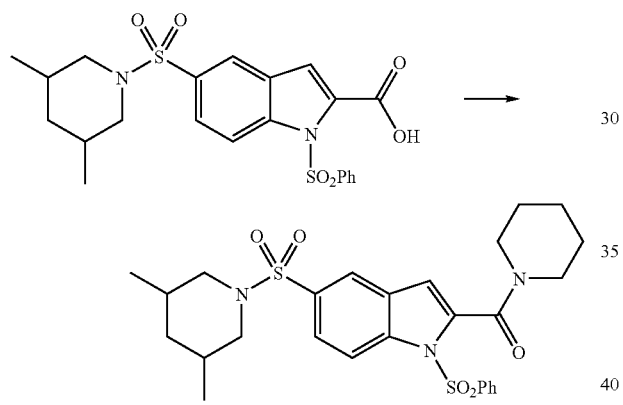

LC/MS (10-99%): M/Z: M$^+$(obs)=544; $t_R$=7.52 min.

5-(Azepane-1-sulfonyl)-1-benzenesulfonyl-1H-indole-2-carboxylic acid benzyl-amide

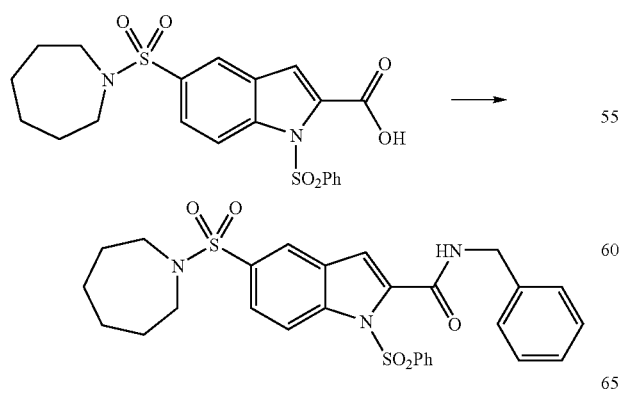

LC/MS (10-99%): M/Z: M$^+$(obs)=552; $t_R$=6.83 min.

1-Benzenesulfonyl-5-(3,5-dimethyl-piperidine-1-sulfonyl)-3-methyl-1H-indole-2-carboxylic acid butyl-methyl-amide

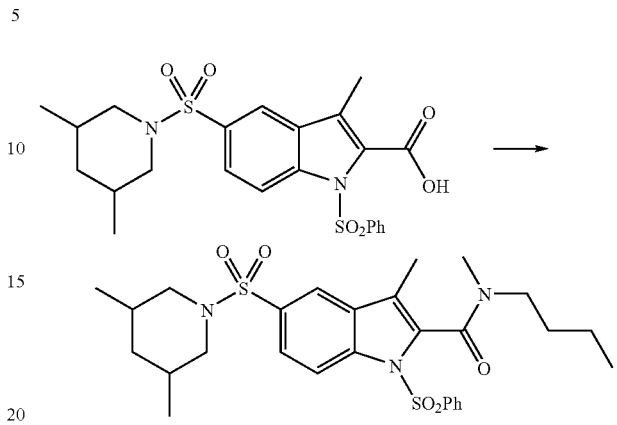

LC/MS (10-99%): M/Z: M$^+$(obs)=560; $t_R$=7.69 min.

General Procedure for the Preparation of 3-R$^5$-1H-indole-2-carboxamides

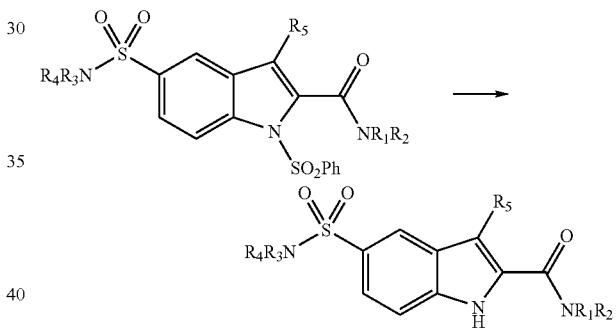

The coupled products were redissolved in MeOH (2 mL) and treated with 2M aqueous NaOH (0.5 mL). The reactions were stirred for 16 h, after which they were diluted with water (2 mL). Most of the MeOH was removed under reduced pressure (Genevac EZ2+) and the remaining mixtures were extracted with CH$_2$Cl$_2$ (2×2 mL, Mettler-Toledo ALLEXis). Finally, removal of the CH$_2$Cl$_2$ under reduced pressure (Genevac EZ2+) afforded the final products in good purity, as shown by LC-MS analysis.

5-(4-Methyl-piperidine-1-sulfonyl)-1H-indole-2-carboxylic acid diisopropylamide

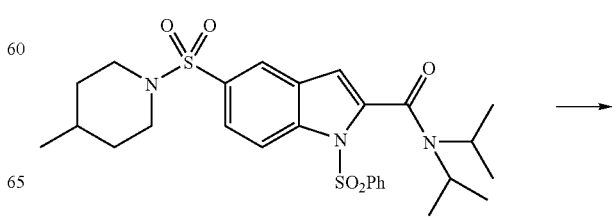

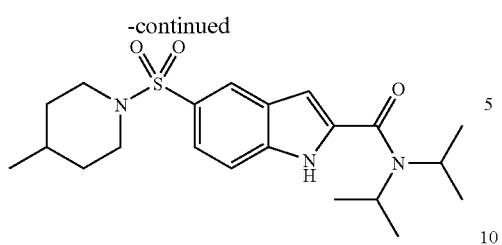

¹H-NMR (300 MHz, CDCl₃): δ 10.11 (s, 1H); 8.11 (d, J=0.8 Hz, 1H); 7.57 (m, 2H); 6.80 (d, J=1.1 Hz, 1H); 3.78-3.74 (m, 2H); 2.23-2.16 (m, 2H); 1.64-1.62 (m, 3H); 1.46 (br. s, 12H); 1.32-1.24 (m, 4H); 0.87 (d, J=5.8 Hz, 3H) ppm.

[5-(3,5-Dimethyl-piperidine-1-sulfonyl)-1H-indol-2-yl]-piperidin-1-yl-methanone

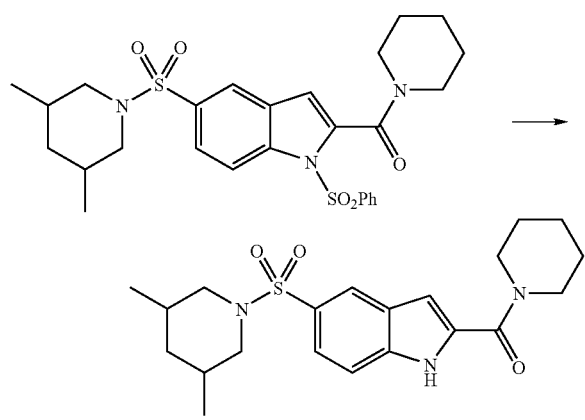

¹H-NMR (300 MHz, CDCl₃): δ 10.53 (s, 1H); 8.12 (d, J=1.4 Hz, 1H); 7.63-7.53 (m, 2H); 6.89 (s, 1H); 3.89 (br.s, 4H); 3.77-3.74 (m, 2H); 1.85-1.62 (m, 11H); 0.82 (d, J=6.3 Hz, 6H); 0.46-0.35 (m, 1H) ppm. LC/MS (10-99%): M/Z: M⁺(obs)=404; t_R=5.77 min.

5-(Azepane-1-sulfonyl)-1H-indole-2-carboxylic acid benzylamide

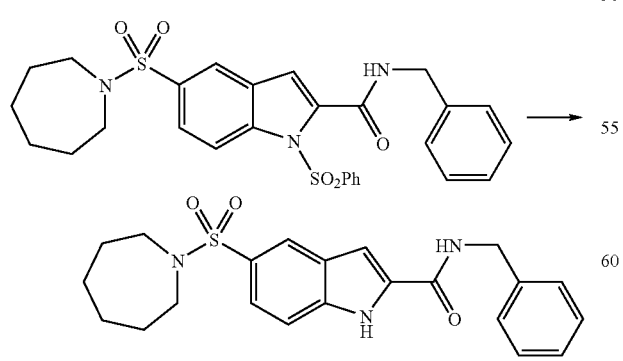

¹H-NMR (300 MHz, DMSO-d₆): δ 12.1 (s, 1H); 8.12 (m, 1H); 7.59-7.52 (m, 2H); 7.35-7.26 (m, 4H); 7.25-7.23 (m, 1H); 4.51 (d, J=5.8 Hz); 3.19-3.15 (m, 4H); 1.58 (br.s 4H); 1.45 (m, 4H) ppm. LC/MS (10-99%): M/Z: M⁺(obs)=412; t_R=5.25 min.

[3-Methyl-5-(4-methyl-piperidine-1-sulfonyl)-1H-indol-2-yl]-(2-methyl-piperidin-1-yl)-methanone

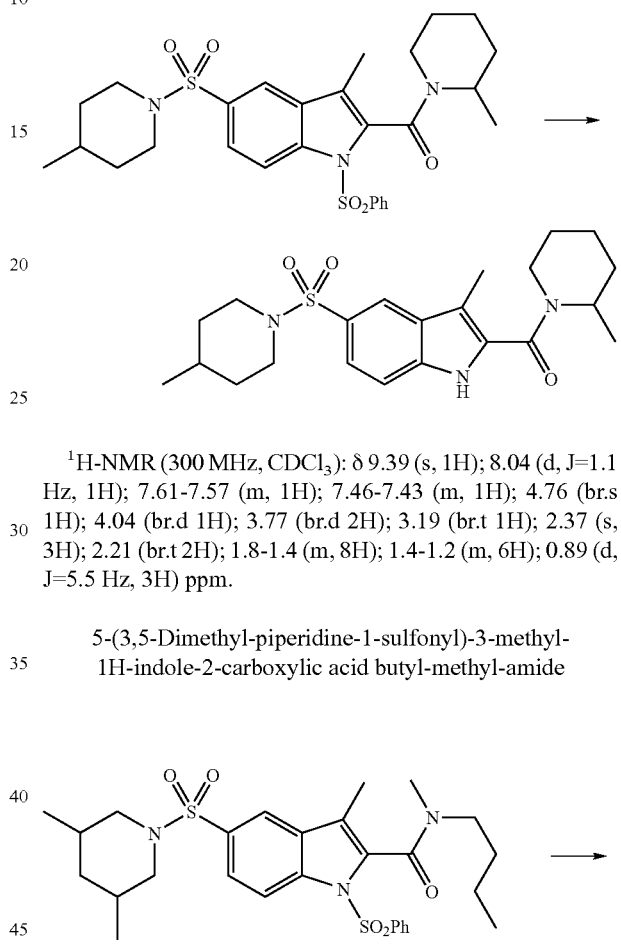

¹H-NMR (300 MHz, CDCl₃): δ 9.39 (s, 1H); 8.04 (d, J=1.1 Hz, 1H); 7.61-7.57 (m, 1H); 7.46-7.43 (m, 1H); 4.76 (br.s 1H); 4.04 (br.d 1H); 3.77 (br.d 2H); 3.19 (br.t 1H); 2.37 (s, 3H); 2.21 (br.t 2H); 1.8-1.4 (m, 8H); 1.4-1.2 (m, 6H); 0.89 (d, J=5.5 Hz, 3H) ppm.

5-(3,5-Dimethyl-piperidine-1-sulfonyl)-3-methyl-1H-indole-2-carboxylic acid butyl-methyl-amide

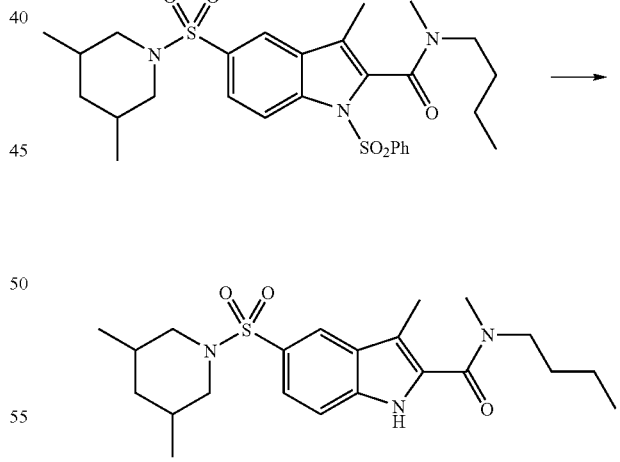

¹H-NMR (300 MHz, CDCl₃): δ 10.53 (s, 1H); 8.01 (d, J=1.1 Hz, 1H); 7.55-7.45 (m, 2H); 3.73 (br.d 2H); 3.52 (br. S, 2H); 3.08 (s, 3H); 2.36 (s, 3H); 1.8-1.1 (m, 9H); 1.0-0.8 (m, 9H); 0.45-0.34 (m, 1H) ppm. LC/MS (10-99%): M/Z: M⁺(obs)=420; t_R=5.99 min.

231

5-(Azepane-1-sulfonyl)-3-methyl-1H-indole-2-carboxylic acid [2-(tetrahydro-pyran-4-yl)-ethyl]-amide

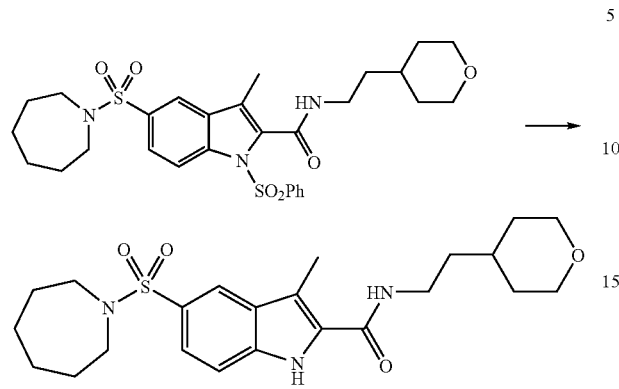

$^1$H-NMR (300 MHz, CDCl$_3$): δ 9.60 (s, 1H); 8.14 (d, J=1.5 Hz, 1H); 7.64 (dd, J=8.5 Hz, 1.5 Hz, 1H); 7.45 (d, J=8.5 Hz, 1H); 6.08 (t, J=5.5 Hz, 1H); 3.97 (dd, J=11.6 Hz, 3.6 Hz, 2H); 3.59 (AB, 2H); 3.39 (t, J=11.0 Hz, 2H); 3.28 (t, J=5.8 Hz, 4H); 2.59 (s, 3H), 1.70-1.57 (m, 15H) ppm.

General Synthetic Scheme 2

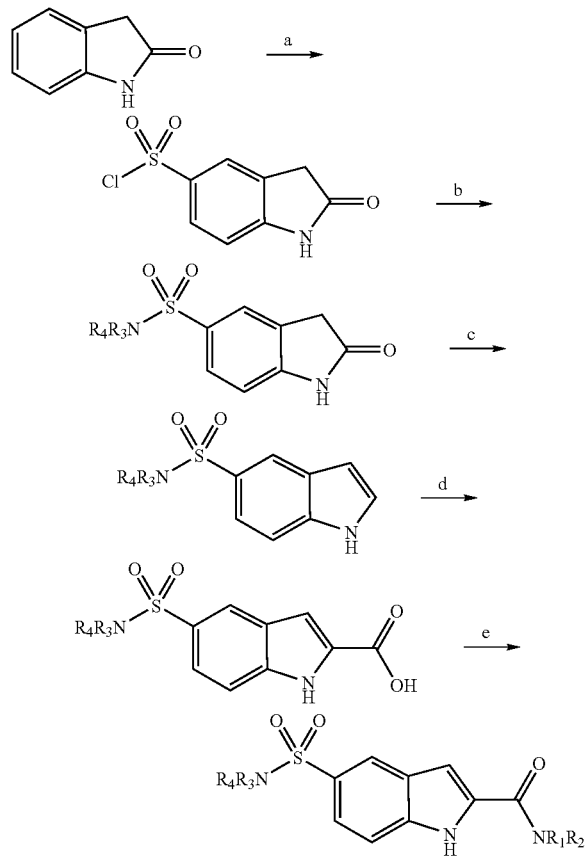

a) ClSO$_3$H
b) HNR$_3$R$_4$, TEA, DCM
c) (i) NaBH$_4$, BF$_3$—OEt$_2$, THF (ii) DDQ, DCM
d) (i) n-BuLi, CO$_2$ (ii) tert-BuLi, CO$_2$
e) (i) SOCl$_2$, DMF, DCM; (ii) HNR$_1$R$_2$, TEA, DCM

232

2-Oxo-2,3-dihydro-1H-indole-5-sulfonyl chloride

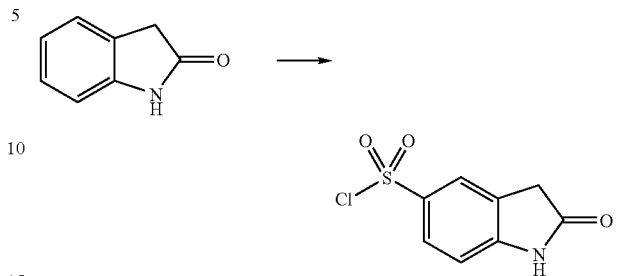

To a solution of chlorosulfonic acid (25 mL, 37.5 mmol) at 0° C. was slowly added oxindole over 40 min. The resulting solution was stirred at RT for 1.5 h and then heated to 50° C. for 10 min until gas evolution ceased. After cooling to RT, the reaction mixture was carefully poured onto ice. A white precipitate was formed which was filtered, washed with ice-water and dried under HV. Yield: 14.35 g (82%). LC/MS (10-99%): M/Z: M$^+$(obs)=232; t$_R$=2.24 min.

General Procedure for the Preparation of 5-aminosulfonyl-1,3-dihydro-indol-2-ones

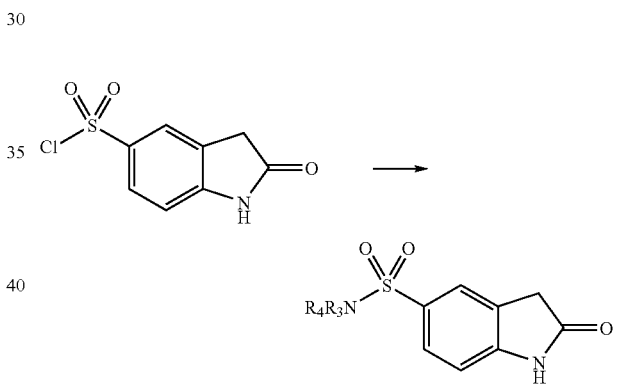

To a solution of the amine (23.8 mmol) and TEA (6.1 mL, 43.6 mmol) in DCM (100 mL) at 0° C. was added the sulfonyl choride (5.0 g, 21.6 mmol) in portions. The reaction mixture was continued to stir at RT for 2 h. The reaction mixture was washed with 1M HCl, water and brine (50 mL each), dried over MgSO$_4$ and concentrated to give the products.

5-(3,5-Dimethyl-piperidine-1-sulfonyl)-1,3-dihydro-indol-2-one

-continued

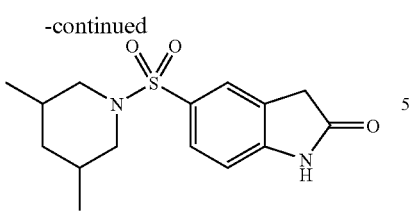

Yield: 6.15 g (92%). ¹H-NMR (400 MHz, DMSO-d⁶) δ 10.81 (s, 1H), 7.58-7.53 (m, 2H), 7.00 (d, J=8.1 Hz, 1H), 3.61 (s, 2H), 3.56 (d, J=6.7 Hz, 2H), 2.89-2.86 (m, 0.3H), 1.94-1.89 (m, 0.3H), 1.69-1.63 (m, 4H), 1.24-1.21 (m, 0.4H), 0.91 (d, J=6.8 Hz, 1H), 0.82 (d, J=5.7 Hz, 5H), 0.52-0.47 (m, 1H) (Mixture of cis- and trans-isomers). LC/MS (10-99%): M/Z: M⁺(obs)=309; $t_R$=2.67 min.

General Procedure for the Preparation of 5-aminosulfonyl-1H-indoles

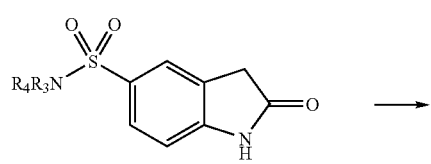

To a suspension of the oxindole (0.65 mmol) in THF (3.5 mL) at 0° C. was added BF₃Et₂O (0.29 mL, 2.28 mmol). After stirring for 10 min at 0° C. NaBH₄ (40 mg, 1.04 mmol) was added in one portion. The resulting solution was slowly warmed up to RT. After 20 h the reaction mixture was quenched by slow addition of water (15 mL) at 0° C. and continued to stir at RT for 30 min. Acidification to pH 1 with 6M HCl was followed by stirring for 30 min. The reaction mixture was then basified to pH 14 with 2M NaOH, stirred for another 30 min. and extracted with EtOAc (3×100 mL). The combined organic extracts were dried over MgSO₄ and concentrated. The crude products (mixture of indole and indoline) were purified by column chromatography (silica, EtOAc in hexanes, 25-50%).

To a solution of the indoline/indole mixtures (0.46 mmol) in THF (9 mL) at 0° C. was added a solution of DDQ (105 mg, 0.46 mmol) in THF (1 mL). After stirring for 1 h at RT, the reaction mixture was concentrated. EtOAc (25 mL) and 1M NaOH (25 mL) were added, the phases were separated and the aqueous layer was extracted with EtOAc (25 mL). The combined organic extracts were washed with brine (2×25 mL), dried over MgSO₄ and concentrated. The crude products were purified by column chromatography (silica, EtOAc in hexanes, 25-5.0%).

5-(3,5-Dimethyl-piperidine-1-sulfonyl)-1H-indole

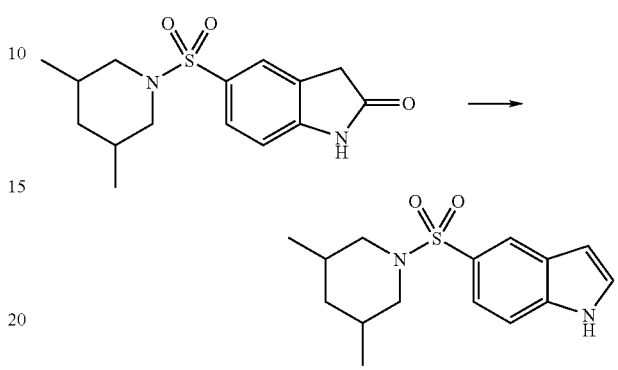

Yield: 101 mg (53% over both steps). ¹H-NMR (400 MHz, DMSO-d⁶): δ 11.64 (s, 1H), 7.99 (d, J=1.5 Hz, 1H), 7.61-7.56 (m, 2H), 7.43 (dd, J=8.5, 1.8 Hz, 1H), 6.68-6.67 (m, 1H), 3.61 (d, J=7.5 Hz, 2H), 2.88-2.85 (m, 0.3H), 1.93-1.89 (m, 0.3H), 1.66-1.56 (m, 4H), 1.20-1.16 (m, 0.4H), 0.91 (d, J=6.8 Hz, 1H), 0.80 (d, J=6.0 Hz, 5H), 0.47-0.38 (m, 1H) (Mixture of cis- and trans-isomers). LC/MS (10-99%): M/Z: M⁺(obs) =293; $t_R$=3.16 min.

General Procedure for the Preparation of 5-aminosulfonyl-1H-indoles-2-carboxylic Acids

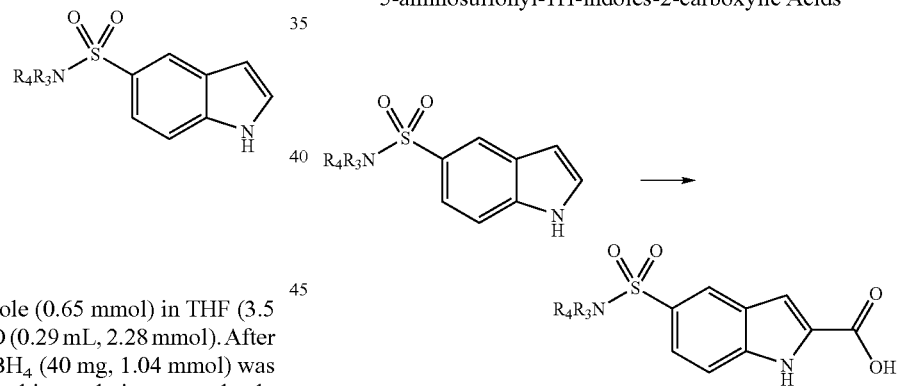

To a solution of the indole (0.68 mmol) in THF (3 mL) at −78° C. was added a solution of n-BuLi (2.5 M in hexanes, 0.29 mL, 0.72 mmol) dropwise. After stirring for 30 Min at this temperature, CO₂ gas was bubbled through the solution at −78° C. for 5 Min upon which the yellow solution turned colorless. The cooling bath was removed and the reaction mixture was warmed up to RT. Solvent was removed under HV with a vacuum trap, and the resulting solid was redissolved in THF (3 mL). After cooling to −78° C. a solution of tert-BuLi (1.7 M in pentane, 0.40 mL, 0.68 mmol) was slowly added over 5 Min. The resulting red solution was continued to stir at −78° C. for 1 h. CO₂ gas was bubbled through the solution for 10 Min, and stirring was continued for 2 h at −78° C. The reaction mixture was quenched by careful addition of water (5 mL). After warming up to RT, the reaction mixture was poured into sat. aqueous NaHCO₃ and extracted with EtOAc (3×25 mL). The combined organic extracts were dried over MgSO₄ and concentrated. The crude products were purified by column chromatography (silica, MeOH in DCM, 0-20%).

5-(3,5-Dimethyl-piperidine-1-sulfonyl)-1H-indole-2-carboxylic acid

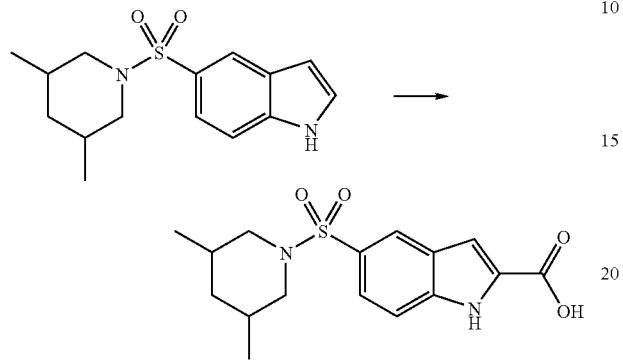

Yield: 55 mg (24%); recovered starting material: 97 mg (42%). LC/MS (10-99%): M/Z: M⁺(obs)=337; $t_R$=2.89 min.

5-(3,5-Dimethyl-piperidine-1-sulfonyl)-1H-indole-2-carboxylic acid diethylamide

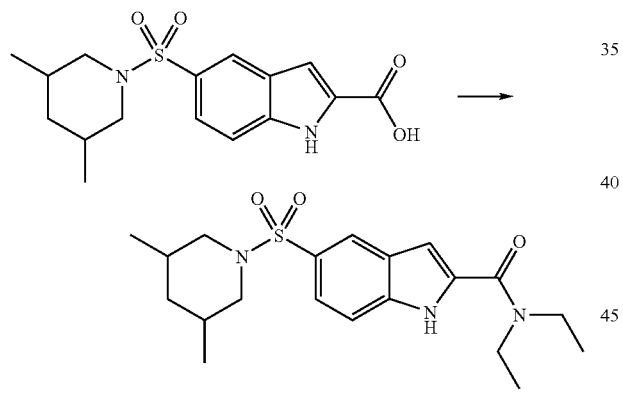

This compound was synthesized following the general procedure for the preparation of 1-Benzenesulfonyl-5-sulfamoyl-3-R⁵-1H-indole-2-carboxamides. ¹H-NMR (400 MHz, DMSO-d 6): δ 12.09 (s, 1H), 8.10-8.07 (m, 1H), 7.62-7.59 (m, 1H), 7.53-7.49 (m, 1H), 7.05-7.03 (m, 1H), 3.62-3.58 (m, 6H), 2.89-2.87 (m, 0.3H), 1.94-1.88 (m, 0.3H), 1.64-1.60 (m, 4H), 1.24-1.16 (m, 6H), 0.91 (d, J=6.8 Hz, 1H), 0.81 (d, J=5.7 Hz, 5H), 0.46-0.44 (m, 1H) (Mixture of cis- and trans-isomers). LC/MS (10-99%): M/Z: M⁺(obs) 392; tR=3.26 min.

General Synthetic Scheme 3

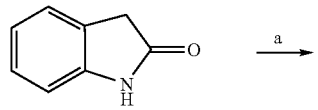

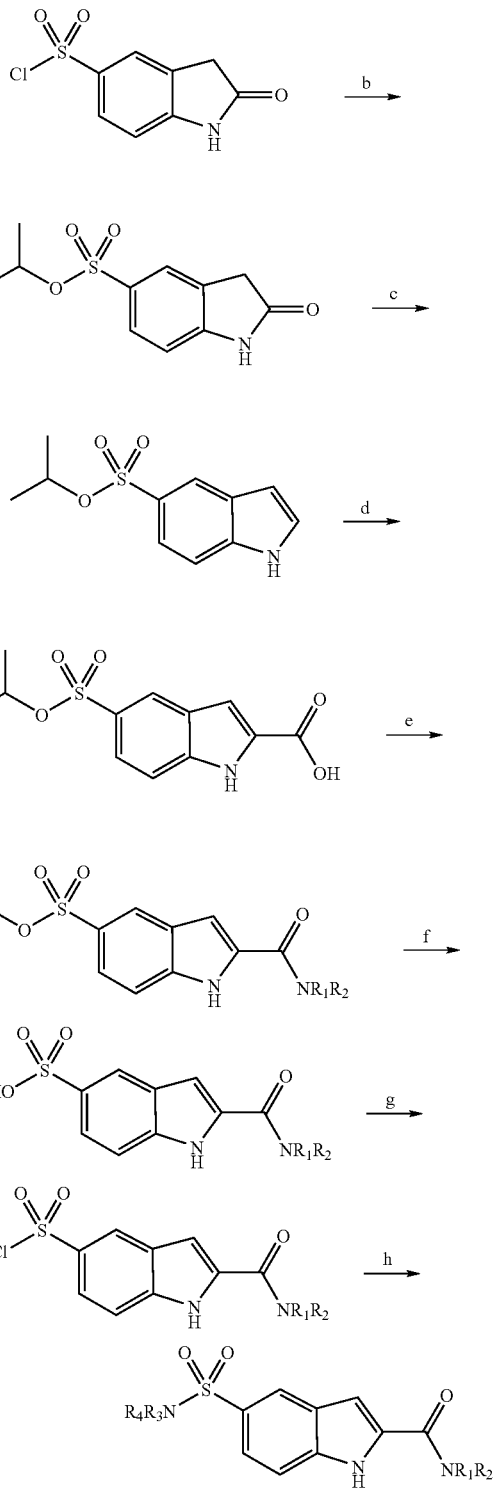

a) ClSO₃H
b) i-PrOH, pyridine
c) (i) NaBH₄, BF₃—OEt₂, THF (ii) DDQ, DCM
d) (i) n-BuLi, CO₂ (ii) tert-BuLi, CO₂
e) (i) SOCl₂, DMF, DCM; (ii) HNR₁R₂, TEA, DCM
f) 1M NaOH, MeOH
g) cyanuric chloride, TEA, acetone, MW: 120° C./600 s
h) HNR₃R₄, pyridine

2-Oxo-2,3-dihydro-1H-indole-5-sulfonic acid isopropyl ester

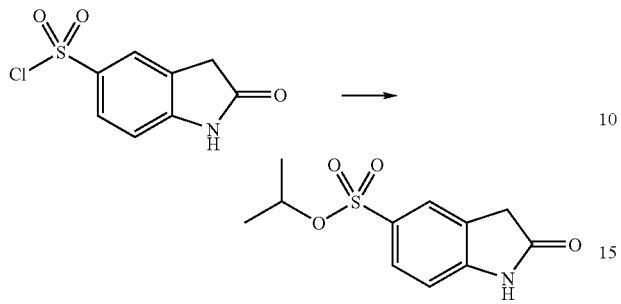

To a solution of 2-propanol (1.8 mL, 23.8 mmol) and pyridine (7.0 mL, 86.4 mmol) at 0° C. was added 2-oxo-2,3-dihydro-1H-indole-5-sulfonyl chloride (5.0 g, 21.6 mmol) in one portion. The resulting suspension was stirred at 0° C. for 45 mins and then warmed RT for 1 h. The reaction mixture was partitioned between DCM and 1M HCl. The organic layer was washed successively with 50 mL of 1M HCl, water, and brine. The organic layers were dried over $MgSO_4$ and concentrated to produce an orange solid. Yield: 4.06 g (74%). $^1$H-NMR (400 MHz, DMSO-d$^6$): δ 10.90 (s, 1H), 7.74 (dd, J=8.2, 1.9 Hz, 1H), 7.70 (s, 1H), 7.01 (d, J=8.2 Hz, 1H), 4.68-4.58 (m, 1H), 3.75-3.69 (m, 2H), 1.19 (d, J=6.2 Hz, 6H). LC/MS (10-99%): M/Z: M$^+$(obs) 256.1; $t_R$=2.10 min.

1H-Indole-5-sulfonic acid isopropyl ester

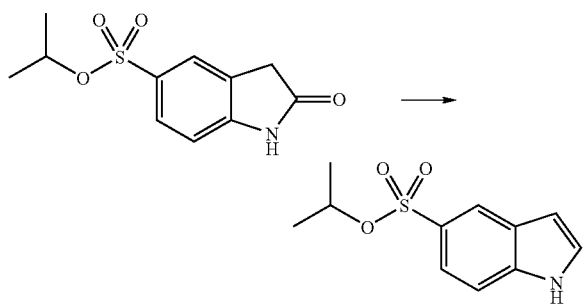

To a suspension of oxindole (3.09 g, 12.1 mmol) in THF (70 mL) at 0° C. was added $BF_3OEt_2$ (5.3 mL, 42.4 mmol) over a 5 min period. After stirring for 10 min, $NaBH_4$ (0.73 g, 19.4 mmol) was added in one portion and slowly warmed to RT overnight. The reaction mixture was quenched by the slow addition of water (270 mL) at 0° C. and stirring for 30 mins. The reaction mixture was acidified with conc. HCl (pH 1), stirred for 30 min, then basified with 1M NaOH (pH 14), and stirred for an additional 30 min. The product was extracted with EtOAc (4×200 mL). The organic layers were dried over $MgSO_4$ and concentrated to produce a crude mixture of the indole and indoline. Yield: 2.01 g (69%).

To a solution of the crude mixture (2.01 g, 8.4 mmol) in THF (150 mL) at 0° C. was added DDQ (1.9 g, 8.4 mmol) portionwise and the reaction mixture stirred at 0° C. for 1 h. The reaction mixture was concentrated and purified by column chromatography (silica, EtOAc in hexanes, 25-50%). Yield: 1.19 g (60% over 2 steps). LC/MS (10-99%): M/Z: M$^+$(obs) 240.5; $t_R$=2.71 min.

5-Isopropoxysulfonyl-1H-indole-2-carboxylic acid

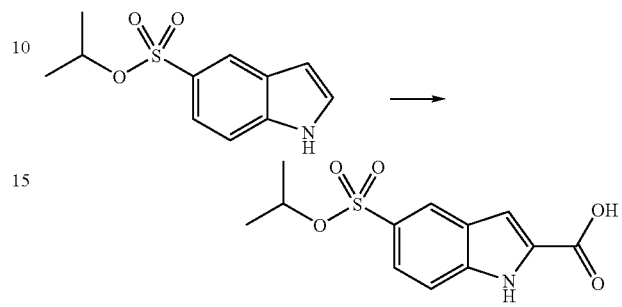

To a solution of the indole (1.51 g, 6.31 mmol) in THF (30 mL) at −78° C. was added a 2.5M solution of n-BuLi in hexanes (2.65 mL, 6.63 mmol) over a 10 min period. The color changed from purple to yellow and the reaction was stirred at −78° C. for 30 min. Carbon dioxide gas was bubbled via syringe through the solution for 10 min and the solution became colorless. The cooling bath was removed, the reaction mixture was warmed to RT, and concentrated under high vacuum with a liquid nitrogen trap. The solids were redissolved in THF (30 mL), cooled to −78° C. again, and a solution of 1.7M tert-BuLi in pentane was added (3.71 mL, 6.31 mmol). The reaction mixture turned red and was stirred at −78° C. for 2.5 h. Carbon dioxide gas was bubbled via syringe through the solution for 10 min and the solution became yellow then colorless. The reaction mixture was stirred in the cooling solution overnight and slowly warmed to RT. The mixture was quenched by the careful addition of water and partitioned between sat. $NH_4Cl$ and EtOAc (3×100 mL). The combined organic solutions were dried over $MgSO_4$, concentrated, and purified by column chromatography (silica, MeOH in DCM, 0-20%). Yield: 526 mg (29%) and 848 mg (56% recovered starting material). $^1$H-NMR (400 MHz, DMSO-d$^6$) δ 8.13 (d, J=1.1 Hz, 1H), 7.55 (d, J=8.7 Hz, 1H), 7.51 (dd, J=8.7, 1.8 Hz, 1H), 6.82 (s, 1H), 4.62-4.53 (m, 1H), 1.14 (d, J=6.2 Hz, 6H). LC/MS (10-99%): M/Z: M$^+$(obs) =284.1; $t_R$=2.47 min.

General Procedure for the Preparation of 2-carbamoyl-1H-indole-5-sulfonic acid isopropyl esters

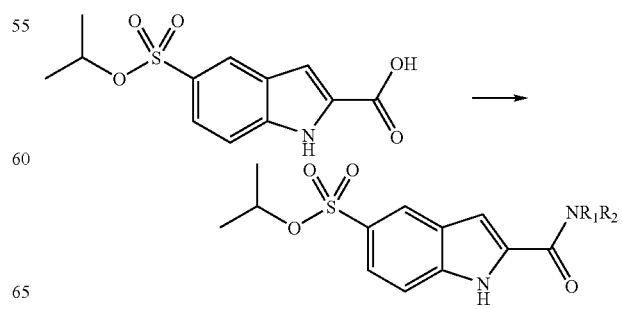

To a solution of the indole 2-carboxylic acid (162 mg, 0.57 mmol) in DCM (5 mL) was added catalytic DMF (10 μL) followed by SO$_2$Cl (0.21 mL, 2.86 mmol) and the reaction mixture heated to 55° C. for 1 h. The reaction mixture was cooled to RT, concentrated and co-evaporated with toluene (2×5 mL) and dried over HV for 15 min. The resulting solids were dissolved in DCM (4 mL) and cooled to 0° C. To the solution was slowly added the amine (3 equivalents, 1.71 mmol) followed by TEA (0.16 mL, 1.14 mmol) in DCM (7.5 mL). The reaction mixture was stirred at RT until completion. The reaction mixtures were partitioned between 1M HCl (30 uL) and DCM (50 mL). The organic layers were washed successively with 30 mL of water and brine. The combined organic solution were dried over MgSO$_4$, concentrated, and purified by column chromatography (silica, EtOAc in hexanes, 25-50%).

2-Diethylcarbamoyl-1H-indole-5-sulfonic Acid Isopropyl Ester

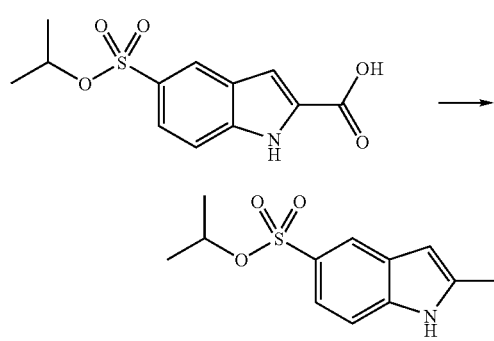

LC/MS (10-99%): M/Z: M$^+$(obs)=339.3; t$_R$=2.85 min.

General Procedure for the Preparation of 2-carbamoyl-1H-indole-5-sulfonic Acids

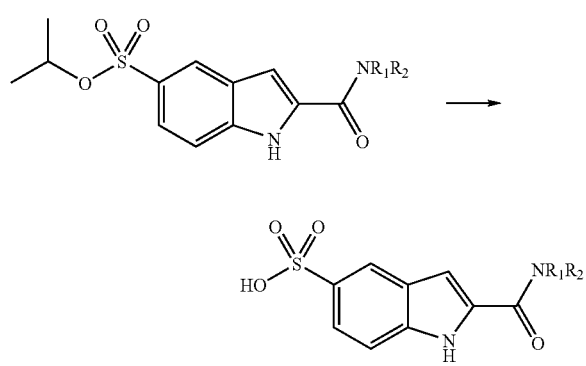

To a solution of the indole (0.43 g, 1.3 mmol) was added NaOH (0.42 g, 10.4 mmol) in MeOH (10 mL) and water (1 mL) and the reaction mixture stirred for 4 d, then heated to 70° C. for 24 h. The reaction mixture was neutralized to pH 7 with 1N HCl and evaporated to dryness to produce the crude sulfonic acid. The crude product was purified by preparative HPLC.

2-Diethylcarbamoyl-1H-indole-5-sulfonic Acid

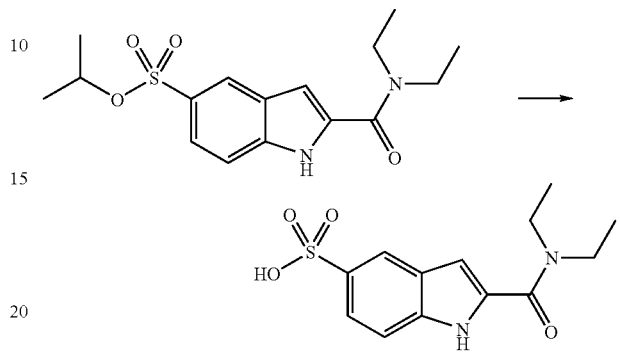

LC/MS (10-99%): M/Z: M$^+$(obs)=297; t$_R$=1.11 min.

General Procedure for the Preparation of 5-sulfamoyl-1H-indole-2-carboxylic Acid Amides

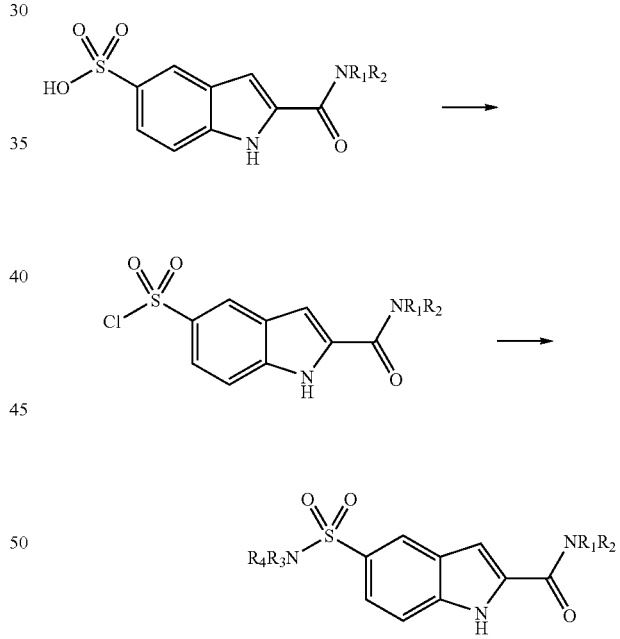

To the sulfonic acid (16 mg, 0.05 mmol) in acetone (0.5 mL) was added cyanuric chloride (10 mg, 0.05 mmol) and TEA (8 μL, 0.05 mmol) and the reaction mixture was microwaved at 120° C. for 600 s. The reaction mixture was filtered, washed with acetone, concentrated, and used directly in the next step.

To a solution of the crude sulfonyl chloride (16 mg, 0.05 mmol) in DCM (1.0 mL) was added the amine (10 equivalents, 0.5 mmol), followed by TEA (2 equivalents, 0.1 mmol) and the reaction mixture was stirred at RT overnight. The reaction mixture was concentrated and purified by HPLC (10-99% gradient of CH$_3$CN in H$_2$0).

241

5-Dipropylsulfamoyl-1H-indole-2-carboxylic acid diethylamide

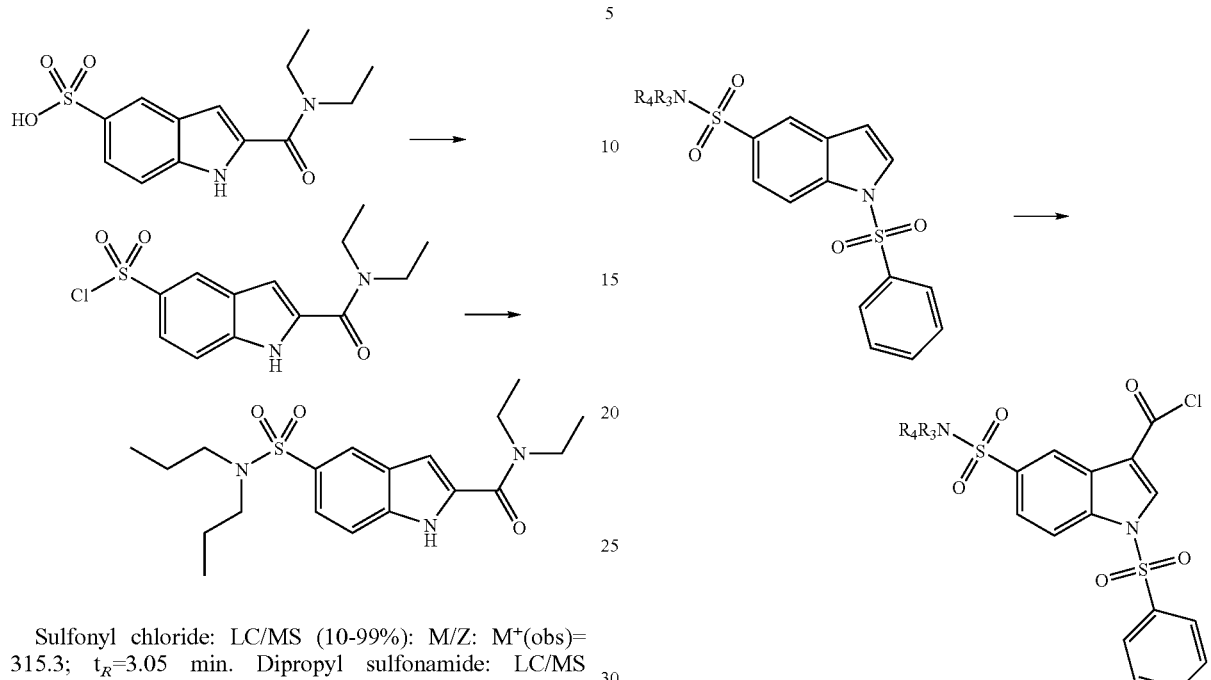

Sulfonyl chloride: LC/MS (10-99%): M/Z: M+(obs)= 315.3; $t_R$=3.05 min. Dipropyl sulfonamide: LC/MS (10-99%): M/Z: M+ (obs)=380.3; $t_R$=3.21 min C-3 Amides

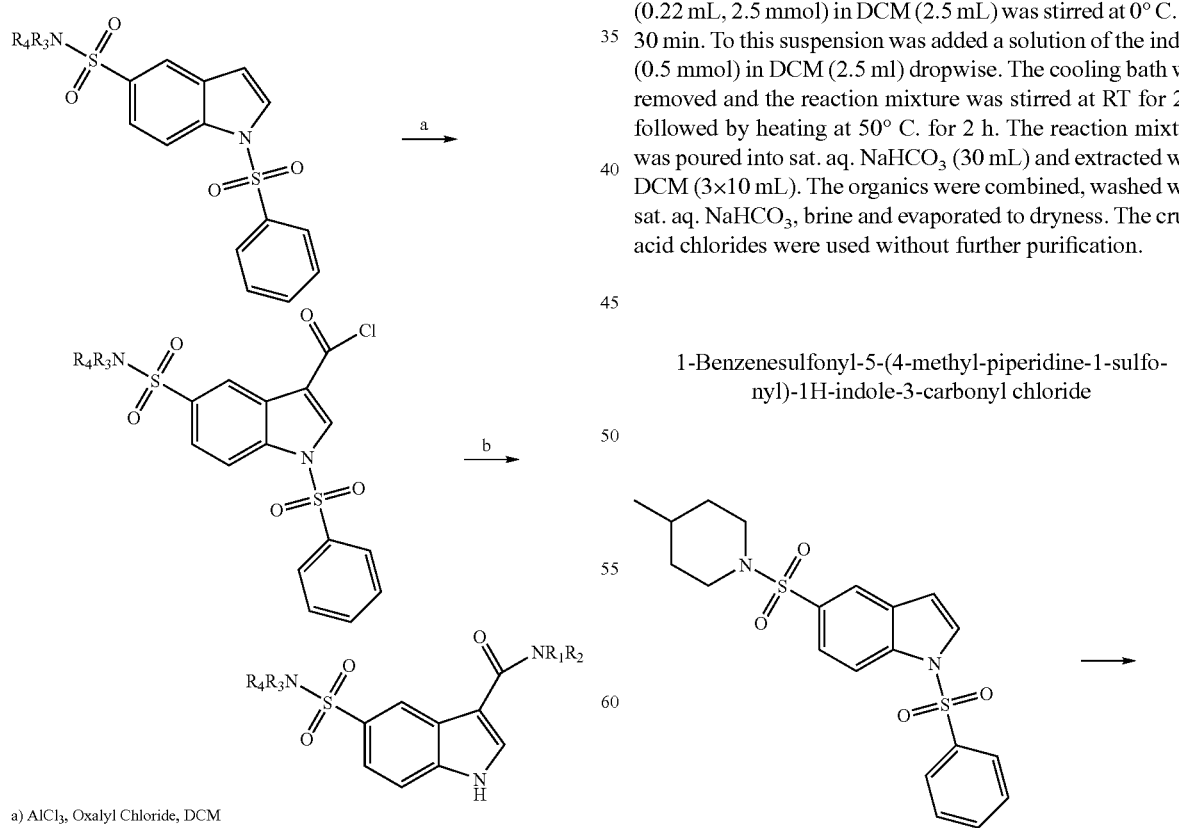

a) AlCl₃, Oxalyl Chloride, DCM
b) (i) HNR₁R₂, TEA, DCM; (ii) NaOH, MeOH

242

General Procedure for the Preparation of 1-Benzene-sulfonyl-5-aminosulfonyl-1H-indole-3-carbonyl Chlorides A solution of AlCl₃ (0.47 g, 2.5 mmol) and oxalyl chloride (0.22 mL, 2.5 mmol) in DCM (2.5 mL) was stirred at 0° C. for 30 min. To this suspension was added a solution of the indole (0.5 mmol) in DCM (2.5 ml) dropwise. The cooling bath was removed and the reaction mixture was stirred at RT for 2 h, followed by heating at 50° C. for 2 h. The reaction mixture was poured into sat. aq. NaHCO₃ (30 mL) and extracted with DCM (3×10 mL). The organics were combined, washed with sat. aq. NaHCO₃, brine and evaporated to dryness. The crude acid chlorides were used without further purification.

1-Benzenesulfonyl-5-(4-methyl-piperidine-1-sulfonyl)-1H-indole-3-carbonyl chloride

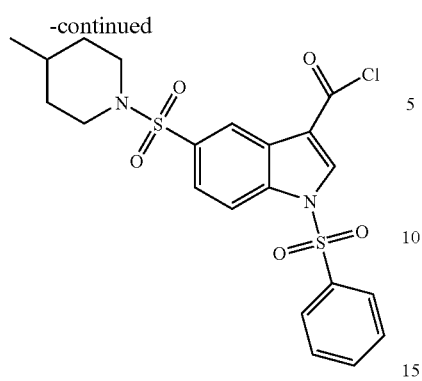

LC/MS (10-99%): M/Z: M⁺(obs)=481; $t_R$=4.03 min (purity=40%).

General Procedure for the Preparation of 5-(4-Methyl-piperidine-1-sulfonyl)-1H-indole-3-carboxylic Acid Amides

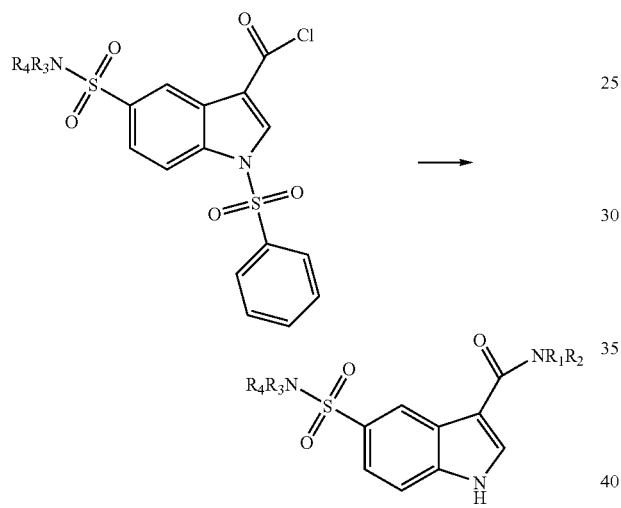

A solution of the acid chloride (0.19 g, 0.1 mmol), amine (0.2 mmol) and TEA (0.03 ml, 0.2 mmol) in DCM (0.3 ml) was stirred at RT for 16 h before evaporating to dryness. The crude material was taken up in MeOH (1 mL)/2.5 N NaOH (0.5 mL) and the stirred solution heated to 60° C. for 2 h. The reaction mixture was treated the 1 N HCl (1 mL) and extracted the EtOAc (2×1 mL). Evaporation and purification by HPLC gave the desired amide products.

5-(4-Methyl-piperidine-1-sulfonyl)-1H-indole-3-carboxylic acid cyclopropylamide

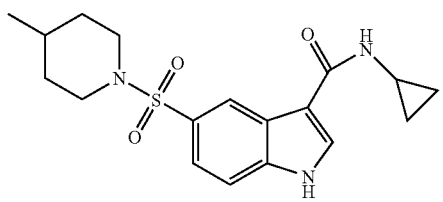

¹H-NMR (400 MHz, CDCl₃) δ 8.12 (s, 1H), 7.68 (dd, J=7.8, 0.9 Hz, 1H), 7.48 (d, J=8.8 Hz, 1H), 6.78 (d, J=0.7 Hz, 1H), 3.91 (s, 3H), 3.78 (dd, J=10.7, 3.8 Hz, 2H), 3.22 (s, 6H), 1.80 (m, 2H), 1.68 (t, J=11.2 Hz, 2H), 1.26 (m, 1H), 0.86 (d, J=6.5 Hz, 6H), 0.43 (m, 1H). LC/MS (10-99%): M/Z: M⁺(obs)=362; $t_R$=2.60 min;

5-(4-Methyl-piperidine-1-sulfonyl)-1H-indole-3-carboxylic acid amide

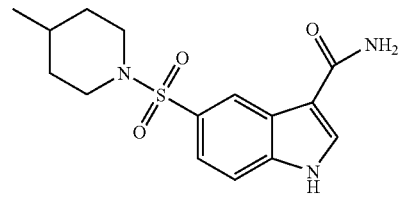

LC/MS (10-99%): M/Z: M⁺(obs)=322; $t_R$=2.32 min 5-(4-Methyl-piperidine-1-sulfonyl)-1H-indole-3-carboxylic acid diisopropylamide

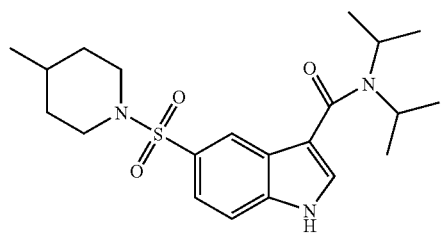

LC/MS (10-99%): M/Z: M⁺(obs)=406; $t_R$=3.23 min (4-Methyl-piperazin-1-yl)-[5-(4-methyl-piperidine-1-sulfonyl)-1H-indol-3-yl]-methanone

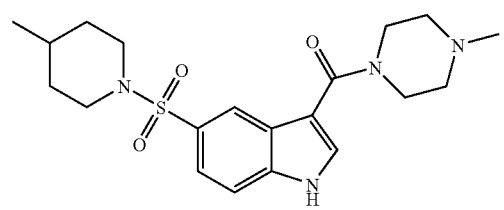

LC/MS (10-99%): M/Z: M⁺(obs)=405; $t_R$=2.01 min

Reduced Amides

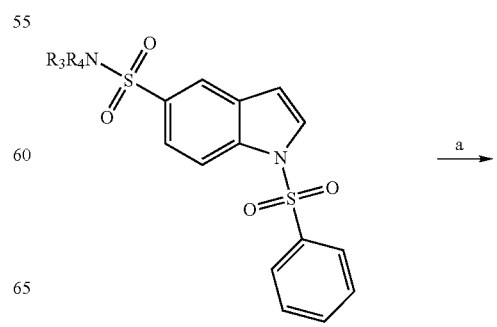

246

1-Benzenesulfonyl-5-(4-methyl-piperidine-1-sulfonyl)-1H-indole-2-carbaldehyde

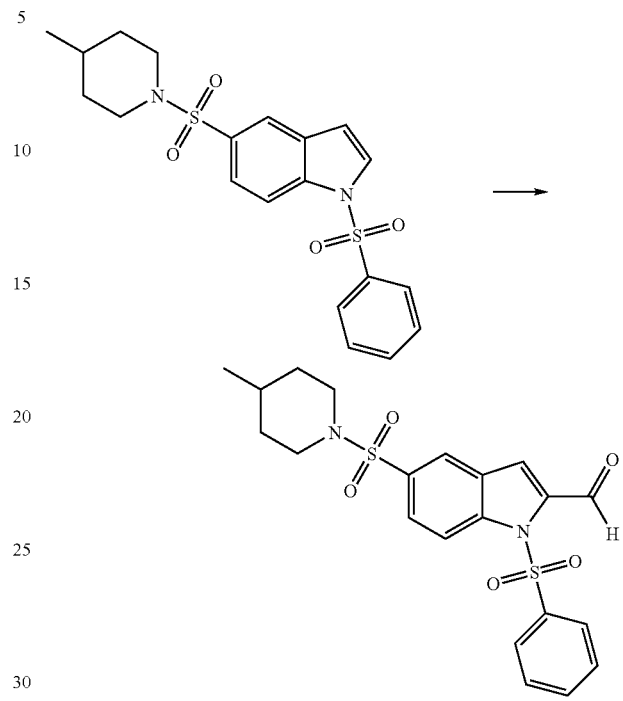

LC/MS (10-99%): M/Z: M⁺(obs)=447; $t_R$=3.67 min (purity 40%).

General Procedure for the Preparation of 5-(4-methyl-piperidine-1-sulfonyl)-1H-indol-2-ylmethyl-amines

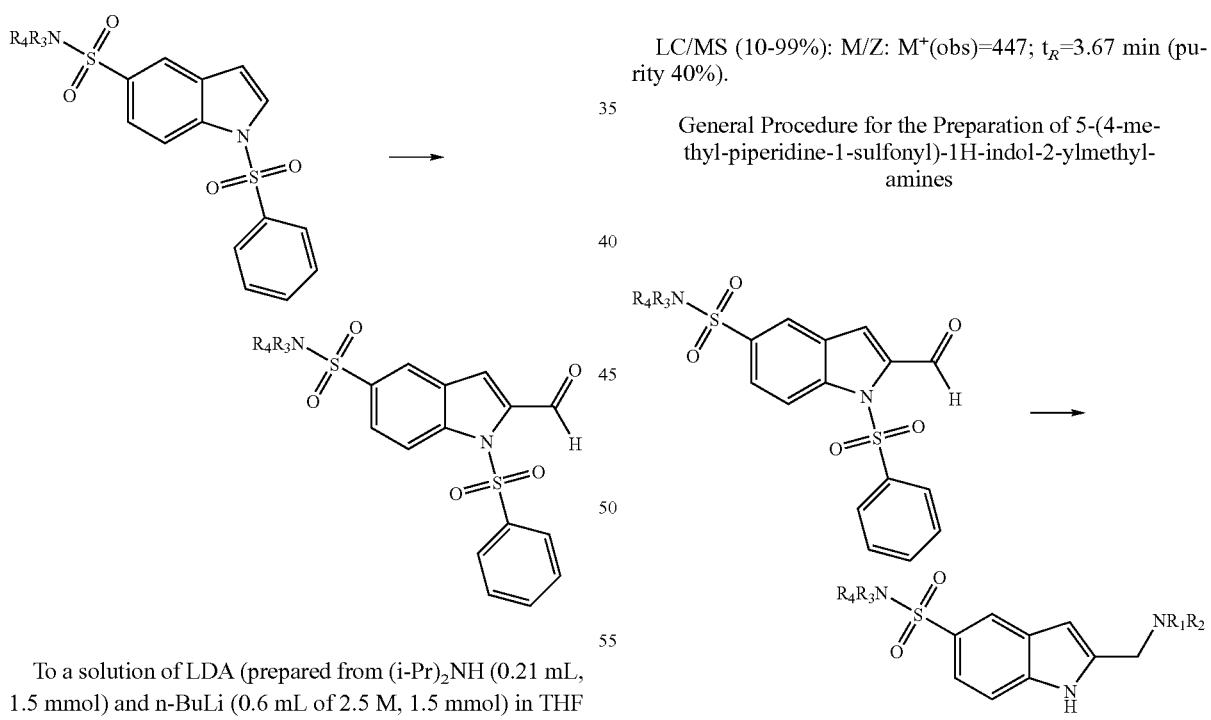

A solution of an aldehyde (0.1 mmol), amine (0.2 mmol), NaBH₃OAc (10 mg, 0.5 mmol) and AcOH (1 drop) in DCE (0.5 mL) was stirred at RT for 16 h. The crude material was taken up in MeOH (1 mL)/2.5 N NaOH (0.5 mL) and the stirred solution was heated to 60° C. for 2 h. To the reaction mixture was added 1 N HCl (1 mL) and extracted the EtOAc (2×1 mL). Evaporation and purification by HPLC gave the desired amine products.

245

-continued

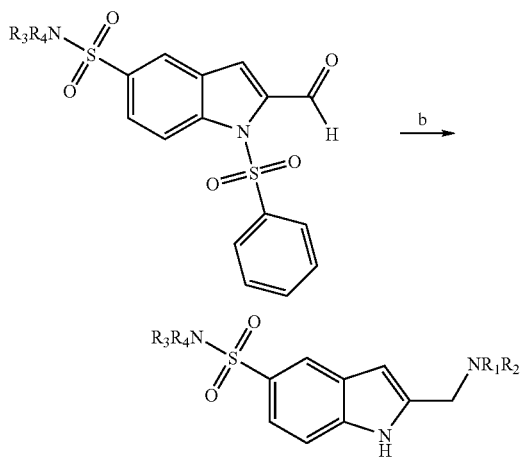

a) (i) LDA, THF; (ii) DMF
b) HNR¹R², NaBH₃CN, AcOH, DCE; (ii) NaOH, MeOH

General Procedure for the Preparation of 1-Benzenesulfonyl-5-aminosulfony)-1H-indole-2-carbaldehydes To a solution of LDA (prepared from (i-Pr)₂NH (0.21 mL, 1.5 mmol) and n-BuLi (0.6 mL of 2.5 M, 1.5 mmol) in THF (10 mL) was added the indole (1.0 mmol) at 0° C. After stirring at 0° C. for 30 min, DMF (0.12 ml, 1.5 mmol) was added in one portion and the reaction mixture was allowed to warm to RT over 2 h. The reaction mixture was poured into water (50 mL) and extracted with EtOAc (3×20 mL). The organics were combined, washed with 1 N HCl (20 mL), brine, dried (NaSO₄) and evaporated to dryness. The crude material was used without further purification.

Cyclopropyl-[5-(4-methyl-piperidine-1-sulfonyl)-1H-indol-2-ylmethyl]-amine

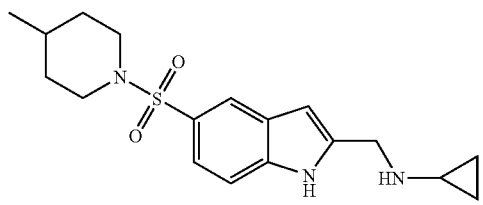

$^1$H-NMR (400 MHz, MeOD) δ 8.08 (d, J=0.9 Hz, 1H), 7.60 (m, 2H), 6.86 (s, 1H), 4.53 (s, 2H), 3.75 (d, J=12.0 Hz, 2H), 2.85 (m, 1H), 2.25 (t, J=11.2 Hz, 2H), 1.70 (d, J=9.9 Hz, 2H), 1.25 (m, 3H), 0.94 (m, 7H). LC/MS (10-99%): M/Z: M$^+$(obs)= 348; t$_R$=2.13 min.

Diethyl-[5-(4-methyl-piperidine-1-sulfonyl)-1H-indol-2-ylmethyl]-amine

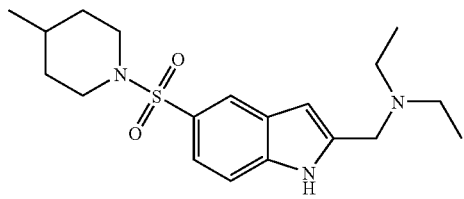

LC/MS (10-99%): M/Z: M$^+$(obs)=364; t$_R$=2.23 min.

5-(4-Methyl-piperidine-1-sulfonyl)-2-piperidin-1-ylmethyl-1H-indole

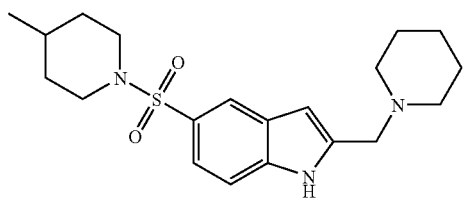

LC/MS (10-99%): M/Z: M$^+$(obs)=376; t$_R$=2.25 min.

2-(4-Methyl-piperazin-1-ylmethyl)-5-(4-methyl-piperidine-1-sulfonyl)-1H-indole

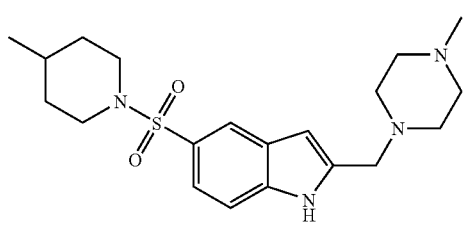

LC/MS (10-99%): M/Z: M$^+$(obs)=391; t$_R$=2.06 min.

C-6 Sulfonamides

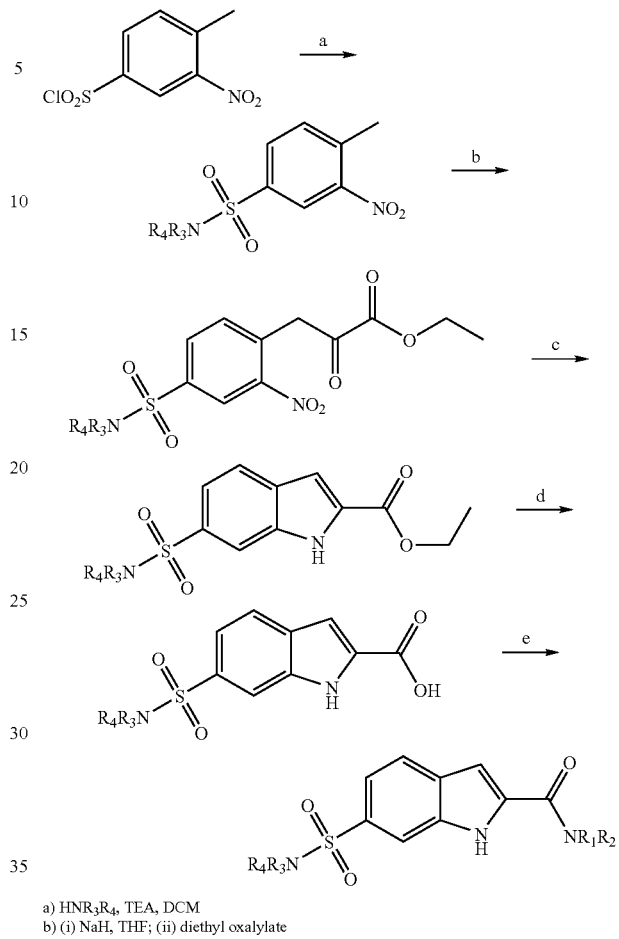

a) HNR$_3$R$_4$, TEA, DCM
b) (i) NaH, THF; (ii) diethyl oxalylate
c) Fe, AcOH
d) NaOH, MeOH
e) (i) SOCl$_2$, DMF, DCM; (ii) HNR$_1$R$_2$, TEA, DCM

General Procedure for the Preparation of 4-methyl-3-nitro-benzene-1-sulfonyl Amines

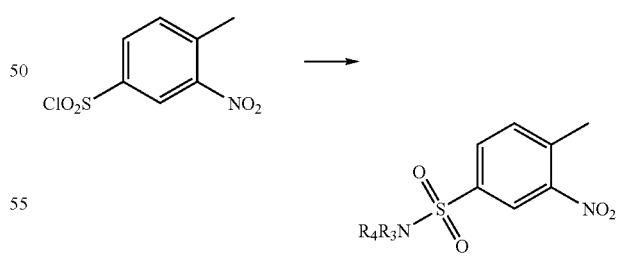

A solution of 4-methyl-3-nitrobenzene-1-sulfonyl chloride (2.36 g, 10 mmol), amine (15 mmol) and TEA (2.1 mL) in DCM (20 mL) was stirred at RT for 16 h. The reaction mixture was poured into 1 M HCl (100 ml) and the layers separated. The aqueous layer was extracted with EtOAc (3×30 mL). All the organic layers were combined, washed with 1 M HCl (2×100 mL), brine, dried (MgSO$_4$) and evaporated to dryness

4-Methyl-1-(4-methyl-3-nitro-benzenesulfonyl)-piperidine

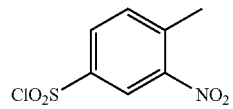  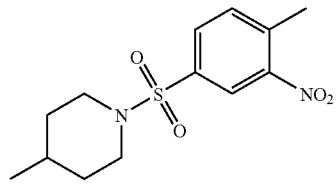

LC/MS (10-99%): M/Z: M⁺(obs)=299; $t_R$=3.40 min.

General Procedure for the Preparation of 3-[4-aminosulfonyl)-2-nitro-phenyl]-2-oxo-propionic Acid Ethyl Ester

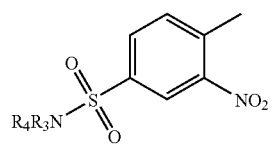  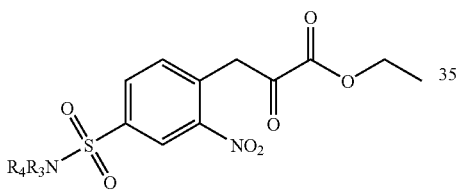

To a solution of 4-methyl-3-nitro-benzene-1-sulfonyl amine (1.0 mmol) in THF (5 mL) at 0° C. was added NaH (0.06 g, 60% in mineral oil) and the reaction mixture was stirred at 0° C. for 1 h. Diethyl oxalate (0.27 ml, 2 mmol) was added in one portion and the cooling bath was removed and the solution was stirred for 2 h. The reaction mixture was then stirred at 60° C. for 16 h. The reaction mixture was poured into water (30 mL) and extracted with EtOAc (3×10 mL). The organics were combined, washed with brine, dried (NaSO₄) and evaporated to dryness. The crude material was used in the next step with our further purification.

3-[4-(4-Methyl-piperidine-1-sulfonyl)-2-nitro-phenyl]-2-oxo-propionic Acid Ethyl Ester

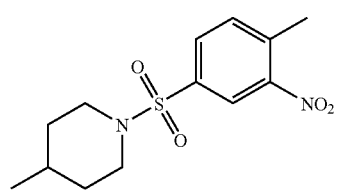 

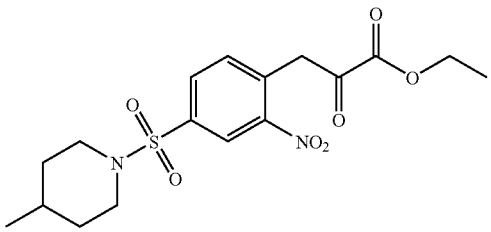

LC/MS (10-99%): M/Z: M⁺(obs)=399; $t_R$=3.39 min.

General Procedure for the Preparation of 6-aminosulfonyl-1H-indole-2-carboxylic Acid Ethyl Esters

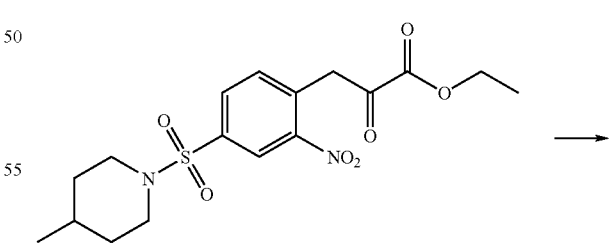

A solution of the sulfonamide (0.5 mmol) and iron (0.14 g, 2.5 mmol) in AcOH (10 ml) was refluxed for 16 h. The solution was poured into sat. aq. Na₂CO₃ (50 ml) and extracted with EtOAc (3×20 ml). The organics were combined, washed with sat. aq. Na₂CO₃, brine, dried (NaSO₄) and evaporated to dryness. The crude material was used in the next step without further purification.

6-(4-Methyl-piperidine-1-sulfonyl)-1H-indole-2-carboxylic Acid Ethyl Ester

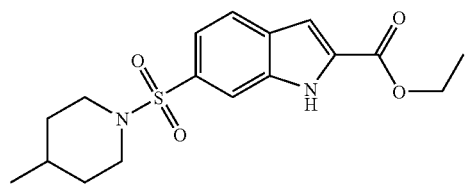

LC/MS (10-99%): M/Z: M⁺(obs)=350; $t_R$=3.46 min.

General Procedure for the Preparation of 6-aminosulfonyl-1H-indole-2-carboxylic Acids

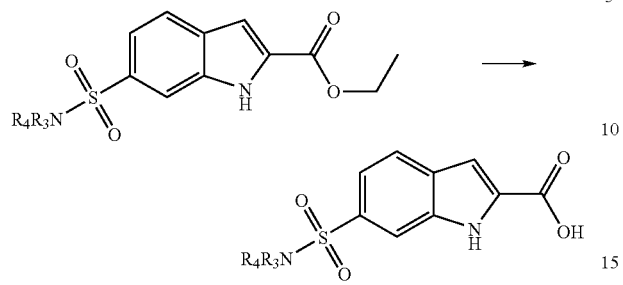

A solution of the indole (0.3 mmol) and 1 M NaOH (0.9 ml, 0.9 mmol) in MeOH (5 mL) was stirred at 60° C. for 4 h. The organics were removed under reduced pressure and the resulting aqueous solution was acidified with 1 M HCl. The precipitate was filtered and desiccated. Purification by column chromatography (10% MeOH in DCM) gave the desired products.

6-(4-Methyl-piperidine-1-sulfonyl)-1H-indole-2-carboxylic acid

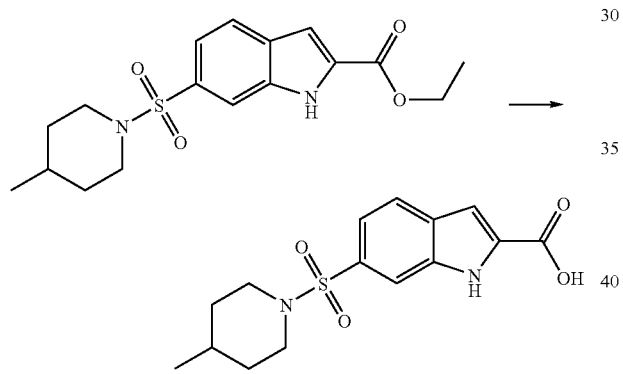

Yield: 50 mg (55%). LC/MS (10-99%): M/Z: M$^+$(obs)=323; t$_R$=2.84 min.

General Procedure for the Preparation of 6-(4-Methyl-piperidine-1-sulfonyl)-1H-indole-2-carboxylic Acid Amides

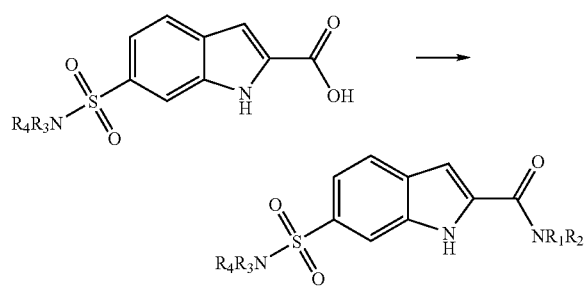

A solution of an acid (0.16 mmol) in DCM (5 ml) and SO$_2$Cl$_2$ (1 ml) was heated to 60° C. for 3 h followed by evaporation to dryness. The residue taken up in toluene (20 ml) and evaporated to dryness (repeated twice more). The material was taken up into DCM (1 ml) and 0.5 mL aliquots were added to an excess of the amine (4 mmol) and stirred at RT for 16 h. The solvents were removed and the material was taken up in 1:1 (DMSO:MeOH). Purification by HPLC gave the desired products.

6-(4-Methyl-piperidine-1-sulfonyl)-1H-indole-2-carboxylic acid dimethylamide

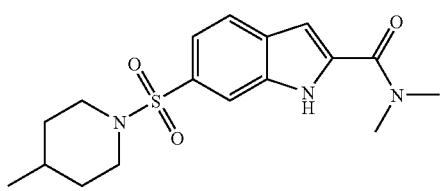

LC/MS (10-99%): M/Z: M$^+$(obs)=350; t$_R$=2.90 min.

6-(4-Methyl-piperidine-1-sulfonyl)-1H-indole-2-carboxylic acid cyclopropylamide

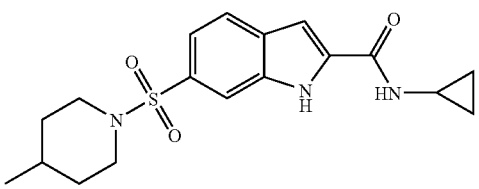

LC/MS (10-99%): M/Z: M$^+$(obs)=362; t$_R$=2.92 min.

N-1 Alkylation (Methylation)

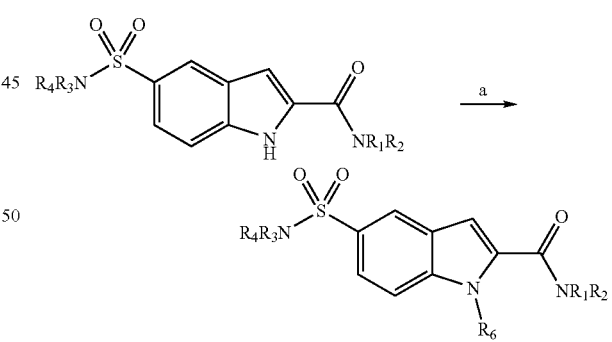

a) (i) NaH, DMF; (ii) R$^6$X

General Procedure for N-1 Alkylation

To a stirred solution of an indole (0.03 mmol) in DMF (0.2 mL) at RT was added NaH (2 mg of 60% in oil, 0.05 mmol) and the reaction mixture stirred for 10 min. MeI (3 µL, 0.05 mmol) was added and the solution stirred at RT for 2 h. The solution was diluted with 1:1 DMSO: MeOH and purification by HPLC gave the desired product.

253

5-(3,5-Dimethyl-piperidine-1-sulfonyl)-1-methyl-1H-indole-2-carboxylic acid dimethylamide

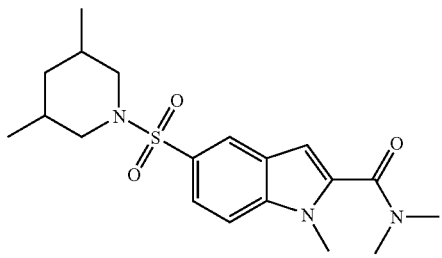

$^1$H-NMR (400 MHz, CDCl$_3$) δ 8.12 (d, J=1.3 Hz, 1H), 7.68 (dd, J=8.7, 1.8 Hz, 1H), 7.48 (d, J=8.8 Hz, 1H), 6.78 (d, J=0.7 Hz, 1H), 3.91 (s, 3H), 3.78 (dd, J=10.7, 3.8 Hz, 2H), 3.22 (s, 6H), 1.80 (m, 2H), 1.68 (m, 2H), 1.25 (m, 1H), 0.86 (d, J=6.5 Hz, 6H), 0.43 (dd, J=24.6, 11.7 Hz, 1H). LC/MS (10-99%): M/Z: M$^+$(obs)=378; t$_R$=3.10 min.

1-Methyl-5-(4-methyl-piperidine-1-sulfonyl)-1H-indole-2-carboxylic acid diethyl amide

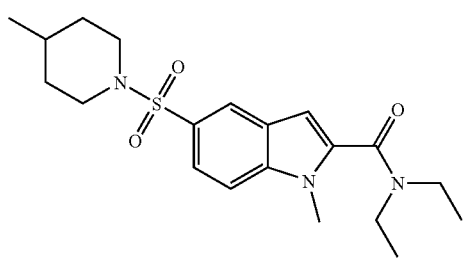

LC/MS (10-99%): M/Z: M$^+$(obs) 392; t$_R$=3.27 min.

[5-(3,5-Dimethyl-piperidine-1-sulfonyl)-1-methyl-1H-indol-2-yl]-piperidin-1-yl-methanone

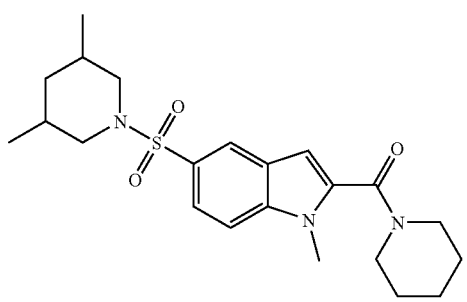

LC/MS (10-99%): M/Z: M$^+$(obs)=418; t$_R$=3.55 min.

254

5-(3,5-Dimethyl-piperidine-1-sulfonyl)-1-methyl-1H-indole-2-carboxylic acid cyclopropylmethyl-propyl-amide

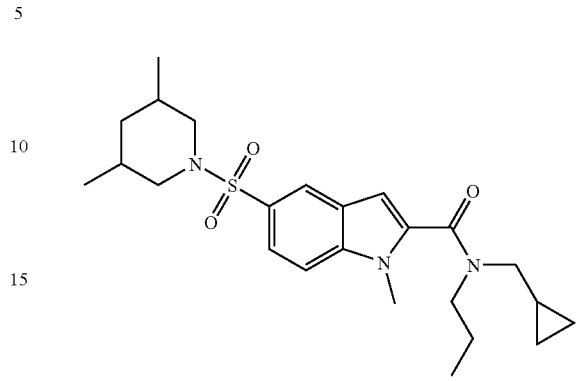

LC/MS (10-99%): M/Z: M$^+$(obs)=446; t$_R$=3.84 min.

N-1 Sulfonamides

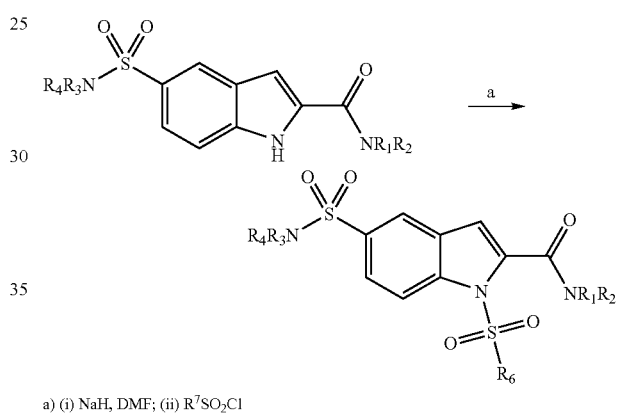

a) (i) NaH, DMF; (ii) R$^7$SO$_2$Cl

General Procedure for the Preparation of N-1 Sulfonamides

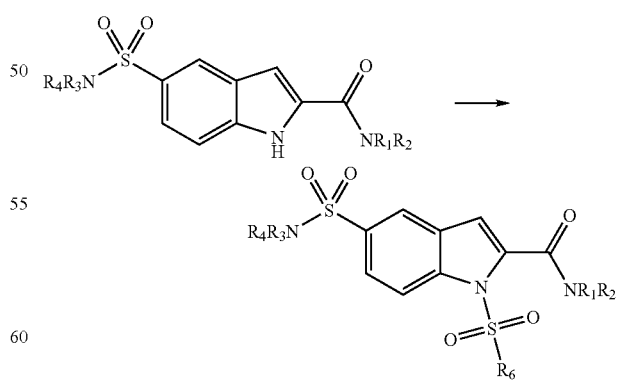

To a stirred solution of an indole (0.1 mmol) in DMF (0.8 mL) at RT was added NaH (8 mg of 60% in oil, 0.2 mmol) and the reaction mixture stirred for 15 min. A 0.2 mL aliquot of this solution was added to the sulfonyl chloride and the reaction was stirred at RT for 16 h. The solution was diluted with 1:1 (DMSO:MeOH) and purification by HPLC gave the desired product.

[5-(3,5-Dimethyl-piperidine-1-sulfonyl)-1-(propane-2-sulfonyl)-1H-indol-2-yl]-piperidin-1-yl-methanone

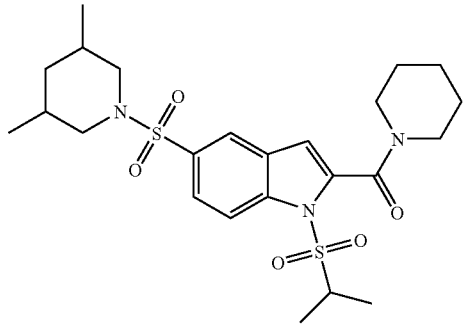

LC/MS (10-99%): M/Z: M+(obs)=509; $t_R$=4.02 min.

[5-(3,5-Dimethyl-piperidine-1-sulfonyl)-1-(propane-1-sulfonyl)-1H-indol-2-yl]-piperidin-1-yl-methanone

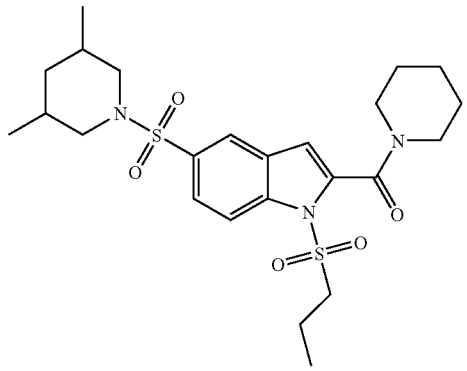

LC/MS (10-99%): M/Z: M+(obs) 510; $t_R$=4.05 min.

[5-(3,5-Dimethyl-piperidine-1-sulfonyl)-1-(4-fluoro-benzenesulfonyl)-1H-indol-2-yl]-piperidin-1-yl-methanone

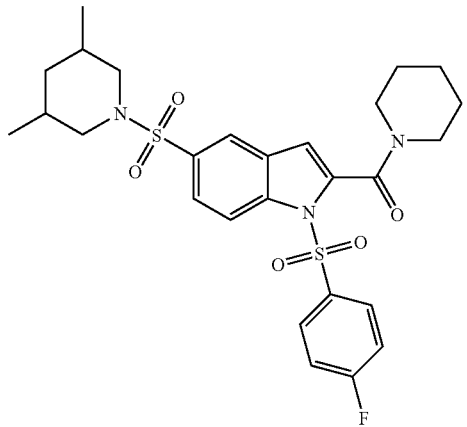

LC/MS (10-99%): M/Z: M+(obs)=562; $t_R$=4.17 min.

[5-(3,5-Dimethyl-piperidine-1-sulfonyl)-1-(4-methoxy-benzenesulfonyl)-1H-indol-2-yl]-piperidin-1-yl-methanone

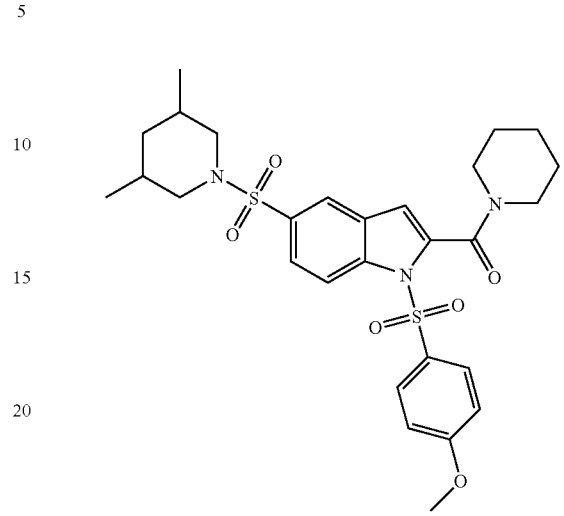

LC/MS (10-99%): M/Z: M+(obs)=574; $t_R$=4.15 min.

N-1 Alkylations and Further Amine Formation

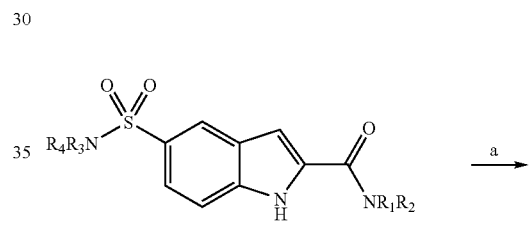

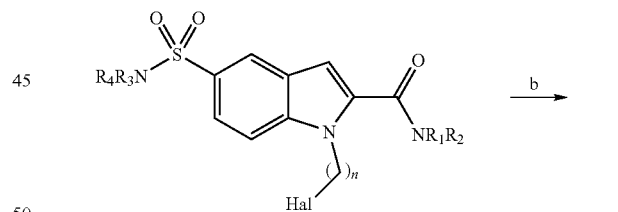

a) (i) NaH, DMF; (ii) Hal(CH$_2$)$_n$Hal
b) HNR'R', (n-Bu)$_4$NI (cat.)

257

General Procedure for N-1 Alkylations Followed by Aminations

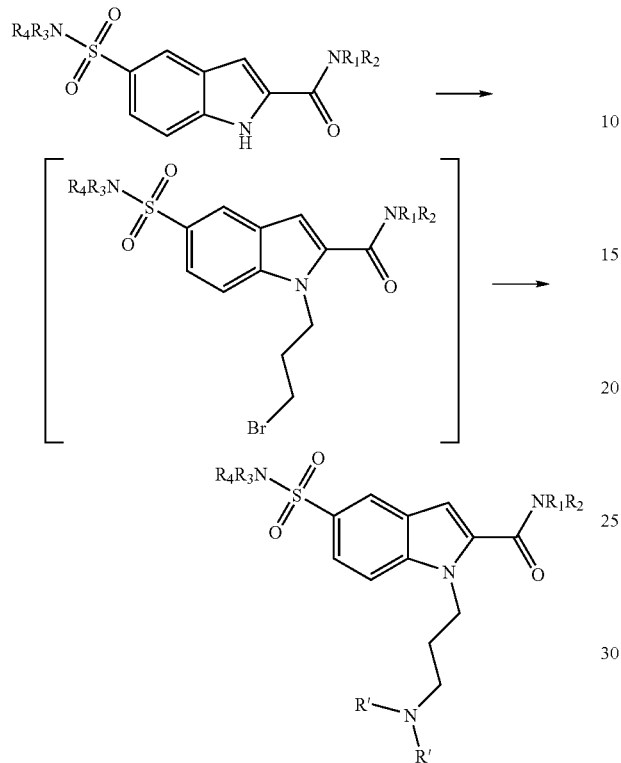

To a stirred solution of an indole (0.05 mmol) in DMF (0.4 mL) at RT was added NaH (4 mg of 60% in oil, 0.4 mmol) and the reaction mixture stirred for 30 min. A 0.2 mL aliquot of this solution was added to a solution of the electrophile (0.05 mmol) in DMF (0.2 mL) and the reaction was stirred at 60° C. for 2 h. To this solution was added the amine (0.25 mmol) and (n-Bu)$_4$NI (1 mg) and the reaction mixture was stirred at 100° C. for 16 h. The solution was diluted with 1:1 (DMSO:MeOH) and purification by HPLC gave the desired product.

5-(3,5-Dimethyl-piperidine-1-sulfonyl)-1-[2-(4-methyl-piperazin-1-yl)-ethyl]-1H-indole-2-carboxylic Acid Diethylamide

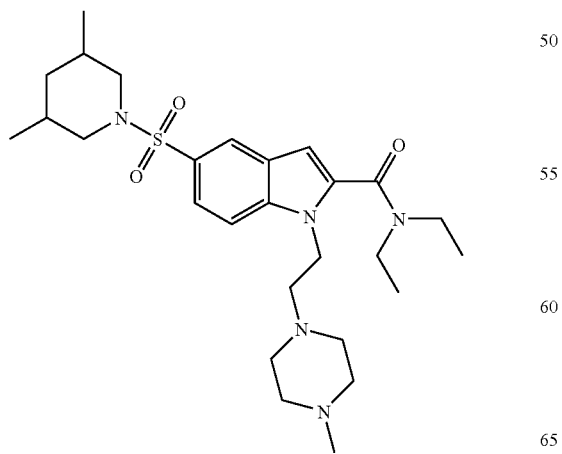

LC/MS (10-99%): M/Z: M$^+$(obs)=517; t$_R$=2.89 min.

258

1-(3-Dimethylamino-propyl)-5-(3,5-dimethyl-piperidine-1-sulfonyl)-1H-indole-2-carboxylic Acid Diethylamide LC/MS (10-99%): M/Z: M$^+$(obs)=477; t$_R$=2.57 min.

5-(3,5-Dimethyl-piperidine-1-sulfonyl)-1-[3-(4-methyl-piperazin-1-yl)-propyl]-1H-indole-2-carboxylic Acid Diethylamide LC/MS (10-99%): M/Z: M$^+$(obs)=531; t$_R$=2.80 min.

N-1 Alkylations (Epichlorohydrin)

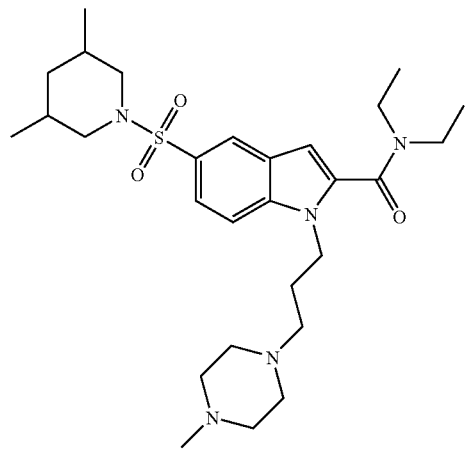

259

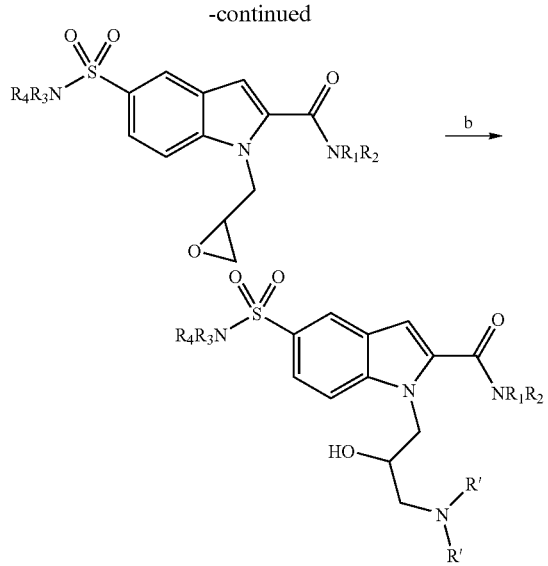

a) (i) NaH, DMF; (ii) epichlorohydrin
b) HNR'R'

General Procedure for N-1 Alkylations with Epichlorohydrin

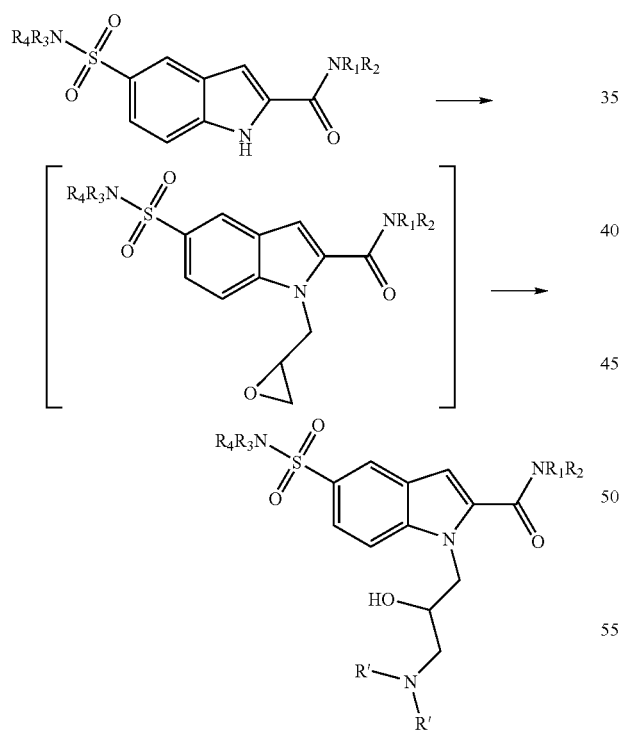

To a stirred solution of an indole (0.05 mmol) in DMF (0.4 mL) at RT was added NaH (4 mg of 60% in oil, 0.4 mmol) and the reaction mixture stirred for 30 min. A 0.2 mL aliquot of this solution was added to a solution of epichlorohydrin (0.03 mL, 0.05 mmol) in DMF (0.2 mL) and the reaction was stirred at 60° C. for 2 h. To this solution was added the amine (0.25 mmol) and the reaction mixture was stirred at 100° C. for 16

260 h. The solution was diluted with 1:1 DMSO MeOH and purification by HPLC gave the desired product.

1-(3-Dimethylamino-2-hydroxy-propyl)-5-(3,5-dimethyl-piperidine-1-sulfonyl)-1H-indole-2-carboxylic acid diethylamide

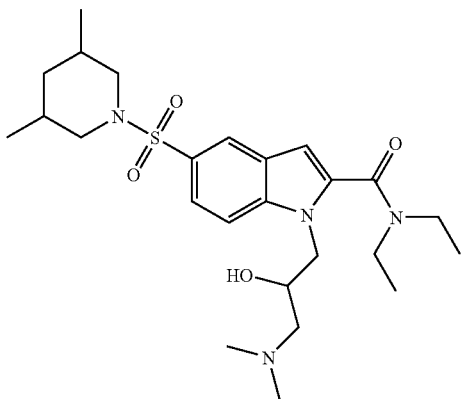

LC/MS (10-99%): M/Z: M$^+$(obs) 493; $t_R$=2.51 min.

5-(3,5-Dimethyl-piperidine-1-sulfonyl)-1-[2-hydroxy-3-(4-methyl-piperazin-1-yl)-propyl]-1H-indole-2-carboxylic acid diethylamide

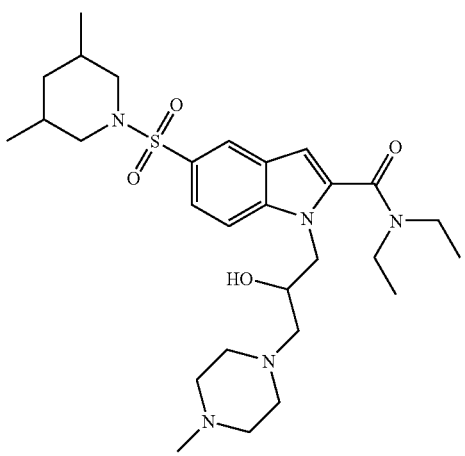

LC/MS (10-99%): M/Z: M$^+$(obs)=547; $t_R$=2.72 min.

Reverse Indole Sulfonamides

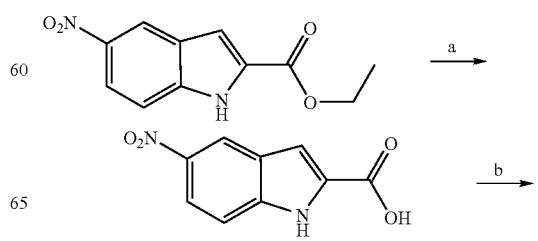

-continued

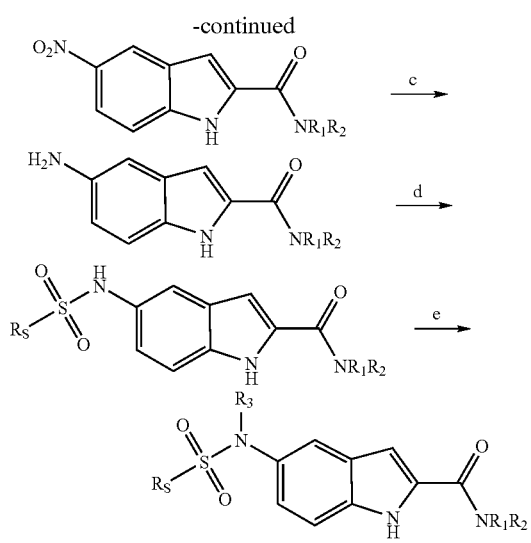

a) NaOH, MeOH
b) (i) SOCl₂, DMF, DCM; (ii) HNR₁R₂, TEA, DCM;
c) Fe, AcOH or Pd/C, H₂, MeOH
d) R$_S$SO₂Cl, Py
e) R₃OH, DEAD, P(Ph)₃, THF

5-Nitro-1H-indole-2-carboxylic Acid

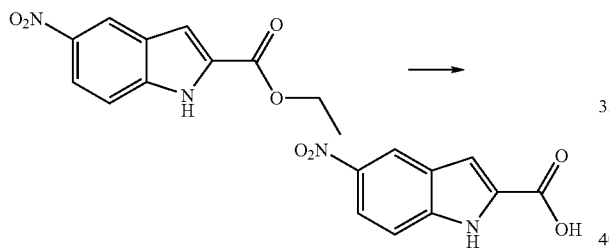

A solution of the indole (2.66 g, 11.4 mmol) and 5 N NaOH (3.4 mL, 17.1 mmol) in THF (10 mL) and MeOH (30 mL) was stirred at 50° C. for 16 h. The solution was reduced by 75% and poured into water (200 ml) and the solution was acidified to pH 1 with 1 N HCl. The precipitate was filtered, washed with water (3×) and desiccated to give the desired product as a brown solid (2.3 g, 98%). LC/MS (10-99%): M/Z: M⁺(obs)= 207; $t_R$=2.29 min.

General Procedure for the Preparation of
5-Nitro-1H-indole-2-carboxylic Acid Amides

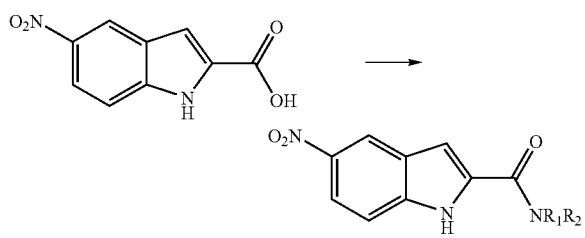

A solution of the indole (2.06 g, 10 mmol), amine (20 mmol) and EDCI (2.11 g, 11 mmol) in DCM (20 ml) and DMF (17 ml) was stirred at RT. At this time more amine (20 mmol) and EDCI (2.11 g, 11 mmol) was added and the reaction mixture was stirred at 60° C. for 16 h. The reaction mixture was poured into 1 M HCl (100 mL) and extracted with EtOAc (3×50 mL). The organics were combined, washed with 1 M HCl (2×100 mL), brine (100 mL), dried (MgSO₄), and evaporated to dryness to give the desired products.

5-Nitro-1H-indole-2-carboxylic Acid
Cyclopropylamide

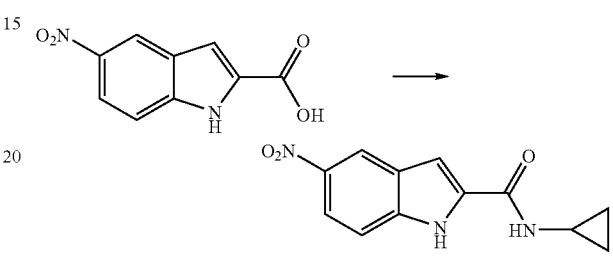

LC/MS (10-99%): M/Z: M⁺(obs) 246; $t_R$=2.41 min.

General Procedure A for the Preparation of
5-Amino-1H-indole-2-carboxylic Acid Amides

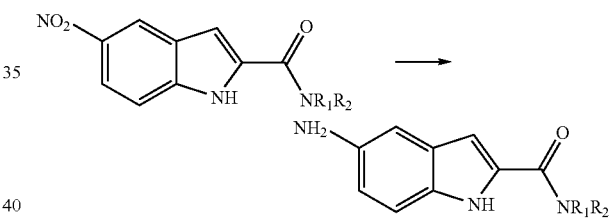

A solution of a nitro compound (3 mmol) and iron (0.83 g, 15 mmol) in AcOH (10 ml) was heated at 100° C. for 16 h. The solution was poured into sat. aq. Na₂CO₃ (50 ml), the pH was adjusted to 10 with solid Na₂CO₃ and the solution was extracted with EtOAc (4×20 ml). The organics were combined, washed with brine, dried (Na2SO4) and evaporated to dryness. Column chromatography (2% to 15% MeOH in DCM) gave the desired products.

5-Amino-1H-indole-2-carboxylic Acid
Cyclopropylamide

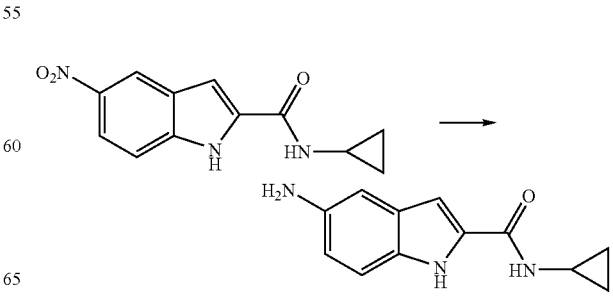

Yield: 300 mg (47%). LC/MS (10-99%): M/Z: M+(obs) =215; $t_R$=0.47 min.

General Procedure B for the Preparation of 5-Amino-1H-indole-2-carboxylic Acid Amides

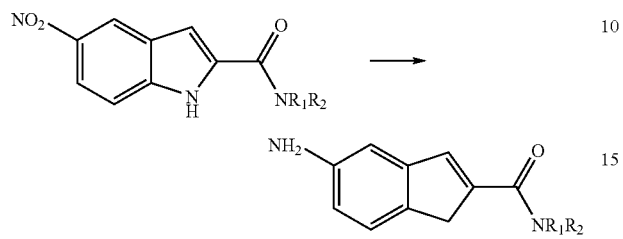

A solution of a nitroindole (1.3 mmol) and Pd/C (30 mg) in MeOH (20 mL) was stirred under an atmosphere of hydrogen for 16 h at RT. The solution was filtered through Celite and the Celite washed with methanol (2×). Evaporation of the solvent gave the desired products.

5-Amino-1H-indole-2-carboxylic Acid Dimethylamide

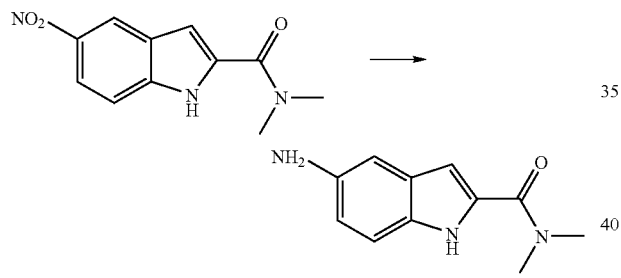

LC/MS (10-99%): M/Z: M+(obs)=204; $t_R$=0.38 min.

General Preparation of 5-Methanesulfonylamino-1H-indole-2-carboxylic Acid Amides

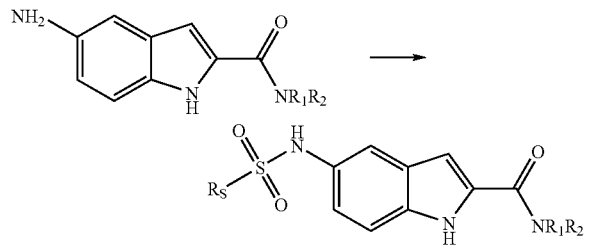

A solution of an aminoindole (0.47 mmol) and a sulfonyl chloride (0.52 mmol) in pyridine (1 mL) was stirred at RT for 16 h. The reaction mixture was diluted with 1:1 DMSO: MeOH (1 mL) and purification by HPLC gave the desired products.

5-Methanesulfonylamino-1H-indole-2-carboxylic Acid Cyclopropylamide

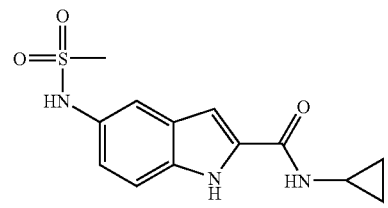

LC/MS (10-99%): M/Z: M+(obs)=294; $t_R$=1.76 min.

5-(Propane-2-sulfonylamino)-1H-indole-2-carboxylic Acid Cyclopropylamide

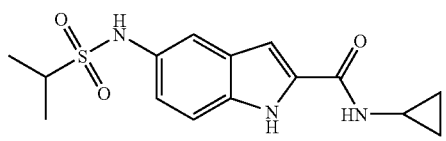

LC/MS (10-99%): M/Z: M+(obs)=322; $t_R$=2.09 min.

5-Benzenesulfonylamino-1H-indole-2-carboxylic Acid Cyclopropylamide

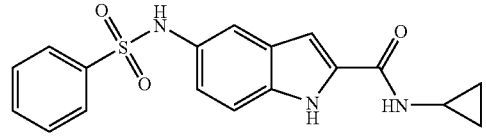

1H-NMR (400 MHz, DMSO-d6) δ 11.53 (s, 1H, NH), 9.87 (s, 1H, NH), 8.40 (d, J=4.0 Hz, 1H, NH), 7.67 (d, J=1.5 Hz, 1H), 7.65 (dd, J=1.7, 1.7 Hz, 1H), 7.58-7.54 (m, 1H), 7.50 (dd, J=6.3, 1.4 Hz, 1H), 7.47 (dd, J=1.4, 1.4 Hz, 1H), 7.24 (d, J=8.7 Hz, 1H), 7.22 (d, J=1.8 Hz, 1H), 6.95 (d, J=1.5 Hz, 1H), 6.88 (dd, J=8.8, 2.1 Hz, 1H), 2.86-2.79 (m, 1H), 0.74-0.69 (m, 2H), 0.58-0.54 (m, 2H). LC/MS (10-99%): M/Z: M+(obs)= 356; $t_R$=2.38 min.

General Procedure for the Alkylation of Sulfonamides

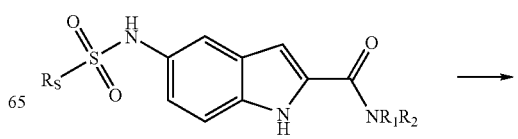

-continued

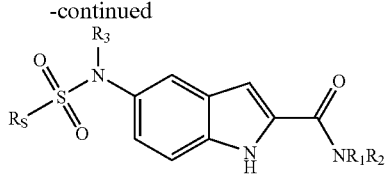

To a stirred solution of the of the indolesulfonamide (0.03 mmol), alcohol (0.1 mmol) and triphenylphosphine (26 mg, 0.1 mmol) in THF (0.3 mL) at 0° C. was added DEAD (12 μL, 0.1 mmol) and the reaction mixture was stirred from 0° C. to RT over 16 h. The reaction mixture was quenched with 0.1 ml AcOH, diluted with 1:1 MeOH: DMSO, and purification by HPLC gave the desired products.

5-(Methanesulfonyl-methyl-amino)-1H-indole-2-carboxylic Acid Cyclopropylamide

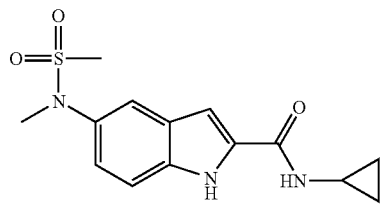

$^1$H-NMR (400 MHz, MeOD) δ 7.68 (d, J=2.0 Hz, 1H), 7.48 (d, J=8.8 Hz, 1H), 7.30 (dd, J=8.8, 2.1 Hz, 1H), 7.09 (s, 1H), 3.35 (s, 3H), 2.93 (s, 3H), 2.86 (m, 1H), 0.83 (m, 2H), 0.68 (m, 2H); LC/MS (10-99%): M/Z: M$^+$(obs)=308; $t_R$=2.03 min.

5-(Methanesulfonyl-propyl-amino)-1H-indole-2-carboxylic Acid Cyclopropylamide

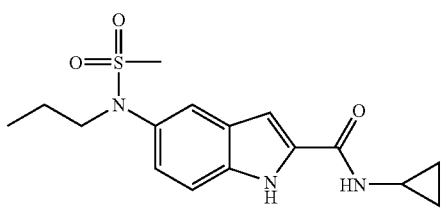

LC/MS (10-99%): M/Z: M$^+$(obs) 336; $t_R$=2.33 min.

5-(Cyclohexyl-methanesulfonyl-amino)-1H-indole-2-carboxylic Acid Cyclopropyl Amide

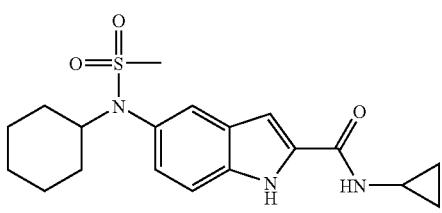

LC/MS (10-99%): M/Z: M$^+$(obs) 376; $t_R$=2.77 min.

5-[Methyl-(propane-2-sulfonyl)-amino]-1H-indole-2-carboxylic Acid Cyclopropyl Amide

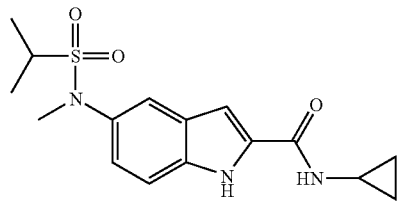

LC/MS (10-99%): M/Z: M$^+$(obs)=336; $t_R$=2.35 min.

5-[Cyclopropylmethyl-(propane-2-sulfonyl)-amino]-1H-indole-2-carboxylic Acid Cyclopropylamide

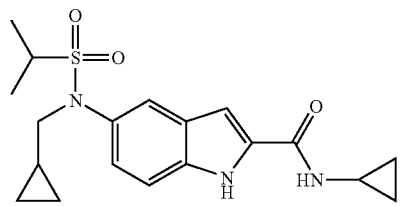

LC/MS (10-99%): M/Z: M$^+$(obs)=376; $t_R$=2.78 min.

5-[(2-Dimethylamino-ethyl)-(propane-2-sulfonyl)-amino]-1H-indole-2-carboxylic Acid Cyclopropylamide

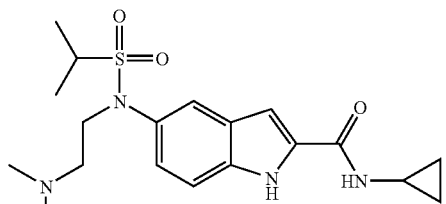

LC/MS (10-99%): M/Z: M$^+$(obs)=3793; $t_R$=1.66 min.

5-[Cyclohexyl-(propane-2-sulfonyl)-amino]-1H-indole-2-carboxylic Acid Cyclo Propylamide

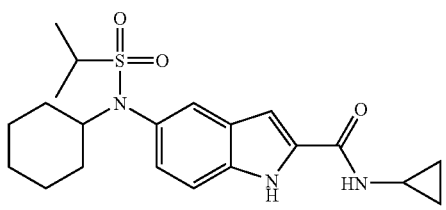

LC/MS (10-99%): M/Z: M$^+$(obs)=404; $t_R$=3.05 min.

267

5-(Benzenesulfonyl-methyl-amino)-1H-indole-2-carboxylic Acid Cyclopropylamide

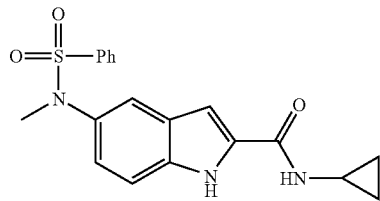

LC/MS (10-99%): M/Z: M⁺(obs)=370; $t_R$=2.71 min.

5-(Benzenesulfonyl-propyl-amino)-1H-indole-2-carboxylic Acid Cyclopropylamide

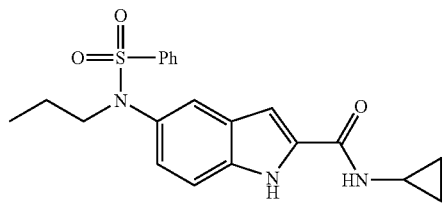

LC/MS (10-99%): M/Z: M⁺(obs)=398; $t_R$=2.94 min.

5-(Benzenesulfonyl-cyclopropylmethyl-amino)-1H-indole-2-carboxylic Acid Cyclo Propylamide

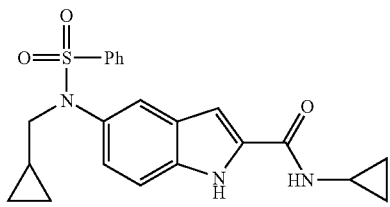

LC/MS (10-99%): M/Z: M⁺(obs) 410; $t_R$=3.02 min.

5-[Benzenesulfonyl-(2-dimethylamino-ethyl)-amino]-1H-indole-2-carboxylic Acid Cyclopropylamide

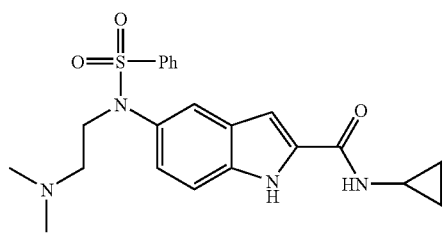

LC/MS (10-99%): M/Z: M⁺(obs) 427; $t_R$=1.93 min.

268

5-(Benzenesulfonyl-cyclohexyl-amino)-1H-indole-2-carboxylic Acid Cyclopropyl Amide

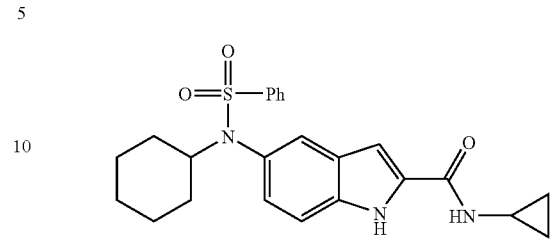

LC/MS (10-99%): M/Z: M⁺(obs) 438; $t_R$=3.31 min.

5-(Benzenesulfonyl-benzyl-amino)-1H-indole-2-carboxylic Acid Cyclopropylamide

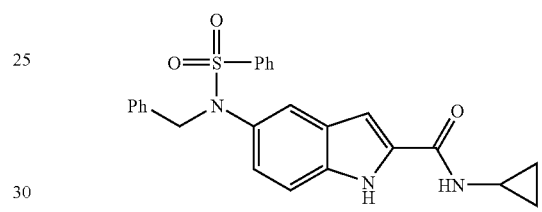

LC/MS (10-99%): M/Z: M⁺(obs)=446; $t_R$=3.15 min.

Synthesis of Sulfones and Sulfoxides

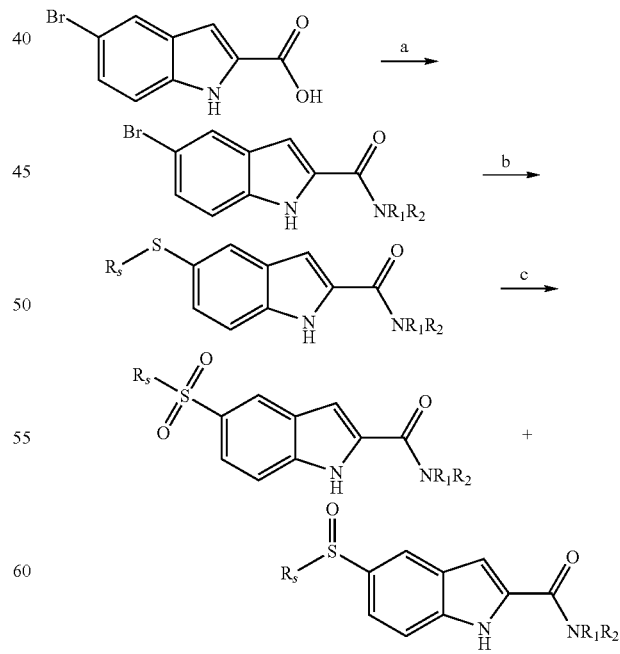

a) (i) SOCl₂, DMF, DCM; (ii) HNR₁R₂, TEA, DCM
b) R$_s$SH, Xantphos, Pd₂dba₃, DⁱPEA, dioxane
c) m-CPBA, DCM

General Procedure for the Preparation of 5-Bromo-1H-indole-2-carboxamides

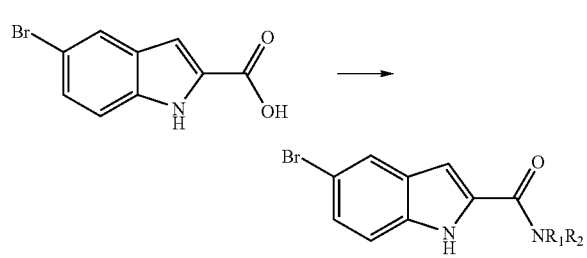

These compounds were synthesized following the general procedure for the preparation of 1-Benzenesulfonyl-5-sulfamoyl-3-$R^5$-1H-indole-2-carboxamides.

5-Bromo-N,N-diethyl-1H-indole-2-carboxamide

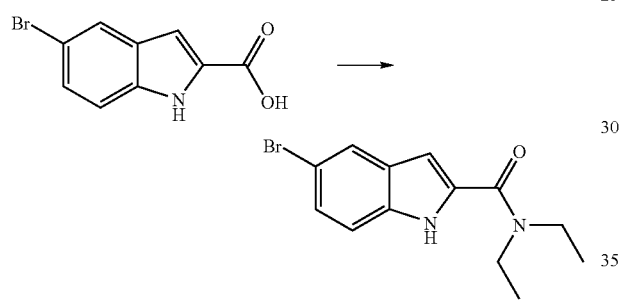

Yellow solid (1.3 g, quant.) LC/MS (10-99%): M/Z: $M^+$(obs)=295; $t_R$=3.15 min.

General Procedure for the Preparation of 5-thioether-1H-indole-2-carboxamides

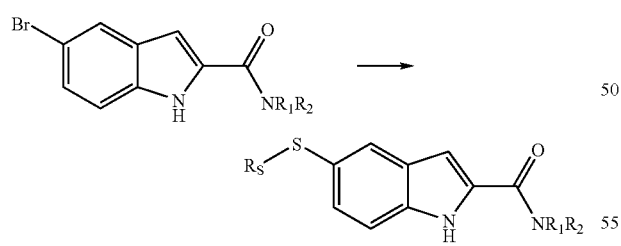

A solution of 5-bromo-1H-indole-2-carboxamide (0.3 mmol), thiol (0.45 mmol), Xantphos (9 mg, 0.015 mmol), $Pd_2dba_3$ (7 mg, 0.075 mmol) and DPEA (0.10 ml, 0.6 mmol) in dioxane (0.5 mL) was stirred at 100° C. for 16 h. The reaction mixture was poured into water (40 ml) and extracted with EtOAc (3×10 ml). The organics were combined, washed with brine, dried ($NaSO_4$) and evaporated to dryness. Purification by column chromatography (0% to 2% MeOH in DCM) gave the desired products.

5-(Cyclohexylthio)-N,N-diethyl-1H-indole-2-carboxamide

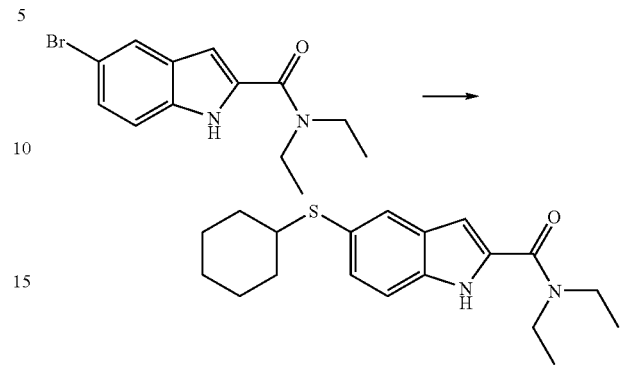

LC/MS (10-99%): M/Z: $M^+$(obs)=331; $t_R$=3.89 min;

General Procedure for the Preparation of 5-sulfinyl-1H-indole-2-carboxamides and 5-sulfonyl-1H-indole-2-carboxamides

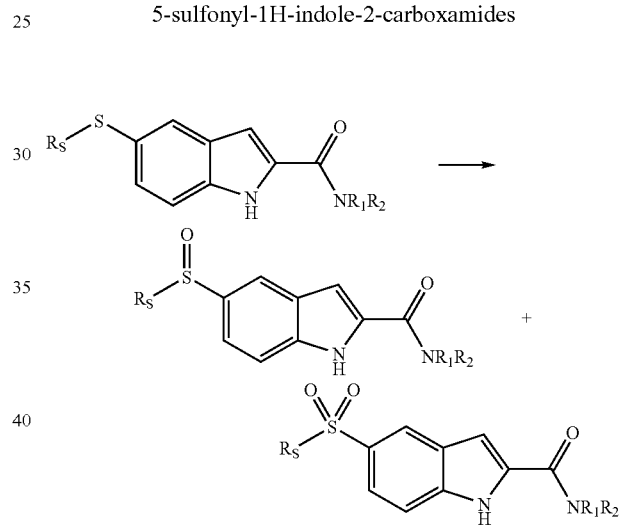

To a solution of a 5-thioether-1H-indole-2-carboxamide (0.13 mmol) in DCM (1 mL) was added m-CPBA (0.057 g, 0.20 mmol) and the reaction mixture stirred for 16 h at RT. The solution was evaporated to dryness and the products separated by HPLC.

5-(Cyclohexylsulfinyl)-N,N-diethyl-1H-indole-2-carboxamide

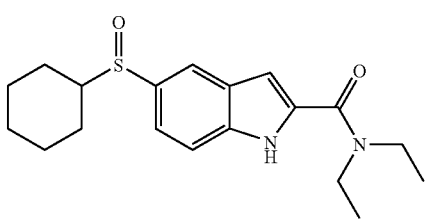

LC/MS (10-99%): M/Z: $M^+$(obs)=347; $t_R$=2.65 min.

5-(Cyclohexylsulfonyl)-N,N-diethyl-1H-indole-2-carboxamide

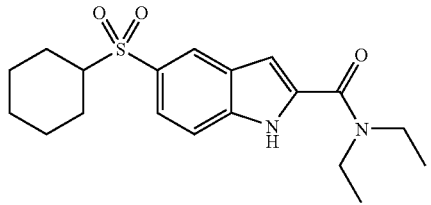

$^1$H-NMR (400 MHz, MeOD) δ 8.25 (s, 1H), 7.67 (m, 2H), 7.05 (s, 1H), 3.70 (s br, 5H), 3.07 (m, 1H), 2.04 (d, J=10.0 Hz, 2H), 1.85 (d, J=10.0 Hz, 2H), 1.68 (d, J=12.8 Hz, 1H), 1.29 (m, 10H); LC/MS (10-99%): M/Z: M$^+$(obs)=362; $t_R$=2.89 min.

Many modifications and variations of the embodiments described herein may be made without departing from the scope, as is apparent to those skilled in the art. The specific embodiments described herein are offered by way of example only.

APPENDIX A

TABLE 2

| Cmpd No. | ANALYTICAL DATA LC-MS M + 1 | LC-RT min |
|---|---|---|
| 1 | 378.0 | 1.965 |
| 2 | 440.0 | 2.054 |
| 3 | 418.0 | 1.898 |
| 5 | 439.0 | 1.921 |
| 6 | 462.0 | 2.149 |
| 7 | 405.0 | 1.967 |
| 8 | 433.0 | 1.792 |
| 9 | 418.0 | 2.473 |
| 10 | 350.0 | 5.864 |
| 11 | 376.0 | 2.25 |
| 12 | 390.0 | 8.259 |
| 13 | 453.0 | 2.039 |
| 14 | 406.0 | 4.814 |
| 15 | 392.0 | 9.097 |
| 16 | 419.0 | 2.119 |
| 17 | 417.0 | 2.216 |
| 18 | 376.0 | 6.377 |
| 20 | 373.1 | 2.21 |
| 21 | 392.0 | 2.18 |
| 22 | 338.0 | 2.376 |
| 23 | 434.0 | 1.839 |
| 24 | 456.5 | 2.19 |
| 25 | 406.3 | 1.84 |
| 26 | 378.0 | 2.529 |
| 27 | 447.0 | 1.84 |
| 29 | 432.0 | 2.614 |
| 30 | 349.0 | 1.738 |
| 31 | 392.0 | 2.118 |
| 32 | 435.0 | 3.4 |
| 33 | 432.0 | 10.61 |
| 34 | 412.0 | 1.867 |
| 35 | 399.0 | 2.94 |
| 36 | 411.0 | 1.813 |
| 37 | 349.0 | 1.965 |
| 38 | 434.0 | 1.973 |
| 40 | 440.0 | 1.999 |
| 41 | 389.0 | 1.889 |
| 42 | 418.0 | 9.929 |
| 43 | 426.0 | 1.998 |
| 44 | 426.0 | 2.109 |

TABLE 2-continued

| Cmpd No. | ANALYTICAL DATA LC-MS M + 1 | LC-RT min |
|---|---|---|
| 46 | 377.0 | 1.913 |
| 47 | 379.0 | 2.037 |
| 48 | 426.0 | 1.927 |
| 49 | 467.0 | 2.114 |
| 50 | 372.1 | 2.21 |
| 51 | 324.0 | 1.799 |
| 52 | 405.0 | 2.1 |
| 53 | 454.0 | 2.145 |
| 54 | 447.0 | 1.791 |
| 55 | 403.0 | 2.062 |
| 56 | 468.0 | 2.439 |
| 58 | 418.0 | 10.237 |
| 59 | 404.0 | 9.046 |
| 60 | 445.0 | 2.414 |
| 61 | 418.0 | 2.332 |
| 62 | 432.0 | 2.737 |
| 64 | 390.0 | 8.074 |
| 65 | 392.0 | 4.116 |
| 66 | 446.0 | 3.15 |
| 67 | 406.0 | 2.183 |
| 68 | 419.0 | 1.834 |
| 69 | 403.0 | 1.965 |
| 71 | 320.3 | 2.01 |
| 72 | 462.0 | 1.777 |
| 74 | 403.0 | 1.97 |
| 75 | 406.0 | 6.768 |
| 77 | 349.0 | 1.721 |
| 78 | 461.0 | 1.925 |
| 80 | 432.0 | 11.065 |
| 81 | 417.0 | 2.079 |
| 82 | 419.0 | 2.066 |
| 83 | 392.0 | 2.075 |
| 84 | 462.0 | 1.771 |
| 87 | 378.0 | 2.097 |
| 88 | 477.0 | 7.626 |
| 89 | 454.0 | 2.364 |
| 90 | 440.0 | 2.006 |
| 91 | 418.0 | 1.997 |
| 92 | 392.0 | 2.118 |
| 94 | 454.0 | 2.322 |
| 95 | 380.0 | 2.123 |
| 96 | 390.0 | 2.016 |
| 97 | 426.0 | 1.928 |
| 98 | 439.0 | 2.029 |
| 99 | 412.0 | 1.87 |
| 100 | 404.0 | 2.199 |
| 101 | 403.0 | 2.074 |
| 102 | 418.0 | 2.331 |
| 103 | 431.0 | 2.23 |
| 104 | 375.0 | 1.873 |
| 105 | 410.0 | 3.02 |
| 106 | 448.0 | 1.847 |
| 107 | 562.0 | 4.14 |
| 108 | 348.0 | 2.13 |
| 110 | 378.0 | 2.097 |
| 111 | 420.0 | 1.79 |
| 112 | 392.0 | 2.215 |
| 113 | 392.0 | 2.085 |
| 115 | 401.3 | 2.71 |
| 116 | 377.0 | 1.857 |
| 117 | 405.0 | 1.981 |
| 119 | 390.0 | 2.13 |
| 120 | 425.0 | 1.872 |
| 121 | 391.0 | 2.06 |
| 122 | 404.0 | 2.148 |
| 124 | 418.0 | 9.91 |
| 125 | 434.0 | 1.853 |
| 126 | 417.0 | 3.278 |
| 127 | 431.0 | 2.216 |
| 128 | 418.0 | 10.152 |
| 130 | 349.0 | 1.745 |
| 131 | 350.0 | 1.833 |
| 133 | 379.1 | 2.29 |
| 135 | 545.3 | 2.44 |

TABLE 2-continued

ANALYTICAL DATA

| Cmpd No. | LC-MS M + 1 | LC-RT min |
|---|---|---|
| 137 | 420.0 | 2.427 |
| 138 | 406.0 | 2.2 |
| 139 | 362.0 | 2.92 |
| 140 | 405.0 | 2.123 |
| 141 | 391.0 | 2.025 |
| 142 | 363.0 | 1.793 |
| 143 | 389.0 | 2.431 |
| 144 | 420.0 | 7.174 |
| 145 | 350.0 | 1.888 |
| 146 | 403.0 | 1.972 |
| 147 | 403.0 | 2.084 |
| 148 | 404.0 | 9.7 |
| 149 | 408.0 | 2.174 |
| 150 | 364.0 | 1.976 |
| 151 | 370.1 | 2.53 |
| 153 | 432.0 | 2.583 |
| 154 | 444.0 | 9.451 |
| 155 | 336.0 | 4.087 |
| 156 | 462.0 | 1.96 |
| 157 | 383.0 | 2.98 |
| 158 | 463.0 | 1.827 |
| 159 | 420.0 | 2.49 |
| 160 | 432.0 | 2.008 |
| 161 | 462.0 | 1.983 |
| 162 | 380.0 | 3.227 |
| 163 | 406.0 | 5.441 |
| 164 | 406.0 | 2.417 |
| 165 | 405.0 | 1.914 |
| 166 | 433.0 | 1.791 |
| 168 | 391.0 | 1.879 |
| 169 | 404.0 | 2.141 |
| 170 | 404.0 | 2.146 |
| 171 | 417.0 | 3.278 |
| 172 | 408.0 | 2.341 |
| 173 | 448.0 | 5.205 |
| 174 | 418.0 | 3.52 |
| 175 | 394.0 | 1.968 |
| 176 | 476.0 | 8.907 |
| 177 | 404.0 | 2.26 |
| 178 | 390.0 | 2.102 |
| 179 | 394.0 | 1.907 |
| 181 | 398.0 | 2.94 |
| 182 | 403.3 | 2.81 |
| 183 | 448.0 | 1.843 |
| 184 | 390.0 | 2.022 |
| 185 | 439.0 | 3.119 |
| 186 | 366.0 | 2.015 |
| 188 | 405.0 | 1.928 |
| 189 | 425.0 | 9.421 |
| 190 | 404.0 | 2.148 |
| 191 | 547.0 | 2.72 |
| 192 | 335.0 | 1.699 |
| 194 | 417.0 | 3.312 |
| 195 | 406.0 | 5.295 |
| 196 | 391.0 | 2.718 |
| 198 | 476.0 | 1.844 |
| 199 | 392.0 | 2.132 |
| 202 | 378.0 | 7.861 |
| 203 | 427.0 | 5.314 |
| 204 | 401.0 | 3.11 |
| 205 | 420.0 | 1.978 |
| 206 | 439.0 | 1.944 |
| 207 | 371.9 | 2.01 |
| 208 | 404.0 | 2.136 |
| 209 | 376.0 | 3.25 |
| 210 | 349.0 | 2.65 |
| 212 | 378.0 | 2.037 |
| 213 | 440.0 | 2.173 |
| 214 | 364.0 | 1.93 |
| 216 | 363.0 | 2.038 |
| 217 | 419.0 | 3.719 |
| 218 | 364.0 | 1.857 |
| 219 | 404.0 | 2.132 |
| 220 | 404.0 | 1.888 |
| 221 | 377.0 | 1.849 |
| 222 | 376.0 | 1.897 |
| 223 | 453.0 | 2.002 |
| 224 | 371.1 | 2.9 |
| 225 | 448.0 | 1.945 |
| 226 | 418.0 | 2.335 |
| 227 | 431.0 | 2.221 |
| 228 | 389.3 | 2.81 |
| 229 | 406.0 | 2.275 |
| 230 | 477.0 | 2.57 |
| 231 | 376.0 | 1.906 |
| 232 | 461.0 | 1.81 |
| 233 | 432.0 | 2.613 |
| 234 | 364.0 | 1.857 |
| 235 | 476.0 | 1.791 |
| 236 | 422.0 | 8.655 |
| 237 | 385.0 | 2.93 |
| 238 | 420.0 | 7.029 |
| 239 | 417.0 | 2.068 |
| 240 | 420.0 | 2.353 |
| 241 | 417.0 | 3.211 |
| 242 | 448.0 | 2.045 |
| 243 | 432.0 | 2.686 |
| 244 | 392.0 | 3.27 |
| 246 | 404.0 | 2.154 |
| 247 | 418.0 | 2.461 |
| 248 | 425.0 | 1.854 |
| 250 | 400.0 | 1.957 |
| 251 | 336.0 | 2.98 |
| 252 | 447.0 | 1.788 |
| 253 | 475.0 | 1.883 |
| 254 | 432.0 | 3.92 |
| 255 | 415.5 | 2.73 |
| 256 | 364.0 | 6.627 |
| 257 | 363.3 | 2.9 |
| 258 | 403.0 | 1.973 |
| 259 | 352.0 | 2.01 |
| 260 | 390.0 | 8.732 |
| 261 | 386.1 | 2.71 |
| 262 | 419.0 | 2.078 |
| 263 | 420.0 | 2.445 |
| 264 | 401.0 | 3.14 |
| 265 | 350.0 | 1.786 |
| 266 | 434.0 | 1.842 |
| 267 | 414.0 | 4.135 |
| 268 | 378.0 | 1.996 |
| 269 | 417.0 | 2.091 |
| 270 | 438.0 | 3.31 |
| 271 | 378.0 | 1.963 |
| 272 | 375.0 | 1.867 |
| 273 | 404.0 | 2.166 |
| 274 | 377.0 | 2.3 |
| 275 | 433.0 | 2.061 |
| 276 | 426.0 | 1.98 |
| 277 | 350.0 | 3.617 |
| 278 | 394.0 | 2.232 |
| 279 | 404.0 | 9.289 |
| 280 | 404.0 | 9.238 |
| 281 | 433.0 | 1.917 |
| 282 | 456.0 | 9.2 |
| 283 | 439.0 | 1.959 |
| 284 | 434.0 | 2.725 |
| 285 | 425.0 | 1.956 |
| 286 | 294.3 | 1.78 |
| 287 | 462.0 | 7.542 |
| 288 | 385.1 | 2.9 |
| 289 | 439.0 | 2.709 |
| 290 | 418.0 | 1.904 |
| 291 | 414.0 | 2.029 |
| 292 | 574.0 | 4.15 |
| 293 | 418.0 | 2.355 |
| 295 | 336.0 | 1.73 |
| 296 | 403.0 | 1.975 |
| 297 | 431.0 | 3.242 |

TABLE 2-continued

ANALYTICAL DATA

| Cmpd No. | LC-MS M + 1 | LC-RT min |
|---|---|---|
| 299 | 462.0 | 1.936 |
| 300 | 404.0 | 2.177 |
| 301 | 363.0 | 1.79 |
| 302 | 386.1 | 1.79 |
| 303 | 335.0 | 1.689 |
| 304 | 390.0 | 1.99 |
| 305 | 412.0 | 8.516 |
| 306 | 322.0 | 2.32 |
| 309 | 417.0 | 2.197 |
| 310 | 364.0 | 1.92 |
| 311 | 390.0 | 2.029 |
| 312 | 369.0 | 2.71 |
| 313 | 404.0 | 1.892 |
| 314 | 493.0 | 2.51 |
| 315 | 377.0 | 1.922 |
| 316 | 379.3 | 2.41 |
| 317 | 440.0 | 2.238 |
| 318 | 428.0 | 2.124 |
| 319 | 417.0 | 2.233 |
| 321 | 420.0 | 2.498 |
| 322 | 422.0 | 1.956 |
| 323 | 453.0 | 3.037 |
| 324 | 403.0 | 1.917 |
| 325 | 406.0 | 9.892 |
| 326 | 364.0 | 2.23 |
| 327 | 434.0 | 1.878 |
| 328 | 451.0 | 1.854 |
| 329 | 417.0 | 3.011 |
| 330 | 432.0 | 2.652 |
| 331 | 431.0 | 2.476 |
| 332 | 364.0 | 1.994 |
| 333 | 418.0 | 2.338 |
| 334 | 418.0 | 2.371 |
| 335 | 433.0 | 1.788 |
| 338 | 405.0 | 2.01 |
| 339 | 418.0 | 2.382 |
| 340 | 425.0 | 1.86 |
| 341 | 392.0 | 2.28 |
| 342 | 417.0 | 2.086 |
| 343 | 476.0 | 2.063 |
| 344 | 461.0 | 2.276 |
| 345 | 419.0 | 1.749 |
| 346 | 477.0 | 1.933 |
| 347 | 418.0 | 9.987 |
| 348 | 403.0 | 2.089 |
| 349 | 516.5 | 3.42 |
| 351 | 461.0 | 1.81 |
| 352 | 406.0 | 4.544 |
| 353 | 364.0 | 5.795 |
| 354 | 389.0 | 1.945 |
| 355 | 419.0 | 1.832 |
| 356 | 436.0 | 1.871 |
| 357 | 425.0 | 2.549 |
| 358 | 403.0 | 2.077 |
| 359 | 406.0 | 5.149 |
| 361 | 392.0 | 4.317 |
| 362 | 431.0 | 2.156 |
| 363 | 420.0 | 1.79 |
| 364 | 403.0 | 2.06 |
| 365 | 350.0 | 1.832 |
| 366 | 403.0 | 2.656 |
| 367 | 378.0 | 2.046 |
| 368 | 389.0 | 1.955 |
| 369 | 406.0 | 2.28 |
| 370 | 392.0 | 3.517 |
| 372 | 392.0 | 3.344 |
| 373 | 453.0 | 2.055 |
| 374 | 531.0 | 2.82 |
| 376 | 418.0 | 2.356 |
| 377 | 405.0 | 3.187 |
| 378 | 432.0 | 2.603 |
| 379 | 417.0 | 2.063 |
| 380 | 350.0 | 2.9 |
| 381 | 439.0 | 1.942 |
| 382 | 411.0 | 1.809 |
| 383 | 434.0 | 1.923 |
| 384 | 363.0 | 2.112 |
| 385 | 419.0 | 5.34 |
| 386 | 405.0 | 1.758 |
| 387 | 510.0 | 4.04 |
| 388 | 392.0 | 2.074 |
| 389 | 403.0 | 2.802 |
| 390 | 417.0 | 2.086 |
| 391 | 418.0 | 3.55 |
| 392 | 404.0 | 2.122 |
| 393 | 454.0 | 2.304 |
| 394 | 399.1 | 2.93 |
| 395 | 377.3 | 3.1 |
| 396 | 498.3 | 2.62 |
| 397 | 426.0 | 2.039 |
| 398 | 552.3 | 3.55 |
| 399 | 352.0 | 1.951 |
| 400 | 363.0 | 1.792 |
| 401 | 454.0 | 2.246 |
| 402 | 390.0 | 2.152 |
| 403 | 477.0 | 1.909 |
| 404 | 419.0 | 2.053 |
| 405 | 447.0 | 2.186 |
| 406 | 418.0 | 2.362 |
| 407 | 405.0 | 1.763 |
| 408 | 420.0 | 1.929 |
| 409 | 418.0 | 2.392 |
| 410 | 463.0 | 1.823 |
| 411 | 378.0 | 8.389 |
| 412 | 389.0 | 1.899 |
| 413 | 418.0 | 2.354 |
| 414 | 404.0 | 2.278 |
| 415 | 476.0 | 1.859 |
| 416 | 425.0 | 1.951 |
| 417 | 404.0 | 2.161 |
| 418 | 419.0 | 1.747 |
| 419 | 559.3 | 2.59 |
| 420 | 419.0 | 2.098 |
| 421 | 502.1 | 3.23 |
| 422 | 391.0 | 2.021 |
| 423 | 406.0 | 2.313 |
| 424 | 417.0 | 2.54 |
| 425 | 431.0 | 3.781 |
| 426 | 399.0 | 2.94 |
| 427 | 404.0 | 2.121 |
| 428 | 356.1 | 2.38 |
| 429 | 406.0 | 1.822 |
| 430 | 440.0 | 2.157 |
| 431 | 337.3 | 2.73 |
| 432 | 450.0 | 2.301 |
| 433 | 426.0 | 2.002 |
| 434 | 362.0 | 2.6 |
| 435 | 364.0 | 3.27 |
| 436 | 403.0 | 2.059 |
| 437 | 403.0 | 2.04 |
| 438 | 336.0 | 1.73 |
| 439 | 490.0 | 1.86 |
| 440 | 417.0 | 2.087 |
| 441 | 440.0 | 2.184 |
| 442 | 349.0 | 1.737 |
| 443 | 420.0 | 10.536 |
| 444 | 338.0 | 1.865 |
| 445 | 440.0 | 2.132 |
| 446 | 418.0 | 2.524 |
| 447 | 378.1 | 2.26 |
| 448 | 403.0 | 1.991 |
| 449 | 434.0 | 8.545 |
| 450 | 391.0 | 1.93 |
| 451 | | |
| 452 | 566.5 | 3.75 |
| 453 | 372.1 | 2.06 |
| 454 | 350.0 | 1.805 |
| 455 | 418.0 | 2.302 |

TABLE 2-continued

ANALYTICAL DATA

| Cmpd No. | LC-MS M + 1 | LC-RT min |
|---|---|---|
| 456 | 406.0 | 1.828 |
| 457 | 389.0 | 1.827 |
| 458 | 408.0 | 1.885 |
| 459 | 404.0 | 9.684 |
| 460 | 404.0 | 9.21 |
| 461 | 378.0 | 3.31 |
| 463 | 446.0 | 3.84 |
| 464 | 440.0 | 9.914 |
| 465 | 418.0 | 10.466 |
| 466 | 432.0 | 2.604 |
| 467 | 448.0 | 2.007 |
| 469 | 364.0 | 1.88 |
| 470 | 510.0 | 4.02 |

NMR data for selected compounds is shown below in Table 2-A:

TABLE 2-A

| Cmpd No. | NMR |
|---|---|
| 47 | 1H-NMR (300MHz, CDCl3): d 8.04(d, J=2Hz, 1H), 7.79 (dd, J=2Hz, 9Hz, 1H), 7.56(d, J=9Hz, 1H), 6.45(d, J=8Hz, 1H), 4.36-4.23(m, 1H), 3.67(br t, 2H), 2.64(s, 3H), 2.25(m, 1H), 1.91(t, J=11Hz, 1H), 1.69(br m, 4H), 1.30(d, J=7Hz, 6H), 0.87(d, J=7 Hz, 3H), 0.83(m, 1H). |
| 94 | 1H-NMR(300 MHz, CDCl3): d 8.09(d, J=2Hz, 1H), 7.83(dd, J=2Hz, 9Hz, 1H), 7.54(d, J=9Hz, 1H), 7.31-7.15(m, 5H), 6.62(br t, 1H), 3.52(q, 7Hz, 2H), 3.29(t, J=6Hz, 4H), 2.74(t, J=7Hz, 2H), 2.64(s, 3H), 2.02(m, 2H), 1.73(br m, 4H), 1.59(m, 4H). |
| 140 | 1H-NMR (300MHz, CDCl3): 10.11(s, 1H); 8.11(d, J=0.8Hz, 1H); 7.57(m, 2H); 6.80(d, J=1.1Hz, 1H); 3.78-3.74(m, 2H); 2.23-2.16(m, 2H); 1.64-1.62(m, 3H); 1.46(br. s, 12H); 1.32-1.24(m, 4H); 0.87(d, J=5.8Hz, 3H) |
| 356 | 1H-NMR (300MHz, CDCl3): d 8.09(d, J=2Hz, 1H), 7.81(dd, J=2Hz, 9Hz, 1H), 7.54(d, J=9Hz, 1H), 4.00(s, 4H), 3.68(br d, 4H), 3.26(q, J=7Hz, 4H), 2.44(s, 3H), 1.81(br t, 4H), 1.13(t, J=7Hz, 6H). |
| 382 | 1H-NMR (300MHz, DMSO-d6): 12.1(s, 1H); 8.12(m, 1H); 7.59-7.52(m, 2H); 7.35-7.26(m, 4H); 7.25-7.23(m, 1H); 4.51(d, J=5.8Hz); 3.19-3.15(m, 4H); 1.58(br.s 4H); 1.45(m, 4H) |
| 389 | 1H-NMR(300 MHz, CDCl3): 10.53(s, 1H); 8.12(d, J=1.4Hz, 1H); 7.63-7.53(m, 2H); 6.89(s, 1H); 3.89(br.s, 4H); 3.77-3.74(m, 2H); 1.85-1.62(m, 11H); 0.82(d, J=6.3Hz, 6H); 0.46-0.35(m, 1H) |
| 393 | 1H-NMR(300MHz, CDCl3): d 8.05(d, J=2Hz, 1H), 7.79(dd, J=2Hz, 9Hz, 1H), 7.53(d, 9Hz, 1H), 7.37-7.24(m, 5H), 6.69(t, J=6Hz, 1H), 3.77-3.70(m, 3H), 2.96(t, J=7Hz, 2H), 2.67(s, 3H), 1.78-1.65(m, 5H), 1.25(t, J=6Hz, 3H), 0.85(d, J=7Hz, 6H), 0.45(q, 13Hz). |

APPENDIX B

TABLE 3

BIOLOGICAL ASSAY DATA

| Cmpd No. | IC50 |
|---|---|
| 1 | ++ |
| 2 | +++ |
| 3 | + |
| 4 | ++ |
| 5 | +++ |
| 6 | +++ |
| 7 | +++ |
| 8 | +++ |
| 9 | +++ |
| 10 | ++ |
| 11 | +++ |
| 12 | ++ |
| 13 | +++ |
| 14 | + |
| 15 | ++ |
| 16 | +++ |
| 17 | ++ |
| 18 | ++ |
| 19 | +++ |
| 20 | + |
| 21 | +++ |
| 22 | + |
| 23 | +++ |
| 24 | + |
| 25 | + |
| 26 | + |
| 27 | ++ |
| 28 | + |
| 29 | +++ |
| 30 | ++ |
| 31 | +++ |
| 32 | +++ |
| 33 | ++ |
| 34 | +++ |
| 35 | ++ |
| 36 | +++ |
| 37 | +++ |
| 38 | ++ |
| 39 | + |
| 40 | +++ |
| 41 | ++ |

TABLE 3-continued

BIOLOGICAL ASSAY DATA

| Cmpd No. | IC50 |
|---|---|
| 42 | +++ |
| 43 | +++ |
| 44 | ++ |
| 45 | +++ |
| 46 | +++ |
| 47 | ++ |
| 48 | +++ |
| 49 | +++ |
| 50 | + |
| 51 | + |
| 52 | ++ |
| 53 | +++ |
| 54 | ++ |
| 55 | +++ |
| 56 | +++ |
| 57 | ++ |
| 58 | ++ |
| 59 | ++ |
| 60 | +++ |
| 61 | ++ |
| 62 | +++ |
| 63 | ++ |
| 64 | ++ |
| 65 | + |
| 66 | ++ |
| 67 | +++ |
| 68 | ++ |
| 69 | ++ |
| 70 | ++ |
| 71 | + |
| 72 | ++ |
| 73 | + |
| 74 | +++ |
| 75 | + |
| 76 | ++ |
| 77 | +++ |
| 78 | ++ |
| 79 | +++ |
| 80 | ++ |
| 81 | +++ |
| 82 | ++ |
| 83 | +++ |
| 84 | +++ |
| 85 | +++ |
| 86 | ++ |
| 87 | +++ |
| 88 | +++ |
| 89 | +++ |
| 90 | +++ |
| 91 | ++ |
| 92 | ++ |
| 93 | +++ |
| 94 | ++ |
| 95 | ++ |
| 96 | ++ |
| 97 | ++ |
| 98 | +++ |
| 99 | None |
| 100 | +++ |
| 101 | +++ |
| 102 | +++ |
| 103 | +++ |
| 104 | ++ |
| 105 | ++ |
| 106 | + |
| 107 | +++ |
| 108 | +++ |
| 109 | + |
| 110 | ++ |
| 111 | ++ |
| 112 | ++ |
| 113 | +++ |
| 114 | ++ |
| 115 | ++ |

TABLE 3-continued

BIOLOGICAL ASSAY DATA

| Cmpd No. | IC50 |
|---|---|
| 116 | ++ |
| 117 | +++ |
| 118 | + |
| 119 | +++ |
| 120 | +++ |
| 121 | ++ |
| 122 | +++ |
| 123 | ++ |
| 124 | ++ |
| 125 | + |
| 126 | +++ |
| 127 | ++ |
| 128 | ++ |
| 129 | ++ |
| 130 | +++ |
| 131 | +++ |
| 132 | + |
| 133 | + |
| 134 | ++ |
| 135 | ++ |
| 136 | ++ |
| 137 | +++ |
| 138 | +++ |
| 139 | ++ |
| 140 | +++ |
| 141 | +++ |
| 142 | +++ |
| 143 | ++ |
| 144 | ++ |
| 145 | + |
| 146 | +++ |
| 147 | +++ |
| 148 | +++ |
| 149 | + |
| 150 | ++ |
| 151 | ++ |
| 152 | ++ |
| 153 | +++ |
| 154 | ++ |
| 155 | + |
| 156 | +++ |
| 157 | ++ |
| 158 | + |
| 159 | ++ |
| 160 | ++ |
| 161 | ++ |
| 162 | + |
| 163 | + |
| 164 | +++ |
| 165 | ++ |
| 166 | + |
| 167 | + |
| 168 | ++ |
| 169 | +++ |
| 170 | +++ |
| 171 | +++ |
| 172 | +++ |
| 173 | ++ |
| 174 | +++ |
| 175 | None |
| 176 | +++ |
| 177 | +++ |
| 178 | ++ |
| 179 | + |
| 180 | +++ |
| 181 | ++ |
| 182 | + |
| 183 | ++ |
| 184 | +++ |
| 185 | +++ |
| 186 | + |
| 187 | ++ |
| 188 | ++ |
| 189 | ++ |

TABLE 3-continued

BIOLOGICAL ASSAY DATA

| Cmpd No. | IC50 |
|---|---|
| 190 | +++ |
| 191 | +++ |
| 192 | +++ |
| 193 | ++ |
| 194 | +++ |
| 195 | + |
| 196 | +++ |
| 197 | + |
| 198 | ++ |
| 199 | +++ |
| 200 | ++ |
| 201 | +++ |
| 202 | ++ |
| 203 | ++ |
| 204 | ++ |
| 205 | ++ |
| 206 | +++ |
| 207 | + |
| 208 | +++ |
| 209 | +++ |
| 210 | + |
| 211 | +++ |
| 212 | +++ |
| 213 | +++ |
| 214 | +++ |
| 215 | ++ |
| 216 | +++ |
| 217 | +++ |
| 218 | ++ |
| 219 | ++ |
| 220 | ++ |
| 221 | ++ |
| 222 | ++ |
| 223 | +++ |
| 224 | ++ |
| 225 | +++ |
| 226 | +++ |
| 227 | +++ |
| 228 | + |
| 229 | +++ |
| 230 | ++ |
| 231 | ++ |
| 232 | ++ |
| 233 | +++ |
| 234 | +++ |
| 235 | ++ |
| 236 | ++ |
| 237 | + |
| 238 | ++ |
| 239 | ++ |
| 240 | +++ |
| 241 | +++ |
| 242 | +++ |
| 243 | ++ |
| 244 | +++ |
| 245 | ++ |
| 246 | +++ |
| 247 | +++ |
| 248 | +++ |
| 249 | ++ |
| 250 | ++ |
| 251 | ++ |
| 252 | ++ |
| 253 | +++ |
| 254 | +++ |
| 255 | + |
| 256 | ++ |
| 257 | + |
| 258 | ++ |
| 259 | + |
| 260 | +++ |
| 261 | + |
| 262 | +++ |
| 263 | +++ |
| 264 | + |
| 265 | ++ |
| 266 | +++ |
| 267 | + |
| 268 | +++ |
| 269 | ++ |
| 270 | ++ |
| 271 | +++ |
| 272 | + |
| 273 | +++ |
| 274 | +++ |
| 275 | +++ |
| 276 | +++ |
| 277 | + |
| 278 | ++ |
| 279 | ++ |
| 280 | ++ |
| 281 | +++ |
| 282 | +++ |
| 283 | +++ |
| 284 | +++ |
| 285 | +++ |
| 286 | + |
| 287 | ++ |
| 288 | ++ |
| 289 | +++ |
| 290 | ++ |
| 291 | ++ |
| 292 | +++ |
| 293 | +++ |
| 294 | +++ |
| 295 | ++ |
| 296 | + |
| 297 | +++ |
| 298 | ++ |
| 299 | ++ |
| 300 | +++ |
| 301 | ++ |
| 302 | + |
| 303 | +++ |
| 304 | +++ |
| 305 | ++ |
| 306 | + |
| 307 | +++ |
| 308 | +++ |
| 309 | +++ |
| 310 | ++ |
| 311 | +++ |
| 312 | ++ |
| 313 | ++ |
| 314 | ++ |
| 315 | +++ |
| 316 | + |
| 317 | +++ |
| 318 | ++ |
| 319 | ++ |
| 320 | ++ |
| 321 | +++ |
| 322 | + |
| 323 | +++ |
| 324 | +++ |
| 325 | +++ |
| 326 | +++ |
| 327 | +++ |
| 328 | + |
| 329 | ++ |
| 330 | +++ |
| 331 | +++ |
| 332 | + |
| 333 | ++ |
| 334 | ++ |
| 335 | +++ |
| 336 | +++ |
| 337 | +++ |

TABLE 3-continued

BIOLOGICAL ASSAY DATA

| Cmpd No. | IC50 |
|---|---|
| 338 | + |
| 339 | +++ |
| 340 | +++ |
| 341 | ++ |
| 342 | +++ |
| 343 | ++ |
| 344 | +++ |
| 345 | +++ |
| 346 | +++ |
| 347 | ++ |
| 348 | ++ |
| 349 | +++ |
| 350 | None |
| 351 | ++ |
| 352 | ++ |
| 353 | ++ |
| 354 | ++ |
| 355 | ++ |
| 356 | + |
| 357 | +++ |
| 358 | ++ |
| 359 | ++ |
| 360 | ++ |
| 361 | + |
| 362 | +++ |
| 363 | ++ |
| 364 | ++ |
| 365 | ++ |
| 366 | +++ |
| 367 | + |
| 368 | +++ |
| 369 | +++ |
| 370 | ++ |
| 371 | ++ |
| 372 | + |
| 373 | +++ |
| 374 | +++ |
| 375 | ++ |
| 376 | +++ |
| 377 | +++ |
| 378 | +++ |
| 379 | ++ |
| 380 | + |
| 381 | +++ |
| 382 | +++ |
| 383 | ++ |
| 384 | +++ |
| 385 | ++ |
| 386 | +++ |
| 387 | +++ |
| 388 | ++ |
| 389 | +++ |
| 390 | +++ |
| 391 | +++ |
| 392 | ++ |
| 393 | +++ |
| 394 | + |
| 395 | ++ |
| 396 | +++ |
| 397 | ++ |
| 398 | +++ |
| 399 | + |
| 400 | + |
| 401 | +++ |
| 402 | + |
| 403 | +++ |
| 404 | ++ |
| 405 | +++ |
| 406 | +++ |
| 407 | +++ |
| 408 | +++ |
| 409 | +++ |
| 410 | ++ |
| 411 | +++ |
| 412 | +++ |
| 413 | +++ |
| 414 | +++ |
| 415 | +++ |
| 416 | +++ |
| 417 | ++ |
| 418 | +++ |
| 419 | ++ |
| 420 | +++ |
| 421 | +++ |
| 422 | +++ |
| 423 | +++ |
| 424 | ++ |
| 425 | +++ |
| 426 | ++ |
| 427 | +++ |
| 428 | + |
| 429 | ++ |
| 430 | +++ |
| 431 | ++ |
| 432 | + |
| 433 | +++ |
| 434 | + |
| 435 | +++ |
| 436 | +++ |
| 437 | + |
| 438 | ++ |
| 439 | +++ |
| 440 | +++ |
| 441 | +++ |
| 442 | ++ |
| 443 | ++ |
| 444 | + |
| 445 | +++ |
| 446 | ++ |
| 447 | + |
| 448 | ++ |
| 449 | ++ |
| 450 | ++ |
| 451 | +++ |
| 452 | +++ |
| 453 | + |
| 454 | +++ |
| 455 | +++ |
| 456 | ++ |
| 457 | ++ |
| 458 | + |
| 459 | ++ |
| 460 | ++ |
| 461 | +++ |
| 462 | +++ |
| 463 | +++ |
| 464 | +++ |
| 465 | ++ |
| 466 | +++ |
| 467 | +++ |
| 468 | ++ |
| 469 | +++ |
| 470 | ++ |

In Table 3,
"+++" = 0-5 µM;
"++" = 5-20 µM;
"+" = <20 µM.

What is claimed is:

1. A compound having formula I-A, formula I-B, or formula I-C:

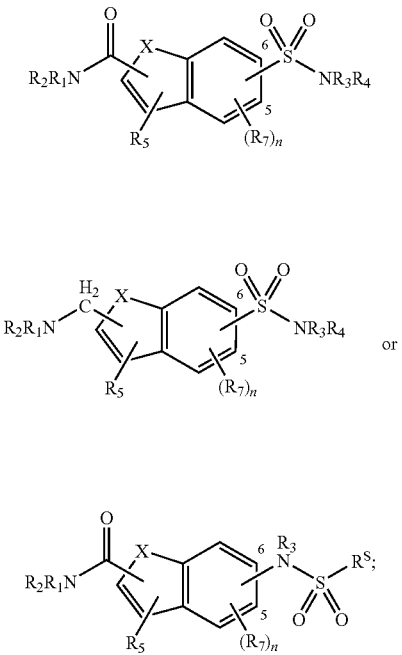

or a pharmaceutically acceptable salt thereof, wherein:

$R_5$ and $R_7$ are independently defined by —$ZR_6$, wherein Z is a bond or is an optionally substituted $C_1$-$C_6$ alkyl, alkenyl, or alkynyl, chain wherein up to two carbon units of Z are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, or —NR'$SO_2$NR'—;

wherein $R_1$, $R_2$, $R_3$, $R_4$ are independently selected from the group consisting of hydrogen, alkyl, substituted alkyl, cycloalkyl, substituted cycloalkyl, heterocyclylalkyl, substituted heterocyclylalkyl, arylalkyl, substituted arylalkyl, heteroarylalkyl, substituted heteroarylalkyl, cycloalkylalkyl, substituted cycloalkylalkyl, polycyclic hydrocarbon, substituted polycyclic hydrocarbon; or $R_1$ and $R_2$ together form an unsubstituted or substituted 3 to 7-membered ring, wherein the members of the ring contain 0-4 heteroatoms selected from nitrogen, oxygen, and sulfur; or $R_3$ and $R_4$ together form a ring wherein together form an unsubstituted or substituted 3 to 7-membered ring, wherein the members of the ring are selected from the group consisting of carbon, nitrogen, oxygen, and sulfur; and the group $SO_2NR_3R_4$ is linked to the phenyl ring either at position 5 or 6;

X is O;

n is 0-3;

$R_6$ is independently R', halogen, $NO_2$, CN, $CF_3$, or $OCF_3$;

$R^S$ is an optionally substituted 5-7 membered, saturated, unsaturated, or aromatic ring having 0-3 heteroatoms selected from N, O, or S;

R' is independently selected from hydrogen or an optionally substituted group selected from a $C_1$-$C_8$ aliphatic group, a 3-8-membered saturated or partially unsaturated ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

2. The compound according to claim 1, wherein $R_3$ and $R_4$ taken together form a 5-7 membered saturated ring, having 0-2 additional heteroatoms selected from nitrogen, oxygen, or sulfur.

3. The compound according to claim 2, wherein $R_3$ and $R_4$ taken together form a 5-7 membered saturated ring having no additional heteroatoms.

4. The compound according to claim 2, wherein $R_3$ and $R_4$ taken together form a 5-7 membered saturated ring having one additional heteroatom.

5. The compound according to claim 2, wherein $R_5$ is hydrogen, or C1-C6 alkyl.

6. The compound according to claim 2, $R_1$ is hydrogen.

7. The compound according to claim 2, wherein $R_1$ is C1-C4 alkyl.

8. The compound according to claim 2, wherein $R_2$ is alkyl, arylalkyl, cycloalkyl, cycloalkenyl, cycloalkyl-alkyl, cycloalkenyl-alkyl, heterocyclyl, heterocyclyl-alkyl, heteroaryl, or heteroarylalkyl, wherein $R_2$ has 0-4 substituents selected from Z—$R_6$.

9. The compound according to claim 8, wherein $R_2$ is an optionally substituted arylalkyl group.

10. The compound according to claim 2, wherein $R_2$ is a cycloalkyl or cycloalkyl-alkyl group wherein $R_2$ has 0-4 substituents selected from Z—$R_6$.

11. The compound according to claim 2, wherein $R_2$ is a cycloalkenyl or cycloalkenyl-alkyl group wherein $R_2$ has 0-4 substituents selected from Z—$R_6$.

12. The compound according to claim 2, wherein $R_2$ is a heterocyclyl, or heterocyclyl-alkyl group wherein $R_2$ has 0-4 substituents selected from Z—$R_6$.

13. The compound according to claim 2, wherein $R_2$ is heteroaryl or heteroaryl-alkyl group, wherein $R_2$ has 0-4 substituents selected from Z—$R_6$.

14. The compound according to claim 2, wherein $R_1$ is C1-C4 alkyl, and $R_2$ is an optionally substituted arylalkyl group.

15. The compound according to claim 2, wherein $R_1$ and $R_2$ taken together form a 5-7 membered heterocyclic ring containing up to two additional heteroatoms selected from oxygen, nitrogen, or sulfur, wherein said ring has 0-4 substituents selected from Z—$R_6$.

16. The compound according to claim 1, wherein said compound is selected from:

| Cmpd No. | Structure |
|---|---|
| 1 | 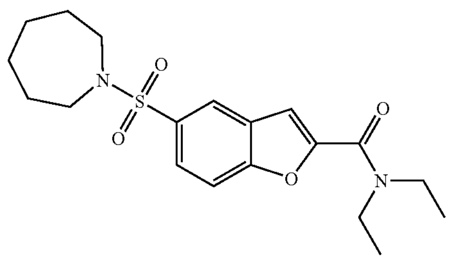 |
| 2 | 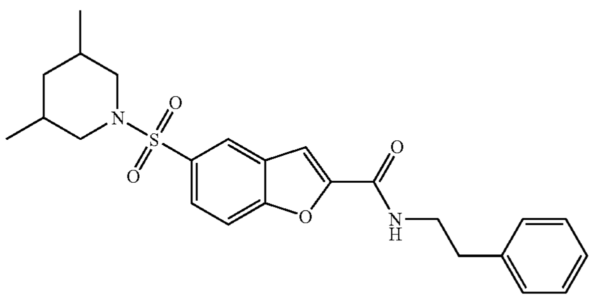 |
| 4 | 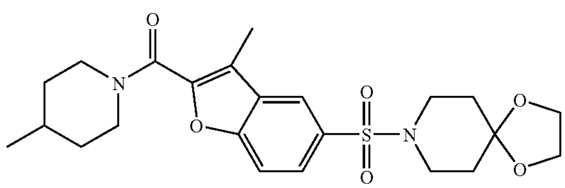 |
| 6 | 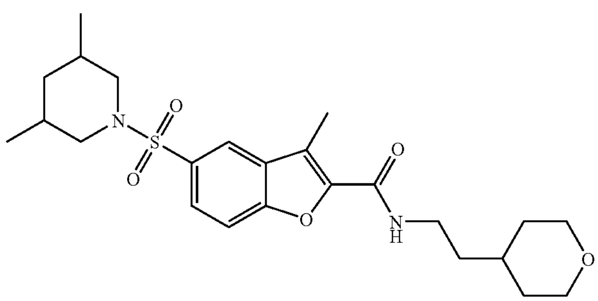 |
| 9 | 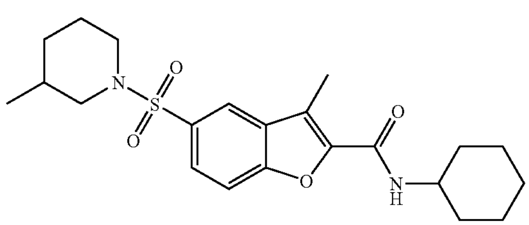 |
| 10 | 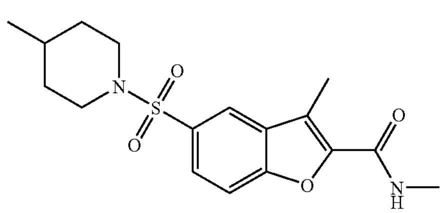 |

-continued

| Cmpd No. | Structure |
|---|---|
| 12 | 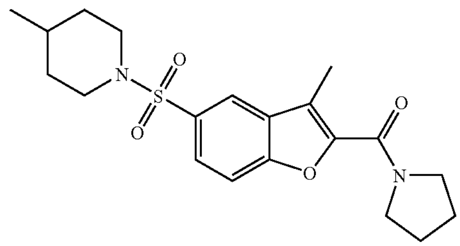 |
| 14 | 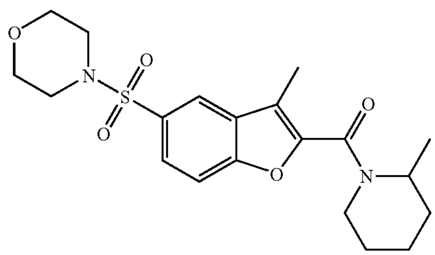 |
| 15 | 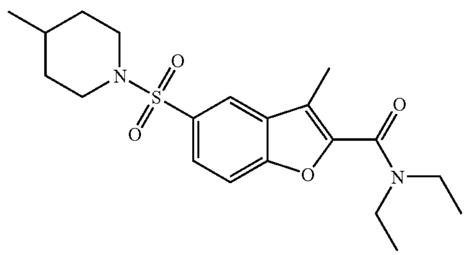 |
| 18 | 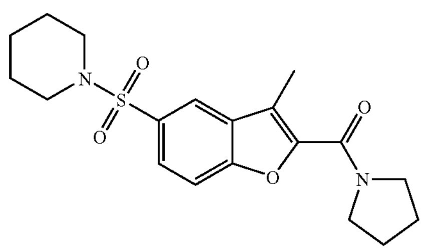 |
| 19 | 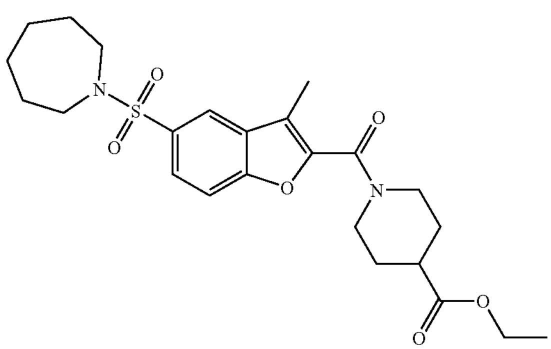 |
| 20 | 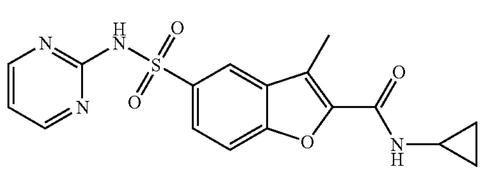 |

| Cmpd No. | Structure |
|---|---|
| 21 | 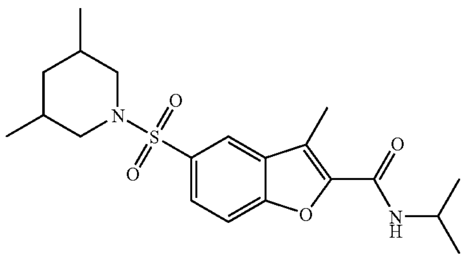 |
| 22 | 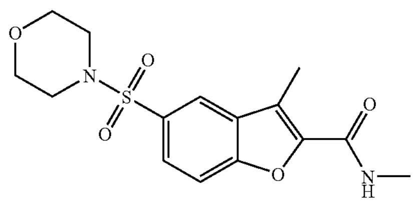 |
| 23 | 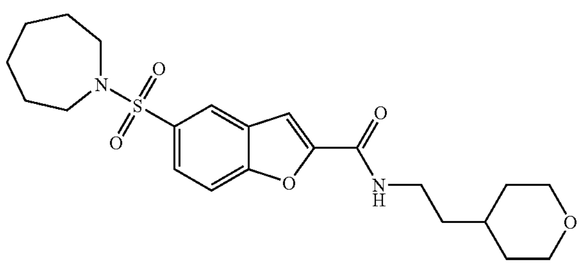 |
| 24 | 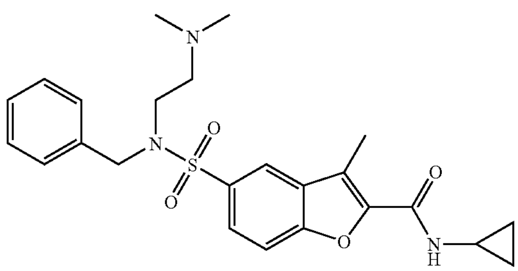 |
| 25 | 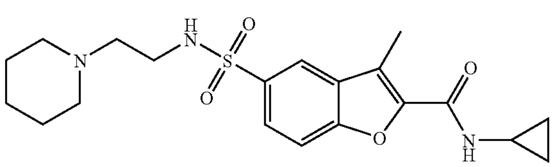 |
| 26 | 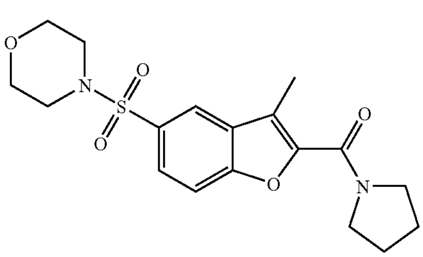 |

-continued
| Cmpd No. | Structure |
|---|---|
| 28 | 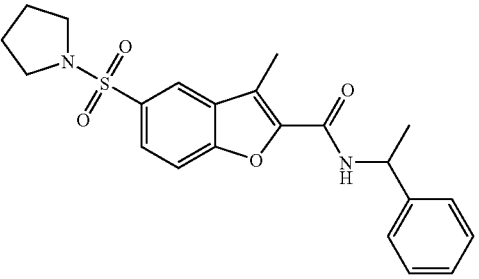 |
| 29 | 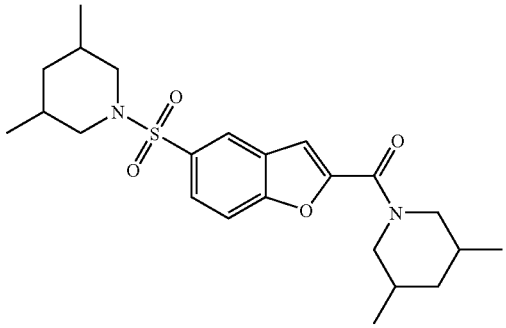 |
| 31 | 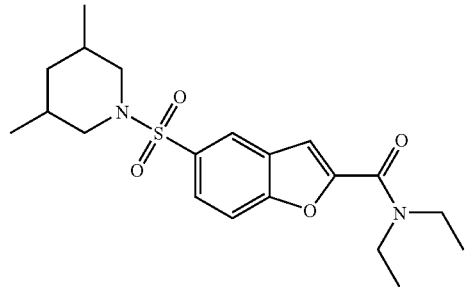 |
| 32 | 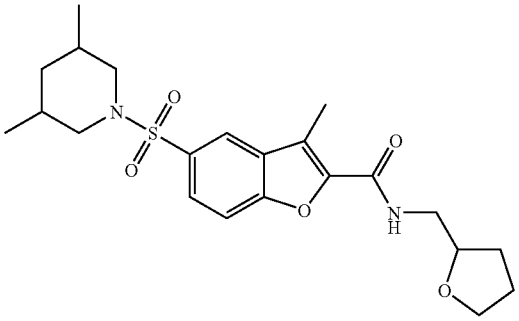 |
| 33 | 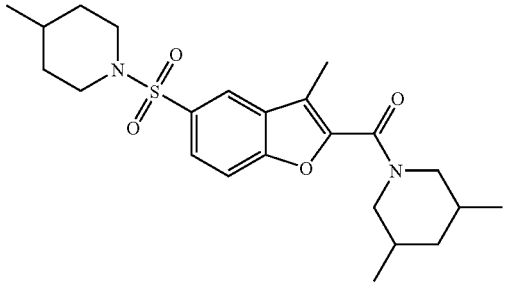 |

-continued
| Cmpd No. | Structure |
|---|---|
| 34 | 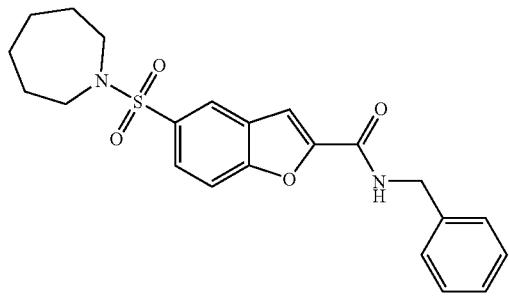 |
| 35 | 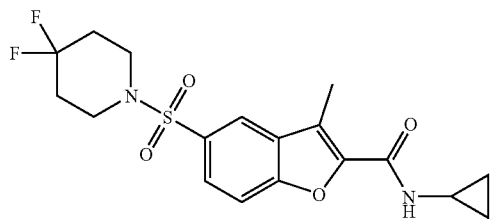 |
| 38 | 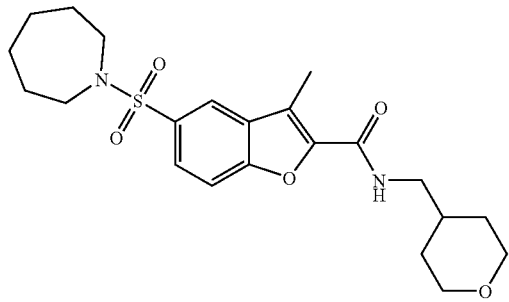 |
| 39 | 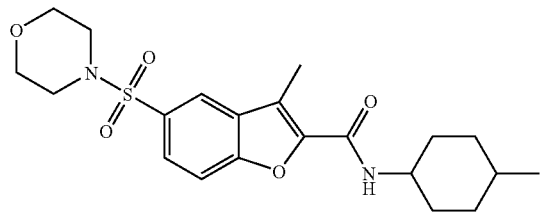 |
| 40 | 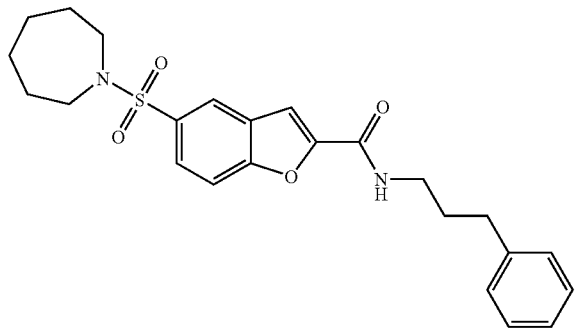 |

| Cmpd No. | Structure |
|---|---|
| 42 | 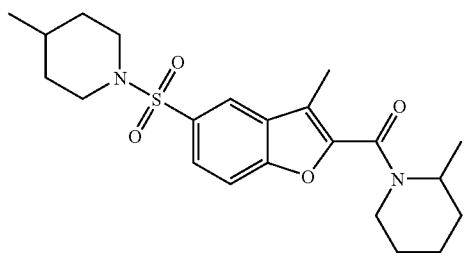 |
| 43 | 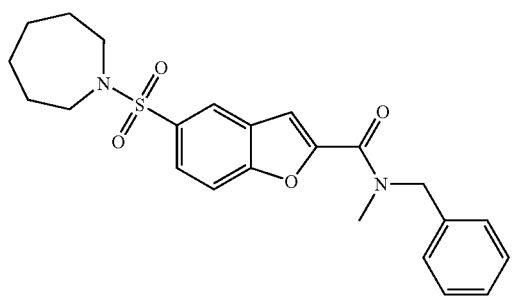 |
| 44 | 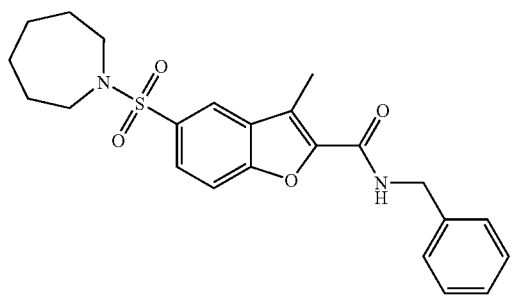 |
| 45 | 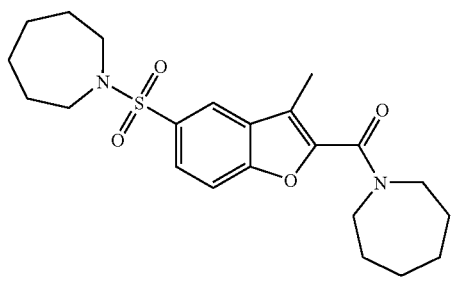 |
| 47 | 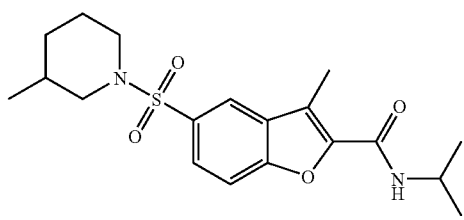 |

-continued
| Cmpd No. | Structure |
|---|---|
| 48 | 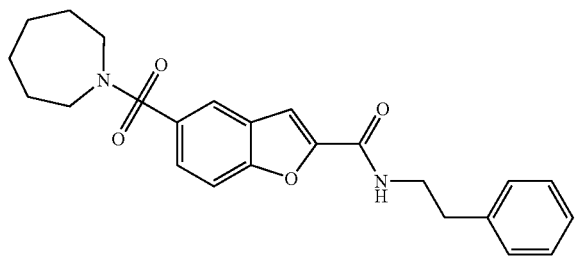 |
| 50 | 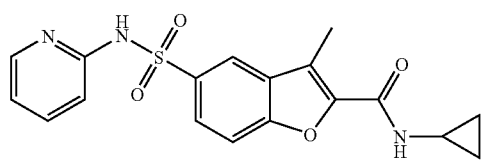 |
| 51 | 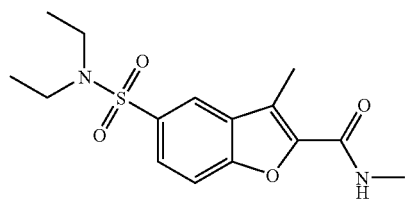 |
| 53 | 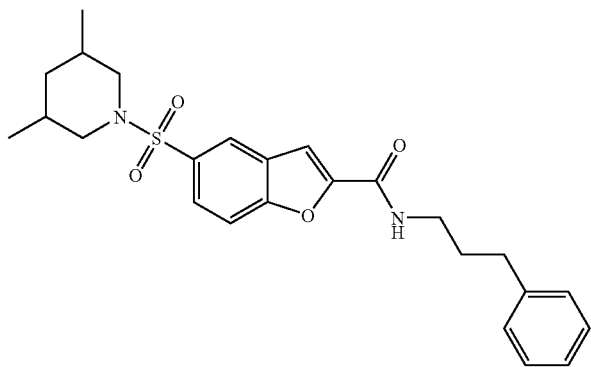 |
| 56 | 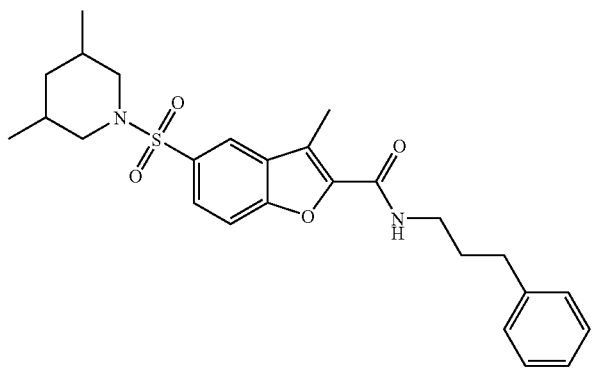 |

-continued
| Cmpd No. | Structure |
|---|---|
| 57 | 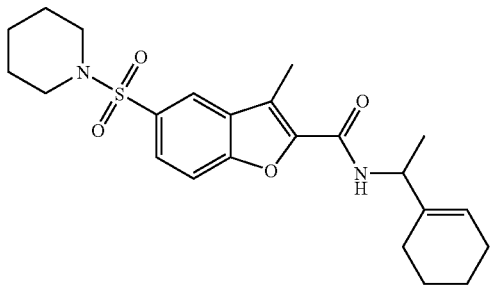 |
| 58 | 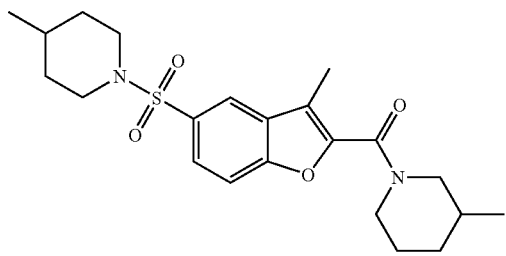 |
| 59 | 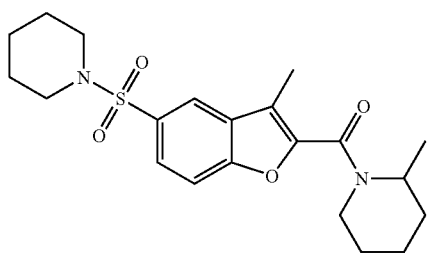 |
| 61 | 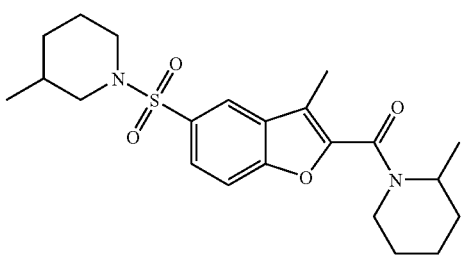 |
| 62 | 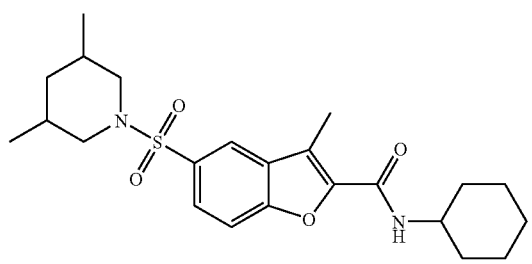 |

-continued
| Cmpd No. | Structure |
|---|---|
| 63 | 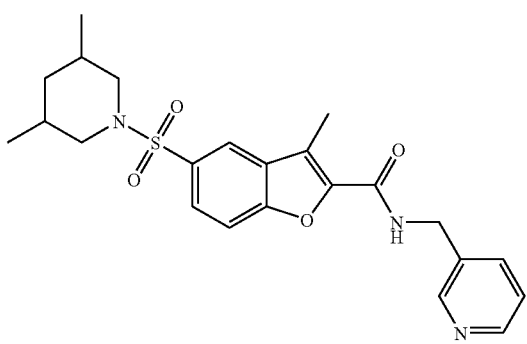 |
| 64 | 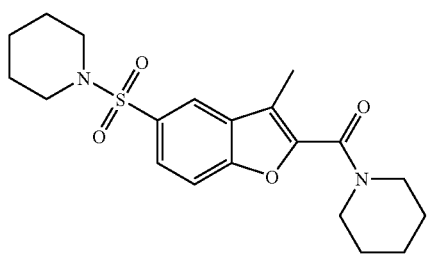 |
| 65 | 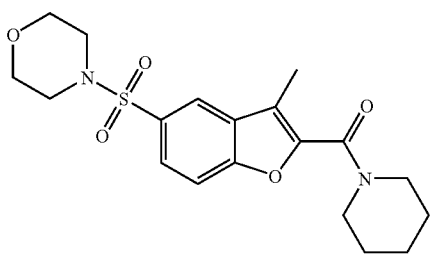 |
| 67 | 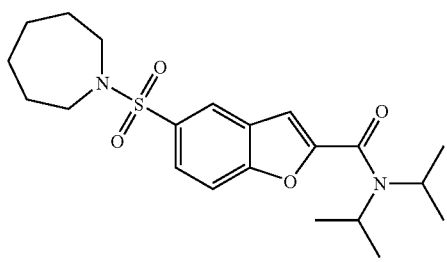 |
| 70 | 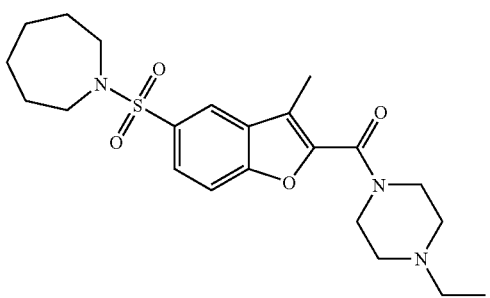 |

-continued

| Cmpd No. | Structure |
|---|---|
| 73 | 3,5-dimethylpiperidin-1-ylsulfonyl-3-methylbenzofuran-2-carboxylic acid (pyridin-2-ylmethyl)amide |
| 75 | 5-(morpholin-4-ylsulfonyl)-3-methyl-N-cyclohexylbenzofuran-2-carboxamide |
| 76 | 5-(piperidin-1-ylsulfonyl)-3-methyl-N-(2-methoxybenzyl)benzofuran-2-carboxamide |
| 79 | 5-(3,5-dimethylpiperidin-1-ylsulfonyl)-3-methyl-N-(3-morpholin-4-ylpropyl)benzofuran-2-carboxamide |
| 80 | 5-(4-methylpiperidin-1-ylsulfonyl)-3-methyl-N-(cyclohexylmethyl)benzofuran-2-carboxamide |

| Cmpd No. | Structure |
| --- | --- |
| 82 | 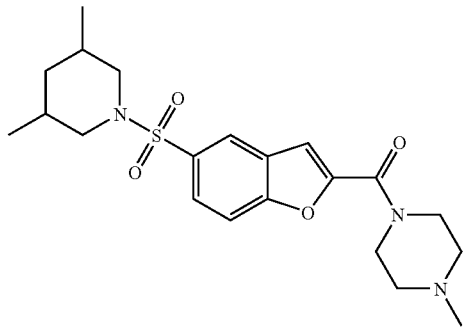 |
| 83 | 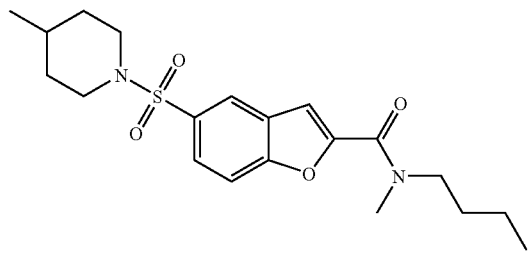 |
| 85 | 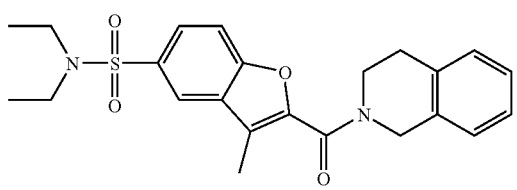 |
| 86 | 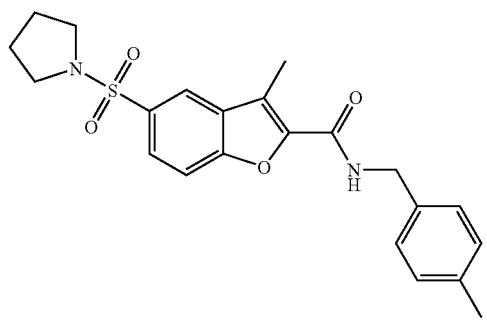 |
| 87 | 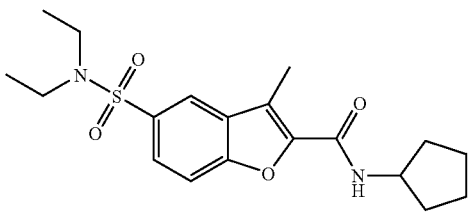 |

-continued

| Cmpd No. | Structure |
|---|---|
| 88 | 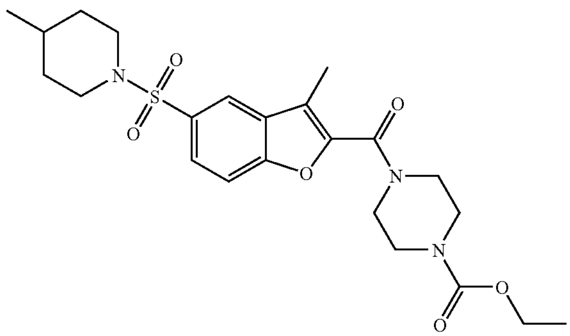 |
| 89 | 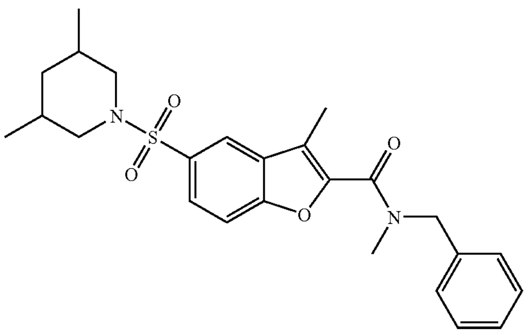 |
| 90 | 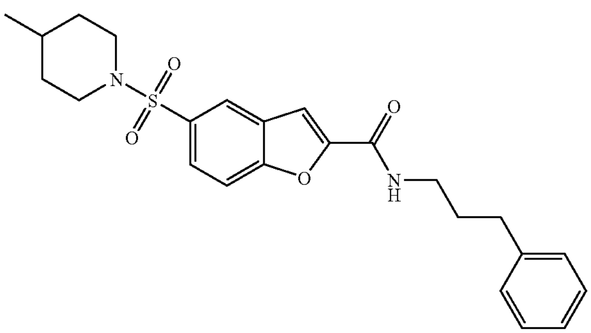 |
| 92 | 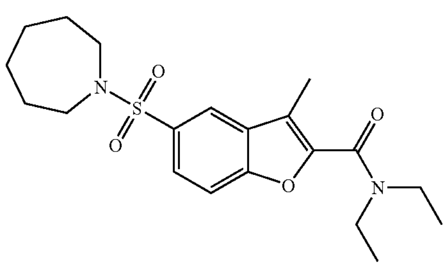 |
| 93 | 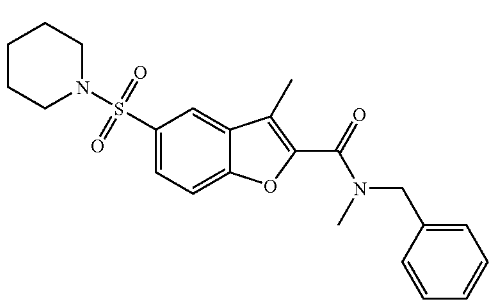 |

-continued
| Cmpd No. | Structure |
|---|---|
| 94 | 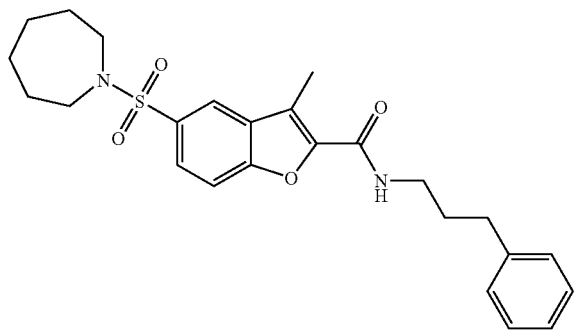 |
| 95 | 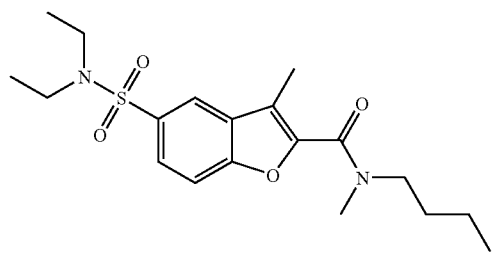 |
| 96 | 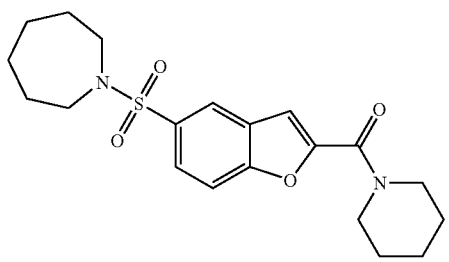 |
| 97 | 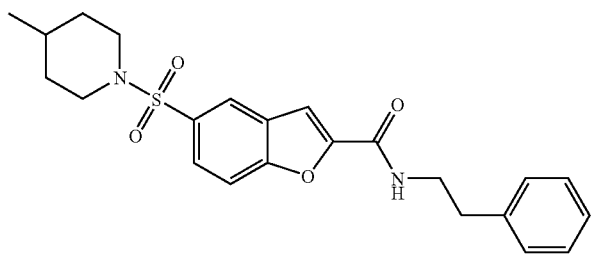 |
| 99 | 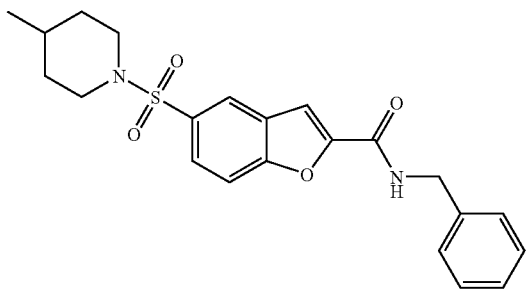 |

-continued

| Cmpd No. | Structure |
|---|---|
| 100 | 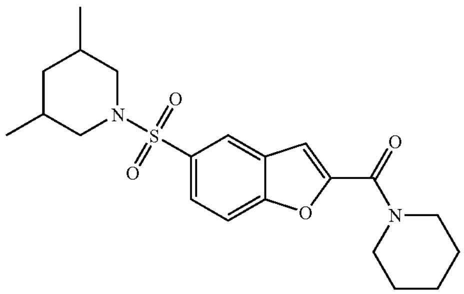 |
| 102 | 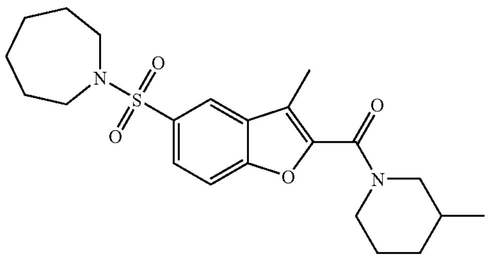 |
| 106 | 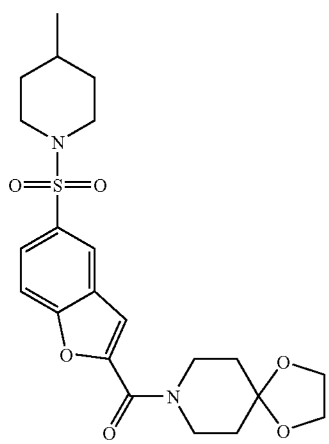 |
| 109 | 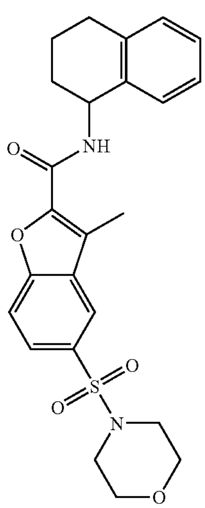 |

-continued
| Cmpd No. | Structure |
|---|---|
| 110 | 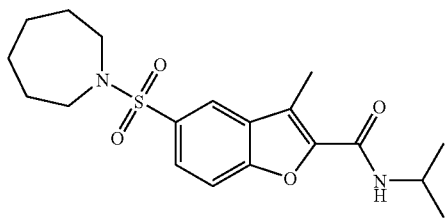 |
| 111 | 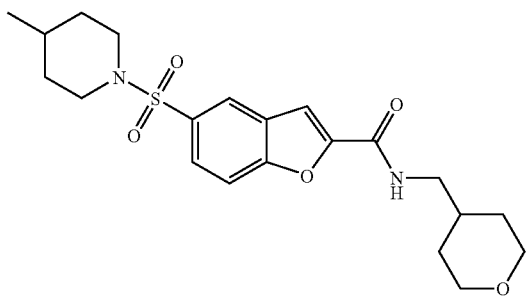 |
| 112 | 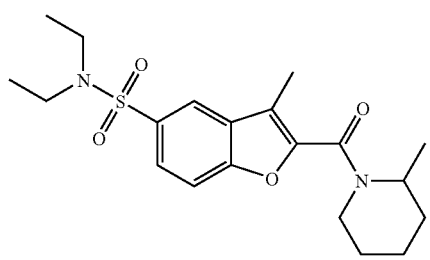 |
| 113 | 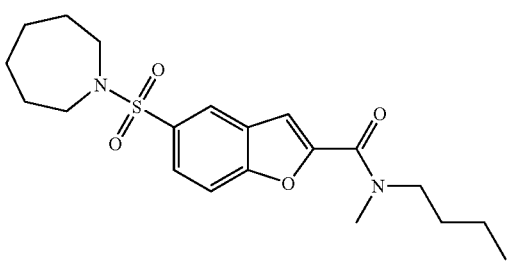 |
| 114 | 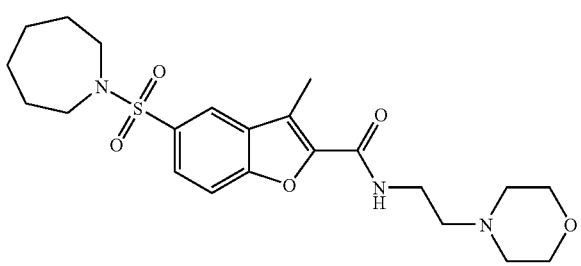 |
| 115 | 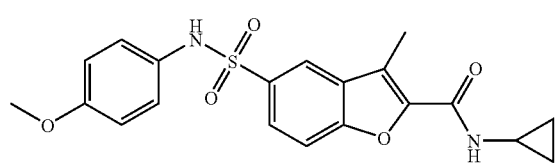 |

| Cmpd No. | Structure |
|---|---|
| 118 | 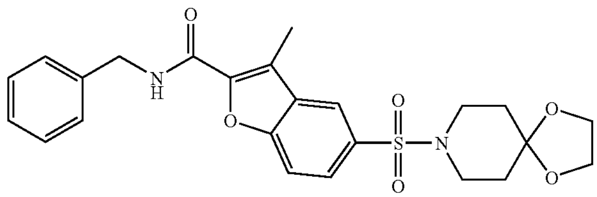 |
| 119 | 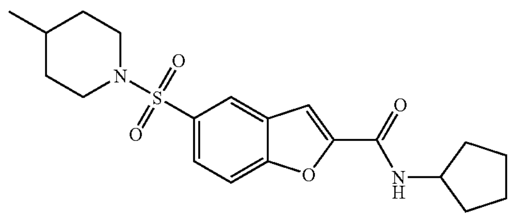 |
| 122 | 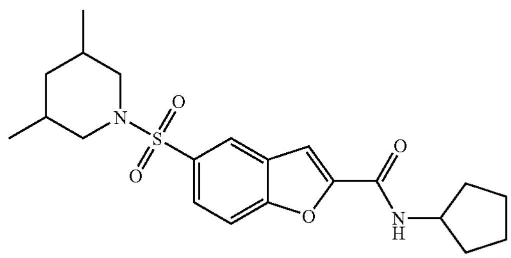 |
| 123 | 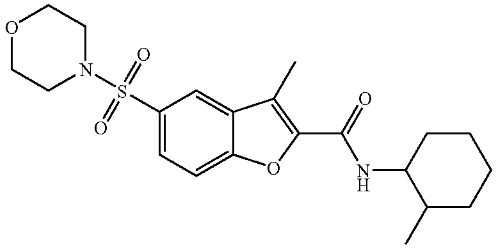 |
| 124 | 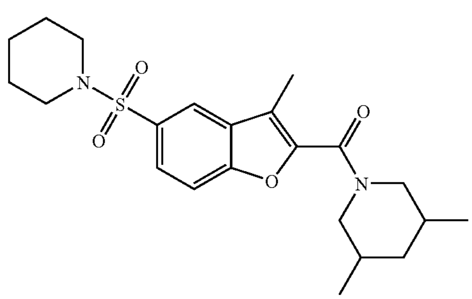 |
| 125 | 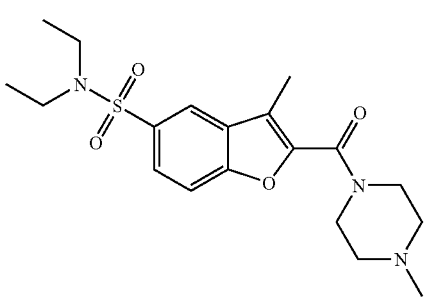 |

-continued

| Cmpd No. | Structure |
|---|---|
| 128 | 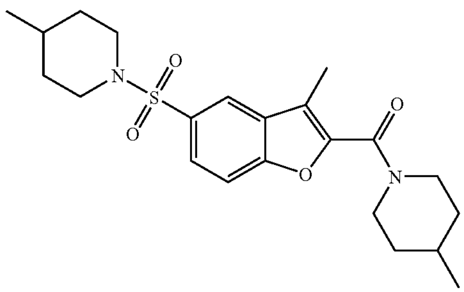 |
| 129 | 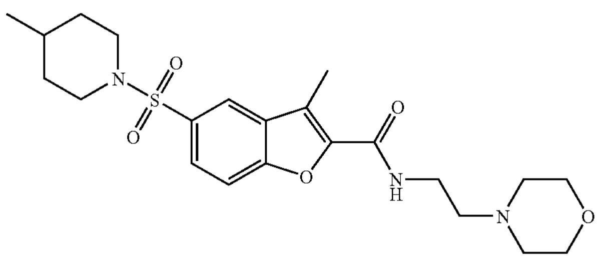 |
| 131 | 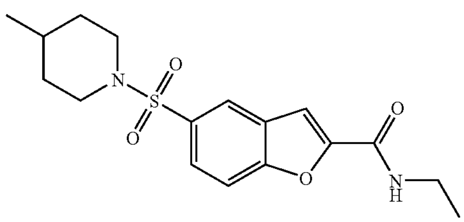 |
| 132 | 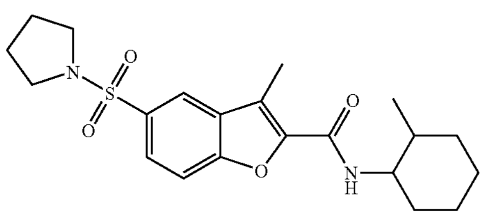 |
| 133 | 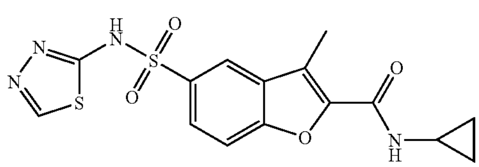 |
| 134 | 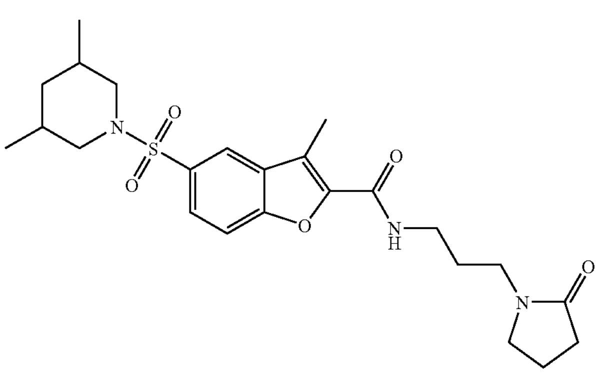 |

-continued
| Cmpd No. | Structure |
|---|---|
| 136 | 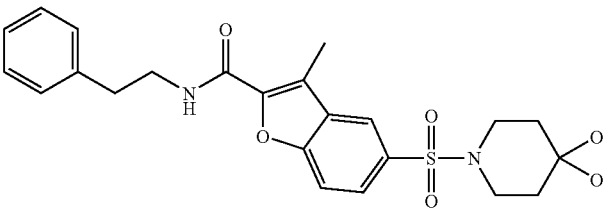 |
| 137 | 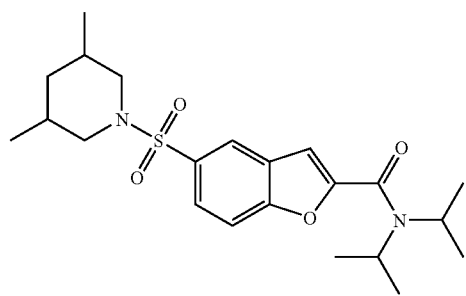 |
| 138 | 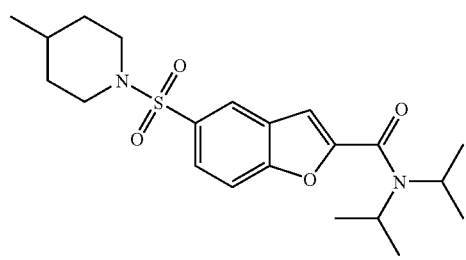 |
| 145 | 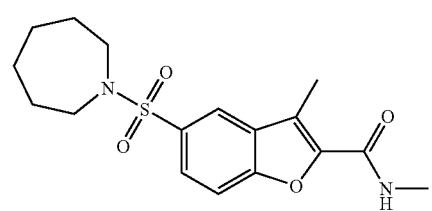 |
| 148 | 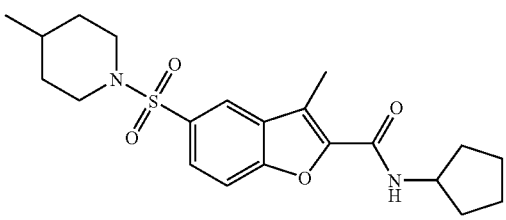 |
| 149 | 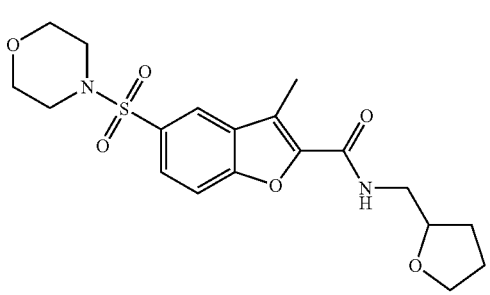 |

-continued
| Cmpd No. | Structure |
|---|---|
| 150 | 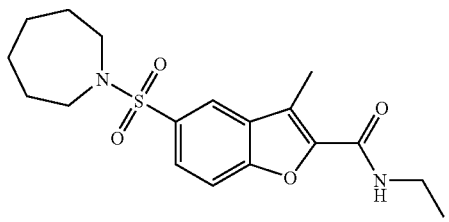 |
| 152 | 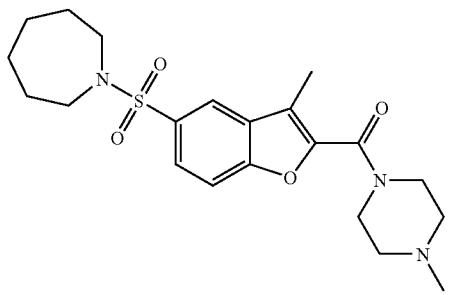 |
| 153 | 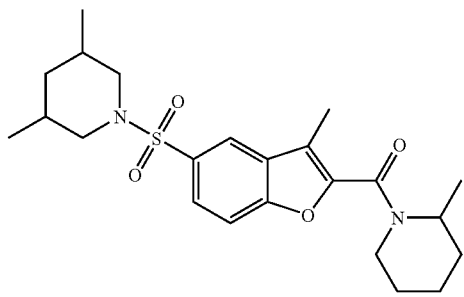 |
| 154 | 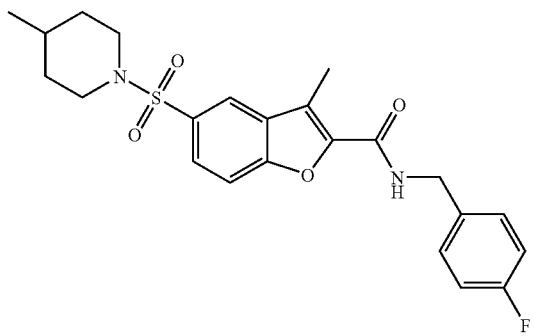 |
| 155 | 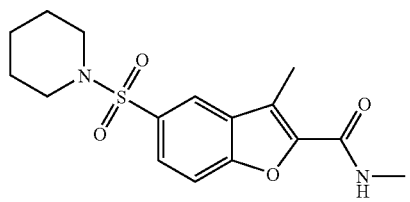 |

-continued
| Cmpd No. | Structure |
|---|---|
| 156 | 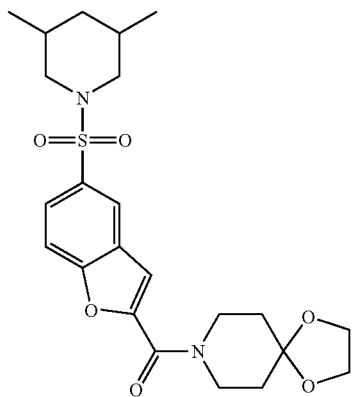 |
| 157 | 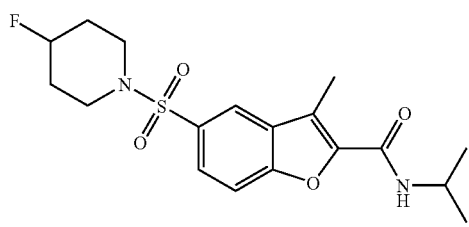 |
| 158 | 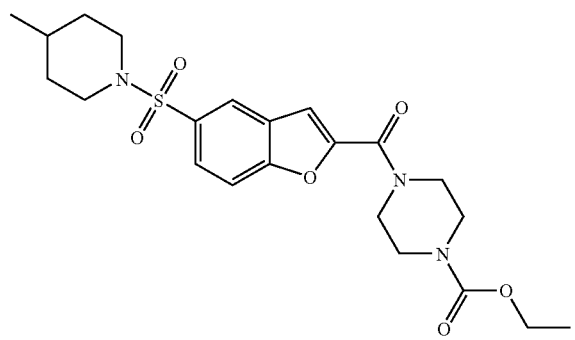 |
| 159 | 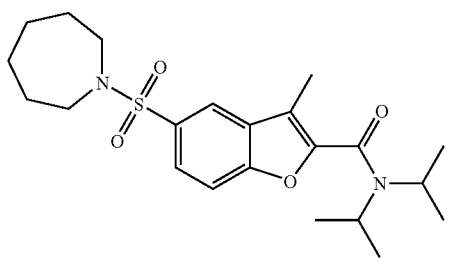 |

-continued

| Cmpd No. | Structure |
|---|---|
| 161 | 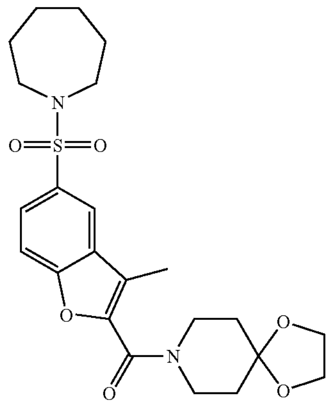 |
| 162 | 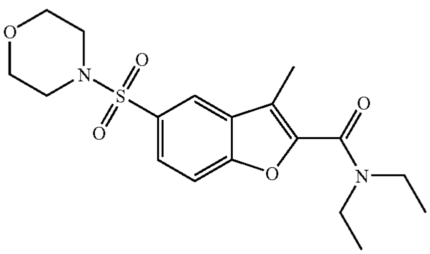 |
| 163 | 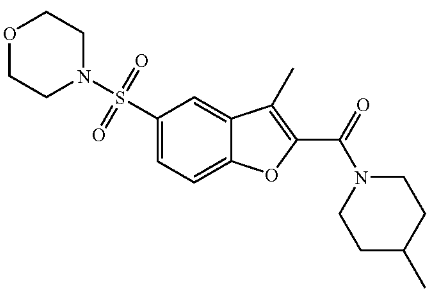 |
| 164 | 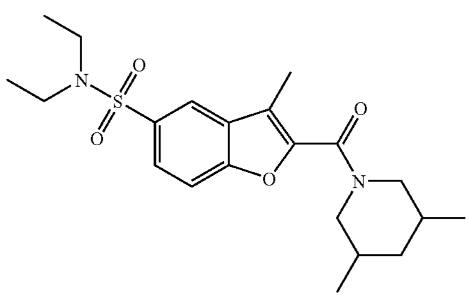 |
| 165 | 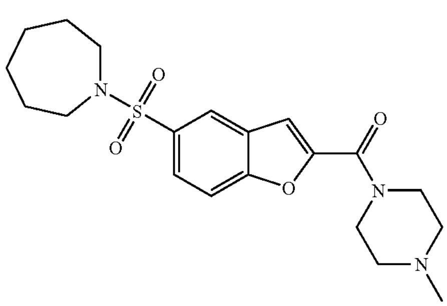 |

-continued
| Cmpd No. | Structure |
|---|---|
| 167 | 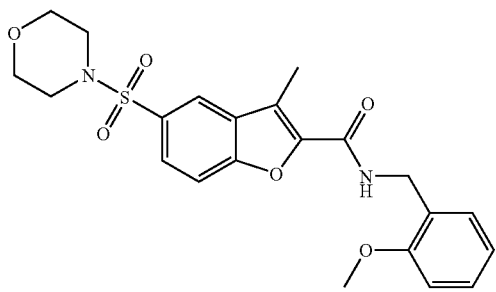 |
| 169 | 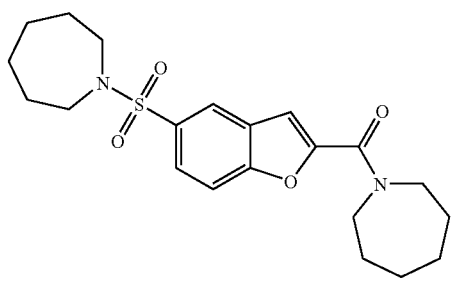 |
| 170 | 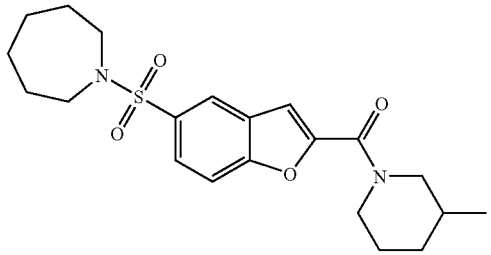 |
| 172 | 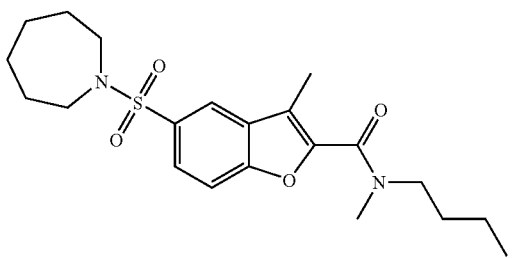 |
| 173 | 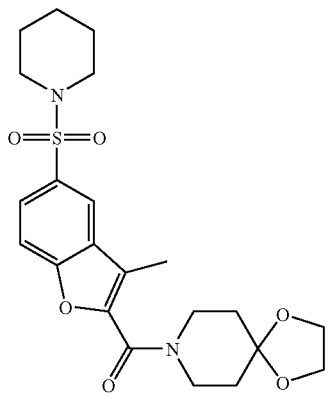 |

-continued
| Cmpd No. | Structure |
|---|---|
| 175 | 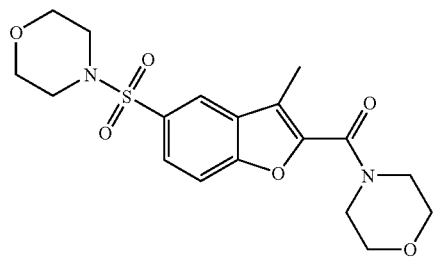 |
| 176 | 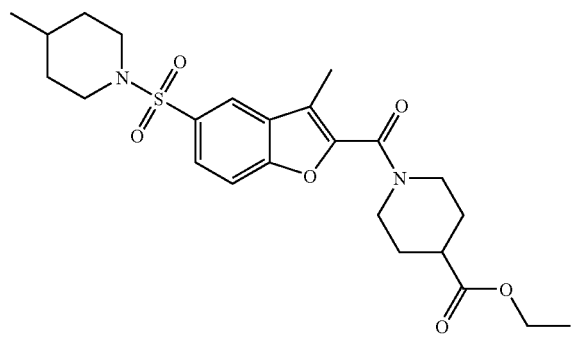 |
| 177 | 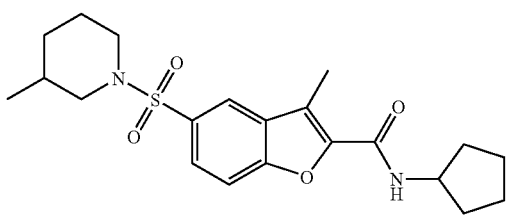 |
| 178 | 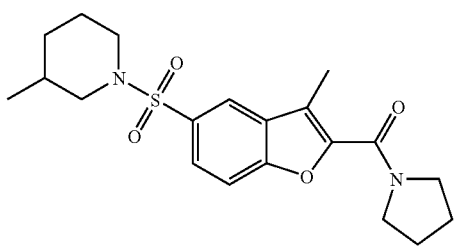 |
| 179 | 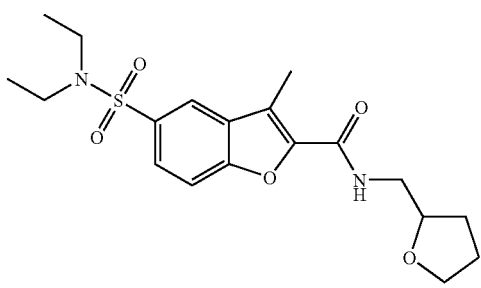 |

-continued
| Cmpd No. | Structure |
|---|---|
| 180 | 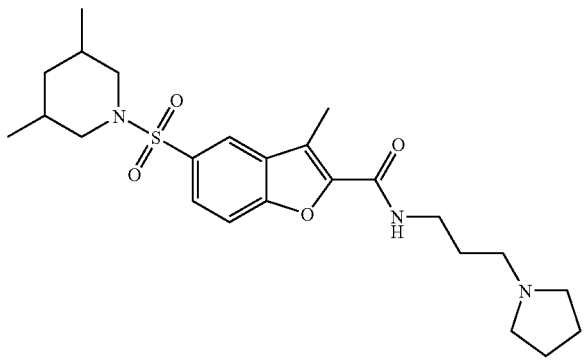 |
| 182 | 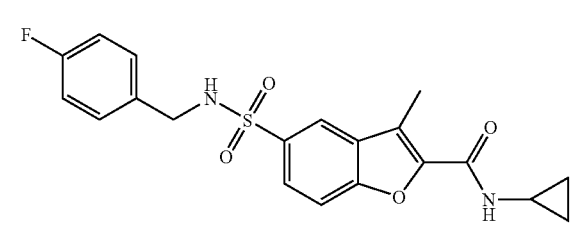 |
| 183 | 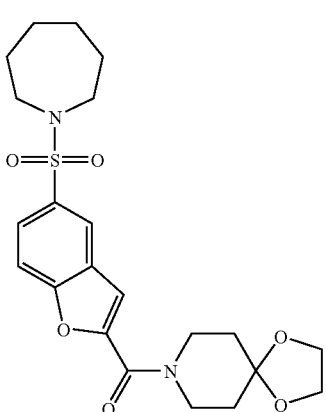 |
| 184 | 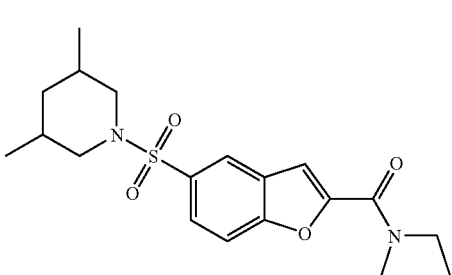 |
| 186 | 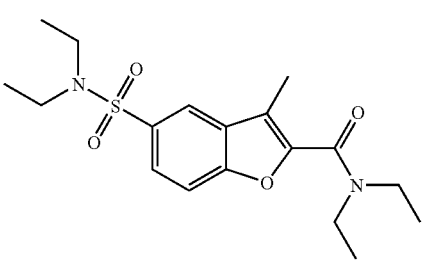 |

| Cmpd No. | Structure |
|---|---|
| 187 | 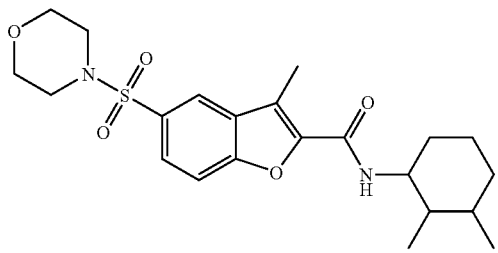 |
| 188 | 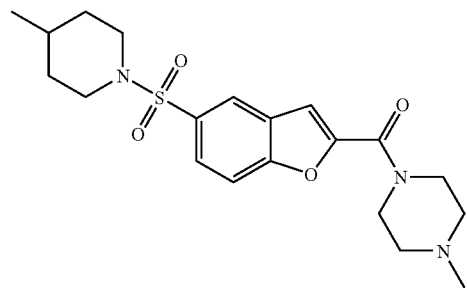 |
| 189 | 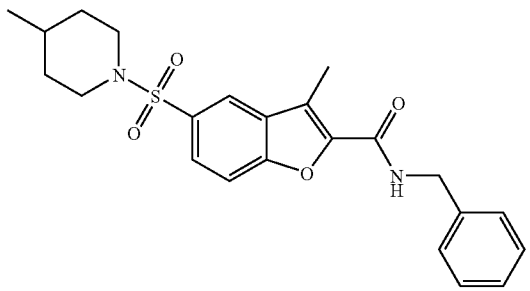 |
| 190 | 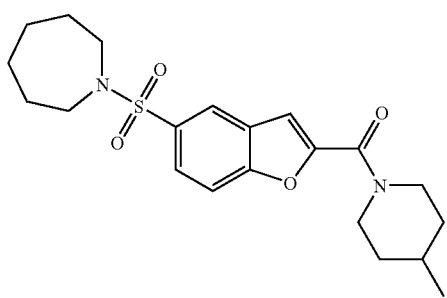 |
| 193 | 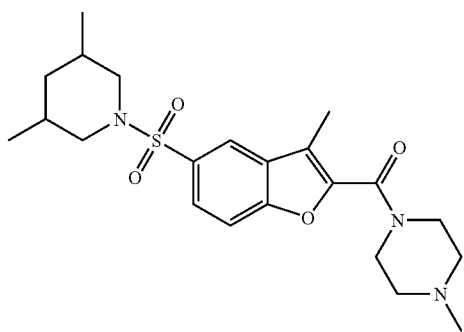 |

-continued

| Cmpd No. | Structure |
|---|---|
| 195 | 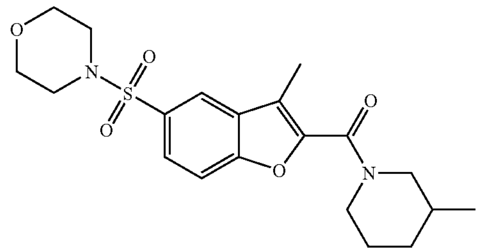 |
| 197 | 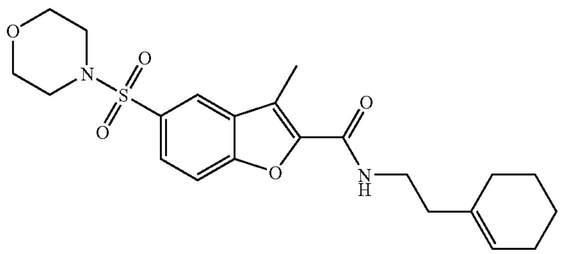 |
| 199 | 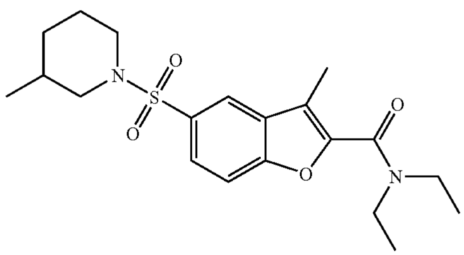 |
| 200 | 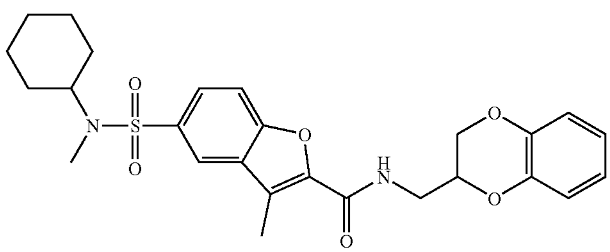 |
| 201 | 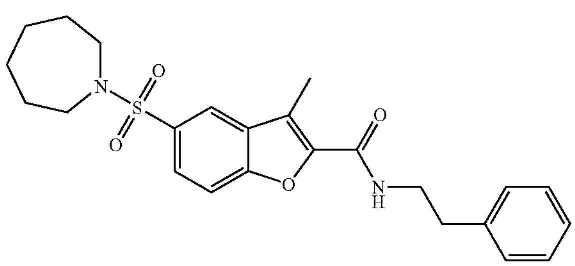 |
| 202 | 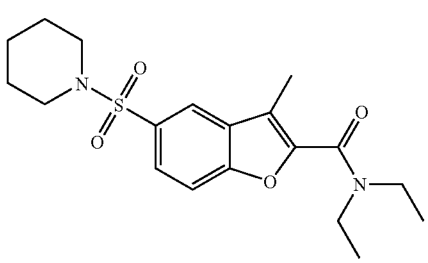 |

-continued
| Cmpd No. | Structure |
|---|---|
| 203 | 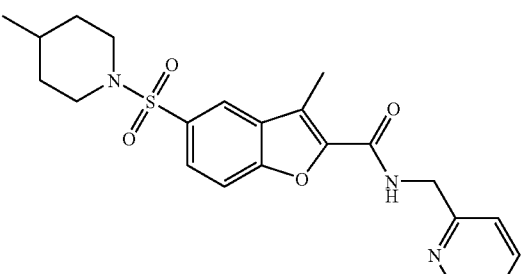 |
| 204 | 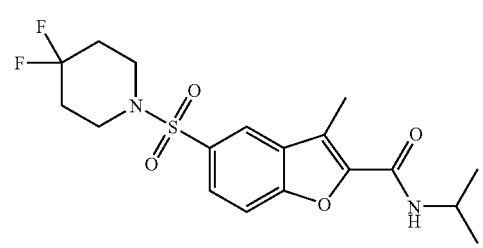 |
| 205 | 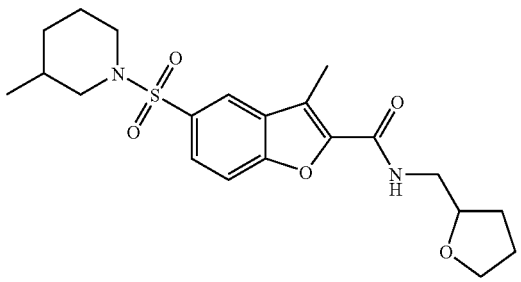 |
| 207 | 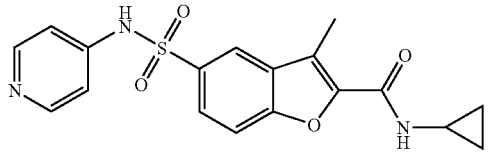 |
| 208 | 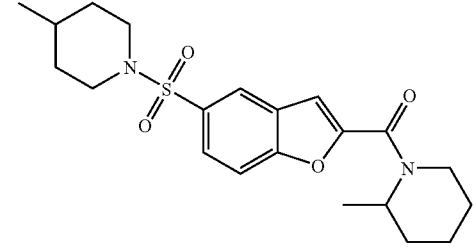 |
| 210 | 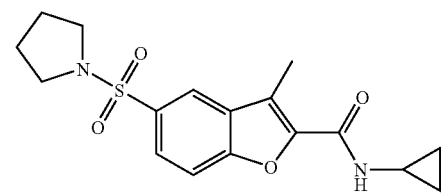 |

-continued
| Cmpd No. | Structure |
|---|---|
| 211 | 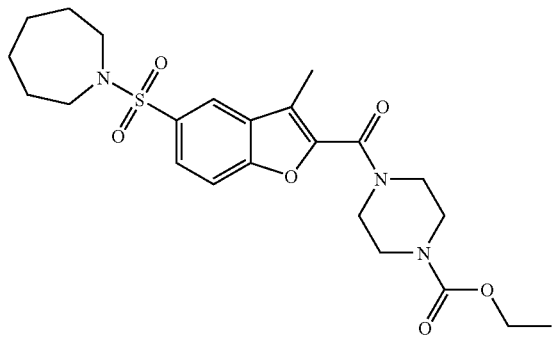 |
| 212 | 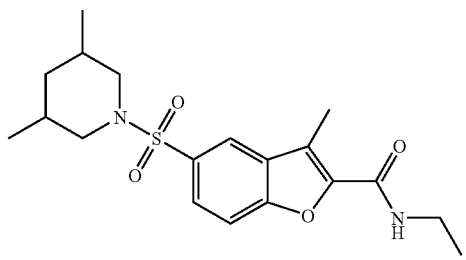 |
| 213 | 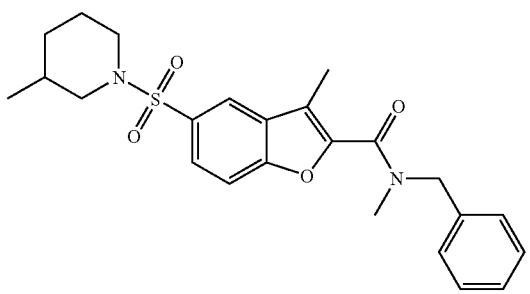 |
| 214 | 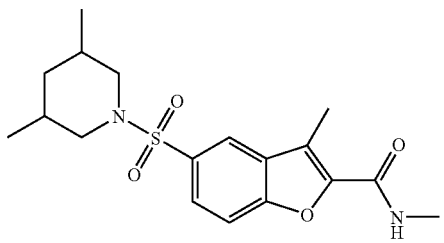 |
| 215 | 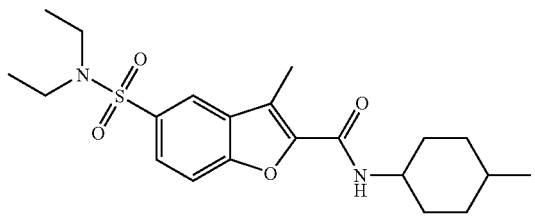 |

| Cmpd No. | Structure |
|---|---|
| 218 | 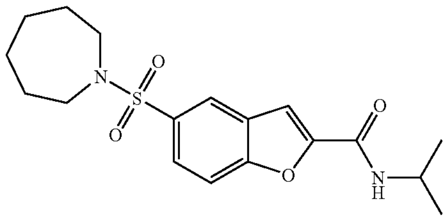 |
| 219 | 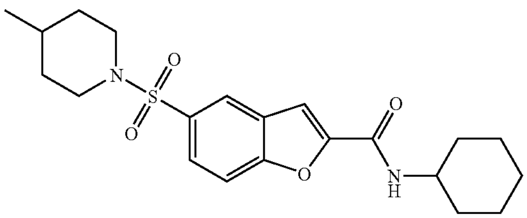 |
| 222 | 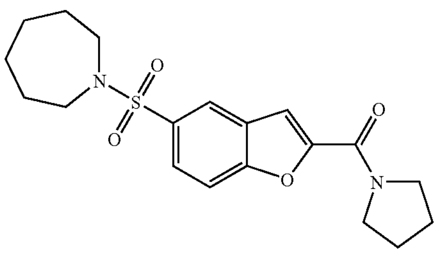 |
| 224 | 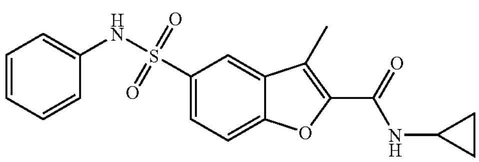 |
| 225 | 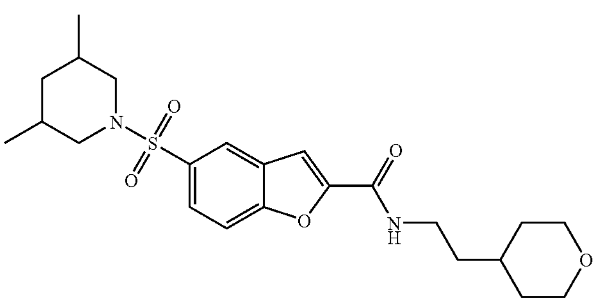 |
| 226 | 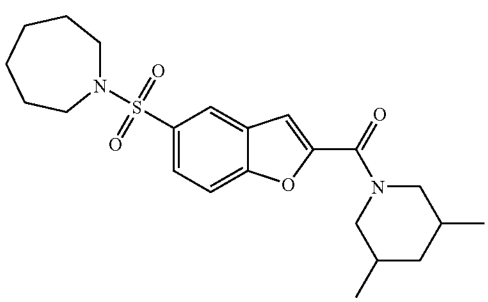 |

-continued
| Cmpd No. | Structure |
|---|---|
| 228 | 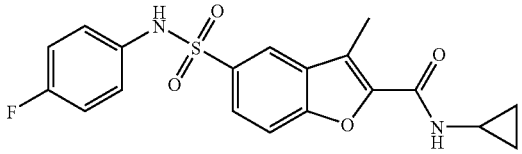 |
| 229 | 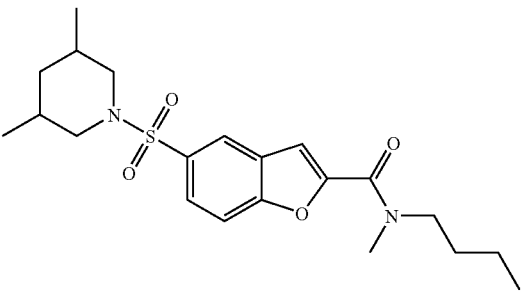 |
| 231 | 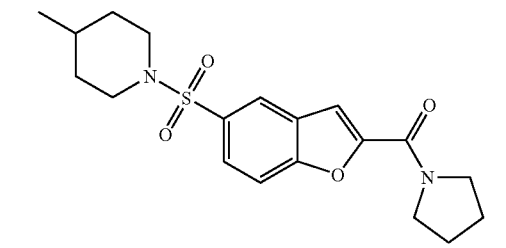 |
| 233 | 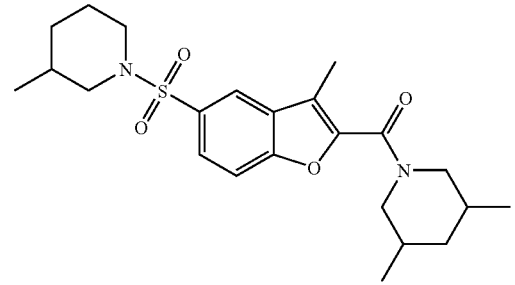 |
| 234 | 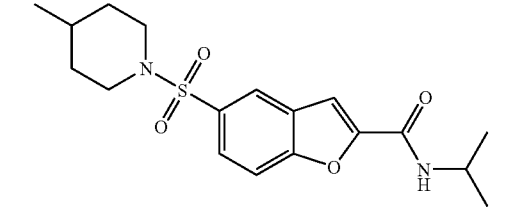 |
| 236 | 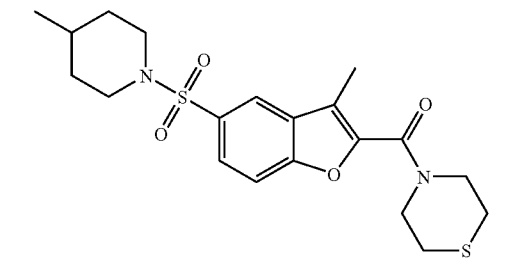 |

-continued
| Cmpd No. | Structure |
|---|---|
| 237 | 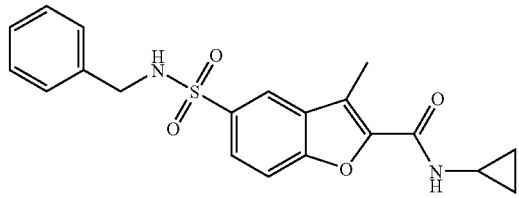 |
| 238 | 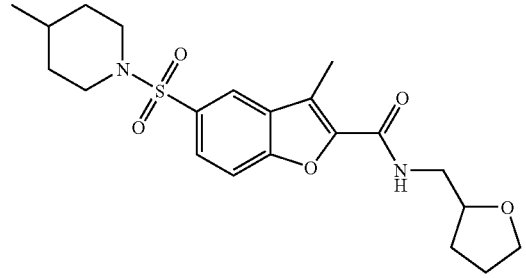 |
| 240 | 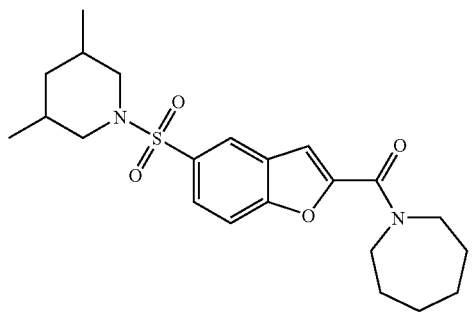 |
| 242 | 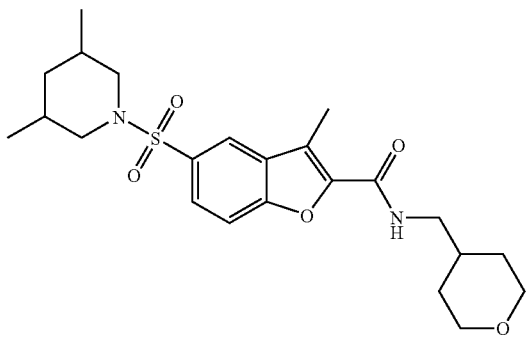 |
| 243 | 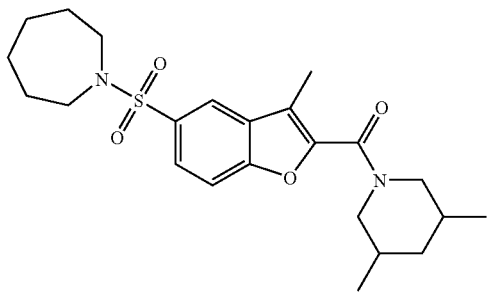 |

-continued
| Cmpd No. | Structure |
|---|---|
| 245 | 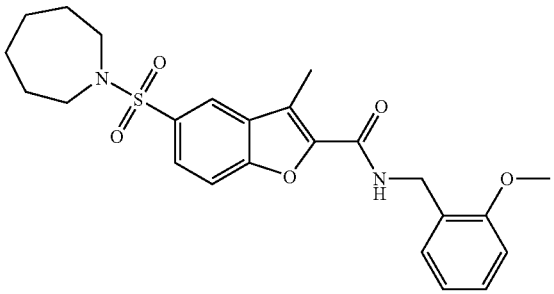 |
| 246 | 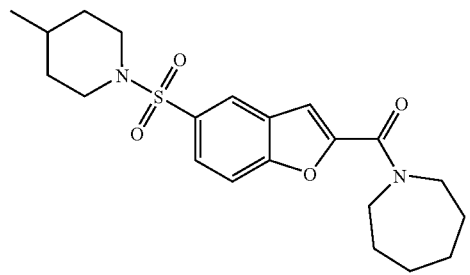 |
| 247 | 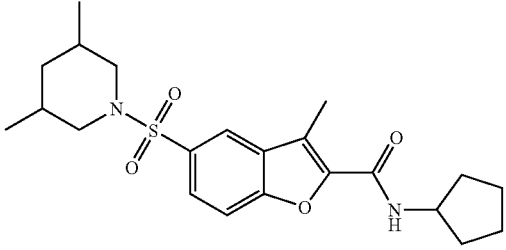 |
| 249 | 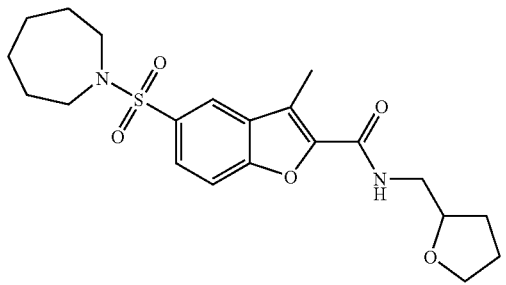 |
| 250 | 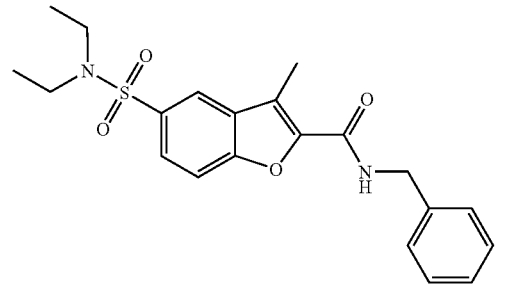 |

-continued
| Cmpd No. | Structure |
|---|---|
| 255 | 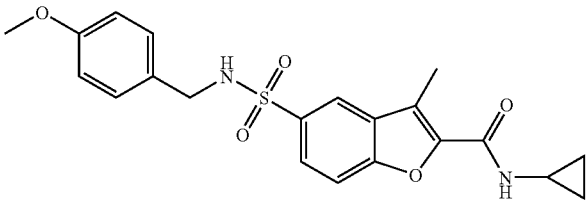 |
| 256 | 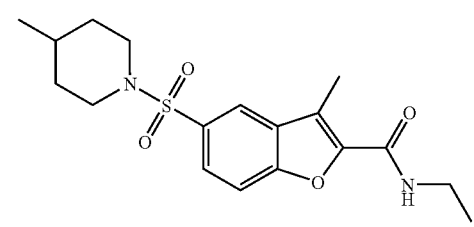 |
| 257 | 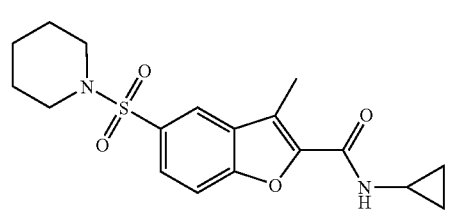 |
| 259 | 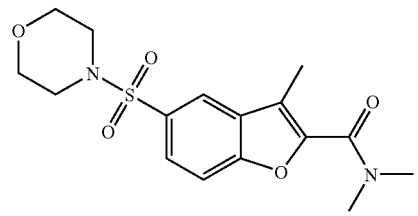 |
| 260 | 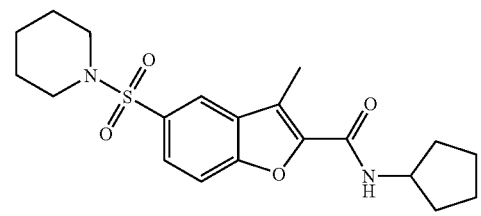 |
| 261 | 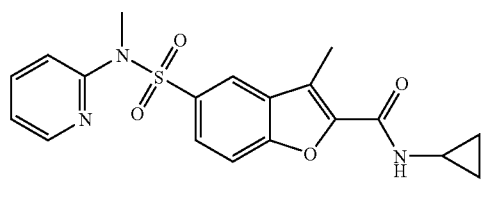 |
| 263 | 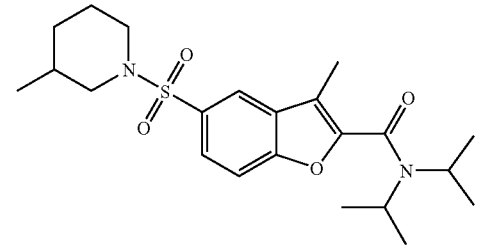 |

-continued

| Cmpd No. | Structure |
|---|---|
| 264 | 3,3-difluoropiperidin-1-ylsulfonyl-3-methylbenzofuran-2-carboxamide, N-isopropyl |
| 265 | azepan-1-ylsulfonyl-benzofuran-2-carboxamide, N-ethyl |
| 266 | 4-methylpiperidin-1-ylsulfonyl-benzofuran-2-carboxamide, N-(2-(tetrahydropyran-4-yl)ethyl) |
| 267 | morpholin-4-ylsulfonyl-3-methylbenzofuran-2-carboxamide, N-benzyl |
| 268 | 4-methylpiperidin-1-ylsulfonyl-benzofuran-2-carboxamide, N,N-diethyl |
| 271 | 3,5-dimethylpiperidin-1-ylsulfonyl-benzofuran-2-carboxamide, N-isopropyl |

-continued
| Cmpd No. | Structure |
|---|---|
| 273 | 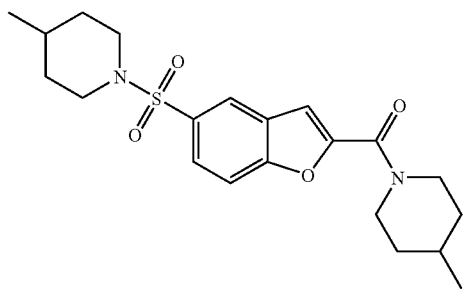 |
| 276 | 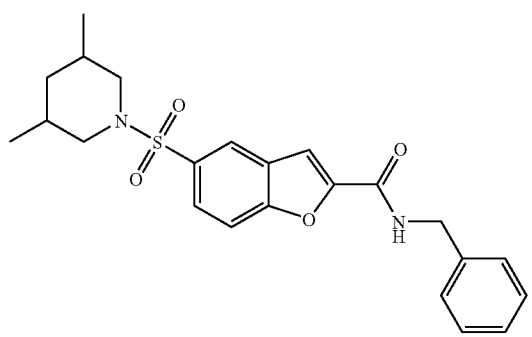 |
| 277 | 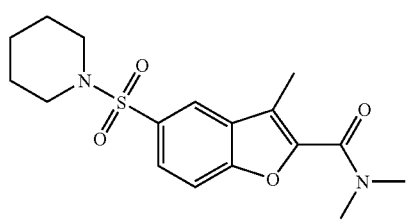 |
| 278 | 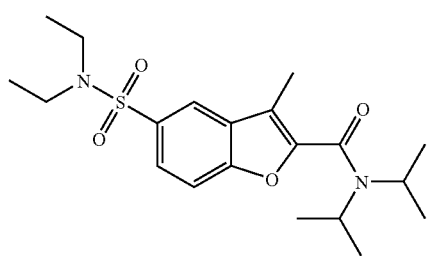 |
| 279 | 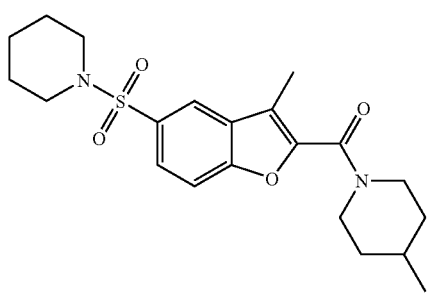 |

-continued

| Cmpd No. | Structure |
|---|---|
| 280 | 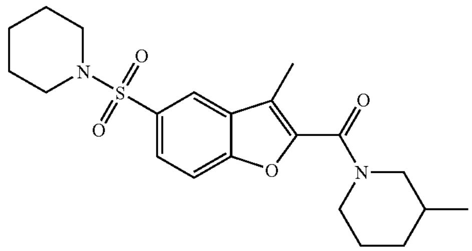 |
| 282 | 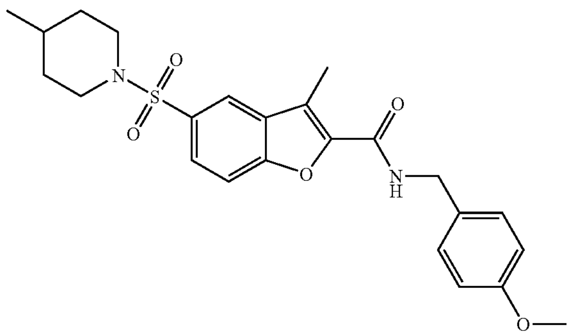 |
| 284 | 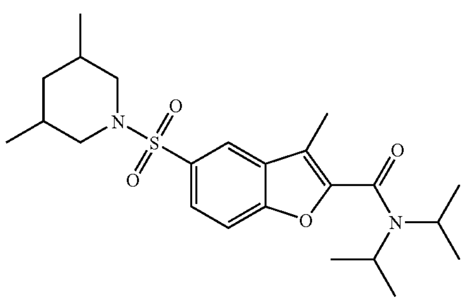 |
| 287 | 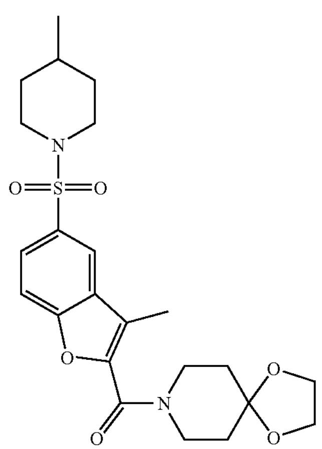 |
| 288 | 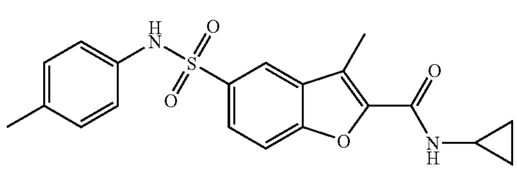 |

-continued
| Cmpd No. | Structure |
|---|---|
| 291 | 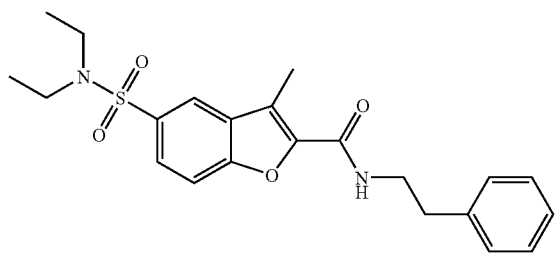 |
| 293 | 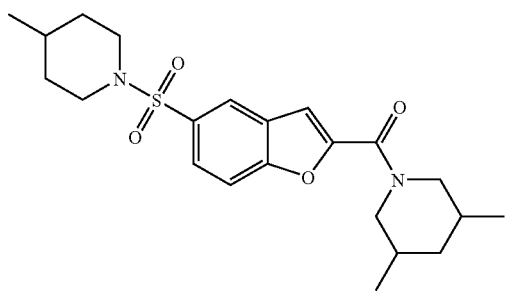 |
| 294 | 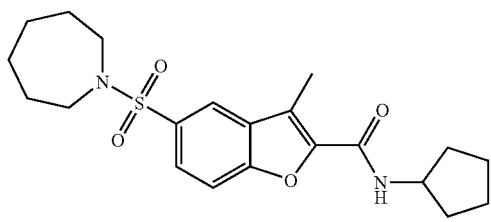 |
| 295 | 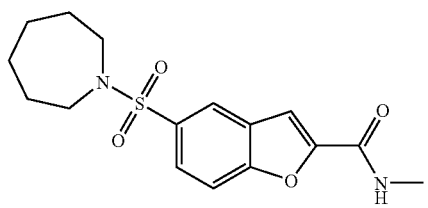 |
| 298 | 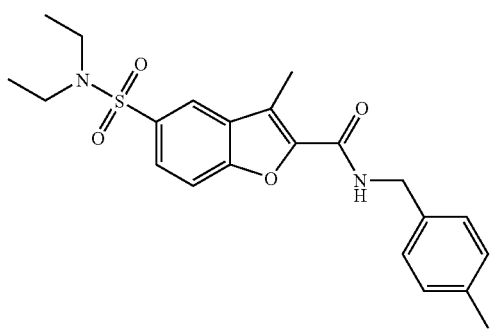 |

-continued
| Cmpd No. | Structure |
|---|---|
| 299 | 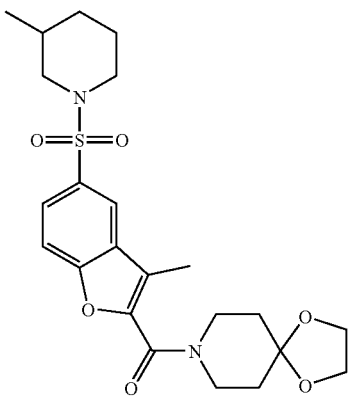 |
| 300 | 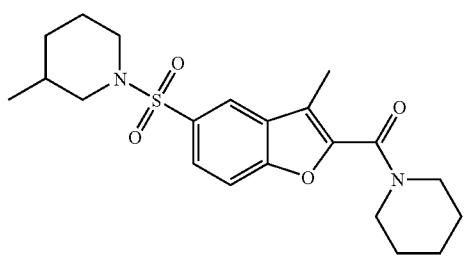 |
| 302 | 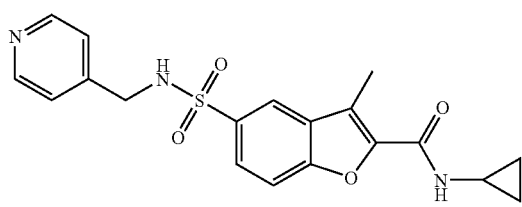 |
| 304 | 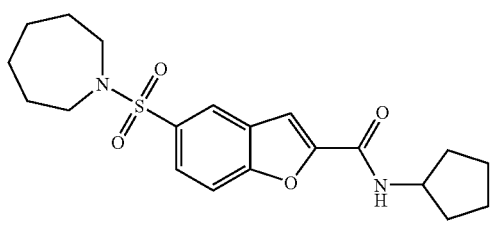 |
| 305 | 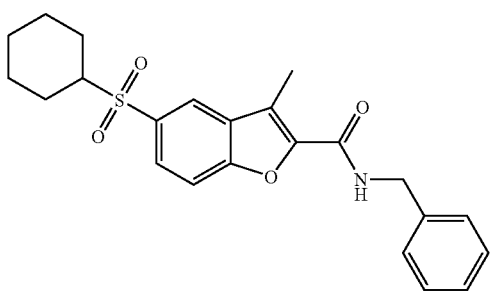 |

-continued

| Cmpd No. | Structure |
|---|---|
| 307 | 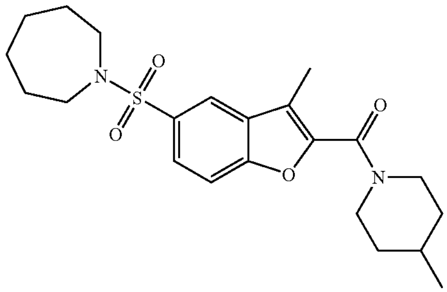 |
| 308 | 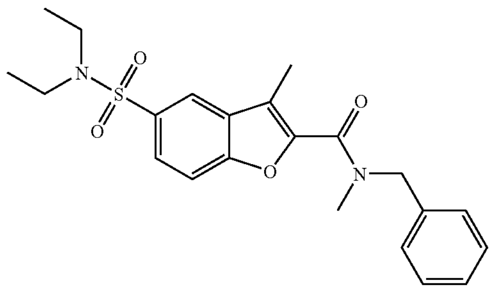 |
| 310 | 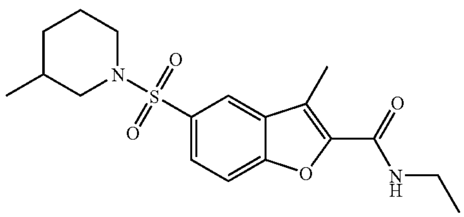 |
| 311 | 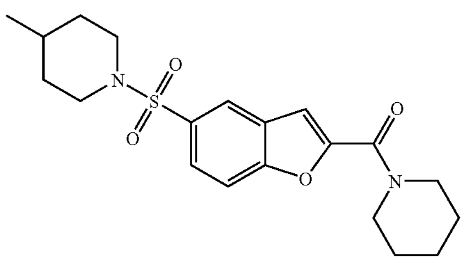 |
| 316 | 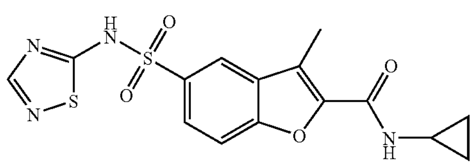 |
| 317 | 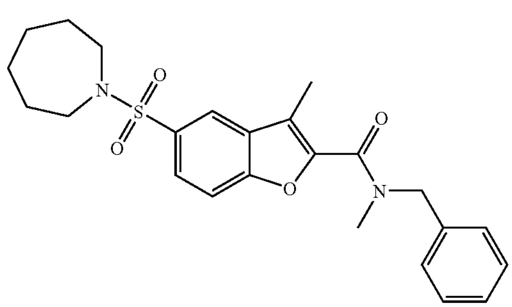 |

-continued
| Cmpd No. | Structure |
|---|---|
| 318 | 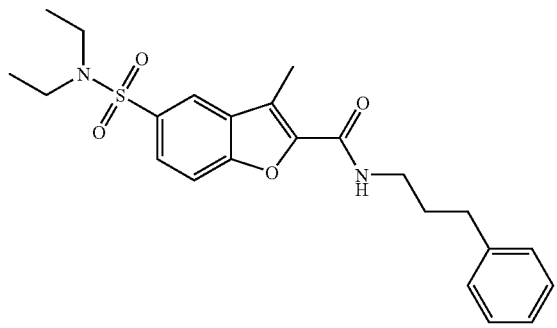 |
| 320 | 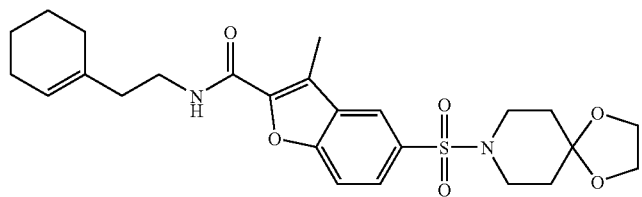 |
| 321 | 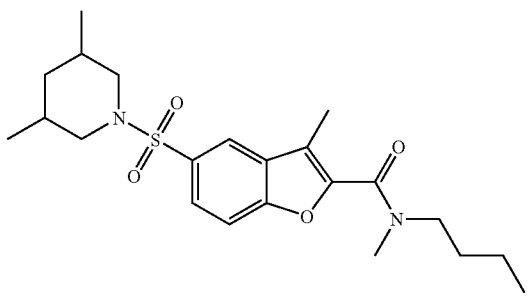 |
| 322 | 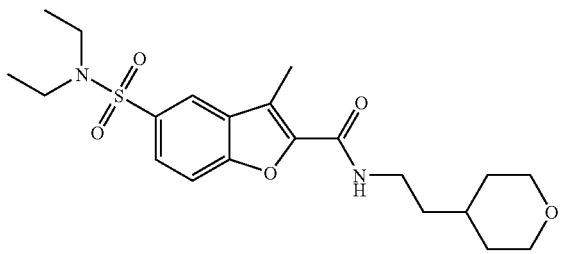 |
| 325 | 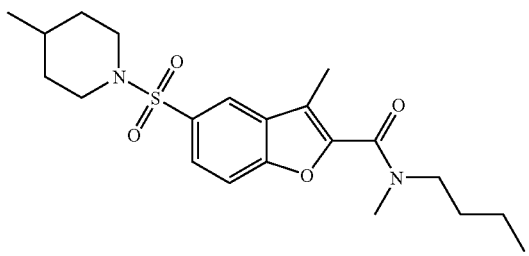 |

-continued

| Cmpd No. | Structure |
|---|---|
| 327 | 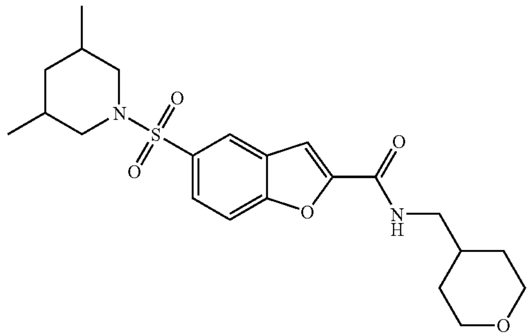 |
| 328 | 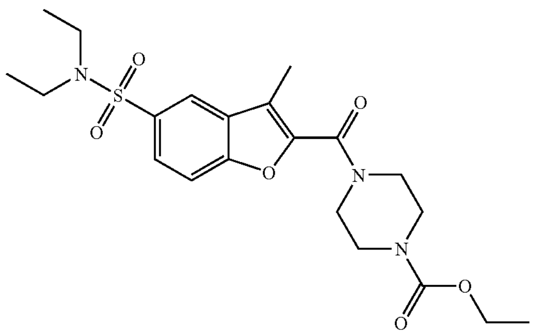 |
| 330 | 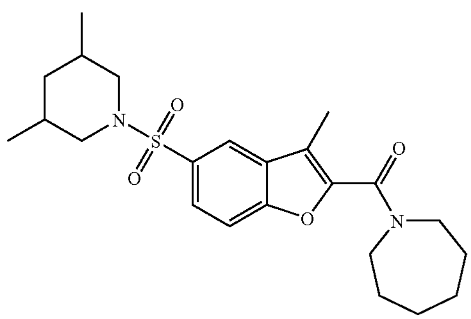 |
| 332 | 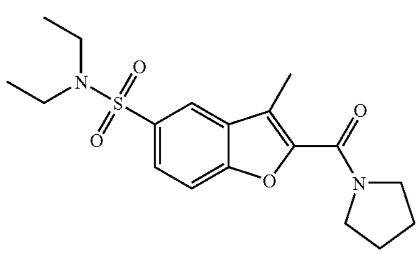 |
| 333 | 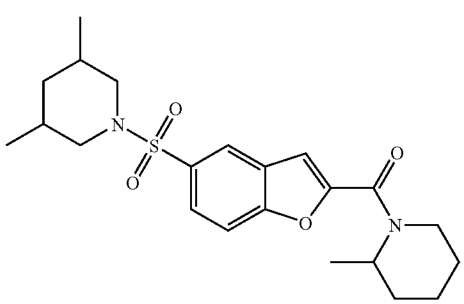 |

-continued
| Cmpd No. | Structure |
|---|---|
| 334 | 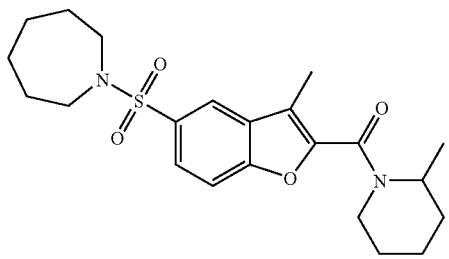 |
| 336 | 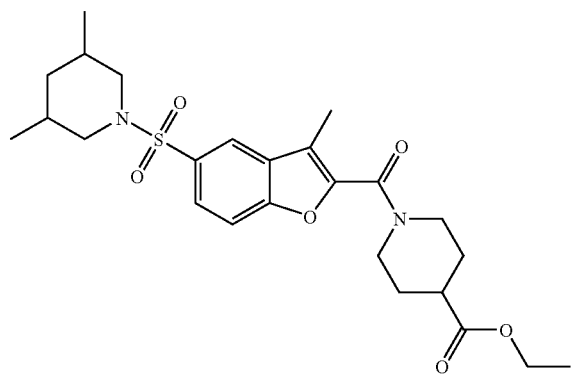 |
| 337 | 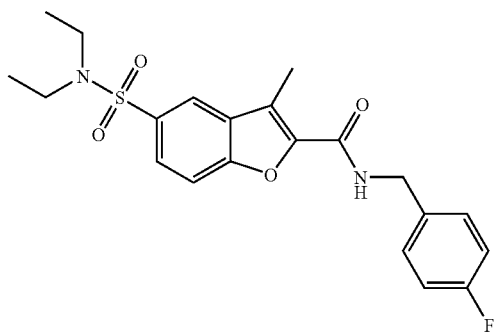 |
| 339 | 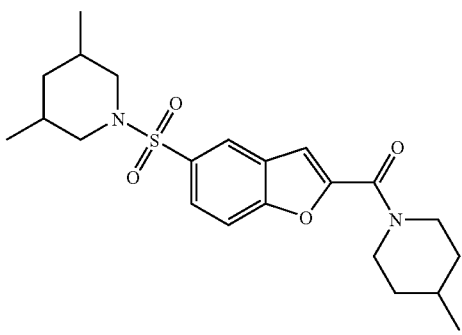 |

-continued
| Cmpd No. | Structure |
|---|---|
| 341 | 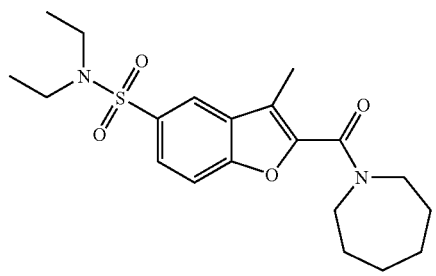 |
| 343 | 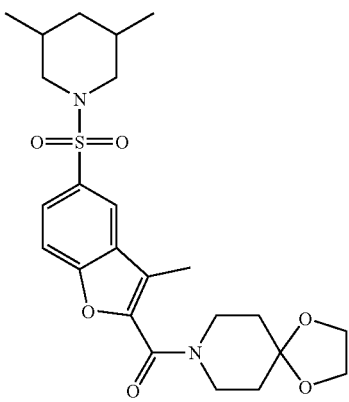 |
| 346 | 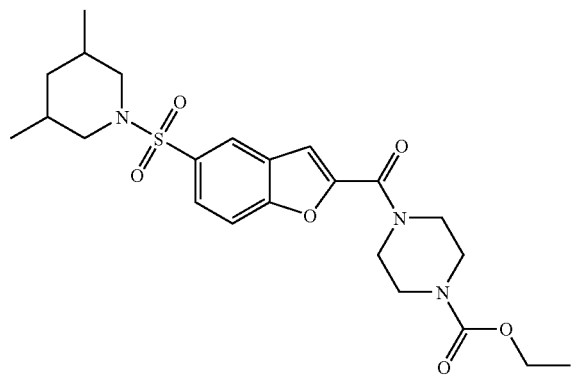 |
| 347 | 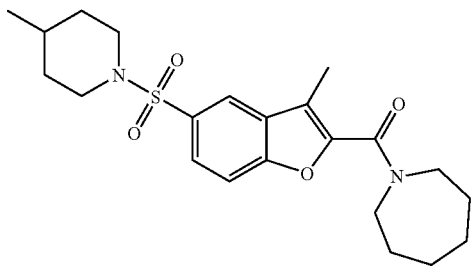 |

-continued
| Cmpd No. | Structure |
|---|---|
| 350 | 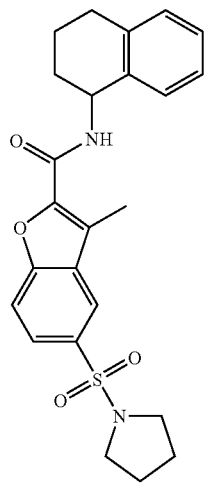 |
| 352 | 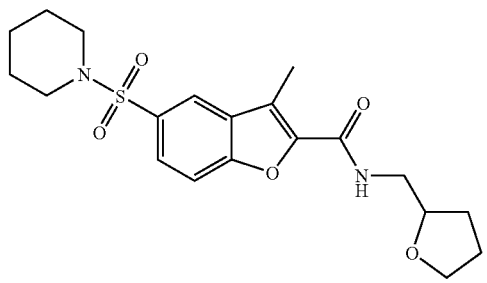 |
| 353 | 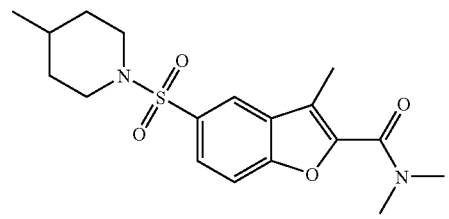 |
| 356 | 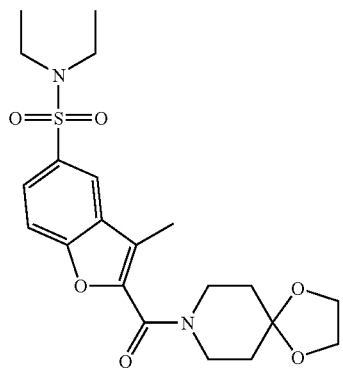 |

-continued

| Cmpd No. | Structure |
|---|---|
| 359 | 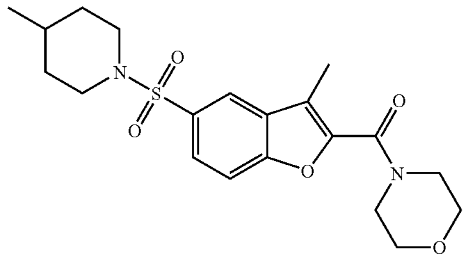 |
| 360 | 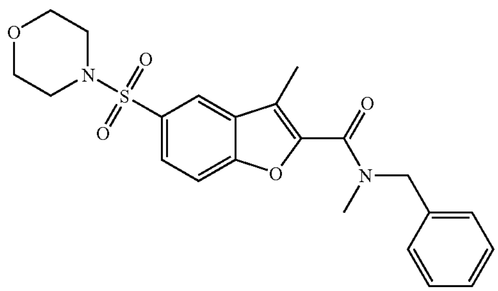 |
| 361 | 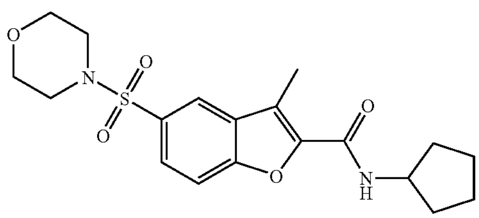 |
| 363 | 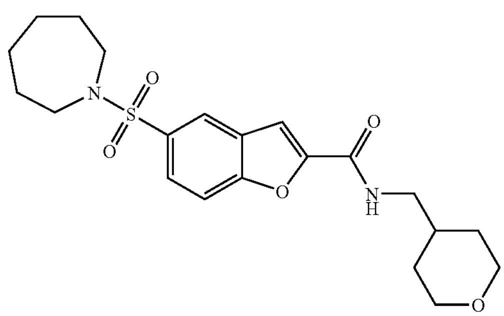 |
| 365 | 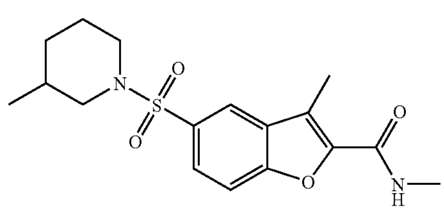 |
| 367 | 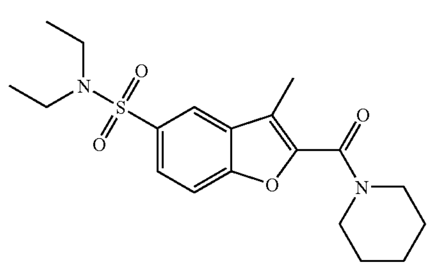 |

-continued
| Cmpd No. | Structure |
|---|---|
| 369 | 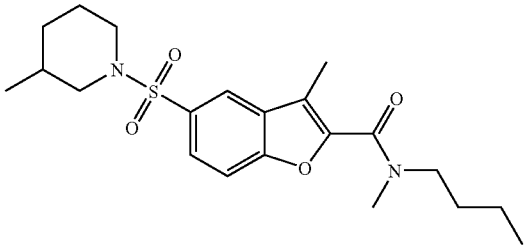 |
| 370 | 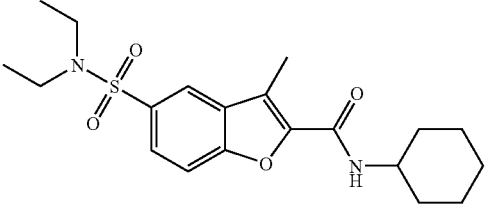 |
| 371 | 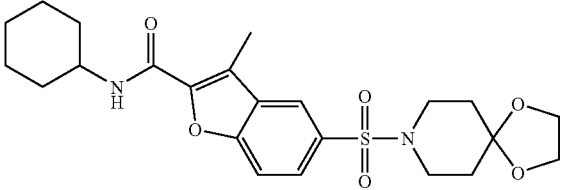 |
| 372 | 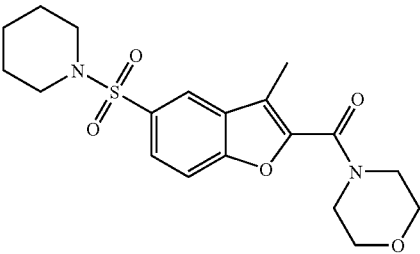 |
| 375 | 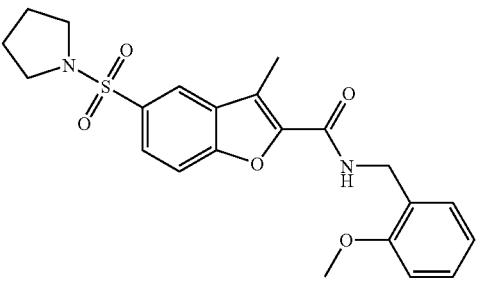 |
| 376 | 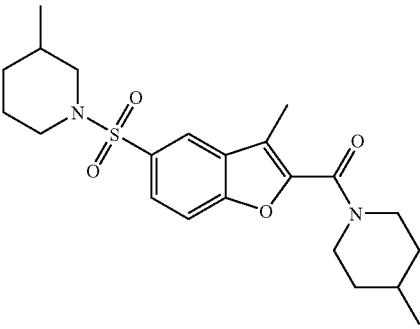 |

-continued
| Cmpd No. | Structure |
|---|---|
| 378 | 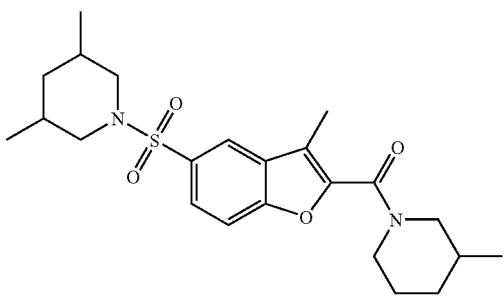 |
| 383 | 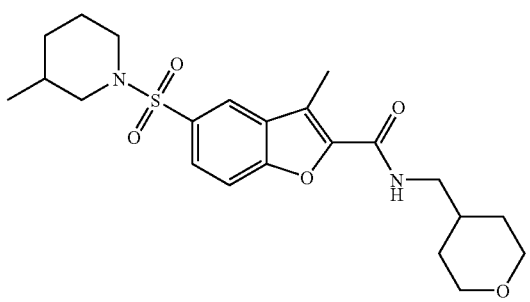 |
| 385 | 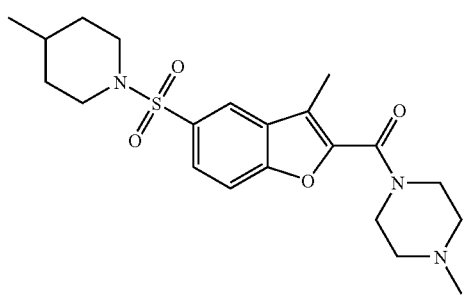 |
| 388 | 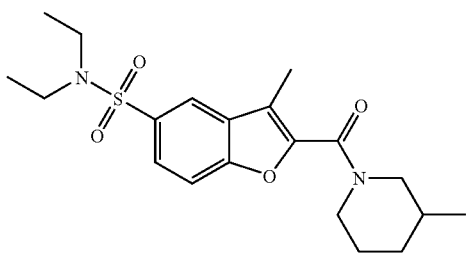 |
| 392 | 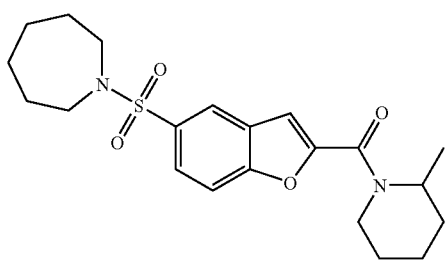 |

-continued
| Cmpd No. | Structure |
|---|---|
| 393 | 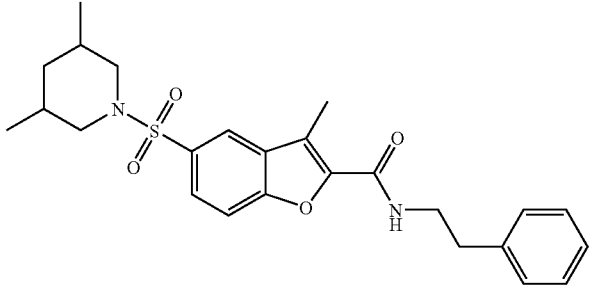 |
| 394 | 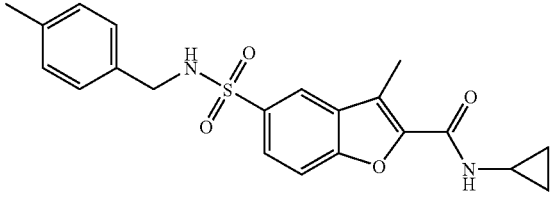 |
| 395 | 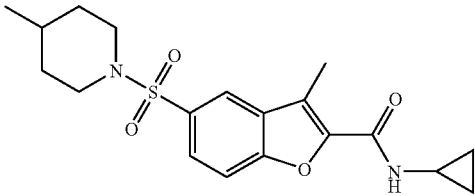 |
| 396 | 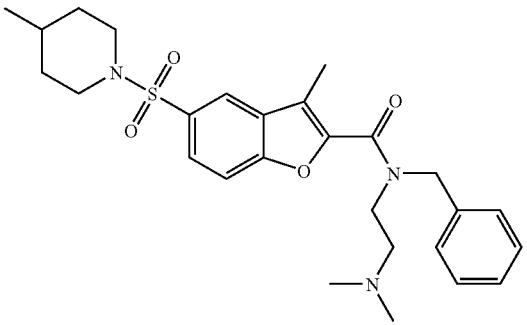 |
| 397 | 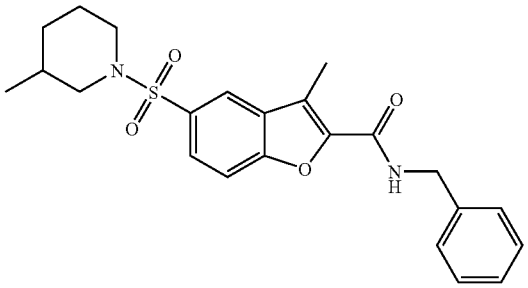 |
| 399 | 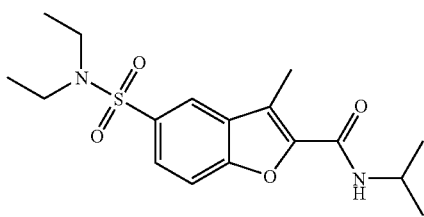 |

-continued
| Cmpd No. | Structure |
|---|---|
| 401 | 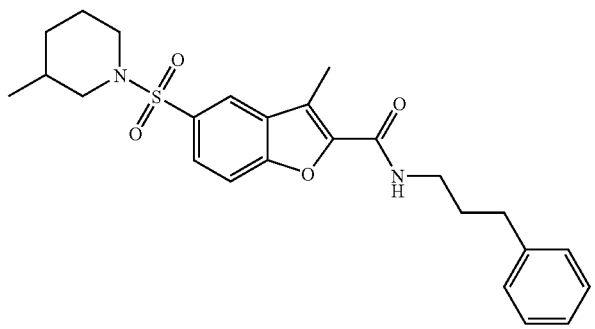 |
| 402 | 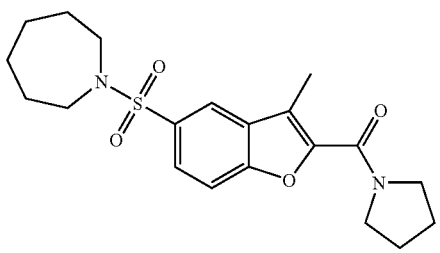 |
| 403 | 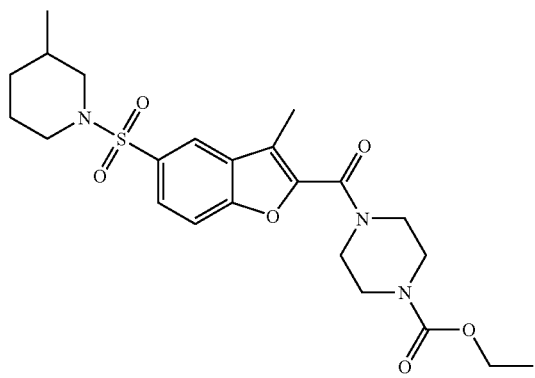 |
| 404 | 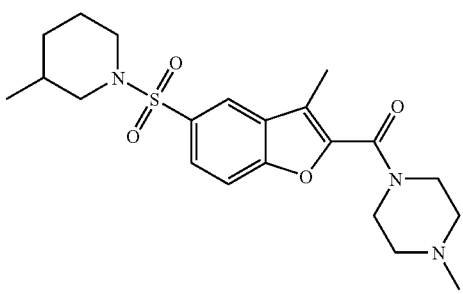 |
| 406 | 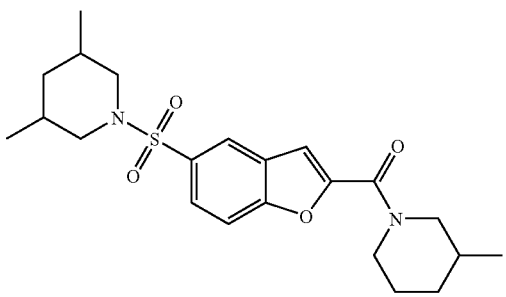 |

-continued
| Cmpd No. | Structure |
|---|---|
| 408 | 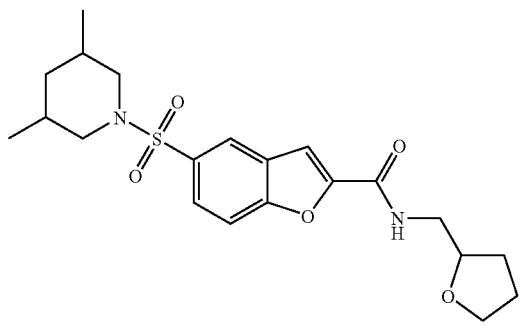 |
| 409 | 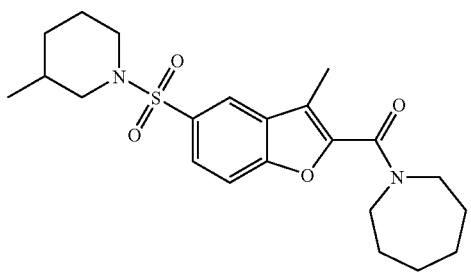 |
| 410 | 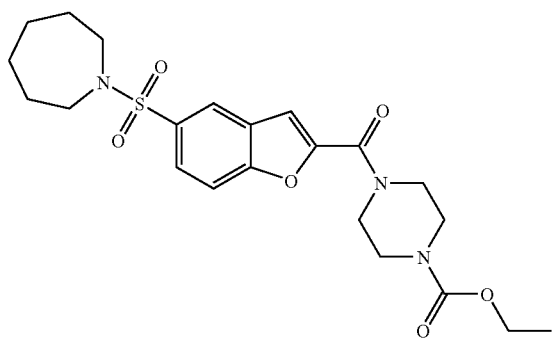 |
| 411 | 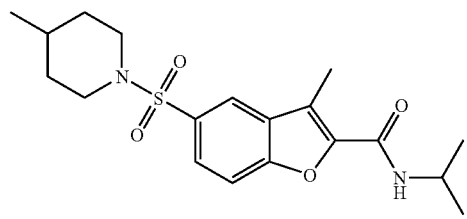 |
| 413 | 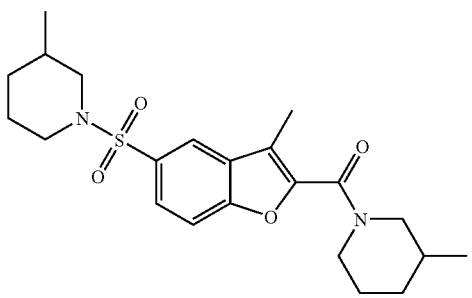 |

-continued

| Cmpd No. | Structure |
|---|---|
| 414 | 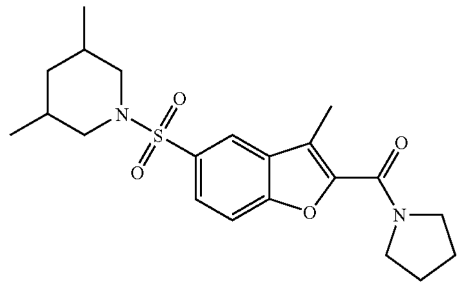 |
| 417 | 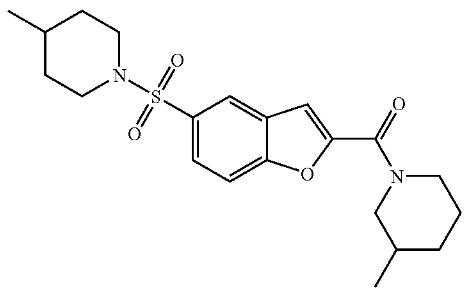 |
| 423 | 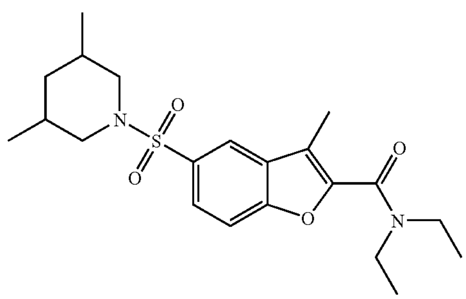 |
| 426 | 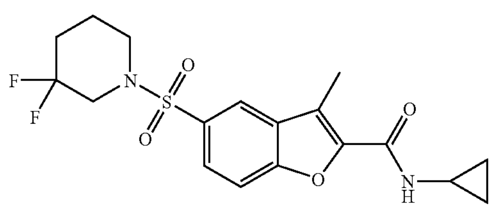 |
| 427 | 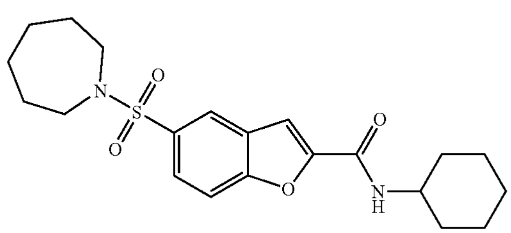 |

-continued

| Cmpd No. | Structure |
|---|---|
| 429 | 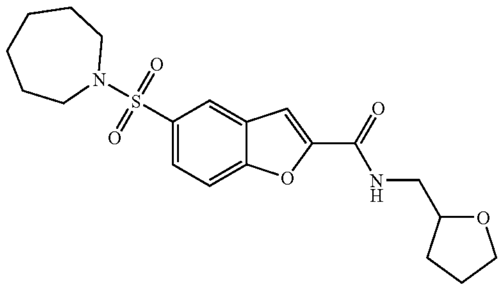 |
| 430 | 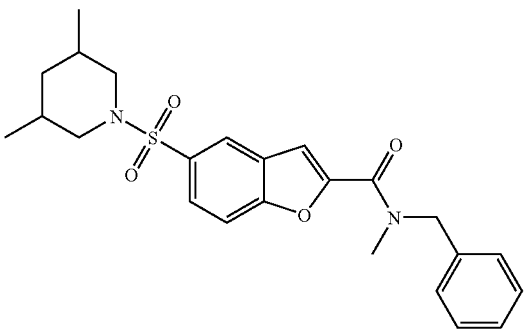 |
| 431 | 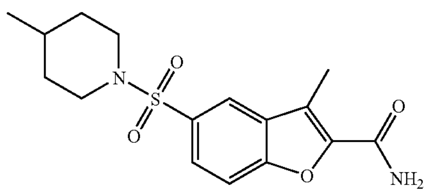 |
| 432 | 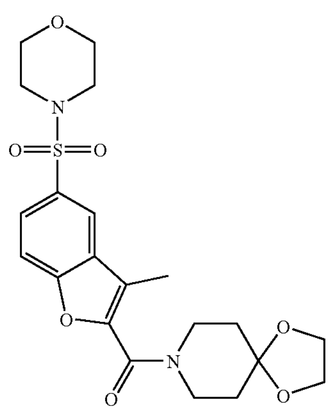 |
| 433 | 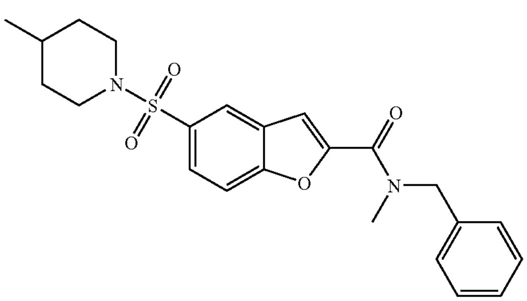 |

| Cmpd No. | Structure |
|---|---|
| 438 | (4-methylpiperidin-1-yl)sulfonyl-benzofuran-2-carboxamide, N-methyl |
| 441 | (3,5-dimethylpiperidin-1-yl)sulfonyl-3-methylbenzofuran-2-carboxamide, N-benzyl |
| 443 | (4-methylpiperidin-1-yl)sulfonyl-3-methylbenzofuran-2-carboxamide, N,N-diisopropyl |
| 444 | (diethylamino)sulfonyl-3-methylbenzofuran-2-carboxamide, N-ethyl |
| 445 | (3-methylpiperidin-1-yl)sulfonyl-3-methylbenzofuran-2-carboxamide, N-phenethyl |
| 446 | (azepan-1-yl)sulfonyl-3-methylbenzofuran-2-carboxamide, N-cyclohexyl |

-continued

| Cmpd No. | Structure |
|---|---|
| 447 | 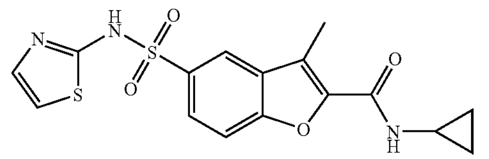 |
| 449 | 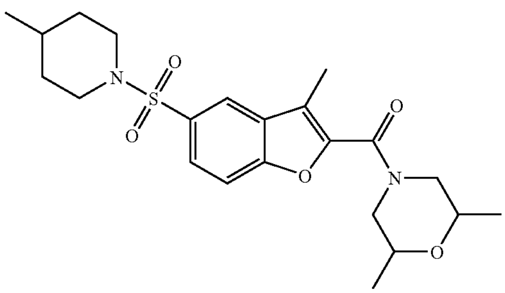 |
| 451 | 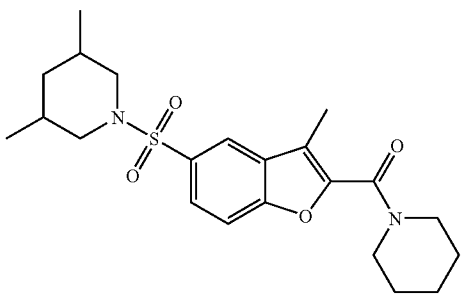 |
| 453 | 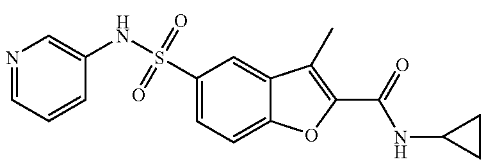 |
| 454 | 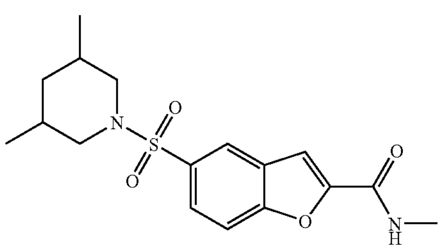 |
| 455 | 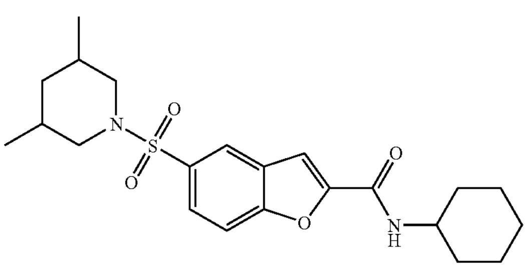 |

-continued
| Cmpd No. | Structure |
|---|---|
| 456 | 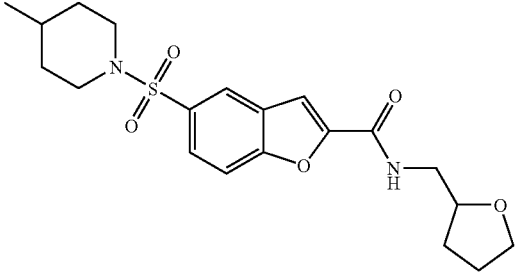 |
| 458 | 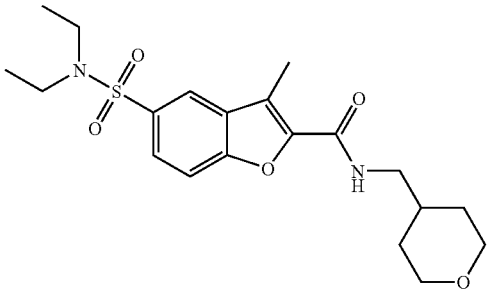 |
| 459 | 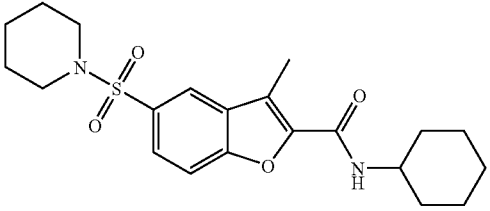 |
| 460 | 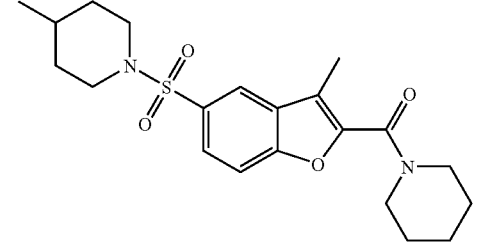 |
| 462 | 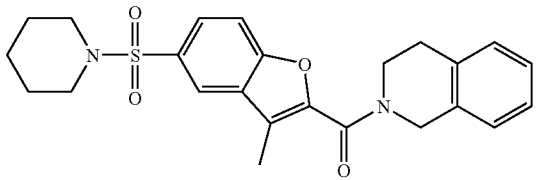 |
| 464 | 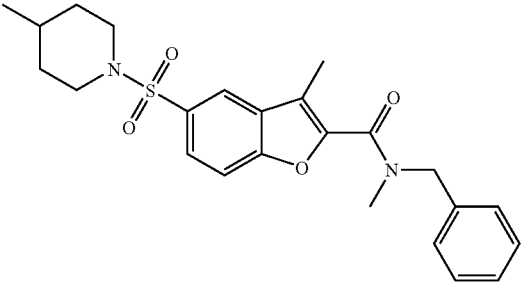 |

-continued
| Cmpd No. | Structure |
|---|---|
| 465 | 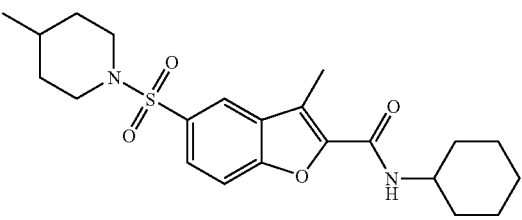 |
| 466 | 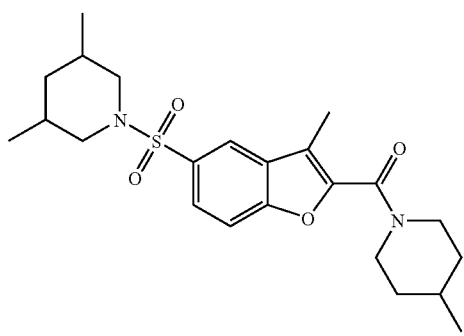 |
| 467 | 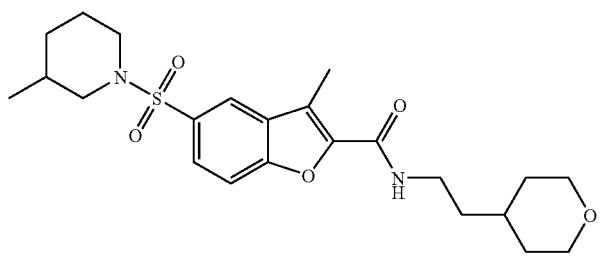 |
| 468 | 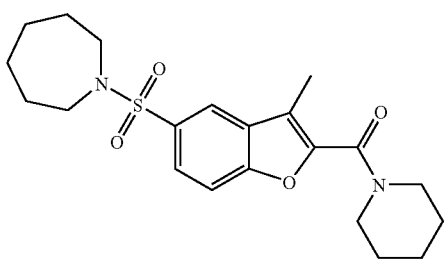 |
| 469 | 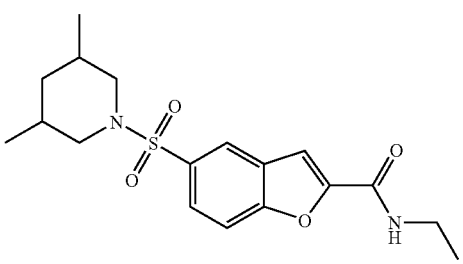 |

17. A compound of formula IV:

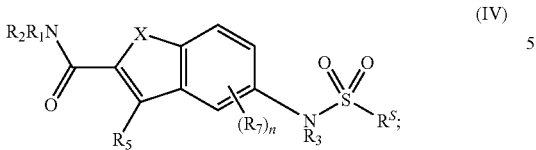

or a pharmaceutically acceptable salt thereof, wherein:
- $R^3$ is C1-C6 aliphatic, C5-C10 cycloaliphatic, or arylalkyl, wherein $R^3$ has 0-4 substituents selected from Z—$R^6$; and
- $R^S$ is aryl optionally substituted with 0-4 substituents selected from Z—$R^6$;
- $R_5$ and $R_7$ are independently defined by —$ZR_6$, wherein Z is a bond or is an optionally substituted $C_1$-$C_6$ alkyl, alkenyl, or alkynyl, chain wherein up to two carbon units of Z are optionally and independently replaced by CO—, —CS—, —COCO—, —CONR'—, —CONR'NR'—, —$CO_2$—, —OCO—, —$NR'CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, $NR'SO_2$—, or —$NR'SO_2NR'$—;
- wherein $R_1$ and $R_2$ are independently selected from the group consisting of hydrogen, alkyl, substituted alkyl, cycloalkyl, substituted cycloalkyl, heterocyclylalkyl, substituted heterocyclylalkyl, arylalkyl, substituted arylalkyl, heteroarylalkyl, substituted heteroarylalkyl, cycloalkylalkyl, substituted cycloalkylalkyl, polycyclic hydrocarbon, substituted polycyclic hydrocarbon; or
- $R_1$ and $R_2$ together form an unsubstituted or substituted 3 to 7-membered ring, wherein the members of the ring contain 0-4 heteroatoms selected from nitrogen, oxygen, and sulfur;
- X is O
- n is 0-3;
- $R_6$ is independently R', halogen, $NO_2$, CN, $CF_3$, or $OCF_3$;
- R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

18. The compound according to claim 17, wherein $R^3$ is C1-C6 alkyl or $R^3$ is C3-C6 cycloalkyl-alkyl.

19. The compound according to claim 17, wherein $R^3$ is arylalkyl.

20. The compound according to claim 17, wherein $R_5$ is hydrogen, or C1-C6 alkyl.

21. The compound according to claim 17, $R_1$ is hydrogen.

22. The compound according to claim 17, wherein $R_1$ is C1-C4 alkyl.

23. The compound according to claim 17, wherein $R_2$ is alkyl, arylalkyl, cycloalkyl, cycloalkenyl, cycloalkyl-alkyl, cycloalkenyl-alkyl, heterocyclyl, heterocyclyl-alkyl, heteroaryl, or heteroarylalkyl, wherein $R_2$ has 0-4 substituents selected from Z—$R_6$.

24. The compound according to claim 23, wherein $R_2$ is an optionally substituted arylalkyl group.

25. The compound according to claim 23, wherein $R_2$ is a cycloalkyl or cycloalkyl-alkyl group wherein $R_2$ has 0-4 substituents selected from Z—$R_6$.

26. The compound according to claim 23, wherein $R_2$ is a cycloalkenyl or cycloalkenyl-alkyl group wherein $R_2$ has 0-4 substituents selected from Z—$R_6$.

27. The compound according to claim 23, wherein $R_2$ is a heterocyclyl, or heterocyclyl-alkyl group wherein $R_2$ has 0-4 substituents selected from Z—$R_6$.

28. The compound according to claim 23, wherein $R_2$ is heteroaryl or heteroaryl-alkyl group, wherein $R_2$ has 0-4 substituents selected from Z—$R_5$.

29. The compound according to claim 17, wherein $R_1$ is C1-C4 alkyl, and $R_2$ is an optionally substituted arylalkyl group.

30. The compound according to claim 17, wherein $R_1$ and $R_2$ taken together form a 5-7 membered heterocyclic ring containing up to two additional heteroatoms selected from oxygen, nitrogen, or sulfur, wherein said ring has 0-4 substituents selected from Z—$R_6$.

31. A pharmaceutical composition comprising a compound selected from claim 1 or 17, and a pharmaceutically acceptable carrier or adjuvant.

* * * * *

UNITED STATES PATENT AND TRADEMARK OFFICE
CERTIFICATE OF CORRECTION

| | | |
|---|---|---|
| PATENT NO. | : 7,569,604 B2 | Page 1 of 1 |
| APPLICATION NO. | : 11/165254 | |
| DATED | : August 4, 2009 | |
| INVENTOR(S) | : Andreas Termin et al. | |

It is certified that error appears in the above-identified patent and that said Letters Patent is hereby corrected as shown below:

On the Title Page

Item (75), line 3, "Nicole Zimmerman" should read --Nicole Zimmermann--

Signed and Sealed this

Twenty-ninth Day of September, 2009

David J. Kappos
*Director of the United States Patent and Trademark Office*